US005710159A

United States Patent [19]
Voss et al.

[11] Patent Number: 5,710,159
[45] Date of Patent: Jan. 20, 1998

[54] INTEGRIN RECEPTOR ANTAGONISTS

[75] Inventors: Matthew Ernst Voss, Lincoln University, Pa.; Prabhakar Kondaji Jadhav, Wilmington, Del.; Joanne Marie Smallheer, Landenberg, Pa.; Douglas Guy Batt, Wilmington, Del.; William John Pitts, Conshohocken; John Wityak, West Grove, both of Pa.

[73] Assignee: The DuPont Merck Pharmaceutical Company, Wilmington, Del.

[21] Appl. No.: 647,132

[22] Filed: May 9, 1996

[51] Int. Cl.⁶ .................... A61K 31/505; C07D 413/06
[52] U.S. Cl. .................. 514/275; 514/303; 514/340; 514/341; 514/370; 514/386; 514/393; 514/394; 514/395; 514/397; 544/331; 546/118; 546/272.1; 548/190; 548/193; 548/194; 548/302.7; 548/304.7; 548/311.1
[58] Field of Search ............... 544/331; 514/275, 514/386, 393, 394, 395, 397, 340, 341, 370, 303; 548/302.7, 304.7, 311.1, 190, 193, 194; 546/272.1, 118

[56] References Cited

U.S. PATENT DOCUMENTS 5,463,071 10/1995 Himmelsbach et al. ............... 548/251

FOREIGN PATENT DOCUMENTS

| 0237082 | 9/1987 | European Pat. Off. . |
| 0525629 | 2/1993 | European Pat. Off. . |
| 9408577 | 4/1994 | WIPO . |
| 9514683 | 6/1995 | WIPO . |

OTHER PUBLICATIONS

CA 115:60756 Silver halide . . . ureylene compounds. Nishizeki et al., 1991.

*Primary Examiner*—Joseph McKane
*Attorney, Agent, or Firm*—Blair Q. Ferguson

[57] ABSTRACT

This invention relates to novel heterocycle compounds including but not limited to 3-[3-[3-(imidazolin-2-yl amino) propyloxy]isoxazol-5-ylcarbonylamino]-2-(benzyloxycarbonylamino)-propionic acid, which are useful as antagonists of the $\alpha_v\beta_3$ and related integrin receptors, to pharmaceutical compositions containing such compounds, processes for preparing such compounds, and to methods of using these compounds, alone or in combination with other therapeutic agents, for the inhibition of cell adhesion and the treatment of angiogenic disorders, inflammation, bone degradation, tumors, metastases, thrombosis, and other cell aggregation-related conditions.

21 Claims, No Drawings

INTEGRIN RECEPTOR ANTAGONISTS

FIELD OF THE INVENTION

This invention relates to novel heterocycles which are useful as antagonists of the $\alpha_v\beta_3$ and related integrin receptors, to pharmaceutical compositions containing such compounds, processes for preparing such compounds, and to methods of using these compounds, alone or in combination with other therapeutic agents, for the inhibition of cell adhesion and the treatment of angiogenic disorders, inflammation, bone degradation, tumors, metastases, thrombosis, and other cell aggregation-related conditions.

BACKGROUND OF THE INVENTION

Angiogenesis or neovascularization is critical for normal physiological processes such as embryonic development and wound repair (Folkman and Shing, J. Biol. Chem. 1992, 267:10931–10934; D'Amore and Thompson, Ann. Rev. Physiol. 1987, 49:453–464). However, angiogenesis occurs pathologically, for example, in ocular neovascularization (leading to diabetic retinopathy, neovascular glaucoma, retinal vein occlusion and blindness), in rheumatoid arthritis and in solid tumors (Folkman and Shing, J. Biol. Chem., 1992, 267:10931–10934; Blood and Zetter, Biochim. Biophys. Acta., 1990, 1032:118–128).

Tumor dissemination, or metastasis, involves several distinct and complementary components, including the penetration and transversion of tumor cells through basement membranes and the establishment of self-sustaining tumor loci in diverse organ systems. To this end, the development and proliferation of new blood vessels, or angiogenesis, is critical to tumor survival. Without neovascularization, tumor cells lack the nourishment to divide and will not be able to leave the primary tumor site (Folkman and Shing, J. Biol. Chem., 1992, 267:10931–10934).

Inhibition of angiogenesis in animal models of cancer has been shown to result in tumor growth suppression and prevention of metastatic growth (Herblin et al., Exp. Opin. Ther. Patents. 1994, 1–14). Many angiogenic inhibitors have been directed toward blocking initial cytokine-dependent induction of new vessel growth, e.g. antibodies to endothelial cell growth factors. However, these approaches are problematic because tumor and inflammatory cells can secrete multiple activators of angiogenesis (Brooks et al., Cell, 1994, 79:1157–1164). Therefore, a more general approach that would allow inhibition of angiogenesis due to a variety of stimuli would be of benefit.

The integrin $\alpha_v\beta_3$ is preferentially expressed on angiogenic blood vessels in chick and man (Brooks et al., Science, 1994, 264:569–571; Enenstein and Kramer, J. Invest. Dermatol., 1994, 103:381–386). Integrin $\alpha_v\beta_3$ is the most promiscuous member of the integrin family, allowing endothelial cells to interact with a wide variety of extracellular matrix components (Hynes, Cell, 1992, 69:11–25). These adhesive interactions are considered to be critical for angiogenesis since vascular cells must ultimately be capable of invading virtually all tissues.

While integrin $\alpha_v\beta_3$ promotes adhesive events important for angiogenesis, this receptor also transmits signals from the extracellular environment to the intracellular compartment (Leavesley et al., J. Cell Biol., 1993, 121:163–170, 1993). For example, the interaction between the $\alpha_v\beta_3$ integrin and extracellular matrix components promotes a calcium signal required for cell motility.

During endothelium injury, the basement membrane zones of blood vessels express several adhesive proteins, including but not limited to von Willebrand factor, fibronectin, and fibrin. Additionally, several members of the integrin family of adhesion receptors are expressed on the surface of endothelial, smooth muscle and on other circulating cells. Among these integrins is $\alpha_v\beta_3$, the endothelial cell, fibroblast, and smooth muscle cell receptor for adhesive proteins including von Willebrand factor, fibrinogen (fibrin), vitronectin, thrombospondin, and osteopontin. These integrins initiate a calcium-dependent signaling pathway that can lead to endothelial cell, smooth muscle cell migration and, therefore, may play a fundamental role in vascular cell biology.

Recently, an antibody to the $\alpha_v\beta_3$ integrin has been developed that inhibits the interaction of this integrin with agonists such as vitronectin (Brooks et al., Science, 1994, 264:569–571). Application of this antibody has been shown to disrupt ongoing angiogenesis on the chick chorioallantoic membrane (CAM), leading to rapid regression of histologically distinct human tumor transplanted onto the CAM (Brooks et al., Cell, 1994, 79:1157–1164). In this model, antagonists of the $\alpha_v\beta_3$ integrin induced apoptosis of the proliferating angiogenic vascular cells, leaving pre-existing quiescent blood vessels unaffected. Thus, $\alpha_v\beta_3$ integrin antagonists have been shown to inhibit angiogenesis. Based on this property, therapeutic utility of such agents is expected in human diseases such as cancer, rheumatoid arthritis and ocular vasculopathies (Folkman and Shing, J. Biol. Chem., 1992, 267:10931–10934).

Increasing numbers of other cell surface receptors have been identified which bind to extracellular matrix ligands or other cell adhesion ligands thereby mediating cell-cell and cell-matrix adhesion processes. These receptors belong to a gene superfamily called integrins and are composed of heterodimeric transmembrane glycoproteins containing $\alpha$- and $\beta$-subunits. Integrin subfamilies contain a common $\beta$-subunit combined with different $\alpha$-subunits to form adhesion receptors with unique specificity. The genes for eight distinct $\beta$-subunits have been cloned and sequenced to date.

Two members of the $\beta_1$ subfamily, $\alpha 4/\beta_1$ and $\alpha 5/\beta_1$ have been implicated in various inflammatory processes. Antibodies to $\alpha 4$ prevent adhesion of lymphocytes to synovial endothelial cells in vitro, a process which may be of importance in rheumatoid arthritis (VanDinther-Janssen et al., J. Immunol., 1991, 147:4207). Additional studies with monoclonal anti-$\alpha 4$ antibodies provide evidence that $\alpha 4/\beta_1$ may additionally have a role in allergy, asthma, and autoimmune disorders (Walsh et al., J. Immunol., 1991, 146:3419; Bochner et al., J. Exp. Med., 1991 173:1553; Yednock et al., Nature, 1992, 356:63). Anti-$\alpha 4$ antibodies also block the migration of leukocytes to the site of inflammation (Issedutz et al., J. Immunol., 1991, 147:4178).

The $\alpha_v/\beta_3$ heterodimer is a member of the $\beta_3$ integrin subfamily and has been described on platelets, endothelial cells, melanoma, smooth muscle cells, and osteoclasts (Horton and Davies, J. Bone Min. Res. 1989, 4:803–808; Davies et al., J. Cell. Biol. 1989, 109:1817–1826; Horton, Int. J. Exp. Pathol., 1990, 71:741–759). Like GPIIb/IIIa, the vitronectin receptor binds a variety of RGD-containing adhesive proteins such as vitronectin, fibronectin, VWF, fibrinogen, osteopontin, bone sialo protein II and thrombosponden in a manner mediated by the RGD sequence. A key event in bone resorption is the adhesion of osteoclasts to the matrix of bone. Studies with monoclonal antibodies have implicated the $\alpha_v/\beta_3$ receptor in this process and suggest that a selective $\alpha_v/\beta_3$ antagonist would have utility in blocking bone resorption (Horton et al., J. Bone Miner. Res., 1993, 8:239–247; Helfrich et al., J. Bone Miner. Res., 1992, 7:335–343).

European Patent Application Publication Number 525629 (corresponds to Canadian Patent Application Publication Number 2,074,685) discloses compounds having the general formula:

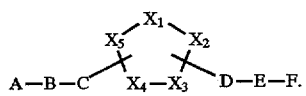

Copending, commonly assigned U.S. patent application Ser. No. 08/337,920 filed Nov. 10, 1994 discloses integrin inhibitors of the general formula shown below:

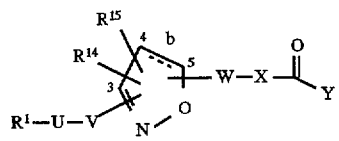

PCT Patent Application WO 94/08577 published Apr. 28, 1994 discloses fibrinogen antagonists, including the isoxazole-containing compound below:

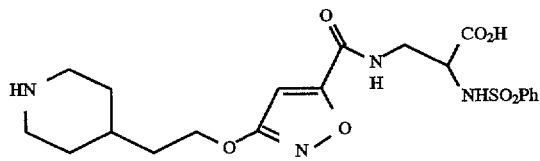

None of the above references teaches or suggests the compounds of the present invention which are described in detail below.

SUMMARY OF THE INVENTION

The present invention provides novel nonpeptide compounds which bind to integrin receptors thereby altering cell-matrix and cell-cell adhesion processes. The compounds of the present invention are useful for the treatment of angiogenic disorders, inflammation, bone degradation, tumors, metastases, thrombosis, and other cell aggregation-related conditions in a meal.

One aspect of this invention provides novel compounds of Formula I (described below) which are useful as antagonists of the $\alpha_v/\beta_3$ or vitronectin receptor. The compounds of the present invention inhibit the binding of vironectin to $\alpha_v/\beta_3$ and inhibit cell adhesion. The present invention also includes pharmaceutical compositions containing such compounds of Formula I, and methods of using such compounds for the inhibition of angiogenesis, and/or for the treatment of angiogenic disorders.

The present invention also provides novel compounds, pharmaceutical compositions and methods which may be used in the treatment or prevention of diseases which involve cell adhesion processes, including, but not limited to, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, ocular vasculopathies, thrombosis, inflammatory bowel disease and other autoimmune diseases.

Also included in the present invention are pharmaceutical kits comprising one or more containers containing pharmaceutical dosage units comprising a compound of Formula I, for the treatment of cell adhesion related disorders, including, but not limited to, angiogenic disorders.

DETAILED DESCRIPTION OF THE INVENTION

The present invention provides novel nonpeptide compounds of Formula I (described below) which bind to integrin receptors thereby altering cell-matrix and cell-cell adhesion processes. The compounds of the present invention are useful for the treatment of angiogenic disorders, inflammation, bone degradation, tumors, metastases, thrombosis, and other cell aggregation-related conditions in a mammal.

One aspect of this invention provides novel compounds of Formula I (described below) which are useful as antagonists of the $\alpha_v/\beta_3$ or vitronectin receptor. The compounds of the present invention inhibit the binding of vitronectin to $\alpha_v/\beta_3$ and inhibit cell adhesion. The present invention also includes pharmaceutical compositions containing such compounds of Formula I, and methods of using such compounds for the inhibition of angiogenesis, and/or for the treatment of angiogenic disorders.

[1] The present invention comprises compounds of the Formula I:

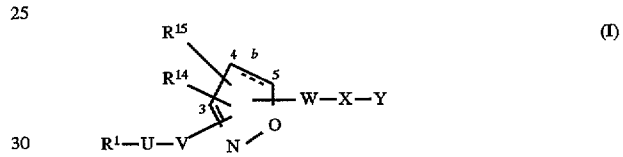

including stereoisomeric forms thereof, or mixtures of stereoisomeric forms thereof, or pharmaceutically acceptable salt or prodrug forms thereof wherein:

b, the bond between carbon atoms numbered 4 and 5, is a carbon-carbon single or double bond;

$R^1$ is selected from:

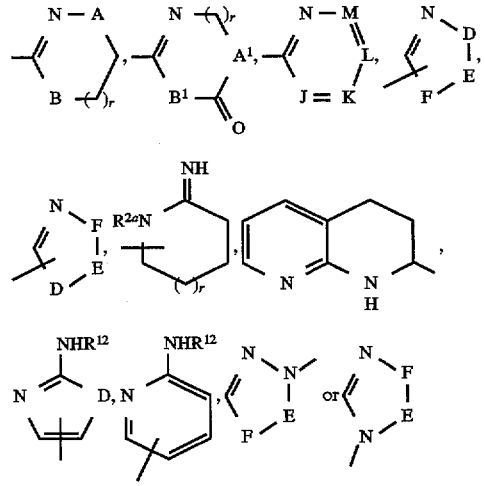

A and B are independently —$CH_2$—, —O—, —$N(R^{12})$—, or —$C(=O)$—;

$A^1$ and $B^1$ are independently —$CH_2$— or -$N(R^{10})$—;

D is —$N(R^{2a})$—, —O—, —S—, —$C(=O)$— or —$SO_2$—; E—F is —$C(R^2)=C(R^3)$—, —$N=C(R^2)$—, —$C(R^2)=N$—, —$N=N$—, or —$C(R^2)_2C(R^3)_2$—;

J, K, L and M are independently selected from —$C(R^2)$— or —N—, provided that at least one of J, K, L and M is —$C(R^2)$—;

$R^2$ and $R^3$ are independently selected from: H, $C_1$–$C_4$ alkoxy, $NR^{11}R^{12}$, =$NR^{12}$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, $C_6$–$C_{10}$ aryl, $C_7$–$C_{11}$ arylalkyl, $C_2$–$C_7$ alkylcarbonyl, $C_6$–$C_{10}$ carbonyl or $C_7$–$C_{11}$ arylcarbonyl;

alternatively, $R^2$ and $R^3$, when substituents on adjacent atoms, can be taken together with the carbon atoms to which they are attached to form a 5–7 membered carbocyclic or 5–7 membered heterocyclic aromatic or nonaromatic ring system, said carbocyclic or heterocyclic ring being optionally substituted with 0–2 $R^7$;

$R^{2a}$ is absent or $R^{12}$;

U is selected from:
—$(CH_2)_n$—,
—$(CH_2)_nO(CH_2)_m$—,
—$(CH_2)_nN(R^{12})(CH_2)_m$—,
—$(CH_2)_nC(=O)(CH_2)_m$—,
—$(CH_2)_nS(O)_p(CH_2)_m$—,
—$(CH_2)_nNHNH(CH_2)_m$—,
—$N(R^{10})C(=O)$—, or
—$C(=O)N(R^{10})$—;
—$N(R^{10})S(O)_p$—, or V is selected from:
—$(CH_2)_n$—,
—$(C_1$–$C_6$ alkylene)-Q—, substituted with 0–3 groups independently selected from $R^{13}$,
—$(C_2$–$C_7$ alkenylene)-Q—, substituted with 0–3 groups independently selected from $R^{13}$,
—$(C_2$–$C_7$ alkynylene)-Q—, substituted with 0–3 groups independently selected from $R^{13}$,
-(phenyl)-Q—, said phenyl substituted with 0–2 groups independently selected from $R^{13}$,
-(pyridyl)-Q—, said pyridyl substituted with 0–2 groups independently selected from $R^{13}$, or
-(pyridazinyl)-Q—, said pyridazinyl substituted with 0–2 groups independently selected from $R^{13}$;

Q is selected from:
—$(CH_2)_n$—,
—$(CH_2)_nO(CH_2)_m$—,
—$(CH_2)_nN(R^{12})(CH_2)_m$—,
—$(CH_2)_nC(=O)(CH_2)_m$—,
—$(CH_2)_nS(O)_p(CH_2)_m$—,
—$(CH_2)_nNHNH(CH_2)_m$—,
—$N(R^{10})C(=O)$—, or
—$C(=O)N(R^{10})$—;

W is selected from:
—$(C(R^4)_2)_qC(=O)N(R^{10})$—,
—$C(=O)$—$N(R^{10})$—$(C(R^4)_2)_q$—;

X is selected from:
a single bond (i.e., X is absent),
—$(C(R^4)_2)_q$—$[C(R^4)(R^8)]_s$—$C(R^4)(R^9)$—;

alternatively, W is

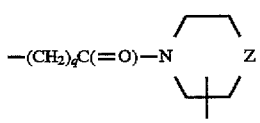

—$(CH_2)_4C(=O)$—N and x is absent or —$CH_2$—

Y is selected from:
—$COR^{20}$, —$SO_3H$, —$PO_3H$, —$CONHNHSO_2CF_3$,
—$CONHSO_2R^{18a}$, —$CONHSO_2NHR^{18b}$,
—$NHCOCF_3$, —$NHCONHSO_2R^{18a}$,
—$NHSO_2R^{18a}$, —$OPO_3H_2$, —$OSO_3H$, —$PO_3H_2$,
—$SO_3H$, —$SO_2NHCOR^{18a}$, —$SO_2NHCO_2R^{18a}$, or

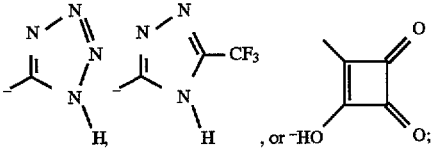

Z is selected from —$CH(R^9)$—, or —$N(R^{16})$—;

$R^4$ is selected from H, $C_1$—$C_{10}$ alkyl, $C_1$–$C_{10}$ alkylcarbonyl, aryl, arylalkyl, cycloalkyl, or cycloalkylalkyl;

alternatively, two $R^4$ groups on adjacent carbon atoms may join to form a bond, thereby to form a carbon-carbon double or triple bond between the adjacent carbon atoms;

$R^5$ is selected from H, $C_1$–$C_6$ alkyl, $C_2$–$C_6$ alkenyl, $C_2$–$C_6$ alkynyl, $C_3$–$C_7$ cycloalkyl, $C_7$–$C_{14}$ bicycloalkyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, $C_1$–$C_6$ alkylcarbonyl, $C_6$–$C_{10}$ aryl, —$N(R^{11})R^{12}$, halo, $CF_3$, CN, $C_1$–$C_6$ alkoxycarbonyl, carboxy, piperidinyl, morpholinyl or pyridinyl;

$R^6$ is selected from:
H, $C_1$–$C_{10}$ alkyl, hydroxy, $C_1$–$C_{10}$ alkoxy, nitro, $C_1$–$C_{10}$ alkylcarbonyl, —$N(R^{11})R^{12}$, cyano, halo, $CF_3$, CHO, $CO_2R^{18b}$, $C(=O)R^{18b}$, $CONR^{17}R^{18b}$, $OC(=O)R^{10}$, $OC(=O)OR^{21}$, $OR^{10}$, $OC(=O)NR^{10}R^{11}$, $OCH_2CO_2R^{10}$, $CO_2CH_2CO_2R^{10}$, $NO_2$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, $S(O)_pR^{11}$, $SO_2NR^{10}R^{11}$, $SiMe_3$, $C_2$ to $C_6$ alkenyl, $C_3$ to $C_{11}$ cycloalkyl, $C_4$ to $C_{11}$ cycloalkylmethyl,
$C_6$ to $C_{10}$ aryl optionally substituted with 1–3 groups selected from halogen, $C_1$–$C_6$ alkoxy, $C_1$–$C_6$ alkyl, $CF_3$, $S(O)_m$Me, or —$NMe_2$;
$C_7$ to $C_{11}$ arylalkyl, said aryl being optionally substituted with 1–3 groups selected from halogen, $C_1$–$C_6$ alkoxy, $C_1$–$C_6$ alkyl, $CF_3$, $S(O)_p$Me, or —$NMe_2$,
methylenedioxy when $R^6$ is a substituent on aryl, or a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:
H, $C_1$–$C_{10}$ alkyl, hydroxy, $C_1$–$C_{10}$ alkoxy, nitro, $C_1$–$C_{10}$ alkylcarbonyl, —$N(R^{11})R^{12}$, cyano, halo, $CF_3$, CHO, $CO_2R^{10}$, $C(=O)R^{10}$, $CONR^{10}R^{11}$, $OC(=O)R^{10}$, $OC(=O)OR^{21}$, $OR^{10}$, $OC(=O)NR^{10}R^{11}$, $OCH_2CO_2R^{10}$, $CO_2CH_2CO_2R^{10}$, $NO_2$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, $S(O)_pR^{11}$, $SO_2NR^{10}R^{11}$, $SiMe_3$, $C_2$ to $C_6$ alkenyl, $C_3$ to $C_{11}$ cycloalkyl, $C_4$ to $C_{11}$ cycloalkylmethyl, $C_6$ to $C_{10}$ aryl, or $C_7$ to $C_{11}$ arylalkyl;

$R^8$ is selected from:
H, $R^6$,
$C_1$–$C_{10}$ alkyl, substituted with 0–3 $R^6$,
$C_2$–$C_{10}$ alkenyl, substituted with 0–3 $R^6$,
$C_2$–$C_{10}$ alkynyl, substituted with 0–3 $R^6$,
$C_3$–$C_8$ cycloalkyl, substituted with 0–3 $R^6$,
$C_5$–$C_6$ cycloalkenyl, substituted with 0–3 $R^6$,
aryl, substituted with 0–3 $R^6$, or
5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^9$ is selected from H, hydroxy, $C_1$–$C_{10}$ alkoxy, nitro, $N(R^{10})R^{11}$, —$N(R^{16})R^{17}$, $OR^{22}$, $C_1$–$C_{10}$ alkyl substituted with 0–3 $R^7$, aryl substituted with 0–3 $R^7$, heteroaryl substituted with 0–3 $R^7$, $C_1$–$C_{10}$ alkylcarbonyl; aryl($C_0$–$C_6$ alkyl)carbonyl, $C_1$–$C_{10}$ alkenyl, $C_1$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, $CO_2R^{18a}$, $C(=O)R^{18a}$, $CONR^{18a}R^{20}$, $SO_2R^{18a}$, or $SO_2NR^{18a}R^{20}$, provided that any of the above alkyl, cycloalkyl, aryl or heteroaryl groups may be unsubstituted or substituted independently with 0–2 $R^7$;

$R^{10}$ is selected from H, $C_1$–$C_8$ alkyl, $C_3$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^4$;

$R^{11}$ is selected from hydrogen, hydroxy, $C_1$ to $C_8$ alkyl, $C_3$–$C_6$ alkenyl, $C_3$ to $C_{11}$ cycloalkyl, $C_4$ to $C_{11}$ cycloalkylmethyl, $C_1$–$C_6$ alkoxy, benzyloxy, $C_6$ to $C_{10}$ aryl, heteroaryl, heteroarylalkyl, $C_7$ to $C_{11}$ arylalkyl, adamantylmethyl, or $C_1$–$C_{10}$ alkyl substituted with 0–2 $R^4$;

alternatively, $R^{10}$ and $R^{11}$ when both are substituents on the same nitrogen atom (as in —$NR^{10}R^{11}$) can be taken together with the nitrogen atom to which they are attached to form a heterocycle selected from:
3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl; said heterocycle being optionally substituted with 0–3 groups selected from: $C_1$–$C_6$ alkyl, $C_6$–$C_{10}$ aryl, heteroaryl, $C_7$–$C_{11}$ arylalkyl, $C_1$–$C_6$ alkylcarbonyl, $C_3$–$C_7$ cycloalkylcarbonyl, $C_1$–$C_6$ alkoxycarbonyl, $C_7$–$C_{11}$ arylalkoxycarbonyl, $C_1$–$C_6$ alkylsulfonyl or $C_6$–$C_{10}$ arylsulfonyl;

$R^{12}$ is selected from:
H, $C_1$–$C_{10}$ alkyl, triphenylmethyl, methoxyphenyldiphenylmethyl, trimethylsilylethoxymethyoxy (SEM), $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl($C_2$–$C_{10}$ alkenyl)sulfonyl, heteroarylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_7$–$C_{11}$ arylcarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylcarbonyl, heteroarylalkylcarbonyl, or aryl($C_1$–$C_{10}$ alkoxy)carbonyl; wherein said aryl groups are optionally substituted with 0–3 substituents selected from the group consisting of:
$C_1$–$C_4$ alkyl, $C_1$–$C_4$ alkoxy, halo, $CF_3$, and $NO_2$;

$R^{13}$ is selected from: H, hydroxy, $C_1$–$C_{10}$ alkoxy, nitro, $N(R^{10})R^{11}$, —$N(R^{16})R^{17}$, $C_1$–$C_{10}$ alkyl substituted with 0–3 $R^7$, aryl substituted with 0–3 $R^7$, heteroaryl substituted with 0–3 $R^7$, or $C_1$–$C_{10}$ alkylcarbonyl;

$R^{14}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^{10}$ or —$C(=O)N(R^{10})R^{11}$;

$R^{15}$ is selected from:
H, $R^6$, —$CO_2R^{10}$, —$C(=O)N(R^{10})R^{11}$;
$C_1$–$C_{10}$ alkoxycarbonyl substituted with 0–2 $R^6$;
$C_1$–$C_{10}$ alkyl, substituted with 0–3 $R^6$;
$C_2$–$C_{10}$ alkenyl, substituted with 0–3 $R^6$;
$C_1$–$C_{10}$ alkoxy, substituted with 0–3 $R^6$;
aryl, substituted with 0–3 $R^6$; or
5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^{16}$ is selected from:
—$C(=O)$—$O$—$R^{18a}$,
—$C(=O)$—$R^{18a}$,
—$C(=O)N(R^{18b})_2$,
—$C(=O)NHSO_2R^{18a}$,
—$C(=O)NHC(=O)R^{18b}$,
—$C(=O)NHC(=O)OR^{18a}$,
—$C(=O)NHSO_2NHR^{18b}$,
—$C(=S)$—$NH$—$R^{18b}$,
—$NH$—$C(=O)$—$O$—$R^{18a}$,
—$NH$—$C(=O)$—$R^{18b}$,
—$NH$—$C(=O)$—$NH$—$R^{18b}$,
—$SO_2$—$O$—$R^{18a}$,
—$SO_2$—$R^{18a}$,
—$SO_2$—$N(R^{18b})_2$,
—$SO_2$—$NHC(=O)OR^{18b}$;

$R^{17}$ is selected from: H, $C_1$–$C_{10}$ alkyl, $C_2$–$C_6$ alkenyl, $C_3$–$C_{11}$ cycloalkyl, $C_4$–$C_{15}$ cycloalkylalkyl, aryl, aryl($C_1$–$C_{10}$ alkyl)-;

$R^{18a}$ is selected from:
$C_1$–$C_8$ alkyl substituted with 0–2 $R^{19}$,
$C_2$–$C_8$ alkenyl substituted with 0–2 $R^{19}$,
$C_2$–$C_8$ alkynyl substituted with 0–2 $R^{19}$,
$C_3$–$C_8$ cycloalkyl substituted with 0–2 $R^{19}$,
aryl substituted with 0–4 $R^{19}$,
aryl($C_1$–$C_6$ alkyl)- substituted with 0–4 $R^{19}$,
a 5–10 membered heterocyclic ring system having 1–3 heteroatoms selected independently from O, S, and N, said heterocyclic ring being substituted with 0–4 $R^{19}$,
$C_1$–$C_6$ alkyl substituted with a 5–10 membered heterocyclic ring system having 1–3 heteroatoms selected independently from O, S, and N, said heterocyclic ring being substituted with 0–4 $R^{19}$;

$R^{18b}$ is selected from $R^{18a}$ or H;

$R^{19}$ is selected from H, halogen, $CF_3$, $CO_2H$, CN, $NO_2$, $NR^{11}R^{12}$, $C_1$–$C_8$ alkyl, $C_2$–$C_6$ alkenyl, $C_2$–$C_6$ alkynyl, $C_3$–$C_{11}$ cycloalkyl, $C_4$–$C_{11}$ cycloalkylalkyl, aryl($C_1$–$C_6$ alkyl)-, $C_1$–$C_6$ alkoxy, $OCF_3$, or $C_1$–$C_4$ alkoxycarbonyl, aryl, —O-aryl, —$SO_2$-aryl, heteroaryl, or —$SO_2$-heteroaryl, wherein said aryl and heteroaryl groups may be substituted with 0–4 groups selected from hydrogen, halogen, $CF_3$, $C_1$–$C_3$ alkyl, or $C_1$–$C_3$ alkoxy;

$R^{20}$ is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ arylalkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, $C_{10}$ to $C_{14}$ (5-aryl-1,3-dioxa-cyclopenten-2-one-yl)methyloxy, $(R^{11})(R^{12})N$—$(C_1$–$C_{10}$ alkoxy)-;

$R^{21}$ is selected from: $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^5$;

$R^{22}$ is selected from:
—C(=O)—$R^{18b}$,
—C(=O)N($R^{18b}$)$_2$,
—C(=O)NHSO$_2$$R^{18a}$,
—C(=O)NHC(=O)$R^{18b}$,
—C(=O)NHC(=O)O$R^{18a}$,
—C(=O)NHSO$_2$NH$R^{18b}$,
—C(=S)—NH—$R^{18b}$,
—SO$_2$—$R^{18a}$,
—SO$_2$—N($R^{18b}$)$_2$,
—SO$_2$—NHC(=O)O$R^{18b}$;

m is 0–2;
n is 0–4;
p is 0–2;
q is 0–4;
r is 0–2;
s is 0–1;

with the following provisos:
(1) when b is a double bond, only one of $R^{14}$ or $R^{15}$ is present and Q and U are not —(CH$_2$)—; and
(2) n, m and q are chosen such that the number of atoms connecting $R^1$ and Y is in the range of 8–14; and
(3) when V is -(phenyl)-Q—, then either: U is not a direct bond (i.e., U is not —(CH$_2$)$_n$— where n=0) or Q is not a direct bond (i.e., Q is not —(CH$_2$)$_n$— where n=0).

[2] Preferred compounds of the present invention are compounds of Formula I:

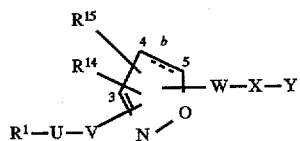

(I)

including stereoisomeric forms thereof, or mixtures of stereoisomeric forms thereof, or pharmaceutically acceptable salt or prodrug forms thereof wherein:

b, the bond between carbon atoms numbered 4 and 5, is a carbon-carbon single or double bond;

$R^1$ is selected from:

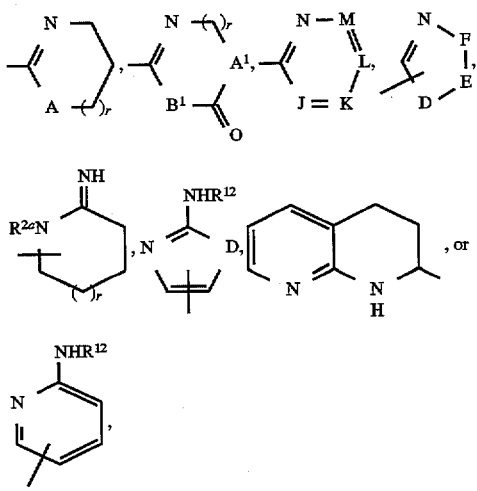

A is selected from —CH$_2$—, or —N($R^{12}$)—;
$A^1$ and B are independently —CH$_2$— or —N($R^{10}$)—;
D is —N($R^{12}$)—, or —S—;
E—F is —C($R^2$)=C($R^3$)—, or —C($R^2$)$_2$C($R^3$)$_2$—;

J is either —C($R^2$)— or —N—, and K, L and M are independently selected from —C($R^2$)— or —C($R^3$)—;

$R^2$ and $R^3$ are independently selected from: H, C$_1$–C$_4$ alkoxy, N$R^{11}R^{12}$, =N$R^{12}$, halogen, NO$_2$, CN, CF$_3$, C$_1$–C$_6$ alkyl, C$_3$–C$_6$ alkenyl, C$_3$–C$_7$ cycloalkyl, C$_4$–C$_{11}$ cycloalkylalkyl, C$_6$–C$_{10}$ aryl substituted with 0–4 $R^7$, C$_7$–C$_{11}$ arylalkyl, C$_2$–C$_7$ alkylcarbonyl, C$_1$–C$_4$ alkoxycarbonyl, or C$_7$–C$_{11}$ arylcarbonyl;

alternatively, $R^2$ and $R^3$ when substituents on adjacent atoms, can be taken together when substituents on adjacent atoms, with the carbon atoms to which they are attached, to form a 5–7 membered carbocyclic or 5–7 membered heterocyclic with the carbon atoms to which they are attached, aromatic or nonaromatic ring system, said carbocyclic or heterocyclic ring being optionally substituted with 0–2 groups selected from C$_1$–C$_4$ alkyl, C$_1$–C$_4$ alkoxy, halo, cyano, amino, CF$_3$ or NO$_2$;

$R^{2a}$ is absent or $R^{12}$;

U is selected from:
—(CH$_2$)$_n$—,
—(CH$_2$)$_n$O(CH$_2$)$_m$—,
—(CH$_2$)$_n$N($R^{12}$)(CH$_2$)$_m$—,
—(CH$_2$)$_n$C(=O)(CH$_2$)$_m$—,
—(CH$_2$)$_n$S(O)$_p$(CH$_2$)$_m$—,
—(CH$_2$)$_n$NHNH(CH$_2$)$_m$—,
—N($R^{10}$)C(=O)—, or
—C(=O)N($R^{10}$)—;
—N($R^{10}$)S(O)$_p$—, or V is selected from:
—(CH$_2$)$_n$—,
—(C$_1$–C$_6$ alkylene)-Q—, substituted with 0–3 groups independently selected from $R^{13}$,
—(C$_2$–C$_7$ alkenylene)-Q—, substituted with 0–3 groups independently selected from $R^{13}$,
—(C$_2$–C$_7$ alkynylene)-Q—, substituted with 0–3 groups independently selected from $R^{13}$,
-(phenyl)-Q—, said phenyl substituted with 0–2 groups independently selected from $R^{13}$,
-(pyridyl)-Q—, said pyridyl substituted with 0–2 groups independently selected from $R^{13}$, or
-(pyridazinyl)-Q—, said pyridazinyl substituted with 0–2 groups independently selected from $R^{13}$;

Q is selected from:
—(CH$_2$)$_n$—,
—(CH$_2$)$_n$O(CH$_2$)$_m$—,
—(CH$_2$)$_n$N($R^{12}$)(CH$_2$)$_m$—,
—(CH$_2$)$_n$C(=O)(CH$_2$)$_m$—,
—(CH$_2$)$_n$S(O)$_p$(CH$_2$)$_m$—,
—(CH$_2$)$_n$NHNH(CH$_2$)$_m$—,
—N($R^{10}$)C(=O)—, or
—C(=O)N($R^{10}$)—;

W is selected from:
—(C($R^4$)$_2$)$_q$C(=O)N($R^{10}$)— or,
—C(=O)—N($R^{10}$)—(C($R^4$)$_2$)$_q$—;

X is selected from:
a single bond (i.e., X is absent) or,
—(C($R^4$)$_2$)$_q$—[C($R^4$)($R^8$)]$_s$—C($R^4$)($R^9$)—;

alternatively, W is

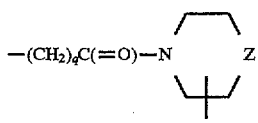

and X is either absent or —CH$_2$—

Y is selected from:
—COR$^{20}$, —SO$_3$H, —PO$_3$H, —CONHNHSO$_2$CF$_3$,
—CONHSO$_2$R$^{18a}$, —CONHSO$_2$NHR$^{18b}$,
—NHCOCF$_3$,
—NHCONHSO$_2$R$^{18a}$, —NHSO$_2$R$^{18a}$, —OPO$_3$H$_2$,
—OSO$_3$H,
—PO$_3$H$_2$, —SO$_3$H, —SO$_2$NHCOR$^{18a}$,
—SO$_2$NHCO$_2$R$^{18a}$, or

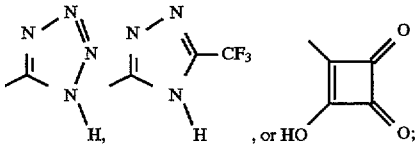

Z is selected from —CH(R$^9$)—, or —N(R$^{16}$)—;

R$^4$ is selected from H, C$_1$–C$_{10}$ alkyl, C$_1$–C$_{10}$ alkylcarbonyl, aryl, arylalkyl, cycloalkyl, or cycloalkylalkyl;
alternatively, two R$^4$ groups on adjacent carbon atoms may join to form a bond, thereby to form a carbon-carbon double or triple bond between the adjacent carbon atoms;

R$^6$ is selected from:
H, C$_1$–C$_{10}$ alkyl, hydroxy, C$_1$–C$_{10}$ alkoxy, nitro, C$_1$–C$_{10}$ alkylcarbonyl, —N(R$^{11}$)R$^{12}$, cyano, halo, CF$_3$, CHO, CO$_2$R$^{18b}$, C(=O)R$^{18b}$, CONR$^{17}$R$^{18b}$, OC(=O)R$^{10}$, OR$^{10}$, OC(=O)NR$^{10}$R$^{11}$, NR$^{10}$C(=O)R$^{10}$, NR$^{10}$C(=O)OR$^{21}$, NR$^{10}$C(=O)NR$^{10}$R$^{11}$, NR$^{10}$SO$_2$NR$^{10}$R$^{11}$, NR$^{10}$SO$_2$R$^{21}$, S(O)$_p$R$^{11}$, SO$_2$NR$^{10}$R$^{11}$,
C$_6$ to C$_{10}$ aryl optionally substituted with 0–3 groups selected from halogen, C$_1$–C$_6$ alkoxy, C$_1$–C$_6$ alkyl, CF$_3$, S(O)$_m$Me, or —NMe$_2$;
C$_7$ to C$_{11}$ arylalkyl, said aryl being optionally substituted with 1–3 groups selected from halogen, C$_1$–C$_6$ alkoxy, C$_1$–C$_6$ alkyl, CF$_3$, S(O)$_p$Me, or —NMe$_2$,
a 5–10 membered heterocyclic ring containing 1–3 N, O, or S heteroatoms, wherein said heterocyclic ring may be saturated, partially saturated, or fully unsaturated, said heterocyclic ring being substituted with 0–2 R$^7$;

R$^7$ is selected from selected from H, C$_1$–C$_4$ alkyl, hydroxy, C$_1$–C$_4$ alkoxy, C$_6$–C$_{10}$ aryl, C$_7$–C$_{11}$ arylalkyl, (C$_1$–C$_4$ alkyl)carbonyl, CO$_2$R$^{18a}$, SO$_2$R$^{11}$, SO$_2$NR$^{10}$R$^{11}$, OR$^{10}$, or N(R$^{11}$)R$^{12}$;

R$^8$ is selected from:
H, CO$_2$R$^{18a}$, C(=O)R$^{18a}$, or CONR$^{17}$R$^{18a}$
C$_1$–C$_{10}$ alkyl, substituted with 0–1 R$^6$,
C$_2$–C$_{10}$ alkenyl, substituted with 0–1 R$^6$,
C$_2$–C$_{10}$ alkynyl, substituted with 0–1 R$^6$,
C$_3$–C$_8$ cycloalkyl, substituted with 0–1 R$^6$,
C$_5$–C$_6$ cycloalkenyl, substituted with 0–1 R$^6$,
aryl, substituted with 0–3 R$^6$, or
5–10 membered heterocyclic ring containing 1–3 N, O, or S heteroatoms, wherein said heterocyclic ring may be saturated, partially saturated, or fully unsaturated, said heterocyclic ring being substituted with 0–2 R$^7$;

R$^9$ is selected from H, hydroxy, C$_1$–C$_{10}$ alkoxy, nitro, N(R$^{10}$)R$^{11}$, —N(R$^{16}$)$^{R17}$, OR$^{22}$, C$_1$–C$_{10}$ alkyl substituted with 0–3 R$^7$, aryl substituted with 0–3 R$^7$, heteroaryl substituted with 0–3 R$^7$, C$_1$–C$_{10}$ alkylcarbonyl; aryl (C$_0$–C$_6$ alkyl)carbonyl, C$_1$–C$_{10}$ alkenyl, C$_1$–C$_{10}$ alkynyl, C$_3$–C$_{10}$ cycloalkyl, C$_3$–C$_{10}$ cycloalkylalkyl, aryl (C$_1$–C$_6$ alkyl)-, heteroaryl(C$_1$–C$_6$ alkyl)-, CO$_2$R$^{18a}$, C(=O)R$^{18a}$, CONR$^{18a}$R$^{20}$, SO$_2$R$^{18a}$, or SO$_2$NR$^{28a}$R$^{20}$, provided that any of the above alkyl, cycloalkyl, aryl or heteroaryl groups may be unsubstituted or substituted independently with 0–2 R$^7$;

R$^{10}$ is selected from H, C$_1$–C$_8$ alkyl, C$_3$–C$_6$ alkenyl, C$_3$–C$_{11}$ cycloalkyl, C$_4$–C$_{11}$ cycloalkylmethyl, C$_6$–C$_{10}$ aryl, C$_7$–C$_{11}$ arylalkyl, or C$_1$–C$_{10}$ alkyl substituted with 0–2 R$^4$;

R$^{11}$ is selected from hydrogen, hydroxy, C$_1$ to C$_8$ alkyl, C$_3$–C$_6$ alkenyl, C$_3$ to C$_{11}$ cycloalkyl, C$_4$ to C$_{11}$ cycloalkylmethyl, C$_1$–C$_6$ alkoxy, benzyloxy, C$_6$ to C$_{10}$ aryl, heteroaryl, heteroarylalkyl, C$_7$ to C$_{11}$ arylalkyl, adamantylmethyl, or C$_1$–C$_{10}$ alkyl substituted with 0–2 R$^4$;

alternatively, R$^{10}$ and R$^{11}$ when both are substituents on the same nitrogen atom (as in —NR$^{10}$R$^{11}$) can be taken together with the nitrogen atom to which they are attached to form a heterocycle selected from:
3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl; said heterocycle being optionally substituted with 0–3 groups selected from: C$_1$–C$_6$ alkyl, C$_6$–C$_{10}$ aryl, heteroaryl, C$_7$–C$_{11}$ arylalkyl, C$_1$–C$_6$ alkylcarbonyl, C$_3$–C$_7$ cycloalkylcarbonyl, C$_1$–C$_6$ alkoxycarbonyl, C$_7$–C$_{11}$ arylalkoxycarbonyl, C$_1$–C$_6$ alkylsulfonyl or C$_6$–C$_{10}$ arylsulfonyl;

R$^{12}$ is selected from:
H, C$_1$–C$_6$ alkyl, triphenylmethyl, methoxyphenyldiphenylmethyl, trimethylsilylethoxymethyoxy (SEM), (C$_1$–C$_6$ alkyl)carbonyl, (C$_1$–C$_6$ alkoxy)carbonyl; (C$_1$–C$_6$ alkyl)aminocarbonyl, C$_3$–C$_6$ alkenyl, C$_3$–C$_7$ cycloalkyl, C$_4$–C$_{11}$ cycloalkylalkyl, aryl, heteroaryl(C$_1$–C$_6$ alkyl)carbonyl, heteroarylcarbonyl, aryl C$_1$–C$_6$ alkyl, (C$_1$–C$_6$ alkyl)carbonyl, or arylcarbonyl, C$_1$–C$_6$ alkylsulfonyl, arylsulfonyl, aryl(C$_1$–C$_6$ alkyl)sulfonyl, heteroarylsulfonyl, heteroaryl(C$_1$–C$_6$ alkyl)sulfonyl, aryloxycarbonyl, or aryl(C$_1$–C$_6$ alkoxy)carbonyl, wherein said aryl groups are substituted with 0–2 substituents selected from the group consisting of C$_1$–C$_4$ alkyl, C$_1$–C$_4$ alkoxy, halo, CF$_3$, and nitro;

R$^{13}$ is selected from: H, hydroxy, C$_1$–C$_{10}$ alkoxy, nitro, N(R$^{10}$)R$^{11}$, —N(R$^{16}$)R$^{17}$, C$_1$–C$_{10}$ alkyl substituted with 0–3 R$^7$, aryl substituted with 0–3 R$^7$, heteroaryl substituted with 0–3 R$^7$, or C$_1$–C$_{10}$ alkylcarbonyl;

R$^{14}$ is selected from H, C$_1$–C$_{10}$ alkyl, C$_2$–C$_{10}$ alkenyl, C$_2$–C$_{10}$ alkynyl, C$_1$–C$_{10}$ alkoxy, aryl, heteroaryl or C$_1$–C$_{10}$ alkoxycarbonyl, CO$_2$R$^{10}$ or —C(=O)N(R$^{10}$) R$^{11}$;

R$^{15}$ is selected from: H, CO$_2$R$^{18a}$, C(=O)R$^{18a}$, CONR$^{18a}$R$^{17}$, —SO$_2$R$^{18a}$, —SO$_2$NR$^{18a}$R$^{17}$, C$_1$–C$_6$ alkyl substituted with 0–1 R$^9$, C$_3$–C$_6$ alkenyl substituted with 0–1 R$^9$, C$_3$–C$_7$ cycloalkyl substituted with 0–1 R$^9$, C$_4$–C$_{11}$ cycloalkylalkyl substituted with 0–1 R$^9$, aryl substituted with 0–1 R$^9$ or 0–2 R$^7$, or aryl (C$_1$–C$_6$ alkyl)- substituted with 0–1 R$^9$ or 0–2 R$^7$;

$R^{16}$ is selected from:
—C(=O)—O—$R^{18a}$,
—C(=O)—$R^{18b}$,
—C(=O)N($R^{18b}$)$_2$,
—C(=O)NHSO$_2$$R^{18a}$,
—C(=O)NHC(=O)$R^{18b}$,
—C(=O)NHC(=O)O$R^{18a}$,
—C(=O)NHSO$_2$NH$R^{18b}$,
—SO$_2$—$R^{18a}$,
—SO$_2$—N($R^{18b}$)$_2$, or
—SO$_2$—NHC(=O)O$R^{18b}$;

$R^{17}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl);

$R^{18a}$ is selected from: $C_1$–$C_8$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl), heteroaryl, or aryl, wherein said aryl or heteroaryl groups are optionally substituted with 0–4 $R^{19}$;

$R^{18b}$ is selected from $R^{18a}$ or H;

$R^{19}$ is selected from H, halogen, CF$_3$, CO$_2$H, CN, NO$_2$, NR$^{11}$R$^{12}$, $C_1$–$C_8$ alkyl, $C_2$–$C_6$ alkenyl, $C_2$–$C_6$ alkynyl, $C_3$–$C_{11}$ cycloalkyl, $C_4$–$C_{11}$ cycloalkylalkyl, aryl ($C_1$–$C_6$ alkyl)-, $C_1$–$C_6$ alkoxy, OCF$_3$, or $C_1$–$C_4$ alkoxycarbonyl, aryl, —O-aryl, —SO$_2$-aryl, heteroaryl, or —SO$_2$-heteroaryl, wherein said aryl and heteroaryl groups may be substituted with 0–4 groups selected from hydrogen, halogen, CF$_3$, $C_1$–$C_3$ alkyl, or $C_1$–$C_3$ alkoxy;

$R^{20}$ is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, $C_{10}$ to $C_{14}$ (5-aryl-1,3-dioxa-cyclopenten-2-one-yl)methyloxy, or ($R^{11}$)($R^{12}$)N—($C_1$–$C_{10}$ alkoxy)-;

$R^{21}$ is selected from: $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^7$;

$R^{22}$ is selected from:
—C(=O)—$R^{18b}$,
—C(=O)N($R^{18b}$)$_2$,
—C(=O)NHSO$_2$$R^{18a}$,
—C(=O)NHC(=O)$R^{18b}$,
—C(=O)NHC(=O)O$R^{18a}$ or,
—C(=O)NHSO$_2$NH$R^{18b}$, m is 0–2;
n is 0–4;
p is 0–2;
q is 0–4;
r is 0–2;
s is 0–1;

with the following provisos:
(1) when b is a double bond, only one of $R^{14}$ or $R^{15}$ is present and Q and U are not —(CH$_2$)—; and
(2) n, m and q are chosen such that the number of atoms connecting $R^1$ and Y is in the range of 8–14; and (3) when V is -(phenyl)-Q—, then either: U is not a direct bond (i.e., U is not —(CH$_2$)$_n$— where n=0) or Q is not a direct bond (i.e., Q is not —(CH$_2$)$_n$— where n=0).

[3] Further preferred compounds of the above invention are compounds of Formula II:

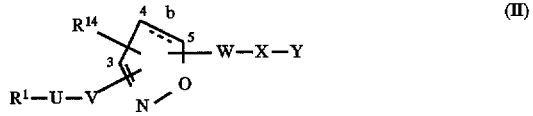

(II)

including enantiomeric or diastereomeric forms thereof, or mixtures of enantiomeric or diastereomeric forms thereof, or pharmaceutically acceptable salt or prodrug forms thereof wherein:

b, the bond between carbon atoms numbered 4 and 5, is a carbon-carbon single or double bond;

$R^1$ is selected from:

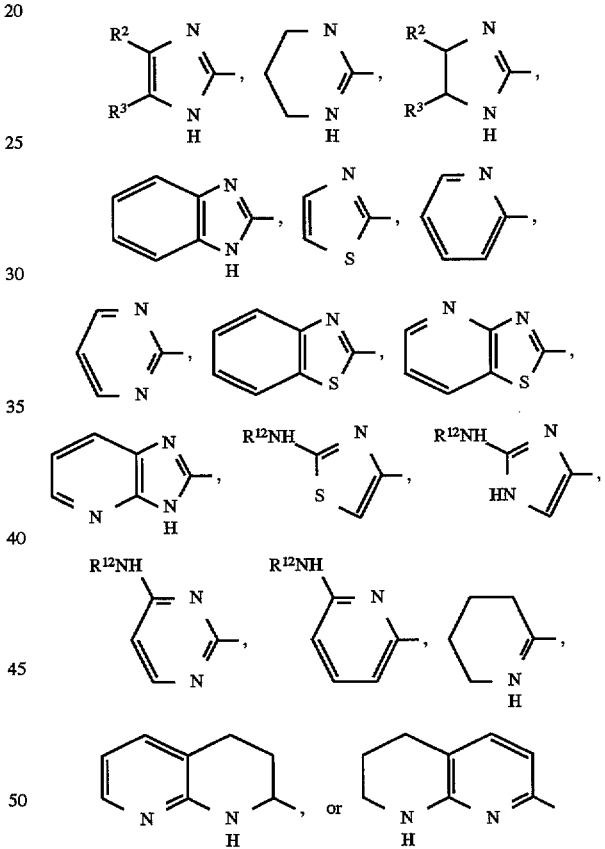

$R^2$ and $R^3$ are independently selected from: H, $C_1$–$C_4$ alkoxy, NR$^{11}$R$^{12}$, halogen, NO$_2$, CN, CF$_3$, $C_1$–$C_6$ alkyl, $C_3$–$C_6$ alkenyl, $C_3$–$C_7$ cycloalkyl, $C_4$–$C_{11}$ cycloalkylalkyl, $C_6$–$C_{10}$ aryl substituted with 0–2 $R^7$, $C_7$–$C_{11}$ arylalkyl, $C_2$–$C_7$ alkylcarbonyl, or $C_7$–$C_{11}$ arylcarbonyl;

alternatively, $R^2$ and $R^3$ can be taken together with the carbon atoms to which they are attached to form a 5–7 membered carbocyclic or 5–7 membered heterocyclic aromatic or nonaromatic ring system, said carbocyclic or heterocyclic ring being optionally substituted with 0–2 $R^7$;

U is selected from:
—(CH$_2$)$_n$—,

—N(R$^{12}$)(CH$_2$)$_m$—,
—N(R$^{10}$)C(=O)—, or
—C(=O)N(R$^{10}$)—;
—N(R$^{10}$)S(O)$_p$—, or

V is selected from:
  —(CH$_2$)$_n$—,
  —(C$_1$–C$_6$ alkylene)-Q—, substituted with 0–3 groups independently selected from R$^{13}$,
  —(C$_2$–C$_7$ alkenylene)-Q—, substituted with 0–3 groups independently selected from R$^{13}$,
  —(C$_2$–C$_7$ alkynylene)-Q—, substituted with 0–3 groups independently selected from R$^{13}$,
  -(phenyl)-Q—, said phenyl substituted with 0–2 groups independently selected from R$^{13}$,
  -(pyridyl)-Q—, said pyridyl substituted with 0–2 groups independently selected from R$^{13}$, or
  -(pyridazinyl)-Q—, said pyridazinyl substituted with 0–2 groups independently selected from R$^{13}$;

Q is selected from:
  —(CH$_2$)$_n$—,
  —(CH$_2$)$_n$O(CH$_2$)$_m$—,
  —(CH$_2$)$_n$N(R$^{12}$)(CH$_2$)$_m$—,
  —N(R$^{10}$)C(=O)—, or
  —C(=O)N(R$^{10}$)—;

W is selected from:
  —(CH$_2$)$_q$C(=O)N(R$^{10}$)—, or
  —C(=O)—N(R$^{10}$)—(CH$_2$)$_q$—;

X is —(CH$_2$)$_q$—CH(R$^8$)—CH(R$^9$)—;

Y is —COR$^{20}$;

R$^6$ is selected from:
  H, C$_1$–C$_4$ alkyl, hydroxy, C$_1$–C$_4$ alkoxy, nitro, C$_1$–C$_6$ alkylcarbonyl, —N(R$^{11}$)R$^{12}$, cyano, halo, CF$_3$, —S(O)$_p$R$^{10}$, CO$_2$R$^{18a}$, CONR$^{17}$R$^{18a}$, —COR$^{18a}$, OR$^{10}$,
  C$_6$ to C$_{10}$ aryl optionally substituted with 0–3 groups selected from halogen, C$_1$–C$_6$ alkoxy, C$_1$–C$_6$ alkyl, CF$_3$, S(O)$_m$Me, or —NMe$_2$;
  a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, benzimidazolyl, piperidinyl, tetrahydrofuranyl, pyranyl, 3H-indolyl, carbazolyl, pyrrolidinyl, piperidinyl, isoxazolinyl, isoxazolyl, or morpholinyl;

R$^7$ is selected from:
  H, C$_1$–C$_4$ alkyl, hydroxy, C$_1$–C$_4$ alkoxy, nitro, C$_1$–C$_4$ alkylcarbonyl, —N(R$^{11}$)R$^{12}$, CO$_2$R$^{18a}$, SO$_2$R$^{11}$, SO$_2$NR$^{10}$R$^{11}$ or OR$^{10}$;

R$^8$ is selected from:
  H, CONR$^{17}$R$^{18a}$, —CO$_2$R$^{18a}$, —COR$^{18a}$
  C$_1$–C$_{10}$ alkyl, substituted with 0–1 R$^6$,
  C$_2$–C$_{10}$ alkenyl, substituted with 0–1 R$^6$,
  C$_2$–C$_{10}$ alkynyl, substituted with 0–1 R$^6$,
  C$_3$–C$_8$ cycloalkyl, substituted with 0–1 R$^6$,
  aryl, substituted with 0–1 R$^6$ or,
  a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, benzimidazolyl, piperidinyl, tetrahydrofuranyl, pyranyl, 3H-indolyl, carbazolyl, pyrrolidinyl, piperidinyl, isoxazolinyl, isoxazolyl or morpholinyl, said heterocycle optionally substituted with 0–2 R$^7$;

R$^9$ is selected from: H or —N(R$^{16}$)R$^{17}$;

R$^{10}$ is selected from H or C$_1$–C$_{10}$ alkyl, or C$_7$–C$_{10}$ arylalkyl;

R$^{11}$ is selected from hydrogen, hydroxy, C$_1$ to C$_8$ alkyl, C$_3$–C$_6$ alkenyl, C$_3$ to C$_{11}$ cycloalkyl, C$_4$ to C$_{11}$ cycloalkylmethyl, C$_1$–C$_6$ alkoxy, benzyloxy, C$_6$ to C$_{10}$ aryl, heteroaryl, heteroarylalkyl, C$_7$ to C$_{11}$ arylalkyl, adamantylmethyl, or C$_1$–C$_{10}$ alkyl substituted with 0–2 R$^4$;

alternatively, R$^{10}$ and R$^{11}$ when both are substituents on the same nitrogen atom (as in —NR$^{10}$R$^{11}$) can be taken together with the nitrogen atom to which they are attached to form a heterocycle selected from:
  3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl; said heterocycle being optionally substituted with 1–3 groups selected from: C$_1$–C$_6$ alkyl, C$_6$–C$_{10}$ aryl, heteroaryl, C$_7$–C$_{11}$ arylalkyl, C$_1$–C$_6$ alkylcarbonyl, C$_3$–C$_7$ cycloalkylcarbonyl, C$_1$–C$_6$ alkoxycarbonyl, C$_7$–C$_{11}$ arylalkoxycarbonyl, C$_1$–C$_6$ alkylsulfonyl or C$_6$–C$_{10}$ arylsulfonyl;

R$^{12}$ is selected from:
  H, C$_1$–C$_6$ alkyl, triphenylmethyl, methoxyphenyldiphenylmethyl, trimethylsilylethoxymethyoxy (SEM), C$_1$–C$_4$ alkoxycarbonyl, C$_1$–C$_6$ alkylcarbonyl, C$_1$–C$_6$ alkylsulfonyl, aryl (C$_1$–C$_4$ alkyl)sulfonyl, arylsulfonyl, aryl, heteroarylcarbonyl, or heteroarylalkylcarbonyl, wherein said aryl groups are substituted with 0–3 substituents selected from the group consisting of: C$_1$–C$_4$ alkyl, C$_1$–C$_4$ alkoxy, halo, CF$_3$, and NO$_2$;

R$^{13}$ is selected from: H, hydroxy, C$_1$–C$_{10}$ alkoxy, N(R$^{10}$)R$^{11}$, —N(R$^{16}$)R$^{17}$, C$_1$–C$_{10}$ alkyl substituted with 0–3 R$^7$, aryl substituted with 0–3 R$^7$, heteroaryl substituted with 0–3 R$^7$, or C$_1$–C$_{10}$ alkylcarbonyl;

R$^{14}$ is selected from H, C$_1$–C$_{10}$ alkyl, C$_2$–C$_{10}$ alkenyl, C$_2$–C$_{10}$ alkynyl, C$_1$–C$_{10}$ alkoxy, aryl, heteroaryl or C$_1$–C$_{10}$ alkoxycarbonyl, CO$_2$R$^{10}$ or —C(=O)N(R$^{10}$)R$^{11}$;

R$^{16}$ is selected from:
  —C(=O)—O—R$^{18a}$,
  —C(=O)—R$^{18b}$,
  —SO$_2$—R$^{18a}$ or,
  —SO$_2$—N(18$^b$)$_2$;

R$^{17}$ is selected from H or C$_1$–C$_4$ alkyl;

R$^{18a}$ is selected from: C$_1$–C$_8$ alkyl, C$_3$–C$_{11}$ cycloalkyl, aryl(C$_1$–C$_6$ alkyl)-, (C$_1$–C$_6$ alkyl)aryl, heteroaryl (C$_1$–C$_6$ alkyl)-, (C$_1$–C$_6$ alkyl)heteroaryl, biaryl(C$_1$–C$_6$ alkyl), heteroaryl, or aryl, wherein said aryl or heteroaryl groups are optionally substituted with 0–2 R$^{19}$;

R$^{18b}$ is selected from R$^{18a}$ or H;

R$^{19}$ is selected from H, halogen, CF$_3$, CO$_2$H, CN, NO$_2$, NR$^{11}$R$^{12}$, C$_1$–C$_8$ alkyl, C$_2$–C$_6$ alkenyl, C$_2$–C$_6$ alkynyl, C$_3$–C$_{11}$ cycloalkyl, C$_4$–C$_{11}$ cycloalkylalkyl, aryl (C$_1$–C$_6$ alkyl)-, C$_1$–C$_6$ alkoxy, OCF$_3$, or C$_1$–C$_4$ alkoxycarbonyl, aryl, —O-aryl, —SO$_2$-aryl, heteroaryl, or —SO$_2$-heteroaryl, wherein said aryl and heteroaryl groups may be substituted with 0–4 groups selected from hydrogen, halogen, CF$_3$, C$_1$–C$_3$ alkyl, or C$_1$–C$_3$ alkoxy;

R$^{20}$ is selected from:
  hydroxy;
  C$_1$ to C$_{10}$ alkoxy;
  methylcarbonyloxymethoxy-;
  ethylcarbonyloxymethoxy-;
  t-butylcarbonyloxymethoxy-;

cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-;
i-propyloxycarbonyloxymethoxy-;
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy-;
(5-(t-butyl)-1,3-dioxacyclopenten-2-on-4-yl)methoxy-;
(1,3-dioxa-5-phenyl-cyclopenten-2-on-4-yl)methoxy-or;
1-(2-(2-methoxypropyl)carbonyloxy)ethoxy-;

$R^{21}$ is selected from $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^4$;

m is 0–2;

n is 0–4;

p is 0–2;

q is 0–1; and r is 0–2;

with the following provisos:
  (1) when b is a double bond, Q and U are not —(CH$_2$)—; and
  (2) n, m and q are chosen such that the number of atoms connecting $R^1$ and Y is in the range of 8–14; and
  (3) when V is -(phenyl)-Q—, then either: U is not a direct bond (i.e., U is not —(CH$_2$)$_n$— where n=0) or Q is not a direct bond (i.e., Q is not —(CH$_2$)$_n$— where n=0).

[4] Still further preferred are compounds of the above invention of Formula IIIa, IIIb or IIIc:

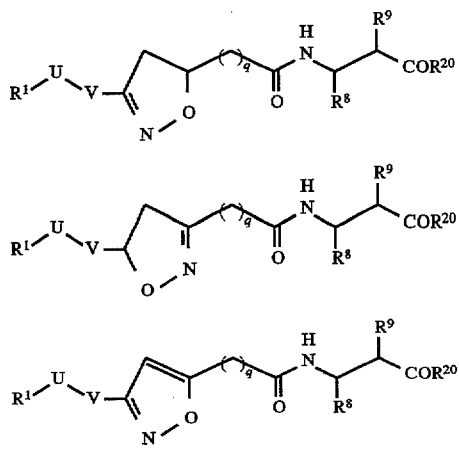

including enantiomeric or diasteriomeric forms thereof, or mixtures of enantiomeric or diasteriomeric forms thereof, or pharmaceutically acceptable salt or prodrug forms thereof wherein:

$R^1$—U taken together are selected from:

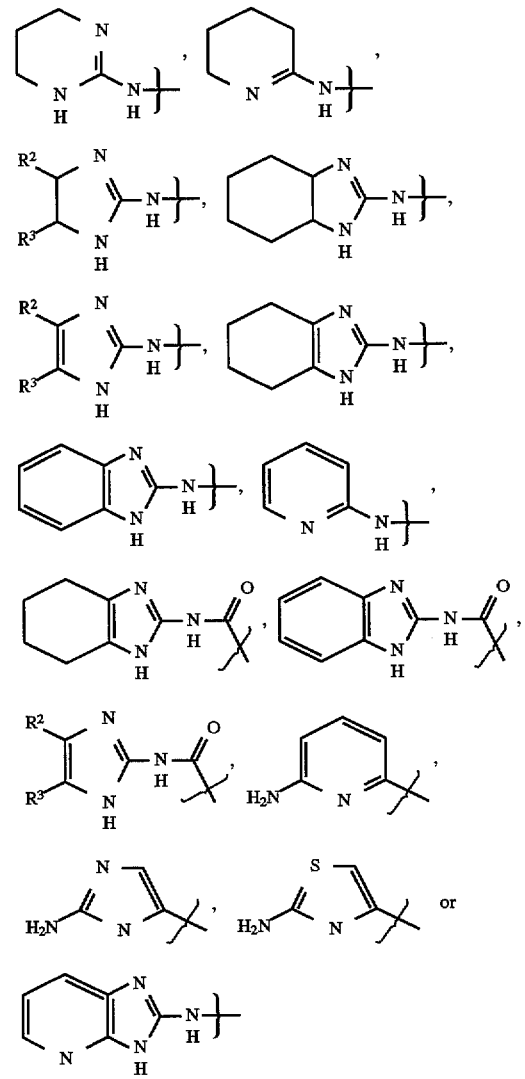

$R^2$ and $R^3$ are independently selected from: H, $C_1$–$C_4$ alkoxy, halogen, $C_1$–$C_6$ alkyl, or $C_3$–$C_6$ alkenyl;

V is selected from:
  —(CH$_2$)$_n$—;
  —($C_1$–$C_6$ alkylene)-Q—, substituted with 0–1 groups independently selected from $R^{13}$ or,
  —($C_2$–$C_7$ alkenylene)-Q—, substituted with 0–1 groups independently selected from $R^{13}$, or
  -(phenyl)-Q—, said phenyl substituted with 0–1 groups independently selected from $R^{13}$, Q is selected from:
  —(CH$_2$)$_n$—,
  —O—,
  —N($R^{12}$)—,
  —N($R^{10}$)C(=O)—, or
  —C(=O)N($R^{10}$)—;

$R^7$ is selected from:
  H, hydroxy, $C_1$–$C_4$ alkoxy, $C_1$–$C_4$ alkylcarbonyl, —N($R^{10}$)($R^{11}$), CO$_2$$R^{18a}$, SO$_2$N($R^{10}$)$R^{11}$, or OR$^{10}$;

$R^8$ is selected from:
  H, CONR$^{17}$R$^{18a}$, $C_1$–$C_{10}$ alkyl, $C_2$–$C_{10}$ alkenyl, $C_2$–$C_{10}$ alkynyl, $C_3$–$C_8$ cycloalkyl, pyridinyl, or aryl, wherein said aryl or pyridinyl groups are optionally substituted with 0–3 substituents selected from the group consisting of: $C_1$–$C_4$ alkyl, $C_1$–$C_4$ alkoxy, aryl, halo, cyano, $CF_3$, and $NO_2$.

$R^9$ is selected from: H or —$NHR^{16}$;

$R^{10}$ is selected from H or $C_1$–$C_{10}$ alkyl;

$R^{11}$ is selected from hydrogen, hydroxy, $C_1$ to $C_8$ alkyl, $C_3$–$C_6$ alkenyl, $C_3$ to $C_{11}$ cycloalkyl, $C_4$ to $C_{11}$ cycloalkylmethyl, $C_1$–$C_6$ alkoxy, benzyloxy, $C_6$ to $C_{10}$ aryl, heteroaryl, heteroarylalkyl, $C_7$ to $C_{11}$ arylalkyl, or adamantylmethyl;

$R^{13}$ is selected from: H, hydroxy, $C_1$–$C_{10}$ alkoxy, $N(R^{10})R^{11}$, —$N(R^{16})R^{17}$, $C_1$–$C_{10}$ alkyl substituted with 0–2 $R^7$, aryl substituted with 0–3 $R^7$, heteroaryl substituted with 0–2 $R^7$, or $C_1$–$C_6$ alkylcarbonyl;

$R^{16}$ is selected from:
—C(=O)—O—$R^{18a}$,
—$SO_2$—$R^{18a}$ or,
—$SO_2$—$NHR^{18a}$;

$R^{18a}$ is selected from: $C_1$–$C_8$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl), heteroaryl, or aryl, wherein said aryl or heteroaryl groups are optionally substituted with 0–2 $R^{19}$;

$R^{19}$ is selected from: H, Br, F, Cl, $CF_3$, CN, $NO_2$, $NHR^{11}$, $C_1$–$C_4$ alkyl, aryl, aryl($C_1$–$C_4$ alkyl)-, $C_1$–$C_4$ alkoxy, $C_1$–$C_4$ alkoxycarbonyl, or —O-aryl, wherein said aryl groups are optionally substituted with 0–3 substituents selected from a group consisting of halogen, $CF_3$, $C_1$–$C_3$ alkyl, or $C_1$–$C_3$ alkoxy;

$R^{20}$ is selected from:
hydroxy;
$C_1$ to $C_{10}$ alkoxy;
methylcarbonyloxymethoxy-;
ethylcarbonyloxymethoxy-;
t-butylcarbonyloxymethoxy-;
cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-;
i-propyloxycarbonyloxymethoxy-;
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy-;
(5-(t-butyl)-1,3-dioxacyclopenten-2-on-4-yl)methoxy-;
(1,3-dioxa-5-phenyl-cyclopenten-2-on-4-yl)methoxy-;
or;
1-(2-(2-methoxypropyl)carbonyloxy)ethoxy-;

n is 0–4;

q is 0–1;

with the proviso that n, and q are chosen such that the number of atoms connecting $R^1$ and $COR^{20}$ is in the range of 8–14;

[5] Specifically preferred compounds of the above invention are compounds of Formula I, including enantiomeric or diasteriomeric forms thereof, or mixtures of enantiomeric or diasteriomeric forms thereof, or pharmaceutically acceptable salt or prodrug forms thereof selected from the group consisting of:

3-[3-[3-(imidazolin-2-ylamino)propyl]isoxazolin-5-ylmethylcarbonylamino]-2-(benzyloxycarbonylamino)propionic acid, 3-[3-[3-(imidazolin-2-ylamino)propyl]isoxazolin-5-ylmethylcarbonylamino]-2-(n-butyloxycarbonylamino)propionic acid, 3-[3-[3-(imidazolin-2-ylamino)propyl]isoxazolin-5-ylmethylcarbonylamino]-2-(phenylsulfonylamino)propionic acid, 3-[3-[3-(imidazolin-2-ylamino)propyl]isoxazolin-5-ylmethylcarbonylamino]-2-(n-butylsulfonylamino)propionic acid, 3-[3-[3-(tetrahydropyrimid-2-ylamino)propyl]isoxazolin-5-ylmethylcarbonylamino]-2-(benzyloxycarbonylamino)propionic acid, 3-[3-[3-(tetrahydropyrimid-2-ylamino)propyl]isoxazolin-5-ylmethylcarbonylamino]-2-(n-butyloxycarbonylamino)propionic acid, 3-[3-[3-(tetrahydropyrimid-2-ylamino)propyl]isoxazolin-5-ylmethylcarbonylamino]-2-(phenylsulfonylamino)propionic acid, 3-[3-[3-(tetrahydropyrimid-2-ylamino)propyl]isoxazolin-5-ylmethylcarbonylamino]-2-(n-butylsulfonyl)aminopropionic acid, 3-[3-[4-(imidazolin-2-ylamino)butyl]isoxazolin-5-ylcarbonylamino]-2-(benzyloxycarbonylamino)propionic acid, 3-[3-[4-(imidazolin-2-ylamino)butyl]isoxazolin-5-ylcarbonylamino]-2-(n-butyloxycarbonylamino)propionic acid, 3-[3-[4-(imidazolin-2-ylamino)butyl]isoxazolin-5-ylcarbonylamino]-2-(phenylsulfonylamino)propionic acid, 3-[3-[4-(imidazolin-2-ylamino)butyl]isoxazolin-5-ylcarbonylamino]-2-(n-butylsulfonylamino)propionic acid, 3-[3-[4-(tetrahydropyrimid-2-ylamino)butyl]isoxazolin-5-ylcarbonylamino]-2-(benzyloxycarbonylamino)propionic acid, 3-[3-[4-(tetrahydropyrimid-2-ylamino)butyl]isoxazolin-5-ylcarbonyl amino]-2-(n-butyloxycarbonylamino)propionic acid, 3-[3-[4-(tetrahydropyrimid-2-ylamino)butyl]isoxazolin-5-ylcarbonylamino]-2-(phenylsulfonylamino)propionic acid, 3-[3-[4-(tetrahydropyrimid-2-ylamino)butyl]isoxazolin-5-ylcarbonylamino]-2-(n-butylsulfonyl)aminopropionic acid, 3-[3-[3-(imidazolin-2-ylamino)propyl]isoxazolin-5-ylcarbonylamino]-2-(benzyloxycarbonylamino)propionic acid, 3-[3-[3-(imidazolin-2-ylamino)propyl]isoxazolin-5-ylcarbonylamino]-2-(phenylsulfonylamino)propionic acid, 3-[3-[3-(tetrahydropyrimid-2-ylamino)propyl]isoxazolin-5-ylcarbonylamino]-2-(benzyloxycarbonylamino)propionic acid, 3-[3-[3-(tetrahydropyrimid-2-ylamino)propyl]isoxazolin-5-ylcarbonylamino]-2-(phenylsulfonylamino)propionic acid, 3-[3-[3-(2-aminothiazol-4-yl)propyl]isoxazolin-5-ylcarbonylamino]-2-(phenylsulfonylamino)propionic acid, 3-[3-[3-(2-aminothiazol-4-yl)propyl]isoxazolin-5-ylcarbonylamino]-2-(benzyloxycarbonylamino)propionic acid, 3-[3-[4-(imidazolin-2-ylamino)butyl]isoxazolin-5-ylcarbonylamino]-2-((2,4,6-trimethylphenyl)sulfonylamino)propionic acid, 3-[3-[4-(tetrahydropyrimid-2-ylamino)butyl]isoxazolin-5-ylcarbonylamino]-2-((2,4,6-tritrimethylphenyl)sulfonylamino)propionic acid, 3-[3-[4-(imidazol-2-ylamino)butyl]isoxazolin-5-ylcarbonylamino]-2-(benzyloxycarbonylamino)-propionic acid, 3-[3-[4-(imidazol-2-ylamino)butyl]isoxazolin-5-ylcarbonylamino]-2-(phenylsulfonylamino)-propionic acid, 3-[3-[4-(imidazol-2-ylamino)butyl]isoxazolin-5-ylcarbonylamino]-2-((2,6-dichlorophenyl)sulfonylamino)propionic acid, 3-[3-[4-(imidazol-2-ylamino)butyl]isoxazolin-5-ylcarbonylamino]-2-((2,4,6-trimethylphenyl)sulfonylamino)propionic acid, 3-[3-[4-(imidazol-2-ylamino)butyl]isoxazolin-5-ylcarbonylamino]-2-((4-biphenyl)sulfonyl-amino)propionic acid, 3-[3-[4-(imidazol-2-ylamino)butyl]isoxazolin-5-ylcarbonylamino]-2-(1-naphthylsulfonylamino)propionic acid, 3-[3-[3-(imidazol-2-ylamino)propyl]isoxazolin-5-ylmethylcarbonylamino]-2-benzyloxycarbonylamino)propionic acid, 3-[3-[3-(imidazol-2-ylamino)propyl]isoxazolin-5-ylmethylcarbonylamino]-2-(phenylsulfonylamino)propionic acid, 3-[3-[3-(imidazol-2-ylamino)propyl]isoxazolin-5-ylmethylcarbonylamino]-2-((2,6-dichlorophenyl)sulfonylamino)propionic acid, 3-[3-[3-(imidazol-2-ylamino)propyl]isoxazolin-5-ylmethylcarbonylamino]-2-((2,4,6-trimethylphenyl)sulfonylamino)propionic acid, 3-[3-[3-(imidazol-2-ylamino)propyl]isoxazolin-5-ylmethylcarbonylamino]-2-((4-biphenyl)sulfonylamino)propionic acid, 3-[3-[3-(imidazol-2-ylamino)propyl]isoxazolin-5-ylmethylcarbonylamino]-2-(1-naphthylsulfonylamino)propionic acid, 3-[3-[2-(imidazol-2-ylamino)ethyl]isoxazolin-5-ylcarbonylamino]-2-(benzyloxycarbonylamino)-propionic acid, 3-[3-[2-(imidazol-2-ylamino)ethyl]isoxazolin-5-ylcarbonylamino]-2-(phenylsulfonylamino)-propionic acid, 3-[3-[2-(imidazol-2-ylamino)ethyl]isoxazolin-5-ylcarbonylamino]-2-((2,6-dichlorophenyl)sulfonylamino)propionic acid, 3-[3-[2-(imidazol-2-ylamino)ethyl]isoxazolin-5-ylcarbonylamino]-2-((2,4,6-trimethylphenyl)sulfonylamino)propionic acid, 3-[3-[2-(imidazol-2-ylamino)ethyl]isoxazolin-5-ylcarbonylamino]-2-((4-biphenyl)sulfonyl-amino)propionic acid, 3-[3-[2-(imidazol-2-ylamino)ethyl]isoxazolin-5-ylcarbonylamino]-2-(1-naphthylsulfonylamino)propionic acid, 3-[3-[3-(imidazol-2-ylaminocarbonyl)propyl]isoxazolin-5-ylcarbonylamino]-2-((2,4,6-trimethylphenyl)sulfonylamino)propionic acid, 3-[3-[3-(2-aminoimidazol-4-yl)propyl]isoxazolin-5-ylcarbonylamino]-2-((2,4,6,trimethylphenyl)sulfonylamino)propionic acid, 3-[3-[2-(2-aminoimidazol-4-yl)ethyl]isoxazolin-5-ylmethylcarbonylamino]-2-((2,4,6,trimethylphenyl)sulfonylamino)propionic acid, 3-[3-[4-(benzimidazol-2-ylamino)butyl]isoxazolin-5-ylcarbonylamino]-2-((2,4,6,trimethylphenyl)sulfonylamino)propionic acid, 3-[3-[3-(benzimidazol-2-ylamino)propyl]isoxazolin-5-ylmethylcarbonylamino]-2-((2,4,6,trimethylphenyl)sulfonylamino)propionic acid, 3-[3-[3-(benzimidazol-2-ylaminocarbonyl)propyl]isoxazolin-5-ylcarbonylamino]-2-((2,4,6,trimethylphenyl)sulfonylamino)propionic acid, 3-[3-[4-(4-methylimidazol-2-ylamino)butyl]isoxazolin-5-ylcarbonylamino]-2-((2,4,6-trimethylphenyl)sulfonylamino)propionic acid, 3-[3-[3-(4-methylimidazol-2-ylamino)propyl]isoxazolin-5-ylmethylcarbonylamino]-2-((2,4,6,trimethylphenyl)sulfonylamino)propionic acid, 3-[3-[4-(4,5-dimethylimidazol-2-ylamino)butyl]-isoxazolin-5-ylcarbonylamino]-2-((2,4,6,trimethylphenyl)sulfonylamino)propionic acid, 3-[3-[3-(4,5-dimethylimidazol-2-ylamino)propyl]-isoxazolin-5-ylmethylcarbonylamino]-2-((2,4,6,trimethylphenyl)sulfonylamino)propionic acid, 3-[3-[3-(4,5-dimethylimidazol-2-ylaminocarbonyl)propyl]isoxazolin-5-ylcarbonylamino]-2-((2,4,6,trimethylphenyl)sulfonylamino)propionic acid, 3-[3-[4-(4,5,6,7-tetrahydrobenzimidazol-2-ylamino)butyl]isoxazolin-5-ylcarbonylamino]-2-((2,4,6,trimethylphenyl)sulfonylamino)propionic acid, 3-[3-[3-(4,5,6,7-tetrahydrobenzimidazol-2-ylamino)propyl]isoxazolin-5-ylmethylcarbonylamino]-2-((2,4,6,trimethylphenyl)sulfonylamino)propionic acid, 3-[3-[4-(pyridin-2-ylamino)butyl]isoxazolin-5-ylcarbonylamino]-2-((2,4,6,trimethylphenyl)sulfonylamino)propionic acid, 3-[3-[3-(pyridin-2-ylamino)propyl]isoxazolin-5-ylmethylcarbonylamino]-2-((2,4,6,trimethylphenyl)sulfonylamino)propionic acid, 3-[3-[3-(2-pyridin-6-yl)propyl]isoxazolin-5-ylcarbonylamino]-2-((2,4,6,trimethylphenyl)sulfonylamino)propionic acid, 3-[3-[2-(2-aminopyridin-6-yl)ethyl]isoxazolin-5-ylmethylcarbonylamino]-2-((2,4,6,trimethylphenyl)sulfonylamino)propionic acid, 3-[3-[3-(7-azabenzimidazol-2-yl)propyl]isoxazolin-5-ylcarbonylamino]-2-((2,4,6,trimethylphenyl)sulfonylamino)propionic acid, 3-[5-[3-(imidazolin-2-ylamino)propyl]isoxazolin-3-ylmethylcarbonylamino]-2-(benzyloxycarbonylamino)-propionic acid, 3-[5-[3-(imidazolin-2-ylamino)propyl]isoxazolin-3-ylmethylcarbonylamino]-2-(n-butyloxycarbonylamino)propionic acid, 3-[5-[3-(imidazolin-2-ylamino)propyl]isoxazolin-3-ylmethylcarbonylamino]-2-(phenylsulfonylamino)propionic acid, 3-[5-[3-(imidazolin-2-ylamino)propyl]isoxazolin-3-ylmethylcarbonylamino]-2-(2,4,6-trimethylphenylsulfonylamino)propionic acid, 3-[5-[3-(imidazolin-2-ylamino)propyl]isoxazolin-3-ylmethylcarbonylamino]-2-(n-butylsulfonylamino)propionic acid, 3-[5-[3-(tetrahydropyrimid-2-ylamino)propyl]isoxazolin-3-ylmethylcarbonylamino]-2-(benzyloxycarbonylamino)propionic acid, 3-[5-[3-(tetrahydropyrimid-2-ylamino)propyl]isoxazolin-3-ylmethylcarbonyl amino]-2-(n-butyloxycarbonylamino)propionic acid, 3-[5-[3-(tetrahydropyrimid-2-ylamino)propyl]isoxazolin-3-ylmethylcarbonylamino]-2-(phenylsulfonylamino)propionic acid, 3-[5-[3-(tetrahydropyrimid-2-ylamino)propyl]isoxazolin-3-ylmethylcarbonylamino]-2-(2,4,6-trimethylphenylsulfonylamino)propionic acid, 3-[5-[3-(tetrahydropyrimid-2-ylamino)propyl]isoxazolin-3-ylmethylcarbonylamino]-2-(n-butylsulfonyl)aminopropionic acid, 3-[5-[4-(imidazolin-2-yl amino)butyl]isoxazolin-3-ylcarbonylamino]-2-(benzyloxycarbonylamino)propionic acid, 3-[5-[4-(imidazolin-2-ylamino)butyl]isoxazolin-3-ylcarbonylamino]-2-(n-butyloxycarbonylamino)propionic acid, 3-[5-[4-(imidazolin-2-ylamino)butyl]isoxazolin-3-ylcarbonylamino]-2-(phenylsulfonylamino)propionic acid, 3-[5-[4-(imidazolin-2-ylamino)butyl]isoxazolin-3-ylcarbonylamino]-2-(n-butylsulfonylamino)propionic acid, 3-[5-[4-(tetrahydropyrimid-2-ylamino)butyl]isoxazolin-3-ylcarbonylamino]-2-(benzyloxycarbonylamino)propionic acid, 3-[5-[4-(tetrahydropyrimid-2-ylamino)butyl]isoxazolin-3-ylcarbonyl amino]-2-(n-butyloxycarbonylamino)propionic acid, 3-[5-[4-(tetrahydropyrimid-2-ylamino)butyl]isoxazolin-3-ylcarbonylamino]-2-(phenylsulfonylamino)propionic acid, 3-[5-[4-(tetrahydropyrimid-2-ylamino)butyl]isoxazolin-3-ylcarbonylamino]-2-(n-butylsulfonyl)aminopropionic acid, 3-[5-[3-(imidazol-2-yl amino)propyl]isoxazolin-3-ylcarbonylamino]-2-(benzyloxycarbonylamino)propionic acid, 3-[5-[3-(imidazolin-2-ylamino)propyl]isoxazolin-3-ylcarbonylamino]-2-(n-propyloxycarbonylamino)propionic acid, 3-[5-[3-(imidazolin-2-ylamino)propyl]isoxazolin-3-ylcarbonylamino]-2-(phenylsulfonylamino)propionic acid, 3-[5-[3-(imidazolin-2-ylamino)propyl]isoxazolin-3-ylcarbonylamino]-2-(n-propylsulfonylamino)propionic acid, 3-[5-[3-(tetrahydropyrimid-2-ylamino)propyl]isoxazolin-3-ylcarbonylamino]-2-(benzyloxycarbonylamino)propionic acid, 3-[5-[3-(tetrahydropyrimid-2-ylamino)propyl]isoxazolin-3-ylmethylcarbonyl amino]-2-(n-propyloxycarbonylamino)propionic acid, 3-[5-[3-(tetrahydropyrimid-2-ylamino)propyl]isoxazolin-3-ylcarbonylamino]-2-(phenylsulfonylamino)propionic acid, 3-[5-[3-(tetrahydropyrimid-2-ylamino)propyl]isoxazolin-3-ylcarbonylamino]-2-(n-propylsulfonyl)aminopropionic acid, 3-[5-[2-(imidazolin-2-ylamino)ethyl]isoxazolin-3-ylcarbonylamino]-2-(phenylsulfonylamino)propionic acid, 3-[5-[4-(pyridin-2-ylamino)butyl]isoxazolin-3-ylcarbonylamino]-2-(phenylsulfonylamino)propionic acid, 3-[5-[4-(pyridin-2-ylamino)butyl]isoxazolin-3-ylcarbonylamino]-2-(2,6-dichlorophenylsulfonylamino)propionic acid, 3-[5-[4-(pyridin-2-ylamino)butyl]isoxazolin-3-ylcarbonylamino]-2-(2,4,6-trimethylphenylsulfonylamino)propionic acid, 3-[5-[4-(pyridin-2-ylamino)butyl]isoxazolin-3-ylcarbonylamino]-2-(4-biphenylsulfonylamino)propionic acid, 3-[5-[4-(pyridin-2-ylamino)butyl]isoxazolin-3-ylcarbonylamino]-2-(1-naphthylsulfonylamino)propionic acid, 3-[5-[3-(2-aminopyridin-6-yl)propyl]isoxazolin-3-ylcarbonylamino]-2-(2,4,6-trimethylphenyl sulfonylamino)propionic acid, 3-[5-[4-(imidazol-2-ylamino)butyl]isoxazolin-3-ylcarbonylamino]-2-(phenylsulfonylamino)-propionic acid, 3-[5-[4-(imidazol-2-ylamino)butyl]isoxazolin-3-ylcarbonylamino]-2-(2,6-dichlorophenylsulfonylamino)propionic acid, 3-[5-[4-(imidazol-2-ylamino)butyl]isoxazolin-3-ylcarbonylamino]-2-(2,4,6-trimethylphenylsulfonylamino)propionic acid, 3-[5-[4-(imidazol-2-ylamino)butyl]isoxazolin-3-ylcarbonylamino]-2-(4-biphenylsulfonylamino)propionic acid, 3-[5-[4-(imidazol-2-ylamino)butyl]isoxazolin-3-ylcarbonylamino]-2-(1-naphthylsulfonylamino)propionic acid, 3-[5-[3-(2-aminoimidazol-4-yl)propyl]isoxazolin-3-ylcarbonylamino]-2-(phenylsulfonylamino)-propionic acid, 3-[5-[3-(2-aminoimidazol-4-yl)propyl]isoxazolin-3-ylcarbonylamino]-2-(2,6-dichlorophenylsulfonylamino)propionic acid, 3-[5-[3-(2-aminoimidazol-4-yl)propyl]isoxazolin-3-ylcarbonylamino]-2-(2,4,6-trimethylphenyl sulfonylamino)propionic acid, 3-[5-[3-(2-aminoimidazol-4-yl)propyl]isoxazolin-3-ylcarbonylamino]-2-(4-biphenylsulfonylamino)propionic acid, 3-[5-[3-(2-aminoimidazol-4-yl)propyl]isoxazolin-3-ylcarbonylamino]-2-(1-naphthylsulfonylamino)propionic acid, 3-[5-[2-(imidazol-2-ylamino)ethyl]isoxazolin-3-ylcarbonylamino]-2-(phenylsulfonylamino)-propionic acid, 3-[5-[2-(imidazol-2-ylamino)ethyl]isoxazolin-3-ylcarbonylamino]-2-(2,6-dichlorophenylsulfonylamino)propionic acid, 3-[5-[2-(imidazol-2-ylamino)ethyl]isoxazolin-3-ylcarbonylamino]-2-(2,4,6-trimethylphenylsulfonylamino)propionic acid, 3-[5-[2-(imidazol-2-ylamino)ethyl]isoxazolin-3-ylcarbonylamino]-2-(4-biphenylsulfonylamino)propionic acid, 3-[5-[2-(imidazol-2-ylamino)ethyl]isoxazolin-3-ylcarbonylamino]-2-(1-naphthylsulfonylamino)propionic acid, 3-[5-[3-(imidazol-2-ylaminocarbonyl)propyl]isoxazolin-3-ylcarbonylamino]-2-(2,4,6-trimethylphenylsulfonylamino)propionic acid, 3-[5-[3-(benzimidazol-2-ylaminocarbonyl)propyl]isoxazolin-3-ylcarbonylamino]-2-(2,4,6-trimethylphenylsulfonylamino)propionic acid, 3-[5-[4-(benzimidazol-2-ylamino)butyl]isoxazolin-3-ylcarbonylamino]-2-(phenylsulfonylamino)propionic acid, 3-[5-[4-(benzimidazol-2-ylamino)butyl]isoxazolin-3-ylcarbonylamino]-2-(2,6-dichlorophenylsulfonylamino)propionic acid, 3-[5-[4-(benzimidazol-2-ylamino)butyl]isoxazolin-3-ylcarbonylamino]-2-(2,4,6-trimethylphenylsulfonylamino)propionic acid, 3-[5-[4-(benzimidazol-2-ylamino)butyl]isoxazolin-3-ylcarbonylamino]-2-(4-biphenylsulfonylamino)propionic acid, 3-[5-[4-(benzimidazol-2-ylamino)butyl]isoxazolin-3-ylcarbonylamino]-2-(1-naphthylsulfonylamino)propionic acid, 3-[5-[4-(4-methylimidazol-2-ylamino)butyl]isoxazolin-3-ylcarbonylamino]-2-(phenylsulfonylamino)propionic acid, 3-[5-[4-(4-methylimidazol-2-ylamino)butyl]isoxazolin-3-ylcarbonylamino]-2-(2,6-dichlorophenylsulfonylamino)propionic acid, 3-[5-[4-(4-methylimidazol-2-ylamino)butyl]isoxazolin-3-ylcarbonylamino]-2-(2,4,6-trimethylphenylsulfonylamino)propionic acid, 3-[5-[4-(4-methylimidazol-2-ylamino)butyl]isoxazolin-3-ylcarbonylamino]-2-(4-biphenylsulfonylamino)propionic acid, 3-[5-[4-(4-methylimidazol-2-ylamino)butyl]isoxazolin-3-ylcarbonylamino]-2-(1-naphthylsulfonylamino)propionic acid, 3-[5-[4-(4,5-dimethylimidazol-2-ylamino)butyl]-isoxazolin-3-ylcarbonylamino]-2-(phenylsulfonylamino)propionic acid, 3-[5-[4-(4,5-dimethylimidazol-2-ylamino)butyl]-isoxazolin-3-ylcarbonylamino]-2-(2,6-dichlorophenylsulfonylamino)propionic acid, 3-[5-[4-(4,5-dimethylimidazol-2-ylamino)butyl]-isoxazolin-3-ylcarbonylamino]-2-(2,4,6-trimethylphenylsulfonylamino)propionic acid, 3-[5-[4-(4,5-dimethylimidazol-2-ylamino)butyl]-isoxazolin-3-ylcarbonylamino]-2-(4-biphenylsulfonylamino)propionic acid, 3-[5-[4-(4,5-dimethylimidazol-2-ylamino)butyl]-isoxazolin-3-ylcarbonylamino]-2-(1-naphthylsulfonylamino)propionic acid, 3-[5-[4-(4,5,6,7-tetrahydrobenzimidazol-2-ylamino)butyl]-isoxazolin-3-ylcarbonylamino]-2-(phenylsulfonylamino)propionic acid, 3-[5-[4-(4,5,6,7-tetrahydrobenzimidazol-2-ylamino)butyl]-isoxazolin-3-ylcarbonylamino]-2-(2,6-dichlorophenylsulfonylamino)propionic acid, 3-[5-[4-(4,5,6,7-tetrahydrobenzimidazol-2-ylamino)butyl]-isoxazolin-3-ylcarbonylamino]-2-(2,4,6-trimethylphenylsulfonylamino)propionic acid, 3-[5-[4-(4,5,6,7-tetrahydrobenzimidazol-2-ylamino)butyl]isoxazolin-3-ylcarbonylamino]-2-(4-biphenylsulfonylamino)propionic acid, 3-[5-[4-(4,5,6,7-tetrahydrobenzimidazol-2-ylamino)butyl]-isoxazolin-3-ylcarbonylamino]-2-(1-naphthylsulfonylamino)propionic acid, 3-[5-[3-(7-azabenzimidazol-2-yl)propyl]isoxazolin-3-ylcarbonylamino]-2-(2,4,6-trimethylphenylsulfonylamino)propionic acid, 3-[5-[4-(imidazol-2-ylamino)butyl]isoxazolin-3-ylcarbonylamino]-2-[(2,6-dimethyl-4-phenyl)phenylsulfonylamino]propionic acid, 3-[5-[4-(4-methylimidazol-2-ylamino)butyl]isoxazolin-3-ylcarbonylamino]-2-[(2,6-dimethyl-4-phenyl)phenylsulfonylamino]propionic acid, 3-[5-[4-(4,5-dimethylimidazol-2-ylamino)butyl]isoxazolin-3-ylcarbonylamino]-2-[(2,6-dimethyl-4-phenyl)phenylsulfonylamino]propionic acid, 3-[5-[4-(4,5,6,7-tetrahydrobenzimidazol-2-ylamino)butyl]isoxazolin-3-ylcarbonylamino]-2-[(2,6-dimethyl-4-phenyl)phenylsulfonylamino]propionic acid, 3-[5-[4-(imidazol-2-ylamino)butyl]isoxazolin-3-ylcarbonylamino]-2-[(2,6-dichloro-4-phenyl)phenylsulfonylamino]propionic acid, 3-[5-[4-(4-methylimidazol-2-ylamino)butyl]isoxazolin-3-ylcarbonylamino]-2-[(2,6-dichloro-4-phenyl)phenylsulfonylamino]propionic acid, 3-[5-[4-(4,5-dimethylimidazol-2-ylamino)butyl]isoxazolin-3-ylcarbonylamino]-2-[(2,6-dichloro-4-phenyl)phenylsulfonylamino]propionic acid, 3-[5-[4-(4,5,6,7-tetrahydrobenzimidazol-2-ylamino)butyl]isoxazolin-3-ylcarbonylamino]-2-[(2,6-dichloro-4-phenyl)phenylsulfonylamino]propionic acid, 3-[5-[4-(imidazol-2-ylamino)butyl]isoxazolin-3-ylcarbonylamino]-3-(phenylsulfonylmethyl)propionic acid, 3-[5-[4-(imidazol-2-ylamino)butyl]isoxazolin-3-ylcarbonylamino]-3-(1-adamantylmethylaminocarbonyl)propionic acid, 3-[5-[4-(imidazol-2-ylamino)butyl]isoxazolin-3-ylcarbonylamino]-3-(3-pyridinyl)propionic acid, 3-[3-[3-(imidazolin-2-yl amino)propyloxy]isoxazol-5-ylcarbonylamino]-2-(benzyloxycarbonylamino)propionic acid, 3-[3-[3-(imidazolin-2-ylamino)propyloxy]isoxazol-5-yl carbonyl amino]-2-(n-butyloxycarbonyl-amino)propionic acid, 3-[3-[3-(imidazolin-2-ylamino)propyloxy]isoxazol-5-yl carbonylamino]-2-(phenylsulfonylamino)propionic acid, 3-[3-[3-(imidazolin-2-ylamino)propyloxy]isoxazol-5-yl carbonyl amino]-2-(n-butylsulfonylamino)-propionic acid, 3-[3-[3-(tetrahydropyrimid-2-ylamino)propyloxy]-isoxazol-5-ylcarbonylamino]-2-(benzyloxycarbonylamino)propionic acid, 3-[3-[3-(tetrahydropyrimid-2-ylamino)propyloxy]-isoxazol-5-ylcarbonyl amino]-2-(n-butyloxycarbonylamino)propionic acid, 3-[3-[3-(tetrahydropyrimid-2-ylamino)propyloxy]-isoxazol-5-ylcarbonylamino]-2-(phenylsulfonylamino) propionic acid, 3-[3-[3-(tetrahydropyrimid-2-ylamino)propyloxy]-isoxazol-5-yl carbonylamino]-2-(n-butylsulfonyl) aminopropionic acid, 3-[3-[2-(imidazolin-2-yl amino)ethyloxy]isoxazol-5-yl carbonylamino]-2-(benzyloxycarbonylamino)-propionic acid, 3-[3-[3-(imidazolin-2-ylamino)ethyloxy]isoxazol-5-yl carbonylamino]-2-(n-butyloxycarbonylamino) propionic acid, 3-[3-[3-(imidazolin-2-ylamino)ethyloxy]isoxazol-5-yl carbonylamino]-2-(phenylsulfonylamino)propionic acid, 3-[3-[3-(imidazolin-2-ylamino)ethyloxy]isoxazol-5-ylcarbonylamino]-2-(n-butylsulfonylamino)propionic acid, 3-[3-[3-(tetrahydropyrimid-2-yl amino)ethyloxy]-isoxazol-5-ylcarbonylamino]-2-(benzyloxycarbonylamino)propionic acid, 3-[3-[3-(tetrahydropyrimid-2-ylamino)ethyloxy]-isoxazol-5-ylcarbonylamino]-2-(n-butyloxycarbonylamino)propionic acid, 3-[3-[3-(tetrahydropyrimid-2-ylamino)ethyloxy]-isoxazol-5-ylcarbonylamino]-2-(phenylsulfonylamino) propionic acid, 3-[3-[3-(tetrahydropyrimid-2-ylamino)ethyloxy]-isoxazol-5-ylcarbonylamino]-2-(n-butylsulfonylamino)propionic acid, 3-[3-[3-(imidazol-2-ylamino)propyloxy]isoxazol-5-ylcarbonylamino]-2-(phenylsulfonylamino)propionic acid, 3-[3-[3-(benzimidazol-2-ylamino)propyloxy]isoxazol-5-ylcarbonylamino]-2-(phenylsulfonylamino)propionic acid, 3-[3-[3-(4-methylimidazol-2-ylamino)propyloxy]-isoxazol-5-ylcarbonylamino]-2-(phenylsulfonylamino) propionic acid, 3-[3-[3-(4,5-dimethylimidazol-2-ylamino)propyloxy]-isoxazol-5-ylcarbonylamino]-2-(phenylsulfonylamino) propionic acid, 3-[3-[3-(4,5,6,7-tetrahydrobenzimidazol-2-ylamino) propyloxy]-isoxazol-5-ylcarbonylamino]-2-(phenylsulfonylamino)propionic acid, 3-[3-[3-(pyridin-2-ylamino)propyloxy]isoxazol-5-ylcarbonylamino]-2-(phenylsulfonylamino)propionic acid, 3-[3-[3-(imidazol-2-ylaminocarbonyl)ethoxy]isoxazol-5-ylcarbonylamino]-2-(phenylsulfonylamino)propionic acid, In the present invention it has been discovered that the compounds of Formula I above are useful as inhibitors of cell-matrix and cell-cell adhesion processes. The present invention includes novel compounds of Formula I and methods for using such compounds for the prevention or treatment of diseases resulting from abnormal cell adhesion to the extracellular matrix which comprises administering to a host in need of such treatment a therapeutically effective amount of such compound of Formula I.

In the present invention it has also been discovered that the compounds of Formula I above are useful as inhibitors of $\alpha_v\beta_3$. The compounds of the present invention inhibit the binding of vitronectin to $\alpha_v\beta_3$ and inhibit cell adhesion.

The present invention also provides pharmaceutical compositions comprising a compound of Formula I and a pharmaceutically acceptable carrier.

The compounds of Formula I of the present invention are useful for the treatment (including prevention) of angiogenic disorders. The term "angiogenic disorders" as used herein includes conditions involving abnormal neovascularization, such as tumor metastasis and ocular neovascularization, including, for example, diabetic retinopathy, neovascular glaucoma, age-related macular degeneration, and retinal vein occlusion, comprising administering to a mammal in need of such treatment a therapeutically effective amount of a compound of Formula I described above.

The compounds of Formula I of the present invention may be useful for the treatment or prevention of other diseases which involve cell adhesion processes, including, but not limited to, inflammation, bone degradation, thromboembolic disorders, restenosis, rheumatoid arthritis, asthma, allergies, adult respiratory distress syndrome, graft versus host disease, organ transplantation rejection, septic shock, psoriasis, eczema, contact dermatitis, osteoporosis, osteoarthritis, atherosclerosis, inflammatory bowel disease and other autoimmune diseases. The compounds of Formula I of the present invention may also be useful for wound healing.

The term "thromboembolic disorders" as used herein includes conditions involving platelet activation and aggregation, such as arterial or venous cardiovascular or cerebrovascular thromboembolic disorders, including, for example, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or such disorders associated with diabetes, comprising administering to a mammal in need of such treatment a therapeutically effective amount of a compound of Formula I described above.

The compounds of the present invention may be used for other ex vivo applications to prevent cellular adhesion in biological samples.

The compounds of the present invention can also be administered in combination with one or more additional therapeutic agents selected from: anti-coagulant or coagulation inhibitory agents, such as heparin or warfarin; anti-platelet or platelet inhibitory agents, such as aspirin, piroxicam, or ticlopidine; thrombin inhibitors such as boropeptides, hirudin or argatroban; or thrombolytic or fibrinolytic agents, such as plasminogen activators, anistreplase, urokinase, or streptokinase.

The compounds of Formula I of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic disorders.

By "therapeutically effective amount" it is meant an amount of a compound of Formula I that when administered alone or in combination with an additional therapeutic agent to a cell or mammal is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term anti-coagulant agents (or coagulation inhibitory agents), as used herein, denotes agents that inhibit blood coagulation. Such agents include warfarin (available as COUMADIN™) and heparin.

The term anti-platelet agents (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam. Piroxicam is commercially available from Pfizer Inc. (New York, N.Y.), as FELDANE™. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include thromboxane-A2-receptor antagonists and thromboxane-A2-synthetase inhibitors, as well as pharmaceutically acceptable salts or prodrugs thereof.

The phrase thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boroarginine derivatives and boropeptides, hirudin and argatroban, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471 651 A2, the disclosures of which are hereby incorporated herein by reference, in their entirety.

The phrase thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 028,489, the disclosures of which are hereby incorporated herein by reference herein, in their entirety. Anistreplase is commercially available as EMINASE™. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the binding of vitronectin or fibrinogen to $\alpha_v\beta_3$. Such compounds may be provided in a commercial kit, for example, for use in pharmaceutical research involving $\alpha_v\beta_3$. The compounds of the present invention may also be used in diagnostic assays involving $\alpha_v\beta_3$.

The compounds herein described may have asymmetric centers. Unless otherwise indicated, all chiral, diastereomeric and racemic forms are included in the present invention. Many geometric isomers of olefins, $C=N$ double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, $R^2$, $R^4$, $R^6$, $R^7$, $R^8$, $R^{12}$, and $R^{14}$, n, etc.) occurs more than one time in any constituent or in any formula, its definition on each occurrence is independent of its definition at every other occurrence. Thus, for example, if a group is shown to be substituted with 0–2 $R^4$, then said group may optionally be substituted with up to two $R^4$ and $R^4$ at each occurrence is selected independently from the defined list of possible $R^4$. Also, by way of example, for the group —N($R^{5a}$)$_2$, each of the two $R^{5a}$ substituents on N is independently selected from the defined list of possible $R^{5a}$. Similarly, by way of example, for the group —C($R^7$)$_2$—, each of the two $R^7$ substituents on C is independently selected from the defined list of possible $R^7$.

When a bond to a substituent is shown to cross the bond connecting two atoms in a ring, then such substituent may be bonded to any atom on the ring. When a bond joining a substituent to another group is not specifically shown or the atom in such other group to which the bond joins is not specifically shown, then such substituent may form a bond with any atom on such other group.

When a substituent is listed without indicating the atom via which such substituent is bonded to the rest of the compound of Formula I, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula I via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_1$-$C_{10}$" denotes alkyl having 1 to 10 carbon atoms); "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, cycloheptyl, cyclooctyl, and adamantyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The terms "alkylene", "alkenylene", "phenylene", and the like, refer to alkyl, alkenyl, and phenyl groups, respectively, which are connected by two bonds to the rest of the structure of Formula I. Such "alkylene", "alkenylene", "phenylene", and the like, may alternatively and equivalently be denoted herein as "-(alkyl)-", "-(alkyenyl)-" and "-(phenyl)-", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; the term "arylalkyl" represents an aryl group attached through an alkyl bridge.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, isoxazolyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolinyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

At used herein, the term "heteroaryl" refers to aromatic heterocyclic groups. Such heteroaryl groups are preferably 5–6 membered monocylic groups or 8–10 membered fused bicyclic groups. Examples of such heteroaryl groups include, but are not limited to pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyrimidinyl, pyridazinyl, benzofuranyl, benzothienyl, benzimidazolyl, quinolinyl, or isoquinolinyl.

As used herein, "pharmaceutically acceptable salts" refer to derivatives of the disclosed compounds wherein the parent compound of Formula I is modified by making acid or base salts of the compound of Formula I. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to Formula I in vivo when such prodrug is administered to a mammalian subject. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula I, and the like. Examples of representative carboxyl and amino prodrugs are included under the definition of $R^2$, $R^3$, and Y.

The pharmaceutically acceptable salts of the compounds of Formula I include the conventional non-toxic salts or the quaternary ammonium salts of the compounds of Formula I formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The disclosures of all of the references cited herein are hereby incorporated herein by reference in their entirety.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

Compounds of Formula I wherein the central heterocycle is a 3,5-disubstituted isoxazoline ring can be conveniently prepared by dipolar cycloaddition of nitrile oxides with appropriate dipolarophiles (for reviews of 1,3-dipolar cycloaddition chemistry, see 1,3-Dipolar Cycloaddition Chemistry (Padwa, ed.), Wiley, New York, 1984; Kanemasa and Tsuge, *Heterocycles* 1990, 30, 719). The requisite nitrile oxides are in turn prepared from the corresponding aldehydes via the intermediate oximes.

Scheme I illustrates one synthetic sequence which will provide the 3,5-isoxazolines of this invention. An appropriately substituted hydroxylamine is treated with NCS in DMF according to the method of Liu, et al. (*J. Org. Chem.* 1980, 45, 3916). The resulting hydroximinoyl chloride is then dehydrohalogenated in situ using TEA to give a nitrile oxide, which undergoes a 1,3-dipolar cycloaddition to a suitably substituted alkene to afford the isoxazoline. Alternatively, the oxime may be oxidatively chlorinated, dehydrochlorinated and the resulting nitrile oxide trapped by a suitable alkene under phase transfer conditions according to the method of Lee (*Synthesis* 1982, 508).

Subsequent hydrolysis of the ester using conventional methods known to one skilled in the art of organic synthesis gives the desired acids. Coupling of the resulting acids to appropriately substituted α- or β-amino esters affords an intermediate which can be deprotected to give compounds of Formula I. The coupling is carried out using any of the many methods for the formation of amide bonds known to one skilled in the art of organic synthesis. These methods include but are not limited to conversion of the acid to the corresponding acid chloride, or use of standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, carbonyldiimidazole method, phosphorus reagents such as BOP-Cl. Some of these methods (especially the carbodiimide) can be enhanced by the addition of 1-hydroxybenzotriazole.

Scheme I

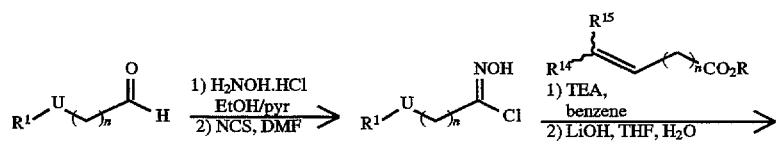

-continued
Scheme I

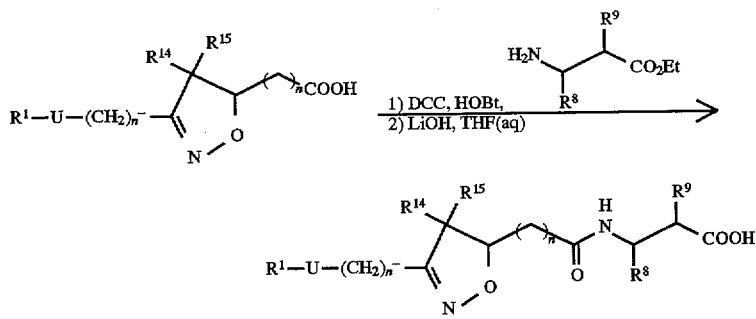

Alternately, as depicted in Scheme Ia, the above sequence can be carried out on an aldehyde bearing a suitably protected functional group which can be converted into $R^1$ after elaboration of the right hand side of the target molecules.

Scheme Ia

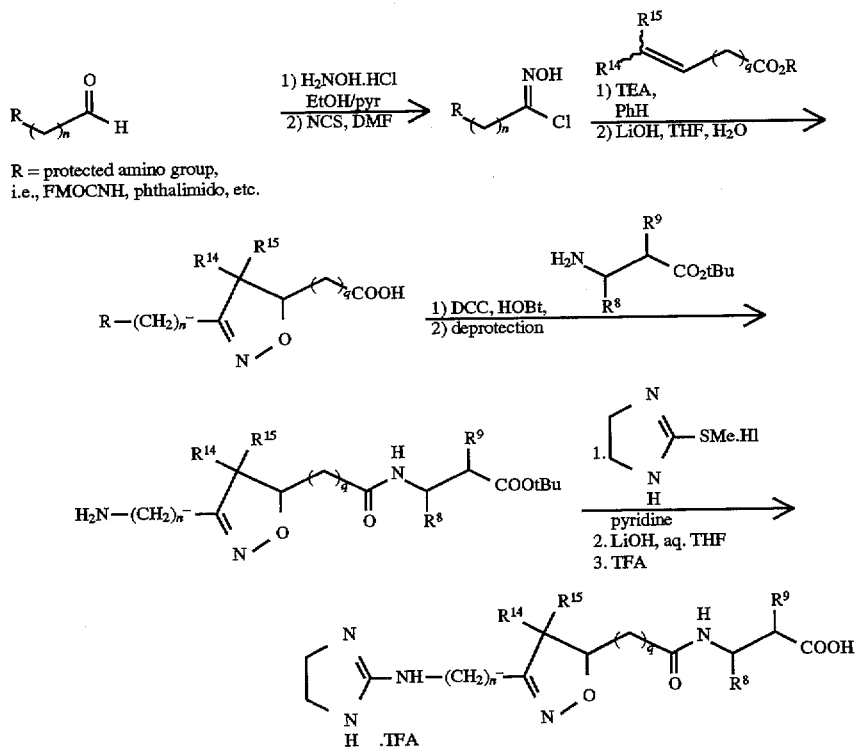

Additional isoxazolinyl acetates useful as starting materials for the preparation of compounds of Formula I, wherein V is -(phenyl)-Q— and Q is other than a single bond, can be prepared by cycloaddition of a suitably substituted chloro or bromooxime with an ester of vinyl acetic acid as shown in Scheme Ib using literature methods or modifications thereof. (D. P. Curran & J. Chao, J. Org. Chem., 1988, 53, 5369–71; J. N. Kim & E. K. Ryu, Heterocycles, 1990, 31, 1693–97).

Scheme Ib

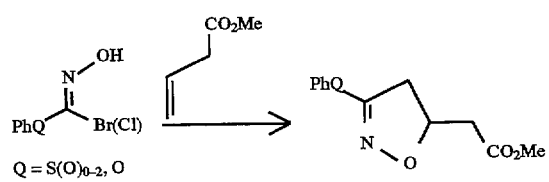

$Q = S(O)_{0-2}, O$

-continued
Scheme Ib

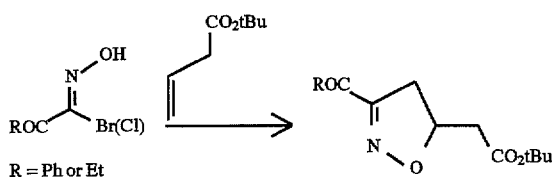

R = Ph or Et

The compounds of the present invention wherein Y is an oxyalkoxy group, e.g. alkoxycarbonyloxyalkoxy, may be prepared by reacting a suitably protected carboxylic acid of Formula I with an e.g. an alkoxycarbonyloxyalkyl chloride in the presence of an iodide source, such as tetrabutylammonium iodide or potassium iodide, and an acid scavenger, such as triethylamine or potassium carbonate, using procedures known to those skilled in the art.

The appropriately substituted racemic β-amino acids may be purchased commercially or, as is shown in Scheme II, Method 1, prepared from the appropriate aldehyde, malonic acid and ammonium acetate according to the procedure of Johnson and Livak (*J. Am. Chem. Soc.* 1936, 58, 299). Racemic β-substituted-β-amino esters may be prepared through the reaction of dialkylcuprates or alkyllithiums with 4-benzoyloxy-2-azetidinone followed by treatment with anhydrous ethanol (Scheme I, Method 2) or by reductive amination of β-keto esters as is described in published PCT patent application W09316038. (Also see Rico et al., J. Org. Chem. 1993, 58, 7948–51.) Enantiomerically pure β-substituted-β-amino acids can be obtained through the optical resolution of the racemic mixture or can be prepared using numerous methods, including: Arndt-Eistert homologation of the corresponding α-amino acids as shown in Scheme II, Method 3 (see Meier, and Zeller, *Angew Chem. Int. Ed. Engl.* 1975, 14, 32; Rodriguez, et al. *Tetrahedron Lett.* 1990, 31, 5153; Greenlee, *J. Med. Chem.* 1985, 28, 434 and references cited within); and through an enantioselective hydrogenation of a dehydroamino acid as is shown in Scheme II, Method 4 (see Asymmetric Synthesis, Vol. 5, (Morrison, ed.) Academic Press, New York, 1985). A comprehensive treatise on the preparation of β-amino acid derivatives may be found in published PCT patent application WO 9307867, the disclosure of which is hereby incorporated by reference.

Scheme II

Method 1

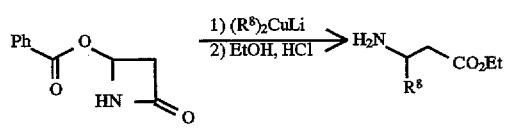

Method 2

-continued
Scheme II

Method 3

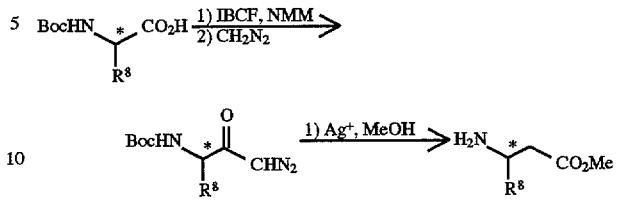

Method 4

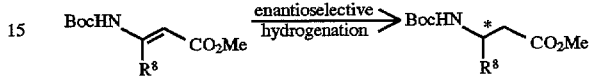

The synthesis of $N^2$-substituted diaminopropionic acid derivatives can be carried out via Hoffman rearrangement of a wide variety of asparagine derivatives as described in Synthesis, 266–267, (1981).

The dipolarophiles used to prepare the compounds of this invention may be prepared by numerous methods. The ω-alkenoic ester class of dipolarophile may be purchased commercially or prepared by oxidation of the corresponding ω-alkenols by the method of Corey and Schmidt (*Tetrahedron Lett.* 1979, 399, Scheme III).

Scheme III

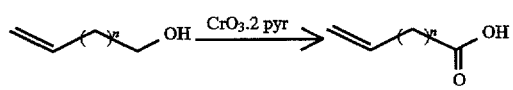

Synthesis of compounds of Formula I which incorporate the isoxazoline ring in the reverse orientation, i.e., a 5,3-disubstituted isoxazoline ring, is shown in Scheme IV. Cycloaddition of an appropriately substituted alkene with t-butylformyloxime using the method described by Gree et al. (Bioorganic and Med. Chem. Lett., 1994, 253) provides the intermediate t-butyl [5-substituted isoxazolin-3-yl] acetate. This ester can be converted to compounds of Formula I using the methods described herein.

Scheme IV

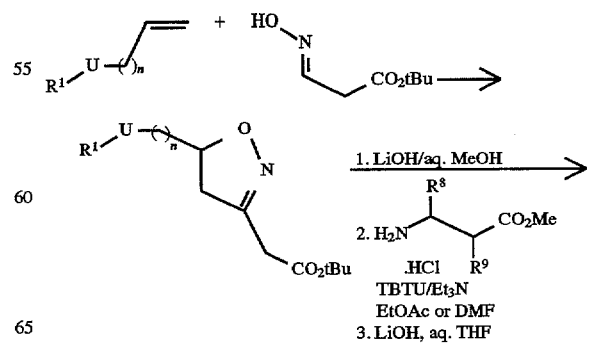

Scheme IV -continued

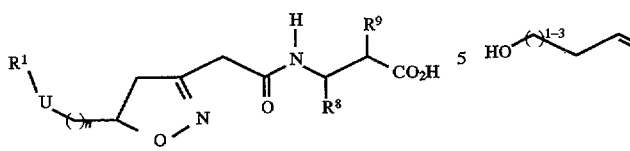

Scheme IVb

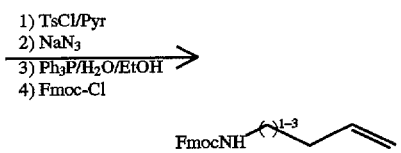

Alternately, as illustrated in Scheme IVa, the reverse isoxazolines may be prepared by reaction of an appropriate nitro ester with an appropriately substituted alkene in the presence of a suitable dehydrating agent such as phenylisocyanate or phosphorus oxychloride in the presence of an organic amine base, such as triethylamine or diisopropylethylamine.

Scheme IVa:

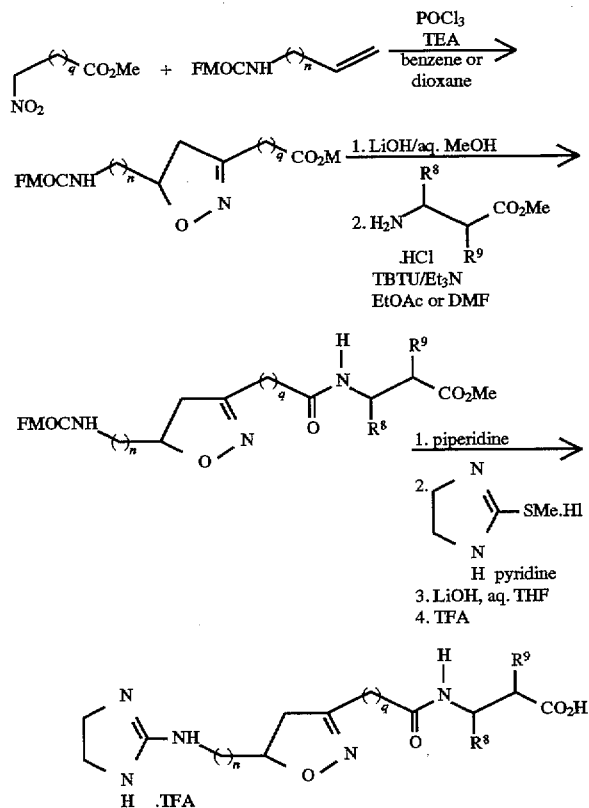

N-protected aminoalkenes useful in the synthesis of compounds of this invention can be prepared from the commercially available alcohols as shown in Scheme IVb, via reaction with a suitable activating agent such as p-toluenesulfonyl chloride in the presence of a base such as pyridine, followed by displacement with sodium azide in a suitable solvent such as DMF. Reduction of the azide by the action of triphenylphosphine in the presence of water (for example see, Scriven, E. F. V., Turnbull, K., Chemical Rev. 1988, 88, 297–360, and the references therein) provides an amine which is suitably protected, for example, Fmoc, Boc or phthalimide group according to literature procedures. (Protecting Groups in Organic Synthesis 2nd Ed. Green, T. W., Wits, P. G. M. pp 309–406. 1991 John Wiley & Sons, Inc. New York)

The appropriate nitroesters are available from commercial sources or can be synthesized according to literature methods (Seebach, D. et al., *Chem. Ber.* 1982, 115, 1705–1720; Chaser. D. W., *Syn. Comm.* 1982, 841–842).

Additional methods for the preparation of compounds of the present invention containing the isoxazoline ring in the reverse orientaion are outlined in Scheme V. An appropriate ω-alkenol can be reacted with commercially available ethyl chorooximidoacetate in a suitable solvent, such as tetrahydrofuran or methylene chloride, in the presence of a suitable base, such as aqueous sodium bicarbonate or triethylamine, to provide the isoxazoline. Alternately the same intermediate is prepared by heating the alkenol in the presence of diethylnitromalonate in refluxing mesitylene or decalin, by the method of Shimizu et al. (*Bull. Chem. Soc. Jpn.* 1985, 58, 2519–2522.) Oxidation of theresulting alcohol the corresponding aldehyde can be achieved by numerous methods described in the literature (for example see Comprehensive Organic Transformations by Larock, R. C., p 604, 605, 607–613. VCH publishers, New York, N.Y., 1989). Reductive amination of the intermediate aldehyde (for suitable methods see, Abdel-Magid, A. F., Maryanoff, C. A., and Carson, K. G., *Tetrahedron Lett.*, 1990, 31, 5595–5598, and references contained therein) with a variety of heteroaryl amines, which may additionally contain suitable protecting groups, provides the substituted amines. Alternatively, depending on the nature of the heterocyclic amine, the reductive amination can be carried out in a two step procedure, wherein initial formation of an imine is carried out by treatment of the aldehyde with the desired amine in the presence of a dehydrating agent such as magnesium sulfate, sodium sulfate, or molecular sieves, in a suitable solvent such as carbon tetrachloride, methylene chloride, benzene or toluene (for example see, Modern Synthetic Reactions 2nd ed. House, H. O., Benjamin/Cummings Publishing Co, Menlo Park, Calif., 1972.). The imine is then subsequently reduced with a variety of reducing agents such as sodium borohydride, sodium cyanoborohydride, or sodium triacetoxyborohydride, in a suitable solvent such as methanol, ethanol, tetrahydrofuran, dioxane or 1,2-dichloroethane, to provide the desired amines.

Hydrolysis of the ester using conventional methods known to one skilled in the art of organic synthesis provides acid intermediates. Coupling of the resulting acids to the appropriately substituted α- or β-amino ester is accomplished using standard coupling reagents, as described above. The esters may be saponified or in the case of tert-butyl esters the acid may be produced either by the action of trifluoroacetic acid with or without an inert solvent such as methylene chloride, or by the action of anhydrous HCl in a solvent such as ether or dioxane. Additional protecting groups may be removed by methods known to one skilled in the art (for example see, Protective Groups in Organic Synthesis 2nd, ed. Greene, T. W., and Wuts, P. G. M., John Wiley & Sons, Inc. New York, 1991).

Scheme V:

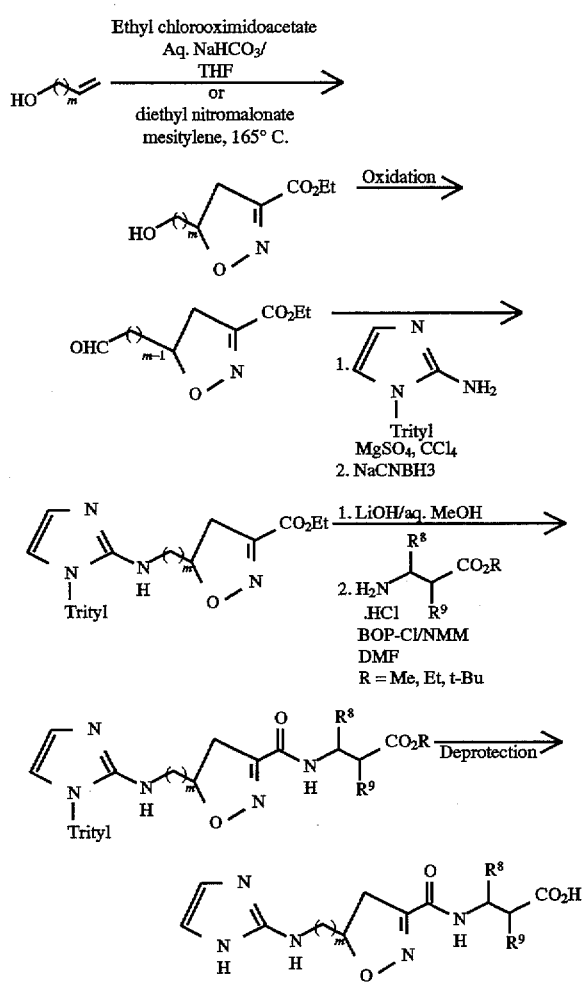

A convenient preparation of suitably protected 2-aminoimidazoles is outlined in Scheme Va.

Scheme Va:

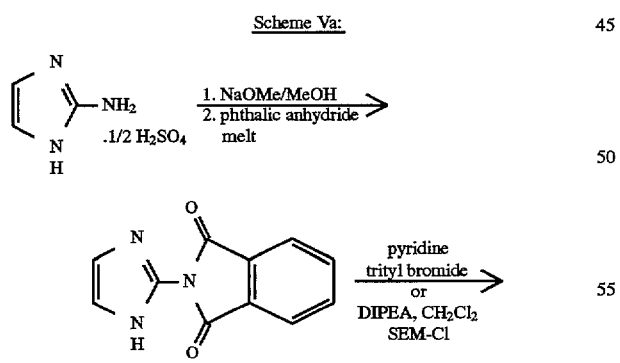

Scheme Va:

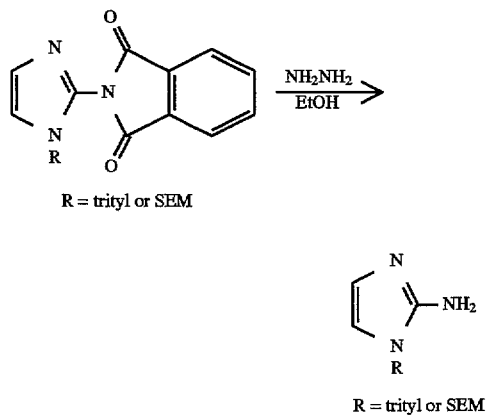

Compounds of formula I wherein b is a double bond can be prepared using one of the routes depicted in Scheme VI. Bromination followed by subsequent dehydrobromination of a suitably substituted methyl 3-(cyanophenyl)isoxazolin-5-ylacetate, prepared as described above, using the method of Elkasaby & Salem (Indian *J. Chem.*, 1980, 19B, 571–575) provides the corresponding isoxazole intermediate. Alternately, this intermediate can be obtained by 1,3-dipolar cycloaddition of a cyanophenylnitrile oxide (prepared from the corresponding chlorooxime as described in Scheme I) with an appropriate alkyne to give the isoxazole directly. Hydrolysis of the ester using conventional methods known to one skilled in the art of organic synthesis provides the acid intermediates. Coupling of the resulting acids to an appropriately substituted α- or β-amino ester is accomplished using standard coupling reagents, as described above. Saponification gives the acids.

Scheme VI

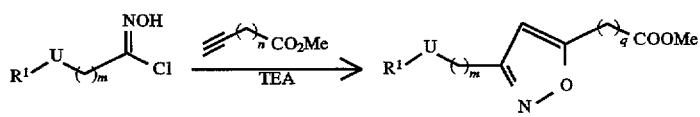

-continued
Scheme VI

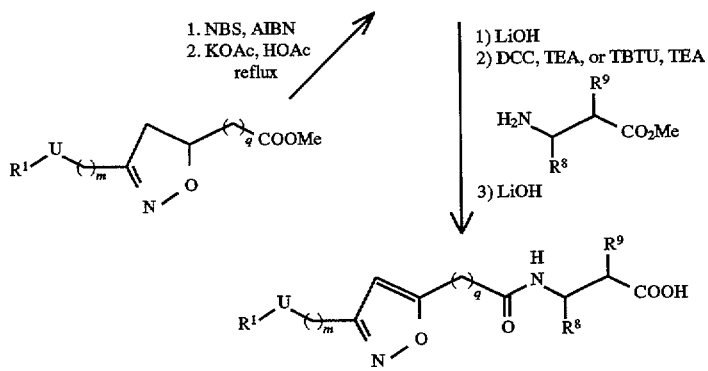

Compounds of Formula I wherein b is a double bond and Q is oxygen can be prepared from commercially available methyl 3-hydroxy-5-isoxazolecarboxylate as illustrated in Scheme VII. Coupling of the hydroxy group to a suitably N-protected amino alcohol can be achieved in one step under Mitsunobu reaction conditions (Hughs, D. L.; Organic Reactions, Volume 42, John Wiley and Sons, 1992, pages 335–656). Alternately, a two step process of activation of the N-protected aminoalcohol as a aryl or alkyl sulfonate ester or by conversion to halide followed by alkylation of the hydroxyisoxazole gives the same result. Bases suitable for this reaction include alkaline hydrogen carbonates, alkaline carbonates, cesium carbonate, alkaline hydrides, and alkaline alcoholates such as sodium ethoxide and potassium t-butoxide. The reaction can be run in a number of different solvents including lower alkyl and branched alcohols, ethereal solvents, or halocarbons, but it proceeds most readily in polar aprotic solvents such as DMF and DMSO. Saponification of the ester using standard conditions known to one skilled in the art provides an acid intermediate which can be converted using the methods described above into compounds of Formula I.

Scheme VII

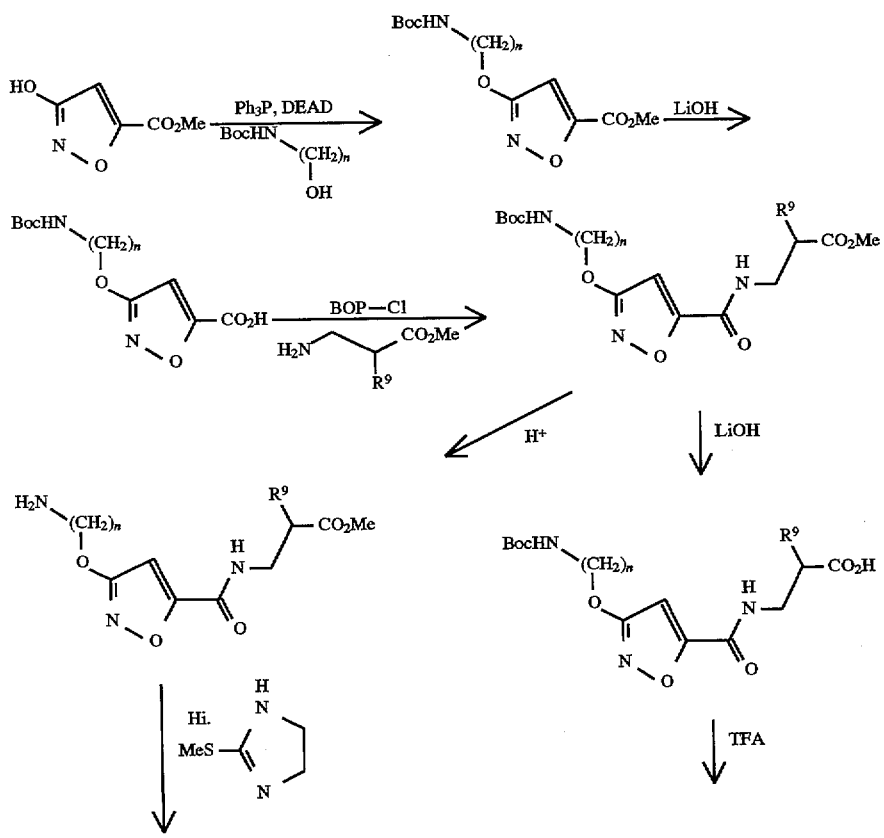

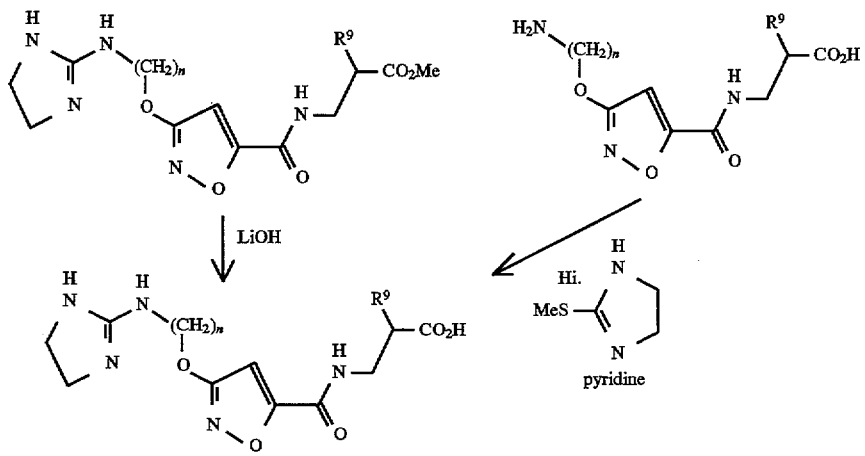

Additional aldehydes useful for the preparation of compounds of formula I in the methods depicted in schemes I–VII can be prepared as illustrated in Scheme VIII below:

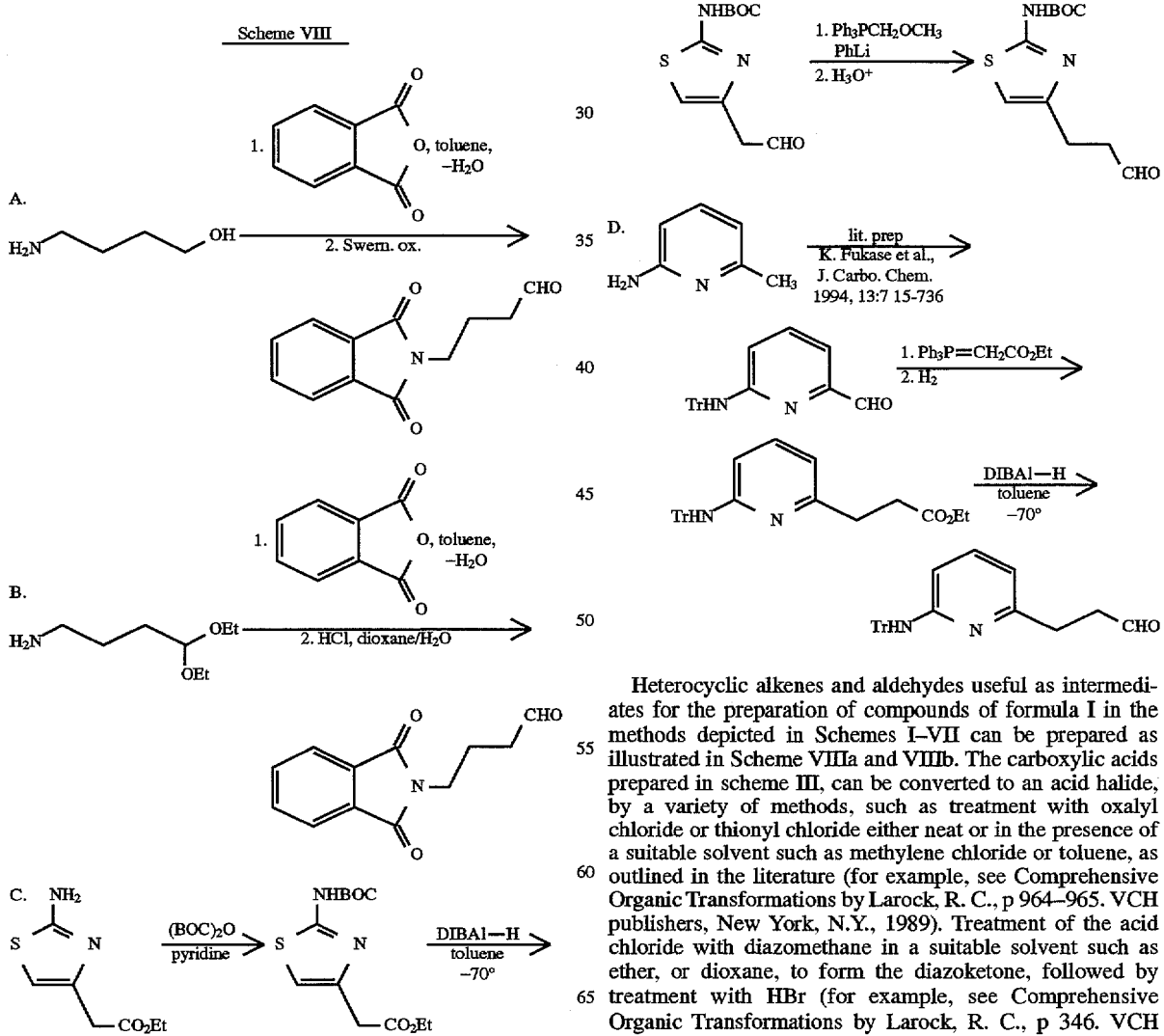

Heterocyclic alkenes and aldehydes useful as intermediates for the preparation of compounds of formula I in the methods depicted in Schemes I–VII can be prepared as illustrated in Scheme VIIIa and VIIIb. The carboxylic acids prepared in scheme III, can be converted to an acid halide, by a variety of methods, such as treatment with oxalyl chloride or thionyl chloride either neat or in the presence of a suitable solvent such as methylene chloride or toluene, as outlined in the literature (for example, see Comprehensive Organic Transformations by Larock, R. C., p 964–965. VCH publishers, New York, N.Y., 1989). Treatment of the acid chloride with diazomethane in a suitable solvent such as ether, or dioxane, to form the diazoketone, followed by treatment with HBr (for example, see Comprehensive Organic Transformations by Larock, R. C., p 346. VCH publishers, New York, N.Y., 1989), provides versatile intermediates for the synthesis of many heterocycles. The examples shown in scheme VIIIa, are for illustration purposes and do not constitute a limitation on the scope of the invention. For example, as illustrated in method A, the α-haloketone can be treated with N-acetylguanidine in a suitable solvent such as acetonitrile from room temperature to reflux, or N,N-dimethylformamide from room temperature to 80° C. according to the method of Little, T. L., and Webber, S. E. (*J. Org. Chem.*, 1994, 59, 7299–7305.) to provide a 2-amino-4-imidazole derivative. Alternatively, treatment of the α-haloketone with thiourea, in the presence of a suitable solvent such as toluene or acetone, at a temperature from 20° C. to the boiling point of the solvent, according to the method of Patt, W. C., Skeean, R. W., and Steinbaugh, B. A., (*Synth. Comm.* 1990, 20, 3097–3102), provides the analogous 2-amino-5-thiazole derivative. The alkenes can be converted by a hydroboration-oxidation procedure (for example, see Comprehensive Organic Transformations by Larock, R. C., p 497–498. VCH publishers, New York, N.Y., 1989), to provide the alcohols. The alcohols can be oxidized to the corresponding aldehydes by numerous published methods (for example see Comprehensive Organic Transformations by Larock, R. C., 604, 605, 607–613. VCH publishers, New York, N.Y., 1989).

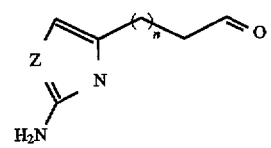

Synthesis of pyridyl-containing alkenes and aldehydes, proceeds as depicted in Scheme VIIIb. The amino group of 2-amino-6-methylpyridine is protected by treatment with 2,6-hexanedione, followed by deprotonation of the methyl group with lithium diisopropylamide according to the method of Breukelman, S. P., Meakins, G. D., and Tirel, M. D. (*J. Chem. Soc. Chem. Comm.* 1982, 800–801.). The lithio intermediate can be trapped with a variety of electrophiles such as formaldehyde, ethylene oxide or 3-(tertbutyldimethylsilyloxy)-1-bromopropane to provide the alcohol intermediates. Oxidation of the alcohol to an aldehyde as described as described in detail above, followed by olefination reaction under any of a number of known conditions, such as, for example, a Wittig reaction or treatment with various titanium reagents provides the alkene intermediates (see Comprehensive Organic Transformations by Larock, R. C., p 173–184. VCH publishers, New York, N.Y., 1989).

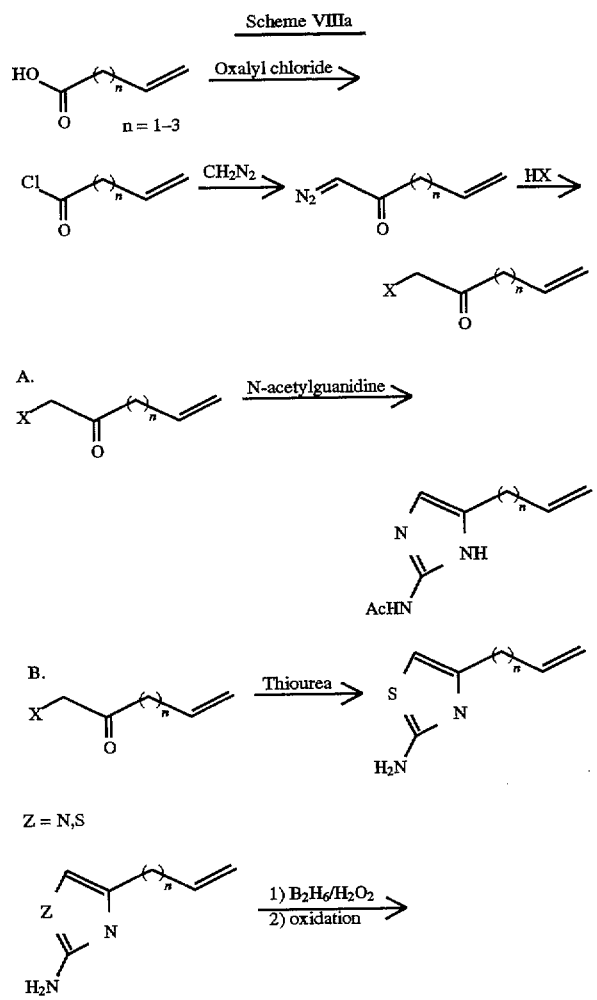

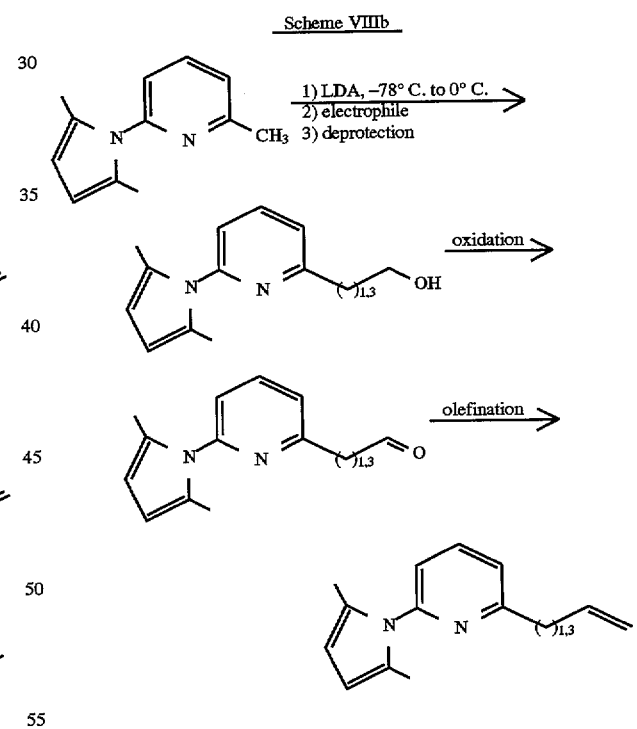

Alternately, reductive amination of the appropriate aldehyde intermediates with heterocyclic amines as shown in method A and method B of Scheme VIIIc, using methods described above, yields the desired amine intermediates. Hydroboration-oxidation of the double bond, followed by oxidation of the alcohol (vide supra) provides additional aldehyde intermediates useful for the synthesis of compounds of this invention. For heterocyclic amines unstable to the hydrogen peroxide required in the hydroboration oxidation procedure, the reductive amination can be carried out on appropriate esterified ω-hydroxy aldehydes, as outlined in method B. Hydrolysis of the esters and oxidation of the alcohol provides the aldehyde.

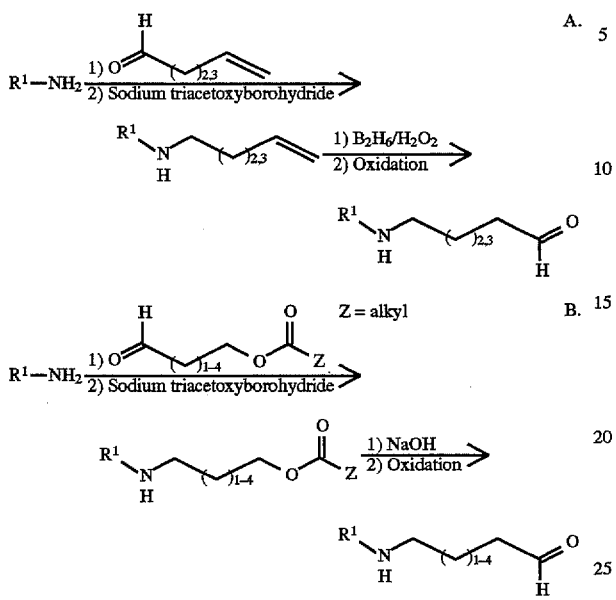

Compounds of Formula I wherein $R^1$ is 2-iminopyrrolidinyl, 2-iminopiperidinyl, or 2-iminoazepinyl can be prepared from the commercially available imides as outlined in Scheme IX.

Additional compounds of formula I where $R^9$ is —$N(R^{16})R^{17}$ can be prepared from the compounds of Schemes I, IA, IV, IVa, and IVb, wherein $R^{16}$ is Cbz (benzyloxycarbonyl), is shown in Scheme X. Selective removal of the Cbz group may be accomplished by hydrogenation using palladium suspended on barium sulfate as the catalyst in a suitable solvent such as methanol or ethanol, with or without a co-solvent, by the method of Nikam, S. S., Kornberg, B. E., Johnson, D. R., and Doherty, A. M. (Tetrahedron Lett. 1995, 36, 197–200). Using this method, the Cbz group can be removed with minimal to no cleavage of the N—O bond contained in the isozazoline rings shown in Scheme X example A, and Scheme X example B.

The resulting amines can be converted to additional compound of formula I by treatment with a wide variety of reagents, for example, acyl halides, chloroformares, isocyanates, sulfonylchlorides, chlorosulfonamides, and sulfonylisocyanates, etc. using standard methods.

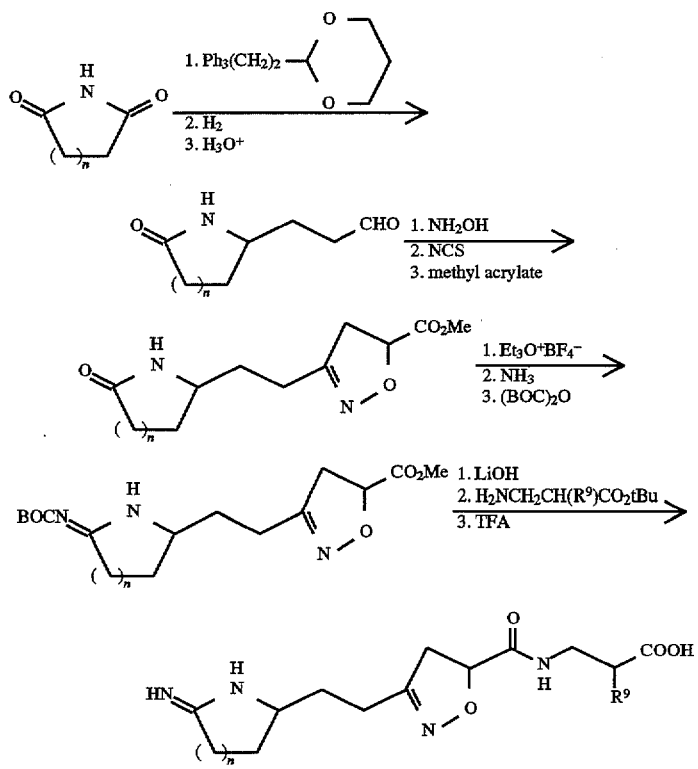

Scheme X

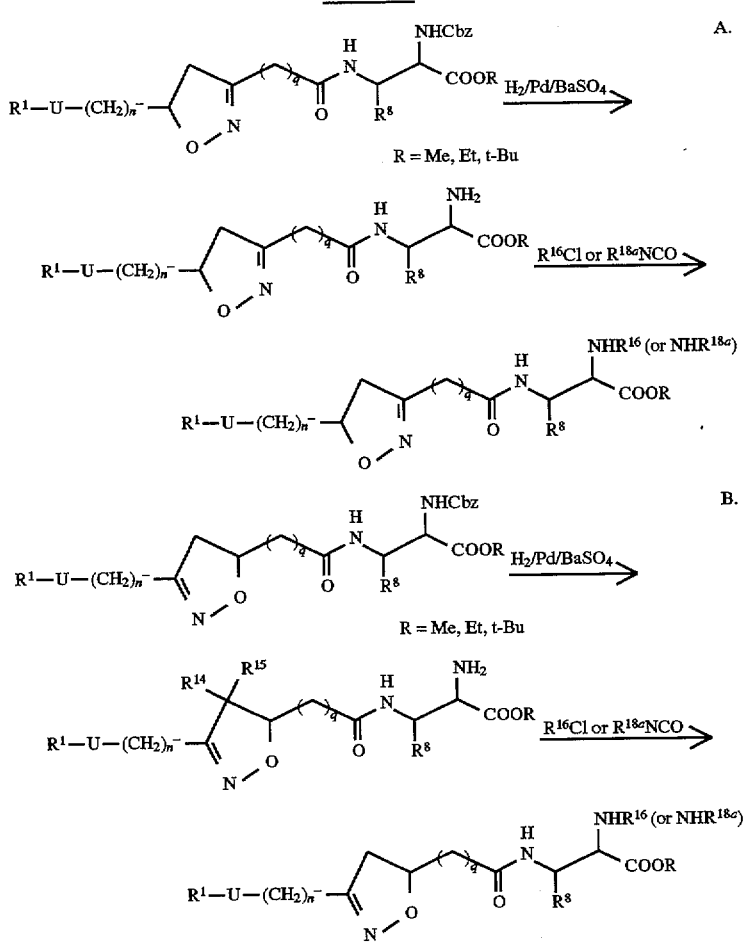

The detailed processes for preparing the compounds of Formula I are illustrated by the following Examples. It is, however, understood that this invention is not limited to the specific details of these examples. Melting points are uncorrected. Proton nuclear magnetic resonance spectra ($^1$H NMR) were measured in chloroform-d (CDCl$_3$) unless otherwise specified and the peaks are reported in parts per million (ppm) downfield from tetramethylsilane (TMS). The coupling patterns are reported as follows: s, singlet; d, doublet; t, triplet; q, quartet; qt, quintet; m, multipier.

EXAMPLE 2

3-[3-[3-(N-3,4,5,6-Tetrahydropyrimidin-2-yl) aminopropyl]-(5R,S)-isoxazoline-5-yl] methylcarbonylamino-2-benzyloxycarbonylaminopropionic acid A. 3-[3-[3-(N-3,4,5,6-Tetrahydropyrimidin-2-yl) aminopropyl]-(5R,S)-isoxazoline-5-yl] methylcarbonylamino-2-benzyloxycarbonylaminopropionic acid The compound of Ex. 16, Part G (199 mg; 0.5 mmol), methyl 3-amino-2-benzyloxycarbonylaminopropionate 147 mg (0.5 mmol), and triethylamine (100 mg; 1 mmol) in 3 ml dimethylformamide was treated with (177 mg; 0.55 mmol) of O-(1H-benzotriazol-1-yl)-N,N,N',N'-tetramethyluronium tetrafluoroborate (TBTU) and the mixture was stirred at room temperature for 18 hours. TLC indicated no starting material; the volatiles were removed under high vaccum. The residue was purified by flash chromatography; 55 g silica gel column using 8% MeOH:CHCl$_3$ followed by 20% to afford the desired product as a white solid (252 mg; 79.9% yield). NMR indicated contamination with triethylamine salt. The compound will be used in the next step without further purification. HRMS calcd. for C$_{24}$H$_{34}$N$_6$O$_6$ ([M+H]$^+$): 503.261808; found: 503.259832.

B. 3-[3-[3-(N-3,4,5,6-Tetrahydropyrimidin-2-yl) aminopropyl]-(5R, S)-isoxazoline-5-yl] methylcarbonylamino-2-benzyloxycarbonylaminopropionic acid A mixture of the compound of Ex. 2, Part A (100 mg; 0.159 mmol) and lithium hydroxide (12 mg; 0.5 mmol) in 2 ml of a 1:1 methanol:water was stirred at room temperature for one hour. TLC indicated dissappearance of starting material. The mixture was diluted with water and washed with hexane. The aqueous layer was neutralized with 1N HCl (0.5 mmol) and then stripped. The residue was purified on a LH20 size exclusion column using 100% methanol as an eluent. The product obtained was lyophilyzed from 2 ml 1N HCl followed by 2 ml distilled water. The desired product was obtained as an off-white solid (59 mg; 70.7% yield). $^1$H NMR (300 MHz CDCl$_3$): 1.721–1.785 (m, 4H); 2.294–2.408 (m, 3H); 2.499 (dd, 1H, J$_1$=14.28 Hz, J$_2$=6.59 Hz); 2.675 (dd, 1H, J$_1$=17.2 Hz, J$_2$=6.23 Hz); 2.984 (dd, 1H, $J_1$=17.2 Hz, $J_2$=10.25 Hz); 3.125 (t, 2H, J=6.59 Hz); 3.225 (m, 4H); 3.343–3.558 (m, 2H); 4.214 (m, 1H); 4.768 (m, 1H); 4.973 (s, 2H); 7.145–7.230 (m, 5H). HRMS calcd. for $C_{23}H_{32}N_6O_6$ ([M+H]$^+$): 489.246158; found: 489.247644.

EXAMPLE 16

3-[3-[3-(N-3,4,5,6-Tetrahydropyrimidin-2-yl) aminopropyl]-(5R,S)-isoxazolin-5-yl] methylcarbonylamino-2-phenylsulfonylaminopropionic acid A. N-(4-Hydroxybutyl)phthalimide:

A solution of 4-amino-1-butanol (5.616 g; 63 mmol) and triethylamine (12.3 ml; 88.2 mmol) in 130 ml tetrahydrofuran was treated with N-carbethoxyphthalimide (13.82 g; 63 mmol). The mixture was refluxed for 18 hours. TLC showed the formation of product (1:1 Ethyl acetate:Hexane Rf=0.3). The mixture was diluted with ethyl acetate and washed with water. The aqueous layer was extracted with more ethyl acetate and the organic layers combined, dried (MgSO$_4$), filtered, concentrated and the residue purified by flash chromatography; 200 g silica gel column using 2:3 ethyl acetate:Hexane followed by 1:1 to provide N-(4-hydroxybutyl)phthalimide as a white solid (9.108 g; 65.9% yield). $^1$H NMR (300 MHz, CDCl$_3$): 1.426 (t, 2H, J=4.93 Hz); 1.597–1.663 (m, 2H); 1.738–1.813 (m, 2H); 3.668–3.768 (m, 4H); 7.715 (m, 2H); 7.838 (m, 2H).

B. N-(4-Oxobutyl)phthalimide:

Oxalyl Chloride (4.01 ml; 46 mmol) in 90 ml dichloromethane was cooled at −78° C. in a dry ice-acetone bath. Dimethylsulfoxide (4.26 ml; 60 mmol) in 22 ml dichloromethane was then added dropwise and the mixture stirred at −78° C. for 30 minutes. N-(4-Hydroxybutyl)phthalimide (9.108 g; 41.5 mmol) in 45 ml dichloromethane was then added and the mixture stirred in the −78° C. bath for 45 minutes. The mixture was then warmed in a 0° C. ice bath and stirred for one hour. Triethylamine (23 g; 230 mmol) in 23 ml dichloromethane was then added and the stirred for an additional 30 minutes. The mixture was worked up by washing with water. The organic layer was separated, dried (MgSO$_4$), filtered, concentrated and the residue purified by flash chromatography; 200 g silica gel column using 1:3 ethyl acetate:Hexane to provide N-(4-oxobutyl)phthalimide as a white solid (7.469 g; 82.8% yield). $^1$H NMR (300 MHz, CDCl$_3$): 2.023 (m, 2H); 2.546 (dt, 2H, $J_1$=7.324 Hz, $J_2$=1.098 Hz); 3.749 (t, 2H, J=6.958 Hz); 7.734 (m, 2H); 7.845 (m, 2H); 9.777 (t, 1H, J=1.099 Hz).

C. 4-(N-Phthaloyl)aminobutyraldehyde oxime:

N-(4-oxobutyl)phthalimide (7.46 g; 34.3 mmol) and triethylamine (17.2 g; 172 mmol) in 75 ml ethanol was treated with hydroxylamine hydrochloride (11.95 g; 172 mmol) and stirred at room temperature for 2 hours. TLC indicated no starting material. The solvent was stripped off and the mixture diluted with ethyl acetate and washed with water. The organic layer was dried (MgSO$_4$), filtered, concentrated and the residue dried in vacuo to afford 4-(N-phthaloyl) aminobutyraldehyde oxime (7.469 g; 73.9% yield). A 2:1 mixture of isomers was obtained and the following is data on the major isomer. $^1$H NMR (300 MHz, CDCl$_3$): 1.856–1.956 (m, 2H); 2.409–2.479 (dt, 2H, $J_1$=7.691 Hz, $J_2$=5.493 Hz); 3.713–3.762 (t, 2H, J=7.324 Hz); 6.769 (t, 1H, J=5.493 Hz); 7.720 (m, 2H); 7.836 (m, 2H).

D. tert-Butyl 3-[3-(N-Phthaloyl)aminopropyl]-(5R,S)-isoxazoline-5-yl acetate:

N-Chlorosuccinimide (3.39 g; 25.4 mmol) and 1 drop of pyridine in 50 ml chloroform was treated with 4-(N-phthaloyl)aminobutyraldehyde oxime (5.89 g; 25.4 mmol) in 25 ml chloroform added over a 5 minute period. After the mixture was completely in solution, it was stirred at room temperature for 1.5 hours. NMR was used to monitor the dissappearance of starting material. The mixture was treated with tert-butyl-3-butenoate (5.42 g; 38.1 mmol) followed by triethylamine 2.70 g (26.7 mmol) added dropwise over a 2 hour period. The mixture was stirred at room temperature for 18 hours and worked up by washing with water, drying the organic layer (MgSO$_4$), filtering, and concentrating. The residue was purified by flash chromatography; 200 g silica gel using 1:5 Ethyl acetate:Hexane followed by 1:3 to provide t-Butyl 3-[3-(N-Phthaloyl)aminopropyl]-(5R,S)-isoxazoline-5-yl acetate (7.469 g; 63.7% yield). $^1$H NMR (300 MHz, CDCl$_3$): 1.430 (s, 9H); 1.967 (m, 2H); 2.355–2.476 (m, 3H); 2.624–2.723 (m, 2H); 3.103 (dd, 1H, $J_1$=16.85 Hz, $J_2$=10.25 Hz); 3.730 (t, 2H, J=6.958 Hz); 4.820–4.879 (m, 1H); 7.712 (m, 2H); 7.813 (m, 2H).

E. tert-Butyl 3-(3-aminopropyl)-(5R,S)-isoxazoline-5-yl acetate:

tert-Butyl 3-[3-(N-phthaloyl)aminopropyl]-(5R,S)-isoxazoline-5-yl acetate (6.025 g; 16.2 mmol) in 200 ml ethanol was treated with hydrazine and the mixture stirred at room temperature for 18 hours. A thick white precipitate that had formed was filtered off and washed with more ethanol. The mother liquor was stripped and diluted with chloroform and washed with water. The organic layer was separated, dried (MgSO$_4$), filtered, concentrated and the residue (3.811 g) purified by flash chromatography; 250 g silica gel column using 10% methanol:chloroform to elute impurities and then 1:1 methanol:chloroform to provide t-Butyl 3-(3-aminopropyl)-(5R,S)-isoxazoline-5-yl acetate (1.0 g; 25.5% yield). $^1$H NMR (300 MHz, CDCl$_3$): 1.398 (bs, 2H); 1.457 (s, 9H); 1.727 (m, 2H); 2.379–2.489 (m, 3H); 2.659–2.784 (m, 4H); 3.114 (dd, 1H, $J_1$=17.21 Hz, $J_2$=10.25 Hz); 4.816–4.919 (m, 1H). HRMS calcd. for $C_{12}H_{22}N_2O_3$ ([M+H]$^+$): 243.170868; found: 234.170966.

F. tert-Butyl 3-[3-(N-3,4,5,6-tetrahydropyrimidin-2-yl) aminopropyl]-(5R,S)-isoxazoline-5-ylacetate:

(tert-Butyl 3-(3-aminopropyl)-(5R,S)-isoxazoline-5-yl acetate 990 mg (4.09 mmol) in 15 ml pyridine was treated with 2-Methylthio-3,4,5,6-tetrahydropyrimidine hydroiodide 1.135 g (4.4 mmol) and the mixture stirred at reflux for 22 hours. TLC indicated no starting material. The mixture was stripped and pumped. The residue was purified by flash chromatography; 130 g silica gel column using 2% MeOH:CHCl$_3$ followed by 4% and finally 6% to elute 923 mg of t-Butyl 3-[3-(N-3,4,5,6-tetrahydropyrimidin-2yl) aminopropyl]-(5R,S)-isoxazoline-5-ylacetate (49.9% yield). $^1$H NMR (300 MHz, CDCl$_3$): 1.460 (s, 9H); 1.897–2.001 (m, 4H); 2.435 (t, 2H, J=6.226 Hz); 2.523 (dd, 1H, $J_1$=15.75 Hz, $J_2$=6.59 Hz); 2.662 (dd, 1H, $J_1$=16.11 Hz, $J_2$=6.59 Hz); 2.779 (dd, 1H, $J_1$=17.40 Hz, $J_2$=7.69 Hz); 3.177 (dd, 1H, $J_1$=17.40 Hz, $J_2$=10.25 Hz); 3.299 (dt, 2H); 3.400 (m, 4H); 4.844–4.949 (m, 1H); 7.518 (s, 2H), 7.623 (t, 1H, J=6.23 Hz). HRMS calcd. for $C_{16}H_{28}N_4O_3$ ([M+H]$^+$): 325.223966; found: 325.223355.

G. 3-[3-(N-3,4,5,6-tetrahydropyrimidin-2-yl)aminopropyl]-(5R,S)-isoxazoline-5-ylacetic acid:

tert-Butyl 3-[3-(N-3,4,5,6-tetrahydropyrimidin-2-yl) aminopropyl]-(5R,S)-isoxazoline-5-ylacetate (885 mg; 1.96 mmol) was treated with 1:1 dichloromethane:trifluoroacetic acid (20 ml) and stirred at room temperature for one hour. TLC indicated no starting material. The mixture was stripped and pumped to afford 3-[3-(N-3,4,5,6-tetrahydropyrimidin-2yl)aminopropyl]-(5R,S)-isoxazoline-5-ylacetic acid as a brown solid (777 mg; 100% yield). $^1$H NMR (300 MHz DMSO-d6): 1.694 (m, 2H); 1.804 (m, 2H);

2.302 (t, 2H, J=7.32 Hz); 2.511 (d, 2H, J=6.59 Hz); 2.681 (dd, 1H, $J_1$=17.21 Hz, $J_2$=7.32 Hz); 3.037–3.152 (m, 3H); 3.231 (m, 4H); 4.693–4.794 (m, 1H); 7.456 (t, 1H, J=5.13 Hz); 7.788 (s, 2H). HRMS calcd. for $C_{12}H_{20}N_4O_3$ ([M+H]$^+$): 269.161366; found: 269.161204.

H. Methyl 3-[3-[3-(N-3,4,5,6-tetrahydropyrimidin-2-yl) aminopropyl]-(5R,S)-isoxazoline-5-yl] methylcarbonylamino-2-phenylsulfonylaminopropionate:

A solution of the compound of Ex. 16, part G (199 mg; 0.5 mmol), methyl 3-amino-2-phenylsulfonylaminopropionate (147 mg; 0.5 mmol), and triethylamine (100 mg; 1 mmol) in 3 ml dimethylformamide was treated with 265 mg (0.6 mmol) of benzotriazol-1-yloxy-tris(dimethylamino) phosphonium hexafluorophosphate (BOP Reagent) and the mixture stirred at room temperature for 18 hours. TLC indicated no starting material; the mixture was pumped to remove most of the dimethylformamide. The residue was purified by flash chromatography; 75 g silica gel column using 15% methanol:chloroform to elute the desired product. NMR indicated contamination with triethylamine salt and some form of the BOP Reagent. The compound was then purified on a LH20 size exclusion column using 100% methanol as the eluent. 113 mg of desired product was obtained with slight contamination from triethylamine salts (35.3% yield). This product was taken on to the next step without further purification.

I. 3-[3-[3-(N-3,4,5,6-Tetrahydropyrimidin-2-yl) aminopropyl]-(5R,S)-isoxazoline-5-yl] methylcarbonylamino-2-phenylsulfonylaminopropionic acid:

A mixture of the compound of Ex. 16, Part H (107 mg; 0.168 mmol) and lithium hydroxide (14 mg; 0.6 mmol) in 2 ml of a 1:1 methanol:water was stirred at room temperature for one hour. TLC indicated dissappearance of the starting material. The mixture was diluted with water and washed with hexane. The aqueous layer was neutralized with 1N HCl (0.6 mmol) and then stripped. The residue was purified on a LH20 size exclusion column using 100% methanol as eluent. The product obtained was lyophilyzed from 2 ml 1N HCl followed by 2 ml distilled water. The desired product was obtained as an off-white solid (68 mg; 76.2% yield). $^1$H NMR (300 MHz CDCl$_3$): 1.646–1.797 (m, 4H); 2.244 (m, 3H); 2.322–2.403 (m, 1H); 3.005 (t, 2H, J=6.96 Hz); 3.153–3.196 (m, 6H); 3.318 (d, 1H, J=5.86 Hz); 3.424 (dd, 1H, $J_1$=13.73 Hz, $J_2$=4.39 Hz); 3.835 (m, 1H); 4.693 (m, 1H); 7.303–7.429 (m, 3H); 7.660 (m, 2H). HRMS calcd. for $C_{21}H_{30}N_6O_6S$ ([M+H]$^+$): 495.202580; found: 495.201869.

EXAMPLE 56

2-benzyloxycarbonylamino-3-[[3-[4-[(N-imidazolin-2-yl)amino]butyl]-(5R,S)-isoxazolin-5-yl] carbonylamino]propionic acid A. 5-Phthalimidopentanol:

A mixture of 10.317 g (100 mmol) 5-amino-1-pentanol and 14.812 g (100 mmol) phthalic anhydride in 200 mL toluene was stirred 18 h under nitrogen at reflux while employing a Dean-Stark trap for removal of water. The reaction was allowed to cool to room temperature and solvent was removed. The residue was flash column chromatographed (1;1 hexanes-ethyl acetate) to provide 19.77 g (84.0 mmol, 84%) of a clear liquid; NMR(CDCl$_3$): 7.66–7.88 (m, 4H), 3.59–3.75 (m, 4H), 1.32–1.79 (m, 6H); Mass spectrum: m/z 234 (M+H).

B. 5-Phthalimidopentanal:

A solution of 260 mL methylene chloride and 10.39 mL (108.22 mmol) oxalyl chloride was stirred in a 1000 mL round bottom flask under nitrogen at –78° C. Added over 10 min was 16 mL dimethyl sulfoxide. Next added over 5 min was 23.61 g (101.21 mmol) of the product obtained from Ex. 56, Step A in 60 mL methylene chloride and the mixture stirred for 15 min. Next added was 60 mL (325.0 mmol) triethylamine and the mixture allowed to warm to room temperature. The mixture was poured into water, extracted with three portions of methylene chloride which were combined, dried, filtered and stripped of solvent to provide 21.22 g (91.7 mmol, 90%) of a clear liquid; NMR(CDCl$_3$): 9.76 (t, 1H), 7.68–7.90 (m, 4H), 3.73 (t, 2H), 2.50 (t, 2H), 1.60–1.81 (m, 4H); Mass spectrum: m/z 232 (M+H).

C. 5-phthalimidopentanal oxime:

A mixture of 20.60 g (89.08 mmol) of the product obtained from Ex. 56, Step B, 250 mL pyridine and 12.27 g (2 equivs) of hydroxylamine hydrochloride was stirred 18 hr under nitrogen at room temperature. Solvent was removed and the residue triturated under water. The resulting solid was filtered and suction dried to provide 12.22 g (49.62 mmol, 55%) of a white solid, mp=120°–123° C.; NMR (CDCl$_3$): 7.69–7.90 (m, 4H), 6.70 and 7.40 (two t, 1H), 7.03 (bs, 1H), 1.50–3.77 (m, 8H); Mass spectrum: m/z 247 (M+H).

D. tert-Butyl-3-[4-phthalimidobutyl]-isoxazolin-5-(R,S)-yl)-carboxylate:

A mixture of 3.50 g (14.212 mmol) of the product obtained from Ex. 56, Step C, 100 mL N,N-dimethylformamide and 1.897 g (14.212 mmol) N-chlorosuccinimide were stirred for 3 h at room temperature under nitrogen. Solvent was removed and the residue flash column chromatographed (2:1 hexanes-ethyl acetate) to provide 3.50 g (12.46 mmol, 87%) of a clear liquid; NMR(CDCl$_3$): 8.50 (bs, 1H), 7.69–7.88(m, 4H), 3.70 (m, 2H), 2.58 (m, 2H), 1.70 (m, 4H); Mass spectrum: m/z 262 ((M+H)–H2O). A mixture of 3.50 g (12.46 mmol) of the product thus obtained, 50 mL tetrahydrofuran, 25 mL water, 3.0 g (excess) t-butyl acrylate and 3.0 g (excess) sodium bicarbonate was stirred 48 h at room temperature under nitrogen. The mixture was poured into water and extracted with three portions of ethyl acetate. The combined organic layers were dried over anhydrous magnesium sulfate, filtered and solvent removed. The residue was flash column chromatographed (3:2 hexanes-ethyl acetate) to provide 2.98 g (8.00 mmol, 64%) of a clear liquid; NMR(CDCl$_3$): 7.70–7.86 (m, 4H), 4.83 (m, 1H), 3.72 (t, 2H), 3.15 (m, 2H), 2.42 (t, 2H), 1.60–1.82 (m, 4H), 1.48 (s, 9H); Mass spectrum: m/z 373 (M+H).

E. tert-Butyl-3-[4-[(N-imidazolin-2-yl)amino]butyl]-(5R, S)-isoxazolin-5-ylcarboxylate, hydroiodide:

A mixture of 2.92 g (7.80 mmol) of the product obtained from Ex. 56, Part D, 100 mL absolute ethanol and 0.75 mL (3 ecluivs) hydrazine was stirred for 18 h at room temperature under nitrogen. Water was added until all dissolved. The mixture was extracted with three portions of ethyl acetate. The combined organic layers were dried over anhydrous magnesium sulfate, filtered and solvent was removed. To the residue was added 1.904 g (7.80 mmol) 2-methylthio-4,5-dihydroimidazole hydroiodide and 100 mL pyridine. The mixture was set at reflux under nitrogen for 18 h. The mixture was allowed to cool to room temperature and the residue flash column chromatographed (1:4 methanol-chloroform) to provide 0.48 g (1.95 mmol, 25 %) of a gum; NMR(CDCl$_3$): 7.90 (bs, 1H), 7.33 (bs, 1H), 4.90 (m, 1H), 1.63–3.80 (m, 14H), 1.47 (s, 9H); Mass spectrum: m/z 311 (free base+H).

F. 3-[4-[(N-imidazolin-2-yl)amino]butyl]-(5R,S)-isoxazolin-5-ylcarboxylic acid, trifluoracetate:

A mixture of 480 mg (1.95 mmol) of the product obtained from Ex. 56, Part E, 15 mL methylene chloride and 1.0 mL (excess) trifluoroacetic acid was stirred for 18 h at room temperature under nitrogen. Solvent was removed and toluene was added. Solvent was removed to provide 240 mg (0.629 mmol, 32 %) of a gum; NMR($d_6$-DMSO): 8.27 (m, 1H), 7.20 (m, 1H), 4.90 (m, 1H), 1.40–3.70 (m, 14H); Mass spectrum: m/z 255 (M+H).

G. tert-Butyl 2-benzyloxycarbonylamino-3-[3-[4-[(N-imidazolin-2-yl)amino]butyl]-(5R,S)-isoxazolin-5-yl]carbonylaminopropionate:

A mixture of 230 mg (0.603 mmol) of the product obtained from Ex. 56, Part F, 217.8 mg (0.740 mmol) (R)-t-butyl-3-amino-2-benzyloxycarbonylaminopropionate, 180 mg (0.930 mmol) of 1-ethyl-3-(3-dimethylaminopropyl)carbodiimide and 26 mg (catalytic) 1-hydroxybenzotriazole hydrate was stirred at room temperature under nitrogen. Added was 10 mL N,N-dimethylformamide followed by 170 mg (1.67 mmol) triethylamine and the mixture stirred 18 h at room temperature under nitrogen. Solvent was removed and the residue flash column chromatographed (1:4 methanol/chloroform) to provide 217 mg (0.329 mmol, 54%) of a gum; NMR(CDCl$_3$/TMS): 8.36 (bs, 1H), 7.68 (bs, 1H), 7.58 (bs, 1H), 7.34 (s, 5H), 6.01 (t, 1H), 5.10 (s, 2H), 4.87 (m, 1H), 1.50–4.38 (m, 17H), 1.41 (s, 9H); Mass spectrum: m/z 531 (free base+H).

H. 2-benzyloxycarbonylamino-3-[3-[4-[(N-imidazolin-2-yl)amino]butyl]-(5R,S)-isoxazolin-5-yl]carbonylaminopropionic acid, trifluoroacetate:

A mixture of 217 mg (0.329 mmol) of the product obtained from Ex. 56, Step H, 50 mL methylene chloride and 50 mL of 0.2M NaOH was placed in a separatory funnel, shaken, and the layers separated. The organic layer was washed two more times with 50 mL portions of 0.2M NaOH. The organic layer was dried over anhydrous magnesium sulfate, filtered and solvent was removed. To the residue was added 10 mL methylene chloride and 0.5 mL (excess) trifluoroacetic acid and the mixture stirred 18 h at room temperature under nitrogen. Solvent was removed and toluene was added. Solvent was removed and the residue triturated under hexanes. The resulting solid was filtered to dryness to provide 127 mg (0.215 mmol, 65%) of the title compound as an off-white solid, mp=100°–6° C.; NMR($d_6$-DMSO): 7.21–8.35 (m, 10H), 1.50–5.12 (m, 20H); Mass spectrum: m/z 475 (M+H).

EXAMPLE 83

2(S)-Benzyloxycarbonylamino-3-[3-(4-(N-[3,4,5,6-tetrahydropyrimidin-2-yl]amino)butyl)isoxazolin-5-(R,S)-ylcarbonyl]aminopropionic acid The title compound was prepared in an analogous manner to the compound of Example 56 by substitution of 2-methylthio-3,4,5,6-tetrahydropyrimidine hydroiodide for 2-methylthio-4,5-dihydroimidazole hydroiodide in Ex. 56, Part E. mp 101°–108° C.

EXAMPLE 110

2(S)-Benzyloxycarbonylamino-3-[3-(3-(N-[3,4,5,6-tetrahydropyrimidin-2-yl]amino)propyl)isoxazolin-5-(R,S)-ylcarbonyl]aminopropionic acid A. 4-Phthalimidobutyraldehyde oxime:

A solution of 4-phthalimidobutyraldehyde (R. Hamilton et al., Tetrahedron Letters, 1993, 34, 2847) (17.38 g, 80 mmol) in pyridine (150 mL) was treated with hydroxylamine hydrochloride (6.67 g, 96 mmol) and stirred at room temperature for 17 h. After concentration, the residue was triturated in water, stirred for 3 h, and filtered to provide the title product as a light tan solid (14.15 g, 76%): NMR (CDCl$_3$) δ 8.06 (b, 1H), 7.85 (m, 2H), 7.70 (m, 2H), 7.46 (t, 0.15H), 6.76 (t, 0.85H), 3.73 (t, 2H), 2.44 (m, 1.7H), 2.28 (m, 0.3H), 1.90 (m, 2H); mass spec (NH$_3$-CI) m/z 233 (M+H$^+$, 100%).

B. tert-Butyl 3-(3-[3-phthalimidopropyl]-isoxazolin-5-(R,S)-yl)-carboxylate:

A mixture of the product of Ex. 110, Part A (2.10 g, 9.05 mmol), N-chlorosuccinimide (1.21 g, 9.05 mmol), pyridine (2 drops), t-butyl acrylate (2.7 mL, 18.10 mmol), and triethylamine (1.5 mL, 10.86 mmol) in 30 mL chloroform was reacted according to the procedure of Ex. 284, Part D to provide the title product (2.40 g, 74%): NMR (CDCl$_3$) δ 7.84 (m, 2H), 7.78 (m, 2H), 4.82 (m, 1H), 3.78 (t, 2H), 3.20 (m, 2H), 2.41 (t, 2H), 2.02 (m, 2H), 1.44 (S, 9H); mass spec (NH$_3$-CI) m/z 376 (M+NH$_4^+$, 100%).

C. 3-(3-[3-phthalimidopropyl]isoxazolin-5-(R,S)-yl)-carboxylic acid:

The product of Ex. 110 step B (500 mg, 1.40 mmol) was reacted with trifluoroacetic acid (5 mL) in 10 mL methylene chloride according to the procedure of Ex. 284, Part E to provide 420 mg (100%) of the title product as a foamy solid: NMR (DMSO-d$_6$) δ 7.81 (m, 2H), 7.78 (m, 2H), 5.40 (b, 1H), 5.02 (m, 1H), 3.79 (t, 2H), 3.30 (m, 2H), 2.42 (t, 2H), 2.00 (q, 2H).

D. tert-Butyl N$^2$-benzyloxycarbonyl-N$^3$-[3-[3-(3-phthalimidopropyl)isoxazolin-5-(R,S)-yl]carbonyl]-2-(S)-2,3-diaminopropionate:

The product of Ex. 110, Part C (420 mg, 1.40 mmol) was reacted with t-butyl N$^2$-benzyloxycarbonyl-2-(S)-2,3-diaminopropionate (412 mg, 1.40 mmol), O-(1H-benzotriazol-1-yl)-N,N,N',N'-tetramethyluronium tetrafluoroborate (450 mg, 1.40 mmol), triethylamine (0.6 mL, 4.20 mmol) in 25 mL ethyl acetate according to the procedure of Ex. 284, Part F to provide 595 mg (66%) of the title product: NMR (CDCl$_3$) δ 7.81 (m, 2H), 7.70 (m, 2H), 7.34 (s, 5H), 7.04 (b, 1H), 5.06 (s, 2H), 4.90 (m, 1H), 4.38 (m, 1H), 3.70 (m, 4H), 3.20 (m, 3H), 2.39 (bt, 2H), 1.98 (m, 2H), 1.40 (s, 9H); mass spec (ESI) m/z 579.4 (M+H$^+$, 100%).

E. tert-Butyl N$^2$-benzyloxycarbonyl-N$^3$-[3-[3-(3-aminopropyl)isoxazolin-5-(R,S)-yl]carbonyl]-2-(S)-2,3-diaminopropionate:

The product of Ex. 110 step D (550 mg, 0.99 mmol) was reacted with hydrazine (0.1 mL, 2.50 mmol) in 5 mL ethanol according to the procedure of Ex. 284 Part G to provide 223 mg (50%) of the title product: NMR (CDCl$_3$) δ 7.38 (m, 5H), 7.04 (b, 1H), 5.80 (dd, 1H), 5.10 (s, 2H), 4.90 (m, 1H), 4.38 (m, 1H), 3.64 (m,2H), 3.40–3.12 (m, 2H), 2.76 (m ,2H), 2.40 (m,2H), 1.72 (m, 2H), 1.50 (s, 9H), 1.46 (b, 2H); mass spec (ESI) m/z 449.5 (M+H$^+$, 100%).

F. tert-Butyl N$^2$-benzyloxycarbonyl-N$^3$-[3-(3-(N-[3,4,5,6-tetrahydropyrimidine-2-yl]amino)propyl)isoxazolin-5-(R,S)-ylcarbonyl]-(S)-2,3-diaminopropionate:

The product of Ex. 110, step E (124 mg, 0.276 mmol) was reacted with 2-methylthio-3,4,5,6-tetrahydropyrimidine hydroiodide (86.0 mg, 0.332 mmol) in 2 mL pyridine according to the procedure of Ex. 284 Part H to provide 30 mg (25%) of the title product: NMR (CDCl$_3$) δ 7.80 (b, 1H), 7.38 (m, 5H), 7.18 (b, 2H), 5.82–5.78 (2b, 1H), 5.10 (s,2H), 4.90 (m, 1H), 4.38 (b, 2H), 3.80 (b, 2H), 3.58–3.10 (m, 9H), 2.42 (b, 2H), 1.95 (b, 2H), 1.42 (s,9H); mass spec (ESI) m/z 531.4 (M+H$^+$, 100%).

G. N2-benzyloxycarbonyl-N³-[3-(3-(N-[3,4,5,6-tetrahydropyrimidine-2-yl]amino)propyl)-isoxazolin-5-(R,S)-ylcarbonyl]-(S)-2,3-diaminopropionic acid:

The product of part F (30 mg, 0.051 mmol) was dissolved in methylene chloride (5 mL) and treated with 0.2 mL trifluoroacetic acid according to the procedure of Ex. 284, Part I, to provide the title product (25 mg, 90%) as a glassy foam: NMR (DMSO-d$_6$) δ 8.36 (s, 1H), 8.20 (m, 1H), 7.60 (m, 2H), 7.38 (bs, 5H), 7.28 (m, 1H), 5.08 (s, 2H), 4.88 (m, 1H), 4.36 (b, 2H), 3.76 (b, 2H), 3.48–3.08 (9H), 2.30 (b,2H), 1.82 (b, 2H); mass spec (ESI) m/z 475.3 (M+H$^+$, 100%).

EXAMPLE 284

2(S)-benzyloxycarbonylamino-3-[2-[3-(2-(N-imidazolin-2-yl)-aminoethyl)isoxazolin-5-(R,S)-yl]ethylcarbonylamino]propionic acid A. 2-(2-Pthalimidoethyl)-1,3-dioxolane:

To a solution of potassium pthalimide (15.20 g, 82.0 mmol) dissolved in 150 mL dimethylformamide was added 2-(2-Bromoethyl)-1,3-dioxolane (14.86 g, 82.0 mmol). After stirring at room temperature for 22 h, the mixture was diluted with excess water and stirred. The resulting white precipitate was collected and dried (17.0 g, 84%): NMR (CDCl$_3$) δ 7.84 (m, 2H), 7.72 (m, 2H), 4.98 (t, 1H), 3.99 (m, 2H), 3.86 (m, 4H), 2.10 (m, 2H); mass spec (NH$_3$-CI) m/z 248.1 (M+H$^+$, 100%).

B. 3-Phthalimidopropionaldehyde:

The product of Ex. 284, part A (17.0 g, 69.0 mmol) was dissolved in dioxane (150 mL) and treated with 1:1 1N HCl/water (200 mL). After stirring at room temperature overnight, the mixture was heated to reflux for 3 h. The reaction was concentrated, neutralized with aqueous NaHCO$_3$, extracted into chloroform, and dried (Na$_2$SO$_4$). Concentration of the solvent provided the title product (14.0 g, 100%): NMR (CDCl$_3$) δ 7.82 (m, 2H), 7.78 (m, 2H), 4.02 (t, 2H), 2.88 (t, 2H).

C. 3-Phthalimidopropionaldehyde oxime:

The product of Ex. 284, part B (14.0 g, 69.0 mmol) was reacted with hydroxylamine hydrochloride (5.80 g, 83.0 mmol) in pyridine (200 mL). After stirring overnight, the pyridine was evaporated and the resultant mixture diluted with water. The precipitate was collected and dried providing the title product as a white solid (8.00 g, 53%): NMR (CDCl$_3$) δ 7.82 (m, 2H), 7.76 (m, 2H), 6.82 (t, 1H), 3.90 (m 4H).

D. tert-Butyl 3-(3-[2-phthalimidoethyl]-isoxazolin-5-(R,S)-yl)-propionate:

The product of Ex. 284, part C (2.69 g, 12.35 mmol) was combined with N-chlorosuccinimide (1.65 g, 12.35 mmol) and pyridine (2 drops) in chloroform (30 mL). After stirring at room temperature for 1 h, t-butyl pentenoate (3.86 g, 24.7 mmol) and triethylamine (2.1 mL, 14.82 mmol) were added and stirring continued at room temperature. After 18 h, the resulting mixture was concentrated and flash chromatographed (7:3 hexane/ethyl acetate) to provide 2.50 g (54%) of the title product: NMR (CDCl$_3$) δ 7.82 (m, 2H), 7.78 (m, 2H), 4.60 (m, 1H), 3.96 (t, 2H), 3.18 (dd,1H) 2.72 (m, 3H), 2.38 (dt, 2H), 1.84 (q, 2H), 1.42 (s, 9H); mass spec (NH$_3$-CI) m/z 373.3 (M+H$^+$, 100%).

E. 3-(3-[2-Phthalimidoethyl]-isoxazolin-5-(R,S)-yl) propionic acid:

The product of Ex. 284, part D (500 mg, 1.34 mmol) was dissolved in 10 mL of methylene chloride and 5 mL trifluoroacetic acid. After 4 h the solution was concentrated to provide the title product as a foamy solid (420 mg, 100%): NMR (DMSO-d$_6$) δ 7.82 (m,2H), 7.76 (m, 2H), 4.62 (m, 1H), 3.96 (t, 2H), 3.20 (m, 1H), 2.78 (m, 3H), 2.56 (m, 2H), 1.96 (q, 2H).

F. tert-Butyl 2(S)-benzyloxycarbonylamino-3-[2-[3-(2-phthalimidoethyl)isoxazolin-5-(R,S)-yl]ethylcarbonylamino]-propionate:

The product of Ex. 284, part E (420 mg, 1.33 mmol) was combined with t-butyl N²-benzyloxycarbonyl-2-(S)-2,3-diaminopropionate (M. Mokotoff and L. Logue, J. Med. Chem., 1981, 24, 554) (390 mg, 1.33 mmol), O-(1H-benzotriazol-1-yl)-N,N,N',N'-tetramethyluronium tetrafluoroborate (430 mg, 1.33 mmol), and triethylamine (0.6 mL, 4.00 mmol) in 25 mL of ethyl acetate. After stirring at room temperature for 20 h, the reaction was concentrated and flash chromatographed (ethyl acetate) to provide 647 mg (86%) of the title product: NMR (CDCl$_3$) δ 7.82 (m, 2H), 7.72 (m, 2H), 7.36 (bs, 5H), 6.06 (b,1H), 5.80 (b, 1H), 5.08 (bd, 2H), 4.60 (b, 1H), 4.37 (b, 1H), 3.97 (bt, 1H), 3.62 (m, 1H), 3.07 (m, 1H), 2.70 (b, 3H), 2.24 (b, 1H), 1.97 (m, 1H), 1.44 (s, 9H); mass spec (ESI) m/z 593.4 (M+H$^+$, 100%).

G. tert-Butyl 2(S)-benzyloxycarbonylamino-3-[2-[3-(2-aminoethyl)isoxazolin-5-(R,S)-yl]ethylcarbonylamino] propionate:

The product of Ex. 284, part F (450 mg, 0.76 mmol) was treated with hydrazine (0.1 mL, 1.90 mmol) in 7 mL of ethanol and stirred at room temperature overnight. The mixture was concentrated and taken up in water, the pH was adjusted to 11 and the resultant extracted with methylene chloride. The organic layer was dried (Na$_2$SO$_4$), filtered, and concentrated providing 250 mg (71%) of the title product as a gummy solid: NMR (CDCl$_3$) δ 7.40 (m,5H), 6.20 (b, 1H), 5.85 (b, 1H), 5.10 (s, 2H), 4.60 (b, 1H), 4.30 (b, 1H), 3.60 (bt, 2H), 3.00–2.96 (m, 3H), 2.60 (2dd, 1H), 2.42 (b, 2H), 2.30 (b, 2H), 2.00–1.80 (m, 2H), 1.58 (bs, 2H), 1.42 (s, 9H); mass spec (ESI) m/z 463.3 (M+H$^+$, 100%).

H. tert-Butyl 2(S)-benzyloxycarbonylamino-3-[2-[3-(2-(N-imidazolin-2-ylamino)ethyl)isoxazolin-5-(R,S)-yl] ethylcarbonylamino]propionate:

The product of Ex. 284, part G (132 mg, 0.290 mmol) was reacted with 2-methylthio-2-imidazoline hydroiodide (84 mg, 0.342 mmol) in 5 mL pyridine over an oil bath heated at 120 C.°. After 18 h the mixture was cooled and concentrated providing the title product (102 mg, 66%): NMR (CDCl$_3$) δ 8.08 (b, 1H), 7.60 (b, 1H), 7.39 (bs, 5H), 7.20 (b, 1H), 6.18 (b, 1H), 5.82 (b 1H), 5.10 (s, 2H), 4.62 (b, 1H), 4.30 (b, 1H), 3.61 (bs, 2H), 3.58 (m, 2H), 3.02–2.94 (m, 3H), 2.60 (m, 1H), 2.40 (b, 2H), 2.30 (b, 2H), 1.94 (m, 2H), 1.40 (s, 9H); mass spec (ESI) m/z 531.5 (M+H$^+$, 100%).

I. 2(S)-benzyloxycarbonylamino-3-[2-[3-(2-(N-imidazolin-2-yl)-aminoethyl)isoxazolin-5-(R,S)-yl] ethylcarbonylamino]propionic acid The product of Ex. 284, part H (100 mg, 0.188 mmol) was dissolved in 2 mL of methylene chloride and 0.2 mL trifluoroacetic acid. After 5 h, the solution was concentrated and triturated with ether to provide 70.0 mg (64%) of the title product: NMR (DMSO-d$_6$) δ 8.20 (m, 1H), 8.04 (m, 1H), 7.53 (bd, 1H), 7.40 (bs, 5H), 5.04 (s, 2H), 4.42 (m,1H), 4.08 (m, 1H), 3.52–3.20 (m, 10H), 3.02 (m, 2H), 2.60 (m, 1H), 2.12 (m, 2H), 1.70 (m, 2H); mass spec (ESI) m/z 475.3 (M+H$^+$, 100%).

General Procedure for synthesis of 1-(9-fluorenylmethoxycarbonylamino)alkenes

A. 1-(p-Toluensulfonyloxy)-3-butene:

3-Butene -1-ol (10.5 g, 0.146 mol) was dissolved in 75 mL of pyridine and cooled in an ice bath. p-Toluenesulfonyl chloride (28.5 g, 0.150 mol) was added slowly. The solution was stirred for 8 h in an ice bath then allowed to stir at room temperature overnight. The solution was poured into saturated NaHCO$_3$ and ice. After the ice melted the mixture was extracted with dichloromethane and the organic layer evaporated to provide the title compound (28.6 g, 86%). ¹H NMR (CDCl₃): δ 2.32–2.44 (m, 2H), 2.45 (s, 3H), 4.05 (t, J=10 Hz, 2H), 5.02–5.12 (m, 2H), 5.60–5.74 (m, 1H), 7.35 (d, J=8 Hz, 2H), 7.78 (d, J=8 Hz, 2H). mass spectrum m/z 311 (M+NH₄, base peak), 294 (M+H).

B. 1-amino-3-butene:

The product of Ex. 637, part A (28.6 g, 0.126 mol) was dissolved in 25 mL of dimethylformamide. Sodium azide (23.5 g, 0.354 mol) was added in several portions and the reaction mixture allowed to stir at room temperature overnight. The reaction mixture was poured into 100 mL of water and 200 mL of diethyl ether and the layers separated. The organic layer was washed with 100 mL of water and 100 mL of brine and dried over magnesium sulfate. The crude azide solution was reacted without further purification. Triphenylphosphine (34.0 g, 0.129 mol) was added and the reaction mixture stirred for 6 h at room temperature. 2.3 mL of water was added to the reaction and the solution was stirred overnight. The diethyl ether layer was distilled and 4.62 g (52%) of the title compound was obtained. ¹H NMR (CDCl₃): δ 1.60 (br s, 2H), 2.20 (q, J=9 Hz, 2H), 2.78 (t, J=9 Hz, 2H), 5.05–5.15 (m, 2H), 5.70–5.84 (m, 1H).

C. 1-(9-Fluorenylmethoxycarbonylamino)-3-butene:

The product of Ex. 637, part B (5.11 g, 65 mmol) was dissolved in 50 mL of tetrahydrofuran and 50 mL of 10% NaHCO₃ and cooled in an ice bath. 9-Fluorenylmethoxycarbonyl chloride (16.8 9, 65 mmol) was added in several portions, after 4 h the ice bath was removed and the reaction mixture allowed to stir at room temperature overnight. The reaction mixture was poured into 200 ml of water and extracted with diethyl ether. The combined organic layers were evaporated to leave a white solid which was purified by flash column chromatography (hexane:ethyl acetate 3:1) to yield 5.4 g (28%) of the desired product. ¹H NMR (CDCl₃) δ 2.22–2.36 (m, 2H), 3.22–3.34 (m, 2H), 4.24 (t, J=8 Hz, 1H), 4.40 (d, J=8 Hz, 1H), 4.60 (br s, 1H), 5.06–5.16 (m, 2H), 5.72–5.84 (m, 1H), 7.26–7.44 (m, 4H), 7.58 (d, J=9 Hz, 2H), 7.78 (d, J=9 Hz, 2H). Mass spectrum: m/z 311 (M+NH₄, base peak), 294, (M+H), HRMS Calcd 294.1494 observed 294.1505.

EXAMPLE 583

2(S)-Benzyloxycarbonylamino-3-[5-(4-(N-[imidazolin-2-yl]amino)butyl)isoxazolin-3-(R,S)-ylcarbonyl]aminopropionic acid:

A. 1-(9-Fluorenylmethoxycarbonylamino)-5-hexene

The title alkene was prepared in 36% yield according to the method described in the above general procedure, except starting with 5-hexene-1-ol. ¹H NMR (CDCl₃) δ 1.34–1.58 (m, 4H), 2.02–2.14 (m, 2H), 3.12–3.24 (m, 2H), 4.20 (t, J=8 Hz, 1H), 4.40 (d, J=8 Hz, 2H), 4.72 (s, 1H), 4.90–5.04 (m, 2H), 5.70–5.84 (m, 1H), 7.26–7.42 (m, 4H), 7.58 (d, J=9 Hz, 2H), 7.76 (d, J=9 Hz, 2H).

B. 3-Methoxycarbonyl-5-[(9-fluorenylmethoxycarbonylamino)butyl]-Δ²-isoxazoline:

1-(9-Fluorenylmethoxycarbonylamino)-5-hexene (2.00 g, 6.22 mmol) and phenylisocyanate (3.70 g, 31.11 mmol) was dissolved in 40 mL of benzene. Thirty drops of diisopropylethylamine was added followed by methyl nitroacetate (1.48 g, 12.44 mmol) and stirred at room temperature for 48 h. The reaction mixture was filtered and the filtrate evaporated. The residue was purified by flash column chromatography (hexane:ethyl acetate 3:1 to 1:1) to yield 1.83 g (70%) of a tan solid. ¹H NMR (CDCl₃) δ 1.32–1.84 (m, 6H), 2.78–2.90 (m, 1H), 3.12–3.34 (m, 3H), 3.86 (s, 3H), 4.20 (t, J=7 Hz, 1H), 4.40 (d, J=7 Hz, 2H), 4.72–4.86 (m, 2H), 7.26–7.42 (m, 4H), 7.58 (d, J=9 Hz, 2H), 7.80 (d, J=9 Hz, 2H). mass spectrum m/z 440 (M+NH₄), 423 (M+H), 244 (base peak).

C. 3-Carboxy-5-[(9-fluorenylmethoxycarbonylamino)butyl]-Δ²-isoxazoline:

The product of Ex. 583, Part B (1.83 g, 4.33 mmol) was dissolved in 50 mL Of tetrahydrofuran and 25 mL of water and cooled in an ice bath. Lithium hydroxide (174 mg, 4.15 mmol) was dissolved in 2 mL of water and added to the tetrahydrofuran/water solution. After approximately 10 min the reaction mixture was quenched with 10% HCl, to pH=3. The mixture was extracted with diethyl ether, dried over magnesium sulfate and evaporated to a syrup. Trituration with benzene:pentane 3:1 and filtration afforded a yellow solid which was recrystalized from benzene chloroform 5:1 to yield 1.18 g (67%) of the title compound as a white powder. ¹H NMR (CDCl₃) δ 1.34–1.82 (m, 6H), 2.80–2.98 (m, 1H), 3.10–3.32 (m, 3H), 4.16–4.30 (m, 1H), 4.40–4.52 (m, 2H), 4.80–4.90 (m, 2H), 6.50 (br s, 1H), 7.26–7.42 (m, 4H), 7.58 (d, J=9 Hz, 2H), 7.76 (d, J=9 Hz, 2H). Mass spectrum m/z 426 (M+NH₄) 382 (M+NH₄—CO₂, base peak) HRMS calcd 409.1763 observed 409.1748.

D. 3-tert-Butyloxycarbonyl-5-[4-(9-fluorenylmethoxycarbonylamino)butyl]-Δ²-isoxazoline The compound of Ex. 583, Part C (715 mg, 1.75 mmol) was dissolved in 2 mL of dichloromethane and cooled in an ice bath. 2 mL of Ca. 3.5M solution of N,N'-diisopropyl-O-t-butyl isourea was added and the reaction mixture stirred for 8 h, and the ice bath removed, and stirred overnight at room temperature. The reaction mixture was cooled in an ice bath and 2 mL of glacial acetic acid was added dropwise, during which time vigorous gas evolution occured. The reaction mixture was diluted with ice water and cautiously neutralized with saturated Na₂CO₃, and extracted three times with ethyl acetate. The organic layer was dried over MgSO₄, filtered and evaporated. The residue was taken up in 20 mL of 1:1 dichloromethane/ethyl acetate and filtered. the filtrate was evaporated and purified by flash column chromatography, CH₂Cl₂:hexane:ethyl acetate, 2:2:1 to yield 375 mg (46%) of the title compound. ¹H NMR (CDCl₃) δ 1.35–1.78 (m, 15H), 2.80, (dd, J=16, 8 Hz, 1H), 3.15–3.30 (m, 3H), 4.22 (t, J=7 Hz, 1H), 4.40 (d, J=7 Hz, 2H), 4.70–4.80 (m, 2H), 7.28–7.44 (m, 4H), 7.60 (d, J=9 Hz, 2H), 7.78 (d, J=9 Hz, 2H). Mass spectrum m/z 482, (M+NH4), 465, (M+).

E. 3-tert-Butyloxycarbonyl-5-(4-aminobutyl)-Δ²-isoxazoline

The compound of Ex. 583, Part D (375 mg, 0.81 mmol) was dissolved in 20 mL of dichloromethane, 0.5 mL of piperidine was added and the reaction mixture stirred overnight at room temperature. The solvent was evaporated and the residue purified by flash column chromatography CH₂Cl₂:isopropanol 2% to CH₂Cl₂:isopropanol 2%:triethylamine:0.5% to yield 163 mg (83%) of the title compound. ¹H NMR (CDCl₃) δ 1.35–1.80 (m, 15 H), 2.40 (br s, 2H), 2.70–2.86 (m, 3H), 3.22 (dd, J=16, 8 Hz, 1H), 4.80 (m, 1H). Mass spectrum m/z 243 (M+H, base peak).

F. 3-tert-Butyloxycarbonyl-5-[4-(imidazolin-2-ylamino)butyl]-Δ²-isoxazoline hydroiodide The compound of Ex. 583, Part E (163 mg, 0.67 mmol) and 2-methylthioimidazoline (180 mg, 0.73 mmol) was dissolved in pyridine and gently refluxed overnight. The solvent was evaporated and the residue purified by preparatory TLC, chloroform, 20% methanol, to yield 100 mg (33%) of the title compound. ¹H NMR (CDCl₃) δ 1.35–1.80 (m, 15H), 2.84 (dd, J=16 Hz, 8 Hz, 1H), 3.20–3.32 (m, 3H), 2.56 (br s, 3H), 3.74 (s, 4H), 4.82 (m, 1H).

Mass spectrum m/z 311 (M (–HI)+H).

G. tert-Butyl-2-benzyloxycarbonylamino-3-[5-[4-[(N-imidazolin-2-yl)amino]butyl-5(R,S)-isoxazolin-3-yl]carbonylamino]propionate:

The compound of Ex. 583, Part F (100 mg, 0.23 mmol) was suspended in 2 mL of dichloromethane and 2 mL of trifluoroacetic acid was added. The reaction mixture was stirred for 1 h. at room temperature and the solvent evaporated to give the brown oil to which was dissolved in 1 mL of DMF. t-Butyl 3-amino-2-S-(benzyloxycarbonylamino)propionate (67 mg, 0.23 mmol) was added followed by benzotriazol-1-yloxytris(dimethylamino)phosphonium hexafluorophosphate (110 mg, 0.24 mmol) and diiosopropylethyl amine (65 mg, 0.50 mmol) and stirred at room temperature overnight. The solvent was evaporated under reduced pressure and the residue purified by preparatory TLC, chloroform, 20% methanol to yield 42 mg, (28%) of the title compound. $^1$H NMR (CDCl$_3$) δ1.35–1.80 (m, 15H), 2.80–3.20 (m, 4H), 3.70 (s, 4H), 4.24 (t, J=5 Hz, 1H), 4.36 (t, J=5 Hz, 1H), 4.78 (m, 1H), 5.10 (s, 2H), 7.35 (s, 5H).

H. 2(S)-benzyloxycarbonylamino-3-[5-(4-(N-[imidazolin-2-yl]amino)butyl) isoxazolin-3-(R,S)-ylcarbonyl] aminopropionic acid:

The product from Ex. 583, Part G was suspended in 2 ml of dichloromethane and 1 mL of trifluoroacetic acid was added. the reaction mixture was stired at room temperature for 1 h. The solvent was evaporated and the residue triturated with diethyl ether to provide the title compound. $^1$H NMR (CDCl$_3$) δ1.32–1.76 (m, 6H), 2.80–2.90 (m, 1H), 3.16–3.80 (m, 6H), 4.40–4.52 (m, 2H), 4.70–4.82 (m, 1H), 5.04–5.16 (m, 1H), 7.24–7.42 (m, 5H). mass spectrum m/z 475.4

EXAMPLE 637

2(S)-Benzyloxycarbonylamino-3-[5-(3-(N-[imidazolin-2-yl]amino)propyl)isoxazolin-3-(R,S)-ylcarbonyl]aminopropionic acid A. 1-(9-Fluorenylmethoxycarbonylamino)-4-pentene:

The title alkene was prepared in 49% yield according to the methods described in the above general procedure, except starting with 4-pentene-1-ol. $^1$H NMR(CDCl$_3$) δ 1.58–1.70 (m, 2H), 2.02–2.16 (m, 2H), 4.22 (t, J=8 Hz, 1H), 4.42 (d, 8 Hz, 2H), 4.75 (br s, 1H), 4.94–5.08 (m, 2H), 5.72–5.84 (m, 1H), 7.26–7.42 (m, 4H), 7.58 (d, J=9 Hz, 2H), 7.78 (d, J=9 Hz, 2H). Mass spectrum m/z 325 (M=NH$_4$, base peak) 308, (M+H). HRMS calcd 308.1650, observed 308.1650.

B. 3-Carboxy-5-[(9-fluorenylmethoxycarbonylamino) propyl]-Δ$^2$-isoxazoline:

The title compound was prepared according to Ex. 583, Part B–C in 58% overall yield starting with 1-(9-Fluorenylmethoxy-carbonylamino)-4-pentene and methyl nitroacetate. $^1$H NMR (DMSO) δ 1.30–1.62 (m, 4H), 2.78 (dd J=16, 8 Hz, 1H), 2.98 (d, J=7 Hz, 2H), 3.20 (dd, J=16, 8 Hz, 1H), 4.20 (t, J=7 Hz, 1H), 4.30 (d, J=7 Hz, 2H), 4.68–4.80 (m, 1H, 7.26–7.44, m, 4H), 7.64 (d, J=9 Hz, 2H), 7.84 (d, J=9 Hz, 2H). 13.40 (br s, 1H).

Mass spectrum m/z 395 (M+H), HRMS calcd 395.1606 observed 395. 1591.

EXAMPLE 667

2-(S)-Benzyloxycarbonylamino-3-[5-(R,S)-(4-(N-(pyridin-2-yl)amino)butyl)isoxazolin-3-ylcarbonyl] aminopropionic acid hydrochloride salt A. 3-Ethoxycarbonyl-5-[-4-(hydroxy)butyl]isoxazoline:

5-Hexene-1-ol (5.0 g, 0.05M) was dissolved in 30 mL of tetrahydrofuran, an aqueous solution of NaHCO$_3$ (29.4 g, 0.35M in 20 mL water) was added and the reaction mixture cooled in an ice bath. Ethyl chlorooximinoacetate (11.4 g, 0.075M) was added over 15 min. in several portions. The reaction mixture was stirred in an ice bath for 6 h. An additional amount of ethyl chlorooximinoacetate (7.75 g, 0.05M) was added and the reaction mixture was allowed to stir overnight, during which time the ice bath melted. The reaction mixture was partitioned between ethyl acetate and water and the organic layer was separated, dried over magnesium sulfate, filtered and evaporated. The crude product was purified by flash column chromatography (hexane/ethyl acetate 3:1) to yield the title compound as a colorless oil (9.22 g, 86%). $^1$H NMR (CDCl$_3$): δ 1.3 (t, J=7 Hz, 3H), 1.40–1.90 (m, 6H) 2.80–2.94 (m, 1H, 3.20–3.54, m, 1H), 3.66 (br s, 2H, 4.34, q, J=7 Hz, 2H), 4.78–4.90 (m, 1H). mass spectrum m/z 233, (M+NH$_4$, base peak), 216, (M+) Alternatively the title compound can be prepared by the following procedure.

5-Hexene-1-ol (5 g, 0.05M) and diethyl nitromalonate (15.4 g, 0.075M) was dissolved in mesitylene (50 mL) and refluxed for 5 h. The solvent was removed in vacuo, and the residue purified by flash column chromatography on silica gel (hexane/ethyl acetate 1:1) to provide the title product (5.11 g, 47.5%).

B. 3-Ethoxycarbonyl-5-[-4-oxobutyl]isoxazoline:

Oxalyl chloride (7.30 g, 0.0575M) was dissolved in anhydrous methylene chloride and cooled to –60° C. in a dry-ice/CHCl$_3$ bath. Dimethylsulfoxide (9.38 g, 0.12M) was dissolved in anhydrous methylene chloride and added dropwise over 30 min. to the solution of oxalyl chloride, and allowed to stir for an additional 30 min. The product of Ex. 667, part A. (10.75 g, 0.05M) was dissolved in anhydrous methylene chloride (30 mL) and added to the reaction mixture dropwise over 45 min, and allowed to stirred for an additional 30 min. Triethylamine (25.25 g, 0.25M) was added dropwise over 15 min. The ice bath was removed and the reaction mixture allowed to warm to room temperature. The reaction mixture was diluted with methylene chloride (100 mL) and washed with water, 1N HCl, water, and brine. The organic layer was separated and dried over magnesium sulfate and evaporated to yield the title compound as a colorless oil (9.54 g, 90%). $^1$H NMR (CDCl$_3$): δ 1.37 (t, J=7 Hz, 3H), 1.60, 1.92 (m, 6H), 2.52 (t J=6 Hz, 2H), 2.80–2.92 (m, 1H, 3.22–3.36, m, 1H), 4.36 (q, J=7 Hz, 2H), 4.74–4.88 (m, 1H, 9.58, s, 1H).

C. 3-Ethoxycarbonyl-5-[4-(-N-(pyridin-2-yl)amino)butyl] isoxazoline

The product of Ex. 667 part B. (9.40 g, 0.044M) was dissolved in dichloroethane (100 mL) and cooled in an ice bath. 2-Aminopyridine (4.57 g, 0.048M) was added followed by the addition of sodium triacetoxyborohydride (14.0 g, 0.066M). The ice bath was removed and the reaction mixture allowed to stir at room temperature for 4 h. The reaction mixture was cautiously poured into a saturated solution of sodium bicarbonate (200 mL), and extracted with ethyl acetate. The organic layer was dried over anhydrous sodium carbonate, filtered and evaporated to yield a semi-solid. The crude product was triturated with a mixture of ether and hexane, and the product collected by filtration (8.93 g, 70%) ¹H NMR (CDCl₃): δ 1.30 (t, J=7 Hz, 3H), 1.40–1.90 (m, 6H, 2.80–2.92, m, 1H), 3.20–3.34 (m, 2H), 4.34 (q, J=7 Hz, 2H), 4.70–4.90 (m, 2H), 6.30 (d, J=9 Hz, 1H), 6.48 (t, J=6 Hz, 1H), 7.42 (t J=6 Hz, 1H), 8.04 (d, J=4 Hz, 1H).

D. 3-Ethoxycarbonyl-5-[4-(N-(pyridin-2-yl)-N-(tert-butyloxycarbonyl)amino)butyl]isoxazoline The product of Ex. 667 part C. (8.93 g, 0.031M) was dissolved in methylene chloride. 4-Dimethylaminopyridine (374 mg, 0.003M) was added followed by di-tert-butyl dicarbonate (14.73 g, 0.067M). The reaction mixture was allowed to stir at room temperature overnight. The mixture was diluted with water and the organic layer separated, dried over magnesium sulfate, filtered and evaporated. The crude product was purified by flash column chromatography (hexane/ethylacetate, 3:1) to yield the title product (9.7 g, 81%). ¹H NMR (CDCl₃): δ 1.38 (t, J=7 Hz, 3H), 1.40–1.90 (m, 15H), 2.76–2.86 (m, 1H), 3.18–3.30 (m, 1H), 3.93 (t, J=7 Hz, 2H), 4.32 (q, J=7 Hz, 2H), 4.70–4.82 (m, 1H), 7.01 (t, J=6 Hz, 1H), 7.54–7.86 (m, 2H), 8.36 (d, J=4 Hz, 1H).

E. 5-[4-(N-(Pyridin-2-yl)-N-(tert-butyloxycarbonyl)amino) butyl]isoxazolin-3-carboxylic acid:

The product of Ex 667 part D, (10.7 g, 0.027M) was dissolved in a mixture of 20 mL of tetrahydrofuran and 20 mL of water, and cooled in an ice bath. Lithium hydroxide (1.73 g, 0.41M) was dissolved in 5 ml of water and added to the ester solution. the reaction mixture was stirred for 45 m. TLC of the reaction mixture (hexane/ethyl acetate, 3:1) indicated that no ester remained. 1M Citric acid solution (40 mL) was added and the mixture was extracted several times with ethyl acetate (until TLC of the organic layer showed no product). The combined orgainic layers were dried over magnesium sulfate, filtered, and evaporated and dried under high vacuum to yield the title product as a light yellow semisolid (9.9 g, 99%). ¹H NMR (CDCl₃): δ 1.24–1.82 (m, 12H), 2.78–2.9 (m, 1H), 3.20–3.32 (m, 1H), 3.90 (t J=7 Hz, 2H), 4.78–4.90 (m, 1H), 7.10 (t J=6 Hz, 1H), 7.52 (d, J=8 Hz, 1H), 7.70 (t, J=6 Hz, 1H), 8.42 (t, J=4 Hz, 1H).

Mass spectrum m/z 364.3 (M+H, base peak)

F. tert-Butyl-2-(S)-benzyloxycarbonylamino-3-[5-(R,S)-(4-(N-(pyridin-2-yl)-N-(tert-butyloxycarbonyl)amino) butylisoxazolin-3-ylcarbonyl]aminopropionate:

tert-Butyl N²-benzyloxycarbonyl-2-(S)-2,3-diaminopropionate (M. Mokotoff and L. Logue, J. Med. Chem., 1981, 24, 554) (2.59 g, 8.806 mmol), and the carboxylic acid from Ex. 667 part E. (3.20 g, 8.806 mmol) were dissolved in N'N'-dimethylformamide (20 mL). N'-methylmorpholine (2.72 g, 26.856 mmol) and benzotriazol-1-yloxy-tris(dimethylamino)phosphonium hexafluorophosphate (4.09 g, 9.246 mmol) were added and the reaction mixture stirred for 48 h at room temperature under nitrogen. Concentration in vacuo to an orange oil which was purified by silica gel flash column chromatography (hexane/ethyl acetate (2:1), to yield the title compound as a pale yellow syrup (4.56 g, 83%). ¹H NMR (CDCl₃): δ 1.35–1.77 (m, 6H), 1.48 (s, 9H), 1.50 (s, 9H), 2.74–2.83 (d of d, J=17.58, 8.05 Hz, 1H), 3.14–3.24 (d of d of d, J=17.58, 8.05, 1.06 Hz, 1H), 3.68–3.79 (m, 2H), 3.90–3.95 (t, J=6.96 Hz, 2H), 4.35–4.41 (m, 1H), 4.67–4.79 (m, 1H), 5.11 (s, 2H)(, 5.66–5.69 d, J=6.96 Hz, 1H), 6.94–6.97 (t, J=5.36 Hz, 1H), 6.98–7.06 (d of d, J=4.76, 1.84 Hz, 1H), 7.28–7.37 (m, 5H), 7.51–7.59 (t of d, J=6.96, 1.84 Hz, 1H), 7.58–7.67 (t of d, J=6.96, 1.83 Hz, 1H), 8.35–8.39 (d of d, J=4.76, 1.83, 1H). Mass spectrum m/z=640.4 (M+H), 264.2 (base peak).

G. 2-(S)-Benzyloxycarbonylamino-3-[5-(R,S)-(4-(N-(pyridin-2-yl)amino)butyl)isoxazolin-3-ylcarbonyl] aminopropionic acid:

The product of Ex. 667 part F (60 mg, 0.094 mmol) was dissolved in 4N HCl in dioxane (2 mL), and stirred at room temperature for 5 h. under nitrogen. The solvent was evaporated in vacuo and the residue purified by reverse phase (C18) HPLC to yield the title compound (39 mg, 87%). ¹H NMR (CDCl₃): δ 1.35–1.77 (m, 6H), 2.74–2.83 (m, 2H), 3.20–3.40 (m, 3H), 3.55–3.80 (m, 3H), 4.40 (br s, 1H), 4.55 (br s, 1H), 5.02 (t, J=8 Hz, 2H), 6.83 (br t, 1H), 7.02 (d, 6 Hz, 1H), 7.28 (s, 5H), 7.78 (d, J=4 Hz, 1H), 7.85 (t, J=5 Hz, 1H). Mass spectrum m/z=484.3. (M+H).

EXAMPLE 669

2-(S)-Phenylsulfonylamino-3-[5-(R,S)-(4-(N-(pyridin-2-yl)amino)butyl)isoxazolin-3-ylcarbonyl] aminopropionic acid trifluoroacetate salt A. Methyl-2-(S)-phenylsulfonylamino-3-[5-(R,S)-(4-(N-(pyridin-2-yl)-N-(tert-butyloxycarbonyl)amino) butylisoxazolin-3-ylcarbonyl]aminopropionate:

Methyl 3-amino-2-phenylsulfonylaminopropionate (Hartman, G. D., Prugh, J. D., Egbertson, M. S., Duggan, M. E. Hoffman, W. PCT Int. Appl WO 9408577 A1 940428) (8.82 g, 24.3 mmol) and the product of Ex 667 part E, (7.15 g, 24.257 mmol) was disolved in N'N'-dimethylformamide (100 ml). N'-Methylmorpholine (7.61 g, 75.197 mmol) and Benzotriazol-1-yloxytris(dimethylamino)phosphonium hexafluorophosphate (12.88 g, 29.108 mmol) were added and the reaction mixture stirred for 15 h. at room temperature under a nitrogen atmosphere. The solvent was removed in vacuo to provide the crude product as an orange syrup which was purified by silica gel flash chromatography (hexane/ethyl acetate, 1:1), to yield the title compound as a light yellow oil (7.31 g, 57%). ¹H NMR (CDCl₃): δ 1.34–1.77 (m, 6H), 1.50 (s, 9H), 2.59–2.68 (d of d, J=22.34, 9.52 Hz, 1H), 2.71–2.83 (d of d of d, J=17.58, 8.42, 2.20 Hz, 1H), 2.88–2.96 (d, J=22.34 Hz, 1H), 2.88–3.25 (d of d of d, J=17.58, 10.62, 3.66 Hz, 1H), 3.59 (s, 3H), 3.62–3.69 (m, 2H), 3.93–3.98 (t, J=7.33 Hz, 2H), 4.06–4.12 (m, 1H), 4.70–4.75 (c, 1H), 5.72–5.75 (d of d, J=7.69, 3.36 Hz, 1H), 7.03–7.07 (d of d and c, J=4.76, 1.84 Hz, 2H), 7.47–7.50 (t, J=8.43 Hz, 3H), 7.52–7.65 (t, J=9.15 Hz, 2H), 7.60–7.70, (d of d, J=3.55, 1.83 Hz, 1H), 7.84–7.86 (d of d, J=6.92, 1.46 Hz, 2H), 8.39–8.41 (d, J=4.76 Hz, 1H). Mass spectrum m/z=604.3 (M+H, base peak).

B. 2-(S)-Phenylsulfonylamino-3-[5-(R,S)-(4-(N-(pyridin-2-yl)N-(tert-butyloxycarbonyl)amino)butylisoxazolin-3-ylcarbonyl]aminopropionic acid:

Lithium hydroxide (0.71 g, 16.952 mmol) dissolved in water (10 ml). In a separate flask the product of ex 669 part A, (7.31 g, 12.109 mmol) was dissolved in a mixture of methyl alcohol (200 mL), water (10 mL). The lithium hydroxide solution was added and the reaction mixture was stirred at room temperature for 72 hrs. The resulting red solution was concentrated in vacuo and partioned between ethyl acetate (100 mL) and water (50 mL). A mixture of 1M Hydrochloric Acid (17 ml) in Citric Acid (100 ml) was added until the pH of the aqeous layer was ca. 4. The organic layer was separated and the aqueous layer extracted with ethyl Acetate (2×30 ml). The combined orgainc layers were dried over anhydrous magnesium sulfate, filtered and the solvent removed in vacuo to provide the title compound as a light yellow oil (6.50 g, 91%). ¹H NMR (CDCl₃): δ 1.34–1.77 (m, 6H), 1.50 (s, 9H), 2.59–2.68 (d of d, J=22.34, 9.52 Hz, 1H), 2.71–2.83 (d of d of d, J=17.58, 8.42, 2.20 Hz, 1H), 2.88–2.96 (d, J=22.34 Hz, 1H), 2.88–3.25 (d of d of d, J=17.58, 10.62, 3.66 Hz, 1H), 3.59 (s, 3H), 3.62–3.69 (m, 2H), 3.93–3.98 (t, J=7.33 Hz, 2H), 4.06–4.12 (c, 1H), 4.70–4.75 (c, 1H), 5.80–5.86 (d of d, J=7.69, 3.36 Hz, 1H), 6.12–6.15 (d, J=8.06 Hz, 1H), 7.03–7.07 (d of d and c, J=4.76, 1.84 Hz, 2H), 7.16–7.19 (d of d, J=6.92, 1.46 Hz, 2H), 7.24–7.28 (t, J=8.43 Hz, 3H), 7.38–7.57 (t and d of d, J=9.15, 4.02, 2.93 Hz, 2H), 7.64–7.70 (c, 1H), 7.83–7.89 (t, J=6.95 Hz, 1H), 8.39–8.41 (d, J=4.76 Hz, 1H). Mass spectrum m/z=590.2 (M+H, base peak).

C. 2-(S)-Phenylsulfonylamino-3-[5-(R,S)-(4-(N-(pyridin-2-yl)amino)butylisoxazolin-3-ylcarbonyl]aminopropionic acid:

Trifluoroacetic acid (10 ml) was added to the product of Ex 669 part B, (6.50 g, 11.023 mmol) and the reaction mixture was stirred for 3 h at room temperature under nitrogen. The solution was concentrated in vacuo then co-concentrated with toluene (3×100 mL). The resulting oil was purified by gradient reverse phase HPLC (Water/Acetonitrile) to yield the title compound as a white powder (4.78 g, 72% yield, 97.7% purity).

$^1$H NMR (CD$_3$OD): δ1.34–1.77 (m, 6H), 1.50 (s, 9H), 2.59–2.68 (d of d, J=22.34, 9.52 Hz, 1H), 2.71–2.83 (d of d of d, J=17.58, 8.42, 2.20 Hz, 1H), 2.88–2.96 (d, J=22.34 Hz, 1H), 2.88–3.25 (d of d of d, J=17.58, 10.62, 3.66 Hz, 1H), 3.30–3.36 (t, J=7.33 Hz, 2H), 3.62–3.69 (m, 2H), 4.06–4.12 (c, 1H), 4.70–4.75 (c, 1H), 5.80–5.86 (d of d, J=7.69, 3.36 Hz, 1H), 6.79–6.85 (d, J=4.76 Hz, 1H), 7.00–7.03 (d of d, J=9.16, 2.56 Hz, 1H), 7.46–7.51 (t, J=7.69 Hz, 2H), 7.57–7.59 (t, J=7.33 Hz, 1H), 7.76–7.87 (d, J=6.96, 4H). Mass spectrum m/z=490.2 (M+H, base peak). High resolution mass spectrum m/z 490.176031.

EXAMPLE 695

[2(S)-Benzyloxycarbonylamino]-3-[5-[(6-aminopyridin-2-yl)propyl]isoxazolin-3-yl] carbonylaminopropionic acid, trifluoroacetate salt A. tert-Butyl-[2(S)-Benzyloxycarbonylamino]-3-[5-[[6-(2,5-dimethylpyrrolyl)pyridin-2-yl]propyl]isoxazolin-3-yl] carbonylaminopropionate:

The product of Ex. 697, Part D (0.43 g, 1.30 mmol) was dissolved in N,N-dimethylformamide (10 mL). (S)-t-Butyl-3-amino-2-benyzloxycarbonylamino-propionate (0.42 g, 1.43 mmol), triethylamine (0.29 g, 2.86 mmol) and O-(1H-benzotriazol-1-yl)-N,N,N',N'-tetramethyluronium tetrafluoroborate (0.46 g, 1.43 mmol), according to the procedure of Ex 284, Part F, to provide the title product (0.33 g, 42%). $^1$HNMR (CDCl$_3$) δ 1.46 (s, 9H), 1.86 (m, 4H), 2.12 (s, 6H), 2.87 (m, 3H), 3.22 (m, 1H), 3.74 (br s, 2H), 4.38 (m, 1H), 4.78 (m, 1H), 5.11 (s, 2H), 5.68, (bs, 1H), 5.89 (s, 2H), 6.97 (bs, 1H), 7.04 (d, 1H), 7.14 (d, 1H), 7.35 (m, 5H), 7.73 (t, 1H). Mass spectrum: (ESI) m/z 604 (M+H)$^+$.

B. [2(S)-Benzyloxycarbonylamino]-3-[5-[(6-aminopyridin-2-yl)propyl]isoxazolin-3-yl]carbonylaminopropionic acid, trifluoroacetate salt:

The compound of Ex. 695, Part A (0.33 g, 0.54 mmol), hydroxylamine hydrochloride (0.75 g, 10.8 mmol, and triethylamine (0.55 g, 5.42 mmol) are dissolved in a 4:1 mixture of isopropanol/water (10.0 mL) and refluxed. After 3.5 h, additional hydroxylamine hydrochloride (0.37 g, 5.40 mmol) and triethylamine (0.27 g, 2.71 mmol) are added, and the reaction mixture refluxed for an additional 4 h. The reaction mixture was cooled and sodium carbonate (0.86 g, 8.13 mol) was added. The reaction mixture was stirred for 16 h, then filtered, and the filtrate concentrated. The crude amine was dissolved in a mixture of methylene chloride (4.0 mL) and trifluoroacetic acid (1.0 mL), and stirred for 16 h. The reaction mixture was concentrated to give a thick yellow oil, which was partitioned between ethyl acetate and water. The organic layer was separated and dried over anhydrous sodium sulfate, filtered and concentrated to give a yellow oil. The crude product was purified by preparative reverse phase HPLC using a gradient, 90:10 to 10:90, water/acetonitrile (0.05% trifluoroacetic acid) as eluent, gave the desired product as a trifluoroacetate salt, 15 mg (5%). $^1$HNMR (CDCl$_3$) δ 1.70 (m, 4H), 2.75 (m, 3H), 3.20 (m, 1H), 3.60 (m, 2H), 4.30 (m, 1H), 4.75 (m, 1H), 5.05 (s, 2H), 6.02 (bs, 1H), 6.59 (d, J=8 Hz, 1H), 6.71 (d, J=8 Hz, 1H), 7.35 (m, 5H), 7.68 (t, J=8 Hz, 1H). Mass spectrum: (ESI) m/z 470(M+H)$^+$.

EXAMPLE 697

[2-Phenylsulfonylammino]-3-[5-[(6-aminopyridin-2-yl)propyl]isoxazolin-3-yl]carbonylaminopropionic acid, trifluoroacetate salt A. 2-(2,5-Dimethyl-1H-pyrrol-1-yl)-6-methylpyridine:

2-Amino-6-methylpyridine (56.4 g, 0.52 mol), 2,5-hexanedione (59.3 g, 0.52 mol) and acetic acid (5.0 mL) were refluxed in toluene (150 mL), under a Dean-Stark trap for 16 h. The mixture was cooled, an additional portion of 2,5-hexanedione (34.0 g, 0.30 mol) was added and reflux resumed for 7 h. The reaction mixture was cooled, and the solvent was evaporated and the residue was disolved in EtOAc and cautiously washed with saturated NaHCO$_3$, and then brine. The organic layer was dried with anhydrous sodium sulfate, filtered and concentrated. The residue was flash column chromotragraphy (silica gel, hexane/ethyl acetate, 85:15) to provide 37.5 g (39%) of the title product.

$^1$H NMR (CDCl$_3$) δ 2.12 (s, 6H), 2.59 (s, 3H), 5.88 (s, 2H), 7.02 (d, J=8 Hz, 1H), 7.15 (d, J=8 Hz, 1H).

Mass spectrum: (ESI) m/z 187(M+H)$^+$.

B. 2-(2,5-dimethyl-1H-pyrrol-yl)-6-(4-pentenyl)pyridine:

The product of Ex 697 part A, (5.0 g, 0.027 mol) was dissolved in anhydrous tetrahydrofuran (45 mL) and cooled to −78° C. A solution of lithium diisopropylamide (0.032 mol) in anhydrous tetrahydrofuran (50 mL) was precooled to 0° C., and added to the reaction mixture. After stirring for 1.5 h at −78° C., 4-bromo-2-butene (3.78 g, 0.028 mol) was added. This mixture was stirred for an additional 0.5 h, and then allowed to warm to ambient temperature. Saturated ammonium chloride (150 mL) was added, the tetrahydrofuran was evaporated, and the aqueous solution extracted with ethyl acetate (150 mL). The combined organic layers were washed with water (150 mL) and brine (100 mL), then dried over sodium sulfate, filtered and concentrated to yield 5.58 g (86%) of the desired product. $^1$H NMR (CDCl$_3$) δ 1.87 (m, 2H), 2.10 (t, J=7.3 Hz, 2H), 2.13 (s, 6H), 2.83 (t, J=7.3 Hz, 2H), 4.99 (m, 2H), 5.83 (m, 1H), 5.89 (s, 2H), 7.02 (d, J=7.7 Hz, 1H), 7.13 (d, J=7.7 Hz, 1H), 7.70 (t, J=7.7 Hz, 1H). Mass spectrum: (ESI) m/z 241(M+H)$^+$.

C. 5-Ethyl[6-[[(2,5-dimethylpyrrolyl)pyridin-2-yl]propyl] isoxazolin-3-yl]carboxylate:

The product of ex 697 part B, (2.4 g, 9.98 mmol) was dissolved in a 2:1 mixture of tetrahydrofuran and water (90 mL). Sodium bicarbonate (5.01 g, 59.6 mmol) and ethyl chlorooximidoacetate (1.5 g, 9.98 mmol), according to the procedure of Ex 667, Part A, to provide the title product (1.01 g, 29%). $^1$H NMR (CDCl$_3$) δ 1.36 (t, 3H), 1.67 (m, 2H), 1.88 (m,2H), 2.12 (s, 6H), 2.85 (m, 3H), 3.25 (m, 1H), 4.33 (q, 2H), 4.84 (m, 1H), 5.89 (s, 2H), 7.04 (d, 1H), 7.14 (d, 2H), 7.73 (t, 1H).

D. [6-[[(2,5-Dimethylpyrrolyl)pyridin-2-yl]propyl] isoxazolin-3-yl]carboxylic acid:

The product of Ex 697 part C, (1.01 g, 2.84 mmol) was hydrolyzed according to the procedure of Ex 667, Part E, to provide the title product (0.86 g, 92%). $^1$H NMR (DMSO) δ 1.61 (m, 2H), 1.76 (m, 2H), 2.04 (s, 6H), 2.79 (m, 3H), 3.22 (m, 1H), 4.77 (m, 1H), 5.78 (s, 1H), 7.20 (d, 1H), 7.30 (d, 1H), 7.88 (t, 1H).

Mass spectrum: (ESI) m/z 328 (M+H)$^+$.

E. Methyl-[2(S)-phenylsulfonylamino]-3-[5-[[6-(2,5-dimethylpyrrolyl)pyidin-2-yl]propyl]isoxazolin-3-yl] carbonylaminopropionate:

The product of Ex. 697, Part D (0.43 g, 1.30 mmol) was dissolved in N,N-dimethyl formamide (10 mL), (S)-methyl-3-amino-2-phenylsulfonylaminopropionate (0.42 g, 1.43 mmol), triethylamine (0.29 g, 2.86 mmol) and O-(1H-benzotriazol-1-yl)-N,N,N',N'-tetramethyluronium tetrafluoroborate (0.46 g, 1.43 mmol), were added according to the procedure of Ex 284, Part F, to provide the title product (0.23 g, 31%). $^1$H NMR (CDCl$_3$) δ 1.85 (m, 4H), 2.13 (s, 6H), 2.79 (m, 1H), 2.88 (t, 2H), 3.23 (m, 1H), 3.67 (m, 1H), 4.11 (m, 1H), 4.79 (m, 1H), 5.76 (m, 1H), 5.89 (s, 2H), 7.02 (bs, 1H), 7.04 (d, 1H), 7.15 (d, 1H), 7.53 (m, 3H), 7.73 (t, 1H), 7.84 (d, 2H). Mass spectrum: (ESI) m/z 568(M+H)$^+$.

F. [2(S)-Phenylsulfonylamino]-3-[5-[(6-aminopyridin-2-yl) propyl]isoxazolin-3-yl]carbonylaminopropionic acid, trifluoroacetate salt:

The product of Ex. 697, Part E, (0.16 g, 0.29 mmol), hydroxylamine hydrochloride (0.40 g, 5.81 mmol), and triethylamine (0.29 g, 2.91 mmol) were dissolved in a 4:1 mixture of isopropanol/water (10.0 mL) and refluxed. After 3.5 h, additional hydroxylamine hydrochloride (0.37 g, 5.40 mmol) and triethylamine (0.27 g, 2.71 mmol) were added, and the reaction mixture refluxed for an additional 4 h. The reaction mixture was cooled and sodium carbonate (0.46 g, 4.36 mol) was added, the mixture was stirred 16 h. The reaction mixture was filtered and concentrated. The crude amine was taken up in a 4:1 mixture of MeOH/water (10.0 mL) and LiOH.H$_2$O (0.012 g, 0.29 mmol) was added. The reaction mixture was stirred 16 h. The methanol was evaporated, and the crude carboxylic acid was dissolved in water and washed with EtOAc. The aqueous phase was adjusted to pH=4.5 with 1M HCl, and the solution absorbed on a pad of C$_{19}$ reverse phase gel. The pad was washed well with H$_2$O and eluted with CH$_3$CN. The CH$_3$CN eluent was concentrated to give an oily solid. Purification by preparative reverse phase HPLC using a gradient 90:10 water/ acetonitrile to 10:90, water/acetonitrile (0.05% trifluoroacetic acid) as eluent, gave the desired product as a TFA salt, 13 mg (8%). $^1$HNMR (CDCl$_3$) δ 1.80 (m, 4H), 2.81 (m,3H), 3.21 (m, 1H), 3.60 (m, 2H), 4.15 (br s, 1H), 4.80 (br s, 1H), 6.75 (d, J=4.5 Hz, 1H), 6.85 (d, J=8.0 Hz, 1H), 7.56 (m, 4H), 7.82 (m, 3H). Mass spectrum: (ESI) m/z 476(M+H)$^+$.

EXAMPLE 849

2-[(S)-((2,4,6-trimethylphenyl)sulfonyl)amino]-3-[5-(R,S)-(4-(N-(pyridin-2-yl)amino)butylisoxazolin-3-ylcarbonyl]aminopropionic acid A. 2-(S)-amino-3-[5-(R,S)-(4-(N-(pyridin-2-yl)-N-(tert-butyloxycarbonyl)amino)butylisoxazolin-3-ylcarbonyl] aminopropionic acid tert-butyl ester:

To the product of example 667 part F, (1.5 g, 2.408 mmol), in methyl alcohol (50 mL) was added Palladium on Barium Sulfate unreduced (0.300 g, 0.482 mmol). The reaction mixture was exposed to hydrogen gas (41 p.s.i.) at room temperature for 15 hours. The reaction mixture was filtered through a celite pad and concentration in vacuo to afforded a light yellow syrup (1.22 g, quantitative yield). $^1$H NMR (CDCl$_3$): δ 1.34–1.76 (m, 6H), 1.46 (s, 9H), 1.48 (s, 9H), 2.29–2.48 (br s, 2H), 2.78–2.87 (d of d,J=17.58, 8.05 Hz, 1H), 3.19–3.28 (d of d of d, J=17.58, 8.05, 1.06 Hz, 1H), 3.59–3.66 (m, 2H), 3.78–3.81 (m, 1H), 3.86–3.91 (t, J=6.96 Hz, 2H), 4.69–4.78 (m, 1H), 6.98–7.02 (d of d, J=4.76, 1.84 Hz, 1H), 7 12–7.14 (t, J=5.36 Hz, 1H), 7.51–7.56 (t of d, J=6.96, 1.84 Hz, 1H), 7.58–7.64 (t of d, J=6.96, 1.83 Hz, 1H), 8.36– 8.38 (d of d, J=4.76, 1.83 Hz, 1H). Mass Spectrum m/z=506.4 (M+H), 197.7 (base peak).

B. 2-[(S)-((2,4,6-trimethylphenyl)sulfonyl)amino]-3-[5-(R, S)-(4-(N-(pyridin-2-yl)amino)butylisoxazolin-3-ylcarbonyl]aminopropionic acid:

The product of example 849 part A, (50 mg, 0.0949 mmol), and pyridine (202 mg, 2.585 mmol) were dissolved in dichloromethane (5 mL). 2,4,6-trimethylbenzenesulfonyl chloride (26 mg, 0.119 mmol) was added and the reaction mixture was stirred at room temperature under nitrogen for 8 h. Saturated aqueous sodium bicarbonate (5 mL) was added and the organic layer was separated, dried over anhydrous sodium carbonate and concentrated in vacuo to a syrup. The product was treated with trifluoroacetic acid (5 ml) at room temperature and stirred for 1 hour. The reaction mixture was concentrated in vacuo to a syrup. Toluene (10 mL) was added and the mixture concentrated in vacuo again. The resulting syrup was submitted to gradient HPLC (Water/ Acetonitrile) The fractions containing the product were concentrated in vacuo and placed on a lyophilization apparatus overnight, to afford the title compound as a white powder (27 mg, 42% over two steps). $^1$H NMR (CD$_3$OD): δ 1.49–1.79 (m, 6H), 2.58 (s, 9H), 2.74–2.82 (d of d, J=17.58, 8.05 Hz, 1H), 3.07–3.16 (d of d of d, J=17.58, 8.05, 1.06 Hz, 1H), 3.31–3.36 (t, J=6.96 Hz, 2H), 3.31–3.65 (d of d, J=13.55, 5.12 Hz, 2H), 4.00–4.06 (m, 1H), 4.74–4.82 (m, 1H), 6.78–6.85 (d of d, J=5.86, 0.73 Hz, 1H), 6.94 (s, 2H), 6.98–7.03 (d of d, J=4.40, 0.05 Hz, 1H), 7 75–7.78 (t, J=5.86 Hz, 1H), 7.81–7.86 (t, J=4.40 Hz, 1H). Mass spectrum m/z=532.2 (M+H , base peak).

EXAMPLE 951

3-{5-[4-(imidazol-2-ylamino)butyl]isoxazoline-3-carbonyl}amino-2S-(2,4,6-trimethylbenzenesulfonylamino)propionic acid trifluoroacetate salt A. 2-Phthalamidoimidazole:

2-Aminoimidazole sulfate (2.64 g, 20 mmol) was dissolved in 200 mL of anhydrous methanol and cooled to −78° C. A 25% solution of sodium methoxide in methanol (4.57 mL, 20 mmol) was added dropwise. The reaction mixture was allowed to warm to room temperature and stirred for an additional 3 hours. The solution was filtered and concentrated on the rotary evaporator to a brown oil (1.6 g, 96.4%). $^1$H NMR (DMSO) δ 5.0 br.s, 2H, 6.32, s, 2H.

Phthalic anhydride (4.14 g, 29.2 mmol) and 2-aminoimidazole (2.32 g, 29.2 mmol) were heated to 170° C. for 15 min. The crude reaction mixture was purified by flash chromatography (gradient chloroform:methanol 95:5–80:20) to yield 4.66 g (75%) of a brown solid. $^1$H NMR (DMSO) δ 7.16 (br.s, 2H), 7.94–8.06 (m, 4H), 12.35 (br s, 1H). Mass spectrum ESI (M+H)$^+$ 214.2

B. 1-Triphenylmethyl-2-phthalamidoimidazole:

The product of Ex. 949, Part A, (4.66 g, 21.9 mmol) was dissolved in 100 mL of anhydrous pyridine and triphenylmethylchloride (9.15 g, 32.82 mmol) was added. The reaction mixture was refluxed for 24 hrs. Pyridine was removed and the residue was purified by flash column chromatography (chloroform:methanol 5–10%) to yield the desired product (2.74 g, 27.5% yield). $^1$H NMR (CDCl$_3$) δ 6.80 (d, J=1.1 Hz, 1H), 7.06 (t, J=7.3 Hz, 3H), 7.17 (t, J=7.7 Hz, 7H), 7.28 (d, 6H, 7.64, s 4H). Mass spectrum NH$_3$-DCI (M+H)$^+$ 456.

C. 1-Triphenylmethyl-2-aminoimidazole:

The product of Ex. 949, Part B, (2.60 g, 5.7 mmol) and hydrazine (1.83 g, 57 mmol) were refluxed in 250 mL of anhydrous ethanol for 1 hr. The reaction mixture was cooled and the solvent removed in vacuo. the solid residue was purified by flash column chromatography (chloroform:methanol 10:1) to yield 1.8 g (97%) of a yellow solid. $^1$H NMR (DMSO) δ 6.26 (d, J=1.8 Hz, 1H), 6.51 (d, J=1.8 Hz, 1H), 7.13 (d, J=7 Hz, 6H), 7.33–7.44 (m, 9H). Mass spectrum NH$_3$-DCI (M+H), 326.

D. 3-Ethoxycarbonyl-5-[4-(1-triphenylmethylimidazol-2-ylamino)butyl]isoxazoline:

1-Triphenylmethyl-2-aminoimidazole (1.43 g, 4.4 mmol), the product of Ex. 667, Part B, (1.034 g, 4.85 mmol) and magnesium sulfate (2.33 g, 19.4 mmol) were stirred in 250 mL of carbon tetrachloride at room temperature. Progress of the reaction was monitored by NMR. After 90 hrs magnesium sulfate was filtered off and triacetoxyborohydride (3.74 g, 17.65 mmol) was added. The reaction mixture was stirred for an additional 48 hrs. Water (100 mL) was added, the organic layer was separated and the water layer was extracted with ethyl acetate. The combined organic layers were concentrated and purified by flash chromatography (ethyl acetate/hexane 1:1, then ethyl acetate, then ethyl acetate:methanol 20:1) to yield the product as a colorless oil (1.7 g, 74%). $^1$H NMR (DMSO) δ 0.84–0.92 (m, 2H), 1.0 (m, 2H), 1.26 (t, J=7.3 Hz, 3H), 1.31–1.48 (m, 2H), 2.70 (dd, J1=17.6 Hz, J2 =8.4 Hz, 1H), 2.90 (q, J=2.3 Hz, 2H), 3.07 (br. s, 1H), 3.20 (dd, J1=11 Hz, J2=17.6 Hz, 1H), 4.25 (q, J=7.3 Hz, 2H), 4.6 (m, 1H), 6.26 (d, J=1.5 Hz, 1H), 7.50 (d, J=1.5 Hz, 1H), 7.09 (m, 6H), 7.33–7.44 (m, 6H). Mass spectrum: NH3-DCI (M+H)$^+$, 523.

E. 5-[4-(1-triphenylmethylimidazol-2-ylamino)butyl]isoxazoline-3-carboxylic acid The product of Ex. 949, Part D (246 mg, 0.47 mmol) was dissolved in of tetrahydrofuran (2 mL). A 0.5N solution of lithium hydroxide (0.94 mL. 0.47 mmol) was added. The reaction mixture was stirred for 1 h, then aqeous 1N HCl (0.47 mL. 0.47 mmol) was added and the solvent was evaporated. The crude product was purified by flash column chromatography (chloroform/methanol 10:1) to yield the product as a white solid (230 mg, 99%). $^1$H NMR (DMSO) δ 0.84–0.1.31 (m, 6H), 2.57 (dd, J$_1$=17.6 Hz, J$_2$=8.4 Hz, 1H), 2.89 (q, J=6.6 Hz, 1H), 3.07 (dd, J$_1$=17.6 Hz, J$_2$=10.6 Hz, 1H), 4.0–4.15 (br.s, 1H), 4.36 (m, 1H), 6.26 (d, J=1.8 Hz, 1H), 6.52 (d, J=1.6 Hz, 1H), 7.10 (d, 6H), 7.34–7.44 (m, 9H). Mass spectrum NH$_3$-DCI (M+H)$^+$ —CO$_2$H, 451.

G. N-(2,4,6 trimethylphenyl)sulfonyl-L-asparagine:

L-Asparagine (20.0 g, 0.15M) was suspended in a mixture of tetrahydrofuran (130 mL) and water (250 mL). Triethylamine (49 g, 0.48M) was added followed by mesitylenesulfonyl chloride (49.7 g, 0.227M), The reaction mixture became slightly exothermic and the solids dissolved over a period of 0.5 h. to yield a yellow solution. The reaction mixture was stirred for 3 h at room temperature, then washed with ether, and methylene chloride. The aqueous layer was separated, and acidified to ca. pH=1.5 with conc. HCl, during which time a thick precipitate formed. After 0.5 h. the product was filtered,washed with water and dried to yield a white solid (34 g, 72%). m.p.=193.5°–195° C. $^1$H NMR (DMSO) δ 2.24 (s, 3H), 2.28 (dd, 1H), 2.45 (dd, 1H), 2.55 (s, 6H), 3.98 (m, 1H), 6.88 (br s, 1H), 6.99 (s, 2H), 7.32 (br s, 1H), 7.82 (d, 2H), 12.58 (br s, 1H). Mass spectrum ESI m/z=315.2, (M+H base peak).

H. 3-Amino-2-(S)-N-(2,4,6 trimethylphenyl) sulfonylaminopropionic acid:

Sodium hydroxide (32 g, 0.80 M), was dissolved in water (200 mL) and cooled in an ice bath. Bromine (19.2 g, 0.12M) was added dropwise over 5 min. and the mixture allowed to stir for 15 min. The product of Ex. 949, Part G, (31.44 g, 0.10M), was added in several portions over a period of ca. 10 min. during which time the yellow color faded. The reaction mixture was gently heated on a steam bath during which time the internal temperature rose to ca. 85° C. After 1 h, the reaction mixture was allowed to cool to room temperature then cooled in an ice bath. The reaction mixture was cautiously acidified to pH=6 with conc. HCl, during which time a solid formed and gas was evolved. The solid was filtered, washed with cold water, and allowed to dry overnight, to yield the product as a white solid (23.9 g, 83%). $^1$H NMR (DMSO) δ 2.26 (s, 3H), 2.59 (s, 6H), 2.80 (dd, 1H), 2.94 (dd, 1H), 3.07 (dd, 1H), 7.06 (s, 2H). Mass spectrum ESI m/z 287.2 (M+H, base peak).

I. tert-Butyl-3-Amino-2-(S)-N-(2,4,6-trimethylphenyl) sulfonylaminopropionate:

The product of Ex. 949, Part H, (11.45 g, 0.04M), was placed in a Parr bottle, and dissolved in dioxane (170 mL), and conc. sulfuric acid (11 mL) was added. The reaction mixture was cooled in a dry ice/acetone bath and ca. 185 ml of isobutylene was added. The bottle was sealed and agitated for 114 h. The bottle was de-pressurized then purged with nitrogen for a brief time. The reaction mixture was poured into a rapidly stirred mixture of water (225 mL) containing sodium hydroxide (17 g) and ether (600 mL) which had been pre-cooled in an ice bath. The layers were separated. The aqueous layer was extracted with additional ether. The pH of the aqueous layer was carefully adjusted with conc. HCl to pH=11 and extracted four times with ether. The organic layers from the pH 11 adjusted extraction were combined, dried with anhydrous sodium sulfate, filtered and evaporated to yield the product as a viscous oil which solidified (8.64 g, 63%).

$^1$H NMR (CDCl$_3$) δ 1.28 (s, 9H), 2.28 (s, 3H), 2.67 (s, 6H), 2.93 (m, 2H), 3.69 (m, 1H), 6.95 (s, 2H).

J. tert-Butyl 3-{5-[4-(1-triphenylmethylimidazol-2-ylamino)butyl]isoxazoline-3-carbonyl}amino-2-(S)-(2,4,6-trimethylbenzenesulfonylamino)propionate:

The product of Ex. 949, Part E, (98 mg, 0.198 mmol) was dissolved in N,N-dimethylformamide (2 mL). The product of Ex 949, Part I, (68 mg, 0.198 mmol), O-(1H-benzotriazol-1-yl)-N,N,N',N'-tetramethyluronium tetrafluoroborate (76 mg, 0.24 mmol) and triethylamine (69 mL, 0.495 mmol) were added and the reaction mixture was stirred at room temperature for 1.5 hrs. The solvent was evaporated and residue was purified by flash chromatography (chloroform/methanol 10:1) to yield the product as a white solid (135 mg, 83%). (NMR***) Mass spectrum (M+H)$^+$ 819.4.

K. 3-{5-[4-(1-Triphenylmethylimidazol-2-ylamino)butyl] isoxazoline-3-carbonyl}amino-2-(S)-(2,4,6-trimethylbenzenesulfonylamino)propionic acid:

The product of Ex. 949, Part J, (130 mg, 0.16 mmol) was dissolved in a 1:1 mixture of trifluoroacetic acid and methylene chloride and stirred at room temperature for 5 hrs. The solvent was evaporated and crude product was purified on reverse phase HPLC (C18) to provide the desired product (75 mg, 73%). $^1$H NMR (acetone) δ 0.99–1.48, m, 6H, 2.27, s, 3H, 2.62, s, 6H, 2.67, m, 1H, 3.04–3.21, m, 1H, 3.31,q, J=6.6 Hz, 3.52–3.74, m, 1H, 4.14, m 1H, 4.60, m, 1H, 5.25, br.s, 1H, 6.70, d, J=2.6 Hz, 6.85, d, 1H, 6.98, s, 2H, 7.14, d, J=2.6 Hz, 7.33, m, 6H, 7.48, m, 9H, 7.68, q, 1H; mass spectrum, NH$_3$-DCI, 763.3, HRMS calc: 763.329094, found: 763.327781.

L. 3-{5-[4-(imidazol-2-ylamino)butyl]isoxazoline-3-carbonyl}amino-2S-(2,4,6-trimethylbenzenesulfonylamino) propionic acid trifluoroacetate salt:

The product of Ex. 949, Part K, (20 mg, 27 μmol) was dissolved in trifluoroacetic acid (2 mL). Water (0.01 mL) was added and the reaction mixture was refluxed for 1 h. The trifluoroacetic acid was evaporated and the crude reaction product was purified on reverse phase HPLC (C18) to yield the desired prodcut as a white solid (10 mg, 58%). $^1$H NMR 1.34–1.66, m 6H, 2.24, s, 3H, 2.53, s 6H, 2.67–2.76, m, 1H, 3.06–3.14, m 1H, 3.20, m, 2H, 3.30–3.48, m, 2H, 3.91, q, 1H, 4.70, m, 1H, 6.50, br,1H, 6.95, s, 2H, 6.95, s, 2H, 7.94, m, 2H, 8.23, m, 1H, 11.9, s, 2H, 12.5–12.8, br., 1H; Mass spectrum, ESI, (M+H)$^+$ 521.4, HRMS; calc. 521.219050, found 521.21823.

EXAMPLE 999j1

2-[(S)-((2,4,6-trimethylphenyl)sulfonyl)amino]-3-[5-(R,S)-(4-(N-(3,4,5,6-tetrahydropyridin-2-yl)amino) butylisoxazolin-3-ylcarbonyl]aminopropionic acid The product of example 849, part B (12 mg, 0.019 mM) was disolved in 50 mL of 1:1 ethyl alcohol and 2-propanol. 5% Palladium on barium sulfate (25 mg) was added and the reaction hydrogenated at 42 psi, at room temperature for 15 h. The reaction mixture was purged with nitrogen, filtered and concentrated in vacuo. The resulting oil was purified by reverse phase HPLC (water/acetonitrile gradient) to yield the title compound as a white powder. (9 mg, 75%) $^1$H NMR (CD$_3$OD) δ1.41–1.58 (m, 2H,), 1.62–1.77 (m, 2H), 1.79–1.86 (m, 2H), 2.26 (s, 3H), 2.57–2.64 (m, 2H), 2.59 (s, 6H), 2.74–3.12 (m, 2H), 3.17–3.23 (m, 2H), 3.26–3.32 (m, 2H), 3.34–3.64 (m, 4H), 4.01–4.06 (m, 1H0, 4.70–4.80 (m, 1H), 6.95 (s, 2H), 8.24–8.26 (q, 1H), 8.81–8.89 (br s, 1H); Mass spectrum, ESI, (M+H)$^+$ 536.5, base peak.

EXAMPLE 1001

3-[[3-[3-[(N-imidazolin-2-yl)amino]proxyloxy] isoxazol-5-yl]carbonylamino]propionic acid A. Methyl 3-[3-(tert-butyloxycarbonylamino)propyloxy]-5-isoxazolecarboxylate:

Diethylazodicarboxylate (1.46 g, 8.39 mmol) was added dropwise to a mixture of methyl 3-hydroxy-5-isoxazolecarboxylate (1 g, 4.55 mmol), triphenylphosphine (1.46 g, 8.39 mmol), and 3-tert-butyloxycarbonylamino-1-propanol (1.50 g, 8.39 mmol) in anhydrous tetrahydrofuran (10 mL) at 0° C. under nitrogen. After 1 h remove the ice bath and warm to room temperature overnight. Dilute with ethyl acetate (75 mL) and wash with water (25 mL), saturated NaHCO$_3$ (25 mL), and brine (25 mL). Dry over MgSO$_4$ then evaporate the solvent in vacuo. The residue was chromatographed over silica gel (75 g, 25 to 60% ethyl acetate/hex) to give the title compound (1.95 g, 95%) as a waxy solid: $^1$H NMR (300 MHz, CDCl$_3$) δ6.53 (s, 1H), 4.74 (bs, 1H), 4.36 (t, 2H), 3.95 (s, 3H), 3.28 (q, 2H), 2.00 (m, 2H), 1.44 (s, 9H); MS (CI-NH$_3$) m/e 318 (M+NH$_4$)$^+$; HRMS calc'd for C$_{13}$H$_{20}$N$_2$O$_6$+H: 301.1400, found 301.1403.

B. 3-[3-(tert-butyloxycarbonylamino)propyloxy]-5-isoxazole carboxylic acid:

Sodium Hydroxide (0.52 g, 13.0 mmol) in water (10 mL) was added in one portion to the product of Ex. 1001, Part A (1.95 g, 6.49 mmol) in methanol (20 mL) at room temperature. After 2 h the methanol was removed in vacuo and the residue was taken up in water (60 mL). The aqueous solution was washed with ether (30 mL, discard), then acidified to pH<2 with 10% HCl. Extraction with ethyl acetate (3×40 mL) was followed by washing the combined organic extracts with brine (40 mL) and drying over MgSO$_4$. The solvent was evaporated in vacuo to provide the desired acid (1.60 g, 86%) as a white solid: $^1$H NMR (300 MHz, CDCl$_3$) δ6.93 (s, 1H), 4.23 (t, 2H), 3.05 (q, 2H), 1.82 (m, 2H), 1.37 (s, 9H); MS (CI-NH$_3$) m/e 304 (M+NH$_4$)$^+$; HRMS calc'd for C$_{12}$H$_{18}$N$_2$O$_6$+H: 287.1243, found 287.1259.

C. Ethyl 3-[3-[3-(tert-butyloxycarbonyl amino)propyloxy] isoxazol-5-ylcarbonylamino]propionate:

Diisopropyethylamine (0.68 g, 5.24 mmol) was added dropwise to the compound of Ex. 1001, Part B (0.5 g, 1.75 mmol), O-(1H-benzotriazol-1-yl)-N,N,N',N'-tetramethyluronium tetrafluoroborate (0.70 g, 1,83 mmol), and ethyl β-alanine hydrochloride (0.28 g, 1.83 mmol) in anhydrous dichloromethane (30 mL) at 0° C. under nitrogen. After the addition was completed the mixture was allowed to warm to room temperature and stirred for 7 h. The reaction was diluted with dichloromethane (75 mL) then washed with water (25 mL), 5% HCl (25 mL), saturated NaHCO$_3$ (25 mL), and brine (25 mL). After drying over MgSO$_4$ the solvent was evaporated in vacuo and the residue chromatographed on silica gel (30 g, 40 to 75% ethyl acetate/hexanes) to provide the title compound (0.23 g, 34%) as a viscous oil: $^1$H NMR (300 MHz, CDCl$_3$) δ 7.05 (bt, 1H), 6.49 (s, 1H), 4.68 (bs, 1H), 4.32 (t, 2H), 4.18 (q, 2H), 3.70 (q, 2H), 3.27 (q, 2H), 2.62 (t, 2H), 1.99 (m, 2H), 1.44 (s, 9H), 1.28 (t, 3H); MS (CI-NH$_3$) m/e 403 (M+NH$_4$)$^+$; HRMS calc'd for C$_{17}$H$_{27}$N$_3$O$_7$+H: 386.1927, found 386.1909.

D. Ethyl 3-[3-(3-aminopropyloxy)isoxazol-5-ylcarbonylamino]propionate:

Trifluoroacetic acid (10 ml) was added in a slow stream to the compound of Ex. 1001, Part C (0.18 g 0.47 mmol) in dichloromethane (10 mL) at room temperature. After 45 min the trifluoroacetic acid was removed in vacuo and the residue was azotopically dried by evaporation in vacuo with toluene (20 mL), then place on a vacuum pump at 0.2 torr overnight. Upon dilution with chloroform the product crystallized out and was isolated as a white solid (0.14 g 75%): $^1$H NMR (300 MHz, CDCl$_3$) δ8.18 (bs, 3H), 7.80 (bt, 1H), 6.51 (s, 1H), 4.32 (m, 2H), 4.11 (q, 2H), 3.65 (q, 2H), 3.17 (m, 2H), 2.6 (t, 2H), 2.18 (m, 2H), 1.23 (t, 3H); MS (CI-NH$_3$) m/e 303 (M+NH$_4$)$^+$; HRMS calc'd for C$_{12}$H$_{29}$N$_3$O$_5$+H: 286.1403, found 286.1404.

E. Ethyl 3-[3-[3-(imidazolin-2-yl amino)propyloxy] isoxazol-5-ylcarbonylamino]propionate:

The compound of Ex. 1001, part D (0.22 g, 0.77 mmol) and 2-methylmercapto-4,5-dihydroimidazole hydroiodide (0.38 g, 1.54 mmol) were combined in ethanol (20 mL) and heated to reflux for 2 hours. The solvent was removed in vacuo and the residue was chromatographed over silica gel (20 g, 9:3:1:0.6, chloroform, methanol, water, acetic acid, lower layer) to provide the desired product (0.13 g, %) as a clear viscous oil: $^1$H NMR (300 MHz, D$_4$-MeOH) δ6.61 (s, 1H), 4.34 (t, 2H), 4.12 (q, 2H), 3.70 (s, 4H), 3.60 (t, 2H), 3.39 (t, 3H), 2.63 (t, 2H), 2.08 (m, 2H), 1,23 (t, 3H); MS (CI-NH$_3$) m/e 354 (M+H)$^+$.

F. 3-[3-[3-(imidazolin-2-ylamino)propyloxy]isoxazol-5-ylcarbonylamino]propionic acid:

Lithium hydroxide (0.5M, 1 mL) was added to the compound of Ex. 1001, part E (0.13 g, 0.25 mmol) in dioxane (2 mL) at room temperature. After 1 h the solution was acidified with HCl in dioxane (4M, 2 mL) and the solvent was removed in vacuo. The residue was chromatographed on silica gel (10 g, 9:3:1:0.6, chloroform, methanol, water, acetic acid, lower layer) and the product fractions were evaporated in vacuo. The product was taken up in methanol (1 mL) and tetrahydrofuran was added slowly. The mixture was stirred overnight and the title product precipitated out as a white solid (32 mg): m.p. 144°–7° C.; $^1$H NMR (300 MHz, $d_6$-DMSO) δ8.81 (bs, 2H), 6.77 (s, 1H), 6.76 (bs, 1H), 4.24 (m, 2H), 3.60 (q, 2H), 3.32 (m, 4H), 3.28 (m, 2H), 2.12 (m, 2H), 1.81 (m, 2H); MS (CI-NH$_3$) m/e 326 (M+H)$^+$; HRMS calc'd for $C_{13}H_{19}N_5O_5$+H: 326.1464, found 326.1462.

EXAMPLE 1003

2(S)-benzyloxycarbonylamino-3-[[3-[2-[(N-imidazolin-2-yl)amino]ethoxy]isoxazol-5-yl] carbonylamino]propionic acid A. [2-(tert-butyloxycarbonylamino)ethyl] methanesulfonate:

Methanesulfonyl chloride (8.2 g 71.6 mmol) in dichloromethane (45 mL) was added dropwise, over 8 min at ambient temperature to a stirring solution of 2-(t-butyloxycarbonylamino)ehtan-1-ol and TEA (9.83 g, 97.3 mmol) in dichloromethane (150 mL). After 2.5 hr the reaction mixture was washed with 1N HCl (2×50 mL), water (2×50 mL), and brine (50 mL) then dried over MgSO$_4$. The solution was filtered, and the solvent evaporated in vacuo to give the title compound (10.37 g, 67%). The resulting waxy solid could be used without further purification: $^1$H NMR (300 MHZ CDCl$_3$) δ 4.9(bs,1H), 4.3(t,2H), 3.3(q,2H) 3.04 (s,1H).

B. 3-[3-(tert-butyloxycarbonylamino)ethyloxy]-5-isoxazole carboxylic acid:

The compound of Ex. 1003. Part A (10.37 g, 43.3 mmol) in dimethylformamide (25 mL) was added dropwise over 10 min to a stirring solution of methyl 3-hydroxy-5-isoxazolecarboxylate and sodium carbonate (5.83 g, 55 mmol). The reaction was heated to 80° C. for 3 h, then stirred at ambient temperture for 18 h. 10% Potassium carbonate (≈200 ml) was added to the reaction mixture and was stirred until the resulting precipitate dissolved. After cooling to 3° C. the solution was acidified to pH≡2 with concentrated HCl. The solid was collected by vacuum filtration, washed with water, then air dried to give the title compound (5.6 g, 47.5%) as a white solid: mp 246° C. vigorous bubbling ~160°–170° C.; $^1$H NMR (300 MHz, CDCl$_3$) δ 6.51(s, 1H), 5.02(m, 1H), 4.35(t, 2H), 3.55(m, 2H), 1.43(s, 1H).

C. Methyl 2-benzyloxycarbonylamino-3-[3-[3-(tert-butyloxycarbonylamino)propyloxy]isoxazol-5-ylcarbonylamino]propionate:

Triethylamine (1.7 g, 16.7 mmol) was added in one portion to a mixture of the compound of Ex. 1003, Part B (1.68 g, 6.2 mmol), 1-(3-dimethylaminopropyl)-3-ethylcarbodiimide hydrochloride (1.8 g, 9.3 mmol), the compound of Ex. 1004, part A (2.14 g, 7.4 mmol) and hydroxybenztriazole (260 mg 1.9 mmol) in anhydrous dimethylformamide (10 mL) at ambient temperature. After 14 h the reaction was diluted with 1N HCl to six time the volume. The acidic solution was then extracted with ethyl acetate (5×30 mL) and the combined organic extracts were washed with 10% K$_2$CO$_3$ (3×50 ml), water (2×25 mL), and brine (25 mL). After drying over MgSO$_4$ the solvent was evaporated in vacuo. The crude product was triturated in 10% K$_2$CO$_3$, filtered, washed with water then air dried. The product thus obtained (1.85 g 59%) was isolated as a white crystaline solid and could be used with out further purification: $^1$H NMR (300 MHz, DMSO) δ 8.95 (m, 1H), 7.78 (d, 1H), 7.36–7.31 (m, 5H) 7.05 (m, 1H), 6.79 (s, 1H) 5.09–4.99 (dd, 2H), 4.35–4.28 (q, 1H), 4,23–4.19 (t, 2H), 3.62 (s, 3H), 3.58–3.56 (m, 2H), 3.32–3.28 (m, 2H), 1.37 (s,9H); MS (DCI-NH$_3$) m/e 524 (M+NH$_4$)$^+$.

D. 2-benzyloxycarbonylamino-3-[3-(2-tert-butyloxycarbonylamino)ethyloxy]isoxazol-5-yl carbonyl amino]propionic acid:

The compound of Ex. 1003, Part C (1.8 g, 3.6 mmol) was saponified using the procedure outlined for Ex. 1, Part C. The acid (0.81 g, 92%) was isolated as a brittle foam: $^1$H NMR (300 MHz, DMSO) δ8.92 (m, 1H) 7.62 (d, 1H) 7.35–7.30 (m,5H) 7.05 (m, 1H), 6.78 (s, 1H) 5.08–4.97 (dd, 2H) 4.27–4.19 (m, 3H) 3.60–3.55 (m 2H) 3.31–3.28 (m, 2H) 1.37 (s, 9H); MS (DCI-NH$_3$) m/e 510 (M+NH$_4$)$^+$.

E. 3-[3-(2-aminoethyloxy])isoxazol-5-ylcarbonylamino]-2-benzyloxycarbonylaminopropionic acid hydrochloride:

A solution of HCl in dioxane (4M, 10 mL) was added to the compound of Ex. 1003, Part C (1.6 g, 3.25 mmol) in 10 ml of dioxane. The mixture was stirred for 3 h at room temperature at which time a white solid had precipatated out. The product was filtered and washed with ether then dried overnight under vacuum (1.25 g, 90%): $^1$H NMR (300 MHz, DMSO) δ12.83 (bs, 1H), 9.06 (t, 1H), 8.24 (bs, 3H), 7.64 (d, 1H), 7.32 (m, 5H), 6.87 (s, 1H), 5.00 (s, 2H), 4.42 (t, 2H), 4.9.2 (m, 1H), 3.56 (m, 2H), 3.21 (m, 2H); MS (CI-NH$_3$); HRMS calc'd for $C_{17}H_{21}N_4O_7$+H: 393.1410, found 391.1391.

F. 2(S)-benzyloxycarbonylamino-3-[3-[2-(imidazolin-2-yl amino)ethyloxy]isoxazol-5-yl carbonyl amino]propionic acid:

2-methylthioimidazolinium iodide (114 mg, 0.5 mmol), the compound of Ex. 1003, Part E (0.10 g, 0.23 mmol), and dimethylamino pyridine (60 mg) were taken up in 1 ml of pyridine then heated to reflux for 2–3 min. The reaction was cooled to between 70°–80° C. and stirred for 24 hr. The solvent was removed in vacuo and the residue chromatographed on silica gel (20 g, 9:3:1:0.6, chloroform, methanol, water, and acetic acid, bottom layer). The product fractions were evaporated in vacuo and the resulting solid recrystallized from methanol/acetone to yield the title compound (33 mg, 31.2%) as a tan solid: mp 226.8° C. dec; $^1$H NMR (300 MHz, DMSO) δ8.82(m, 1H), 7.33 (m, 5H) 6.75 (d, 1H) 4.99 (s, 2H) 4.30–4.27(m, 2H), 3.58–3.52(m,7H), 3.33(m,1H); Mass Spec (ESI) m/e 461 (M+H)$^+$; HRMS calc'd for $C_{20}H_{25}N_6O_7$+H: 461.1784, found 461.1789.

EXAMPLE 1004

2(S)-benzyloxycarbonylamino-3-[[3-[3-[(N-imidazolin-2-yl)amino]propyloxy]isoxazol-5-yl] carbonylamino]propionic acid A. Methyl 3-amino-2(S)-(benzyloxycarbonyl) aminopropionate hydrochloride:

A solution of 4N HCl in dioxane (20 mL) was added to 3-amino-2-(benzyloxycarbonyl)aminopropanoic acid (2.39 g, 10 mmol) in methanol (20 mL) and the solution was stirred for 2 hours. The solvents was removed in vacuo to give the methyl ester (2.74 g, 95%) as a white solid product. NMR (DMSO-d$_6$): δ 8.38 (b, 3H); 7.96 (d, 1H); 7.38 (m, 5H); 5.05 (s, 2H); 4.44 (m, 1H); 3.66 (s, 3H); 3.14 (m, 2H)

B. Methyl 2-benzyloxycarbonylamino-3-[3-[3-(tert-butyloxycarbonylamino)propyloxy]isoxazol-5-ylcarbonylamino]propionate:

Diisopropylethylamine (0.54 g, 4.17 mmol) was added dropwise to a mixture of the compound of Ex. 1001, Part B (1.0 g, 3.48 mmol), 1-(3-dimethylaminopropyl)-3- ethylcarbodiimide hydrochloride (0.70 g, 3.65 mmol), and the compound of Example 1004, Part A (1.0 g, 3.48 mmol) in anhydrous dimethylformamide (10 mL) at 0° C. under nitrogen. After 48 h the reaction was diluted with water (75 mL) then extraced with ethyl acetate (3×30 mL). The combined organic extracts were washed with water (2×25 mL) and brine (25 mL). After drying over $MgSO_4$ the sovent was evaporated in vacuo and the residue chromatographed on silica gel (30 g, 30 to 75% ethyl acetate/hexanes) to provide the title compound (0.90 g, 50%) as a viscous oil: $^1$H NMR (300 MHz, $CDCl_3$) δ 7.35 (m, 5H), 7.03 (bt, 1H), 6.49 (s, 1H), 5.78 (d, 1H), 5.13 (s, 1H), 4.73 (bt, 1H), 4.54 (q, 1H), 4.35 (t, 2H), 3.86 (t, 2H), 3.79 (s, 3H), 3.28 (q, 2H), 1.99 (m, 2H), 1.44 (s, 9H); MS ($CI-NH_3$) m/e 538 $(M+NH_4)^+$; HRMS calc'd for $C_{24}H_{32}N_4O_9$+H: 521.2248, found 521.2266.

C. 3-[3-[3-(tert-butyloxycarbonylamino)propyloxy] isoxazol-5-yl carbonyl amino]-2-benzyloxycarbonylaminopropionic acid:

The compound of Ex. 1004, Part B (0.9 g, 1.73 mmol) was saponified using the procedure outlined for Example 1001, Part C. The acid (0.81 g, 92%) was isolated as a brittle foam: $^1$H NMR (300 MHz, DMSO) δ 8.91 (bt, 1H), 7.62 (d, 1H), 7.34 (m, 5H), 6.91 (bt, 1H), 6.78 (s, 1H), 5.03 (dd, 2H), 4.22 (m, 3H), 3.59 (m, 2H), 3.05 (q, 2H), 1.84 (m, 2H), 1.37 (s, 9H); MS ($CI-NH_3$) m/e 524 $(M+NH_4)^+$; HRMS calc'd for $C_{23}H_{30}N_4O_9$+H: 507.2091, found 507.2105.

D. 3-[3-(3-aminopropyloxy])isoxazol-5-ylcarbonylamino]-2(S)-benzyloxycarbonylaminopropionic acid hydrochloride:

A solution of HCl in dioxane (4M, 10 mL) was added to the compound of Example 1004 Part C (0.81 g, 1.60 mmol) dropwise. The mixture was stirred for 3 h at room temperature, at which time a white solid had precipatated out. The product was filtered then washed with ether and dried overnight under vacuum (0.58 g, 82%): $^1$H NMR (300 MHz, DMSO) δ12.83 (s, 1H), 8.98 (t, 1H), 7.88(bs, 3H), 7.64 (d, 1H), 7.34 (m, 5H), 6.83 (s, 1H), 5.03 (s, 2H), 4.31 (t, 2H), 4.27 (m, 1H), 3.40 (m, 2H), 2.92 (m, 2H), 2.04 (m, 2H); MS ($CI-NH_3$) m/e 407 $(M+H)^+$; HRMS calc'd for $C_{18}H_{22}N_4O_7$+H: 407.1567, found 407.1553.

E. 3-[3-[3-(imidazolin-2-yl amino)propyloxy]isoxazol-5-yl carbonyl amino]-2-benzyloxycarbonylaminopropionic acid hydroiodide:

The compound of Ex. 1004, Part D (0.42 g, 0.95 mmol) and 2-methylmercapto-4,5-dihydroimidazole hydroiodide (0.35 g, 1.42 mmol) were combined in pyridine (2 mL) and heated to reflux for 4 h. Additional 2-methylmercapto-4,5-dihydroimidazole hydroiodide (0.35 g, 1.42 mmol) was added and the heating was continued for 2 h. The pyridine was removed in vacuo and the residue was chromatographed over silica gel (25 g, 9:3:1:0.6, chloroform, methanol, water, acetic acid, lower layer). The product fractions were combined and the solvent removed in vacuo. The residue was taken up in DMSO (1.5 ml) followed by addition of methanol (3 mL) then the slow addition of tetrahydrofuran (40 mL). The mixture was stirred for 30 min then filtered to provide the title compound (0.19 g, 34%) as a tan solid: m.p. 201°-2° C. (dec); $^1$H NMR 10.14 (bs, 1H), 9.64 (bs, 1H), 8.87 (bt, 1H), 7.34 (m, 5H), 6.78 (d, 1H), 6.75 (s, 1H), 5.00 (s, 2H), 4.22 (t, 2H), 3.85 (q, 1H), 3.56 (s, 4H), 3.55 (m, 1H), 3.23 (m, 3H), 1.92 (m, 2H); MS (esi) m/e 475 $(M+H)^+$; HRMS calc'd for $C_{21}H_{26}N_6O_7$+H: 475.1941, found 475.1942.

Using the above procedures and modifications known to one skilled in the art of organic synthesis the following additional examples of Tables 1–5 may be prepared.

TABLE 1

| Ex. No. | $R^1$-U | m | n | $R^8$ | $R^9$ | MS |
|---|---|---|---|---|---|---|
| 1 | tetrahydropyrimidin-2-ylamino | 3 | 1 | H | H | |
| 2 | tetrahydropyrimidin-2-ylamino | 3 | 1 | H | NHCbz | 489.2 |
| 3 | tetrahydropyrimidin-2-ylamino | 3 | 1 | H | NHtBOC | |
| 4 | tetrahydropyrimidin-2-ylamino | 3 | 1 | H | $NHCO_2$-nBu | |
| 5 | tetrahydropyrimidin-2-ylamino | 3 | 1 | H | $NHCO_2Et$ | |
| 6 | tetrahydropyrimidin-2-ylamino | 3 | 1 | H | $NHCO_2Me$ | |
| 7 | tetrahydropyrimidin-2-ylamino | 3 | 1 | H | $NHCO(CH_2)_nPh$ | |
| 8 | tetrahydropyrimidin-2-ylamino | 3 | 1 | H | NHCOtBu | |
| 9 | tetrahydropyrimidin-2-ylamino | 3 | 1 | H | NHCO-n-$C_5H_{11}$ | |
| 10 | tetrahydropyrimidin-2-ylamino | 3 | 1 | H | NHCO-n-$C_4H_9$ | |
| 11 | tetrahydropyrimidin-2-ylamino | 3 | 1 | H | $NHCOCH_2CH_3$ | |
| 12 | tetrahydropyrimidin-2-ylamino | 3 | 1 | H | $NHCOCH_3$ | |
| 13 | tetrahydropyrimidin-2-ylamino | 3 | 1 | H | $NHSO_2CH_3$ | |
| 14 | tetrahydropyrimidin-2-ylamino | 3 | 1 | H | $NHSO_2CH_2CH_3$ | |

TABLE 1-continued $$R^1-U-(CH_2)_m-C(=N-O)-CH_2-(CH_2)_n-C(=O)-NH-CHR^8-CHR^9-COOH$$

| Ex. No. | R¹-U | m | n | R⁸ | R⁹ | MS |
|---|---|---|---|---|---|---|
| 15 | tetrahydropyrimidin-2-ylamino | 3 | 1 | H | NHSO₂n-Bu | |
| 16 | tetrahydropyrimidin-2-ylamino | 3 | 1 | H | NHSO₂Ph | 495.2 |
| 17 | tetrahydropyrimidin-2-ylamino | 3 | 1 | H | NHSO₂C₆H₄(4-CH₃) | |
| 18 | tetrahydropyrimidin-2-ylamino | 3 | 1 | H | NHSO₂Bn | |
| 19 | tetrahydropyrimidin-2-ylamino | 3 | 1 | H | NHCO(2-pyridyl) | |
| 20 | tetrahydropyrimidin-2-ylamino | 3 | 1 | H | NHCO(3-pyridyl) | |
| 21 | tetrahydropyrimidin-2-ylamino | 3 | 1 | H | NHCO(4-pyridyl) | |
| 22 | tetrahydropyrimidin-2-ylamino | 3 | 1 | H | NHCOCH₂(2-pyridyl) | |
| 23 | tetrahydropyrimidin-2-ylamino | 3 | 1 | H | NHCOCH₂(3-pyridyl) | |
| 24 | tetrahydropyrimidin-2-ylamino | 3 | 1 | H | NHCOCH₂(4-pyridyl) | |
| 25 | tetrahydropyrimidin-2-ylamino | 3 | 1 | H | NHCO₂CH₂(2-pyridyl) | |
| 26 | tetrahydropyrimidin-2-ylamino | 3 | 1 | H | NHCO₂CH₂(3-pyridyl) | |
| 27 | tetrahydropyrimidin-2-ylamino | 3 | 1 | H | NHCO₂CH₂(4-pyridyl) | |
| 28 | imidazolin-2-ylamino | 3 | 1 | H | H | |
| 29 | imidazolin-2-ylamino | 3 | 1 | H | NHCbz | |
| 30 | imidazolin-2-ylamino | 3 | 1 | H | NHtBOC | |
| 31 | imidazolin-2-ylamino | 3 | 1 | H | NHCO₂-nBu | |
| 32 | imidazolin-2-ylamino | 3 | 1 | H | NHCO₂Et | |
| 33 | imidazolin-2-ylamino | 3 | 1 | H | NHCO₂Me | |
| 34 | imidazolin-2-ylamino | 3 | 1 | H | NHCO(CH₂)ₙPh | |
| 35 | imidazolin-2-ylamino | 3 | 1 | H | NHCOtBu | |
| 36 | imidazolin-2-ylamino | 3 | 1 | H | NHCO-n-C₅H₁₁ | |
| 37 | imidazolin-2-ylamino | 3 | 1 | H | NHCO-n-C₄H₉ | |
| 38 | imidazolin-2-ylamino | 3 | 1 | H | NHCOCH₂CH₃ | |
| 39 | imidazolin-2-ylamino | 3 | 1 | H | NHCOCH₃ | |
| 40 | imidazolin-2-ylamino | 3 | 1 | H | NHSO₂CH₃ | |
| 41 | imidazolin-2-ylamino | 3 | 1 | H | NHSO₂CH₂CH₃ | |
| 42 | imidazolin-2-ylamino | 3 | 1 | H | NHSO₂n-Bu | |
| 43 | imidazolin-2-ylamino | 3 | 1 | H | NHSO₂Ph | |
| 44 | imidazolin-2-ylamino | 3 | 1 | H | NHSO₂C₆H₄(4-CH₃) | |
| 45 | imidazolin-2-ylamino | 3 | 1 | H | NHSO₂Bn | |
| 46 | imidazolin-2-ylamino | 3 | 1 | H | NHCO(2-pyridyl) | |
| 47 | imidazolin-2-ylamino | 3 | 1 | H | NHCO(3-pyridyl) | |
| 48 | imidazolin-2-ylamino | 3 | 1 | H | NHCO(4-pyridyl) | |
| 49 | imidazolin-2-ylamino | 3 | 1 | H | NHCOCH₂(2-pyridyl) | |

TABLE 1-continued $$R^1-U-(CH_2)_m-C(=N-O)-CH_2-CH(-(CH_2)_n-C(=O)-NH-CR^8(R^9)-C(=O)-OH)$$

| Ex. No. | R¹-U | m | n | R⁸ | R⁹ | MS |
|---|---|---|---|---|---|---|
| 50 | imidazolin-2-ylamino | 3 | 1 | H | NHCOCH$_2$(3-pyridyl) | |
| 51 | imidazolin-2-ylamino | 3 | 1 | H | NHCOCH$_2$(4-pyridyl) | |
| 52 | imidazolin-2-ylamino | 3 | 1 | H | NHCO$_2$CH$_2$(2-pyridyl) | |
| 53 | imidazolin-2-ylamino | 3 | 1 | H | NHCO$_2$CH$_2$(3-pyridyl) | |
| 54 | imidazolin-2-ylamino | 3 | 1 | H | NHCO$_2$CH$_2$(4-pyridyl) | |
| 55 | tetrahydropyrimidin-2-ylamino | 4 | 0 | H | H | |
| 56 | tetrahydropyrimidin-2-ylamino | 4 | 0 | H | NHCbz | 489.3 |
| 57 | tetrahydropyrimidin-2-ylamino | 4 | 0 | H | NHtBOC | |
| 58 | tetrahydropyrimidin-2-ylamino | 4 | 0 | H | NHCO$_2$-nBu | |
| 59 | tetrahydropyrimidin-2-ylamino | 4 | 0 | H | NHCO$_2$Et | |
| 60 | tetrahydropyrimidin-2-ylamino | 4 | 0 | H | NHCO$_2$Me | |
| 61 | tetrahydropyrimidin-2-ylamino | 4 | 0 | H | NHCO(CH$_2$)$_n$Ph | |
| 62 | tetrahydropyrimidin-2-ylamino | 4 | 0 | H | NHCOtBu | |
| 63 | tetrahydropyrimidin-2-ylamino | 4 | 0 | H | NHCO-n-C$_5$H$_{11}$ | |
| 64 | tetrahydropyrimidin-2-ylamino | 4 | 0 | H | NHCO-n-C$_4$H$_9$ | |
| 65 | tetrahydropyrimidin-2-ylamino | 4 | 0 | H | NHCOCH$_2$CH$_3$ | |
| 66 | tetrahydropyrimidin-2-ylamino | 4 | 0 | H | NHCOCH$_3$ | |
| 67 | tetrahydropyrimidin-2-ylamino | 4 | 0 | H | NHSO$_2$CH$_3$ | |
| 68 | tetrahydropyrimidin-2-ylamino | 4 | 0 | H | NHSO$_2$CH$_2$CH$_3$ | |
| 69 | tetrahydropyrimidin-2-ylamino | 4 | 0 | H | NHSO$_2$n-Bu | |
| 70 | tetrahydropyrimidin-2-ylamino | 4 | 0 | H | NHSO$_2$Ph | |
| 71 | tetrahydropyrimidin-2-ylamino | 4 | 0 | H | NHSO$_2$C$_6$H$_4$(4-CH$_3$) | |
| 72 | tetrahydropyrimidin-2-ylamino | 4 | 0 | H | NHSO$_2$Bn | |
| 73 | tetrahydropyrimidin-2-ylamino | 4 | 0 | H | NHCO(2-pyridyl) | |
| 74 | tetrahydropyrimidin-2-ylamino | 4 | 0 | H | NHCO(3-pyridyl) | |
| 75 | tetrahydropyrimidin-2-ylamino | 4 | 0 | H | NHCO(4-pyridyl) | |
| 76 | tetrahydropyrimidin-2-ylamino | 4 | 0 | H | NHCOCH$_2$(2-pyridyl) | |
| 77 | tetrahydropyrimidin-2-ylamino | 4 | 0 | H | NHCOCH$_2$(3-pyridyl) | |
| 78 | tetrahydropyrimidin-2-ylamino | 4 | 0 | H | NHCOCH$_2$(4-pyridyl) | |
| 79 | tetrahydropyrimidin-2-ylamino | 4 | 0 | H | NHCO$_2$CH$_2$(2-pyridyl) | |
| 80 | tetrahydropyrimidin-2-ylamino | 4 | 0 | H | NHCO$_2$CH$_2$(3-pyridyl) | |
| 81 | tetrahydropyrimidin-2-ylamino | 4 | 0 | H | NHCO$_2$CH$_2$(4-pyridyl) | |
| 82 | imidazolin-2-ylamino | 4 | 0 | H | H | |
| 83 | imidazolin-2-ylamino | 4 | 0 | H | NHCbz | 475.3 |
| 84 | imidazolin-2-ylamino | 4 | 0 | H | NHtBOC | |

TABLE 1-continued $$R^1-U-(CH_2)_m-\underset{N-O}{C}-CH_2-(CH_2)_n-\underset{O}{C}-\underset{H}{N}-\underset{R^8}{\overset{R^9}{C}}-\underset{O}{C}-OH$$

| Ex. No. | R¹-U | m | n | R⁸ | R⁹ | MS |
|---|---|---|---|---|---|---|
| 85 | imidazolin-2-ylamino | 4 | 0 | H | NHCO$_2$-nBu | |
| 86 | imidazolin-2-ylamino | 4 | 0 | H | NHCO$_2$Et | |
| 87 | imidazolin-2-ylamino | 4 | 0 | H | NHCO$_2$Me | |
| 88 | imidazolin-2-ylamino | 4 | 0 | H | NHCO(CH$_2$)$_n$Ph | |
| 89 | imidazolin-2-ylamino | 4 | 0 | H | NHCOtBu | |
| 90 | imidazolin-2-ylamino | 4 | 0 | H | NHCO-n-C$_5$H$_{11}$ | |
| 91 | imidazolin-2-ylamino | 4 | 0 | H | NHCO-n-C$_4$H$_9$ | |
| 92 | imidazolin-2-ylamino | 4 | 0 | H | NHCOCH$_2$CH$_3$ | |
| 93 | imidazolin-2-ylamino | 4 | 0 | H | NHCOCH$_3$ | |
| 94 | imidazolin-2-ylamino | 4 | 0 | H | NHSO$_2$CH$_3$ | |
| 95 | imidazolin-2-ylamino | 4 | 0 | H | NHSO$_2$CH$_2$CH$_3$ | |
| 96 | imidazolin-2-ylamino | 4 | 0 | H | NHSO$_2$n-Bu | |
| 97 | imidazolin-2-ylamino | 4 | 0 | H | NHSO$_2$Ph | |
| 98 | imidazolin-2-ylamino | 4 | 0 | H | NHSO$_2$C$_6$H$_4$(4-CH$_3$) | |
| 99 | imidazolin-2-ylamino | 4 | 0 | H | NHSO$_2$Bn | |
| 100 | imidazolin-2-ylamino | 4 | 0 | H | NHCO(2-pyridyl) | |
| 101 | imidazolin-2-ylamino | 4 | 0 | H | NHCO(3-pyridyl) | |
| 102 | imidazolin-2-ylamino | 4 | 0 | H | NHCO(4-pyridyl) | |
| 103 | imidazolin-2-ylamino | 4 | 0 | H | NHCOCH$_2$(2-pyridyl) | |
| 104 | imidazolin-2-ylamino | 4 | 0 | H | NHCOCH$_2$(3-pyridyl) | |
| 105 | imidazolin-2-ylamino | 4 | 0 | H | NHCOCH$_2$(4-pyridyl) | |
| 106 | imidazolin-2-ylamino | 4 | 0 | H | NHCO$_2$CH$_2$(2-pyridyl) | |
| 107 | imidazolin-2-ylamino | 4 | 0 | H | NHCO$_2$CH$_2$(3-pyridyl) | |
| 108 | imidazolin-2-ylamino | 4 | 0 | H | NHCO$_2$CH$_2$(4-pyridyl) | |
| 109 | tetrahydropyrimidin-2-ylamino | 3 | 0 | H | H | |
| 110 | tetrahydropyrimidin-2-ylamino | 3 | 0 | H | NHCbz | 475.3 |
| 111 | tetrahydropyrimidin-2-ylamino | 3 | 0 | H | NHtBOC | |
| 112 | tetrahydropyrimidin-2-ylamino | 3 | 0 | H | NHCO$_2$-nBu | |
| 113 | tetrahydropyrimidin-2-ylamino | 3 | 0 | H | NHCO$_2$Et | |
| 114 | tetrahydropyrimidin-2-ylamino | 3 | 0 | H | NHCO$_2$Me | |
| 115 | tetrahydropyrimidin-2-ylamino | 3 | 0 | H | NHCO(CH$_2$)$_n$Ph | |
| 116 | tetrahydropyrimidin-2-ylamino | 3 | 0 | H | NHCOtBu | |
| 117 | tetrahydropyrimidin-2-ylamino | 3 | 0 | H | NHCO-n-C$_5$H$_{11}$ | |
| 118 | tetrahydropyrimidin-2-ylamino | 3 | 0 | H | NHCO-n-C$_4$H$_9$ | |
| 119 | tetrahydropyrimidin-2-ylamino | 3 | 0 | H | NHCOCH$_2$CH$_3$ | |

TABLE 1-continued $$R^1-U-\overset{(CH_2)_m}{\underset{N-O}{\diagdown}}\overset{}{\diagup}(CH_2)_n-\overset{H}{\underset{O}{N}}-\overset{R^9}{\underset{R^8}{\overset{}{\diagup}}}\overset{OH}{\underset{O}{\diagdown}}$$

| Ex. No. | R¹-U | m | n | R⁸ | R⁹ | MS |
|---|---|---|---|---|---|---|
| 120 | tetrahydropyrimidin-2-ylamino | 3 | 0 | H | NHCOCH₃ | |
| 121 | tetrahydropyrimidin-2-ylamino | 3 | 0 | H | NHSO₂CH₃ | |
| 122 | tetrahydropyrimidin-2-ylamino | 3 | 0 | H | NHSO₂CH₂CH₃ | |
| 123 | tetrahydropyrimidin-2-ylamino | 3 | 0 | H | NHSO₂n-Bu | |
| 124 | tetrahydropyrimidin-2-ylamino | 3 | 0 | H | NHSO₂Ph | 481.2 |
| 125 | tetrahydropyrimidin-2-ylamino | 3 | 0 | H | NHSO₂C₆H₄(4-CH₃) | |
| 126 | tetrahydropyrimidin-2-ylamino | 3 | 0 | H | NHSO₂Bn | |
| 127 | tetrahydropyrimidin-2-ylamino | 3 | 0 | H | NHCO(2-pyridyl) | |
| 128 | tetrahydropyrimidin-2-ylamino | 3 | 0 | H | NHCO(3-pyridyl) | |
| 129 | tetrahydropyrimidin-2-ylamino | 3 | 0 | H | NHCO(4-pyridyl) | |
| 130 | tetrahydropyrimidin-2-ylamino | 3 | 0 | H | NHCOCH₂(2-pyridyl) | |
| 131 | tetrahydropyrimidin-2-ylamino | 3 | 0 | H | NHCOCH₂(3-pyridyl) | |
| 132 | tetrahydropyrimidin-2-ylamino | 3 | 0 | H | NHCOCH₂(4-pyridyl) | |
| 133 | tetrahydropyrimidin-2-ylamino | 3 | 0 | H | NHCO₂CH₂(2-pyridyl) | |
| 134 | tetrahydropyrimidin-2-ylamino | 3 | 0 | H | NHCO₂CH₂(3-pyridyl) | |
| 135 | tetrahydropyrimidin-2-ylamino | 3 | 0 | H | NHCO₂CH₂(4-pyridyl) | |
| 136 | imidazolin-2-ylamino | 3 | 0 | H | H | |
| 137 | imidazolin-2-ylamino | 3 | 0 | H | NHCbz | 461.2 |
| 138 | imidazolin-2-ylamino | 3 | 0 | H | NHtBOC | |
| 139 | imidazolin-2-ylamino | 3 | 0 | H | NHCO₂-nBu | |
| 140 | imidazolin-2-ylamino | 3 | 0 | H | NHCO₂Et | |
| 141 | imidazolin-2-ylamino | 3 | 0 | H | NHCO₂Me | |
| 142 | imidazolin-2-ylamino | 3 | 0 | H | NHCO(CH₂)ₙPh | |
| 143 | imidazolin-2-ylamino | 3 | 0 | H | NHCOtBu | |
| 144 | imidazolin-2-ylamino | 3 | 0 | H | NHCO-n-C₅H₁₁ | |
| 145 | imidazolin-2-ylamino | 3 | 0 | H | NHCO-n-C₄H₉ | |
| 146 | imidazolin-2-ylamino | 3 | 0 | H | NHCOCH₂CH₃ | |
| 147 | imidazolin-2-ylamino | 3 | 0 | H | NHCOCH₃ | |
| 148 | imidazolin-2-ylamino | 3 | 0 | H | NHSO₂CH₃ | |
| 149 | imidazolin-2-ylamino | 3 | 0 | H | NHSO₂CH₂CH₃ | |
| 150 | imidazolin-2-ylamino | 3 | 0 | H | NHSO₂n-Bu | |
| 151 | imidazolin-2-ylamino | 3 | 0 | H | NHSO₂Ph | |
| 152 | imidazolin-2-ylamino | 3 | 0 | H | NHSO₂C₆H₄(4-CH₃) | |
| 153 | imidazolin-2-ylamino | 3 | 0 | H | NHSO₂Bn | |
| 154 | imidazolin-2-ylamino | 3 | 0 | H | NHCO(2-pyridyl) | |

TABLE 1-continued

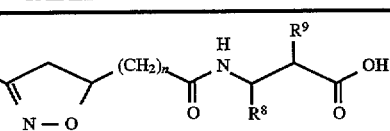

| Ex. No. | R¹-U | m | n | R⁸ | R⁹ | MS |
|---|---|---|---|---|---|---|
| 155 | imidazolin-2-ylamino | 3 | 0 | H | NHCO(3-pyridyl) | |
| 156 | imidazolin-2-ylamino | 3 | 0 | H | NHCO(4-pyridyl) | |
| 157 | imidazolin-2-ylamino | 3 | 0 | H | NHCOCH$_2$(2-pyridyl) | |
| 158 | imidazolin-2-ylamino | 3 | 0 | H | NHCOCH$_2$(3-pyridyl) | |
| 159 | imidazolin-2-ylamino | 3 | 0 | H | NHCOCH$_2$(4-pyridyl) | |
| 160 | imidazolin-2-ylamino | 3 | 0 | H | NHCO$_2$CH$_2$(2-pyridyl) | |
| 161 | imidazolin-2-ylamino | 3 | 0 | H | NHCO$_2$CH$_2$(3-pyridyl) | |
| 162 | imidazolin-2-ylamino | 3 | 0 | H | NHCO$_2$CH$_2$(4-pyridyl) | |
| 172 | pyridin-2-ylamino | 3 | 1 | H | NHCbz | 484.2 |
| 173 | pyridin-2-ylamino | 3 | 1 | H | NHCO$_2$-n-Bu | |
| 174 | pyridin-2-ylamino | 3 | 1 | H | NHSO$_2$Ph | |
| 175 | pyridin-2-ylamino | 3 | 1 | H | NHSO$_2$-Ph | |
| 176 | pyridin-2-ylamino | 4 | 0 | H | NHCbz | 484.4 |
| 177 | pyridin-2-ylamino | 4 | 0 | H | NHCO$_2$-n-Bu | |
| 178 | pyridin-2-ylamino | 4 | 0 | H | NHSO$_2$Ph | |
| 179 | pyridin-2-ylamino | 4 | 0 | H | NHSO$_2$-nBu | |
| 180 | pyridin-2-ylamino | 3 | 0 | H | NHCbz | |
| 181 | pyridin-2-ylamino | 3 | 0 | H | NHCO$_2$-n-Bu | |
| 182 | pyridin-2-ylamino | 3 | 0 | H | NHSO$_2$Ph | |
| 183 | pyridin-2-ylamino | 3 | 0 | H | NHSO$_2$-nBu | |
| 184 | imidazol-2-ylamino | 3 | 1 | H | NHCbz | |
| 185 | imidazol-2-ylamino | 3 | 1 | H | NHCO$_2$-n-Bu | |
| 186 | imidazol-2-ylamino | 3 | 1 | H | NHSO$_2$Ph | |
| 187 | imidazol-2-ylamino | 3 | 1 | H | NHSO$_2$-nBu | |
| 188 | imidazol-2-ylamino | 4 | 0 | H | NHCbz | |
| 189 | imidazol-2-ylamino | 4 | 0 | H | NHCO$_2$-n-Bu | |
| 190 | imidazol-2-ylamino | 4 | 0 | H | NHSO$_2$Ph | |
| 191 | imidazol-2-ylamino | 4 | 0 | H | NHSO$_2$-nBu | |
| 192 | imidazol-2-ylamino | 3 | 0 | H | NHCbz | |
| 193 | imidazol-2-ylamino | 3 | 0 | H | NHCO$_2$-n-Bu | |
| 194 | imidazol-2-ylamino | 3 | 0 | H | NHSO$_2$Ph | |
| 195 | imidazol-2-ylamino | 3 | 0 | H | NHSO$_2$-nBu | |
| 196 | thiazol-2-ylamino | 3 | 1 | H | NHCbz | |
| 197 | 2-aminopyridin-6-yl | 3 | 1 | H | NHCO$_2$-n-Bu | |
| 198 | 2-aminopyridin-6-yl | 3 | 1 | H | NHSO$_2$Ph | |
| 199 | 2-aminopyridin-6-yl | 3 | 1 | H | NHSO$_2$-nBu | |
| 200 | 2-aminopyridin-6-yl | 4 | 0 | H | NHCbz | |
| 201 | 2-aminopyridin-6-yl | 4 | 0 | H | NHCO$_2$-n-Bu | |
| 202 | 2-aminopyridin-6-yl | 4 | 0 | H | NHSO$_2$Ph | |
| 203 | 2-aminopyridin-6-yl | 4 | 0 | H | NHSO$_2$-nBu | |
| 204 | 2-aminopyridin-6-yl | 3 | 0 | H | NHCbz | |
| 205 | 2-aminopyridin-6-yl | 3 | 0 | H | NHCO$_2$-n-Bu | |
| 206 | 2-aminopyridin-6-yl | 3 | 0 | H | NHSO$_2$Ph | |
| 207 | 2-aminopyridin-6-yl | 3 | 0 | H | NHSO$_2$-nBu | |
| 208 | 2-aminopyridin-3-yl | 2 | 0 | H | NHCbz | |
| 209 | 2-aminopyridin-3-yl | 2 | 0 | H | NHCO$_2$-n-Bu | |
| 210 | 2-aminopyridin-3-yl | 2 | 0 | H | NHSO$_2$Ph | |
| 211 | 2-aminopyridin-3-yl | 2 | 0 | H | NHSO$_2$-nBu | |
| 212 | 2-aminothiazol-4-yl | 3 | 1 | H | NHCbz | |
| 213 | 2-aminothiazol-4-yl | 3 | 1 | H | NHCO$_2$-n-Bu | |
| 214 | 2-aminothiazol-4-yl | 3 | 1 | H | NHSO$_2$Ph | |
| 215 | 2-aminothiazol-4-yl | 3 | 1 | H | NHSO$_2$-nBu | |
| 216 | 2-aminothiazol-4-yl | 4 | 0 | H | NHCbz | |
| 217 | 2-aminothiazol-4-yl | 4 | 0 | H | NHCO$_2$-n-Bu | |
| 218 | 2-aminothiazol-4-yl | 4 | 0 | H | NHSO$_2$Ph | |
| 219 | 2-aminopyridin-6-yl | 4 | 0 | H | NHSO$_2$-nBu | |
| 220 | 2-aminothiazol-4-yl | 3 | 0 | H | NHCbz | |
| 221 | 2-aminothiazol-4-yl | 3 | 0 | H | NHCO$_2$-n-Bu | |
| 222 | 2-aminothiazol-4-yl | 3 | 0 | H | NHSO$_2$Ph | |
| 223 | 2-aminothiazol-4-yl | 3 | 0 | H | NHSO$_2$-nBu | |
| 224 | 2-aminothiazol-4-yl | 3 | 1 | H | NHCbz | |
| 225 | 2-aminothiazol-4-yl | 3 | 1 | H | NHCO$_2$-n-Bu | |

TABLE 1-continued $$R^1-U\underset{N-O}{\overset{(CH_2)_m}{\diagdown}}(CH_2)_n\underset{O}{\overset{H}{\underset{|}{N}}}\underset{R^8}{\overset{R^9}{\underset{|}{C}}}\underset{O}{\overset{OH}{\diagdown}}$$

| Ex. No. | R¹-U | m | n | R⁸ | R⁹ | MS |
|---|---|---|---|---|---|---|
| 284 | imidazolin-2-ylamino | 2 | 2 | H | NHCbz | 475.3 |
| 285 | imidazolin-2-ylamino | 2 | 2 | H | NHCO₂-n-Bu | |
| 286 | imidazolin-2-ylamino | 2 | 2 | H | NHSO₂Ph | |
| 287 | imidazolin-2-ylamino | 2 | 2 | H | NHSO₂-nBu | |
| 288 | tetrahydropyrimidin-2-ylamino | 2 | 2 | H | NHCbz | 489.4 |
| 289 | tetrahydropyrimidin-2-ylamino | 2 | 2 | H | NHCO₂-n-Bu | |
| 290 | tetrahydropyrimidin-2-ylamino | 2 | 2 | H | NHSO₂Ph | |
| 291 | tetrahydropyrimidin-2-ylamino | 2 | 2 | H | NHSO₂-nBu | |
| 292 | benzimidazol-2-ylamino | 4 | 0 | H | NHCbz | |
| 293 | benzthiazol-2-ylamino | 4 | 0 | H | NHCbz | |
| 296 | imidazol-4-ylamino | 4 | 0 | H | NHCbz | |
| 303 | 2-iminopyrrolidin-5-yl | 3 | 1 | H | NHCbz | |
| 304 | 2-iminopyrrolidin-5-yl | 3 | 1 | H | NHSO₂Ph | |
| 305 | 2-iminopyrrolidin-5-yl | 3 | 0 | H | NHCbz | |
| 306 | 2-iminopyrrolidin-5-yl | 3 | 0 | H | NHSO₂Ph | |
| 307 | 2-iminopyrrolidin-5-yl | 2 | 1 | H | NHCbz | |
| 308 | 2-iminopyrrolidin-5-yl | 2 | 1 | H | NHSO₂Ph | |
| 309 | 2-iminopiperidin-6-yl | 3 | 1 | H | NHCbz | |
| 310 | 2-iminopiperidin-6-yl | 3 | 1 | H | NHSO₂Ph | |
| 311 | 2-iminopiperidin-6-yl | 3 | 0 | H | NHCbz | |
| 312 | 2-iminopiperidin-6-yl | 3 | 0 | H | NHSO₂Ph | |
| 313 | 2-iminopiperidin-6-yl | 2 | 1 | H | NHCbz | |
| 314 | 2-iminopiperidin-6-yl | 2 | 1 | H | NHSO₂Ph | |
| 315 | 2-iminoazepin-7-yl | 3 | 1 | H | NHCbz | |
| 316 | 2-iminoazepin-7-yl | 3 | 1 | H | NHSO₂Ph | |
| 317 | 2-iminoazepin-7-yl | 3 | 0 | H | NHCbz | |
| 318 | 2-iminoazepin-7-yl | 3 | 0 | H | NHSO₂Ph | |
| 319 | 2-iminoazepin-7-yl | 2 | 1 | H | NHCbz | |
| 320 | 2-iminoazepin-7-yl | 2 | 1 | H | NHSO₂Ph | |
| 321 | benzimidazol-2-ylamino | 4 | 0 | n-Bu | H | |
| 322 | benzthiazol-2-ylamino | 4 | 0 | n-Bu | H | |
| 325 | imidazol-4-ylamino | 4 | 0 | n-Bu | H | |
| 335 | thiazol-2-ylamino | 4 | 0 | H | NHCbz | 490.4 |
| 340 | imidazolin-2-ylamino | 4 | 0 | H | NHSO₂(2,4,6-trimethylphenyl) | |
| 341 | imidazolin-2-ylamino | 4 | 0 | H | NHSO₂(2,4,6-trichlorophenyl) | |
| 342 | imidazolin-2-ylamino | 4 | 0 | H | NHSO₂(2,6-dichlorophenyl) | |
| 343 | imidazolin-2-ylamino | 4 | 0 | H | NHSO₂(2-chloro-6-methylphenyl) | |
| 344 | imidazolin-2-ylamino | 4 | 0 | H | NHSO₂C₆H₄(2-CH₃) | |
| 345 | imidazolin-2-ylamino | 4 | 0 | H | NHSO₂C₆H₄(2-Br) | |
| 346 | imidazolin-2- | 4 | 0 | H | NHSO2[4-(2,6- | |

TABLE 1-continued

[Structure: R¹—U—(CH₂)ₘ—C(=N-O)—CH₂—(CH₂)ₙ—C(=O)—NH—CHR⁸—CHR⁹—C(=O)—OH]

| Ex. No. | R¹-U | m | n | R⁸ | R⁹ | MS |
|---|---|---|---|---|---|---|
| | ylamino | | | | dimethylphenyl)phenyl | |
| 347 | imidazolin-2-ylamino | 4 | 0 | H | NHSO₂C₆H₄(4-Ph) | |
| 348 | imidazolin-2-ylamino | 4 | 0 | H | NHSO₂[4-(3,5-dimethyl)isoxazolyl] | |
| 349 | imidazolin-2-ylamino | 4 | 0 | H | NHSO₂(1-napthyl) | |
| 350 | imidazolin-2-ylamino | 4 | 0 | H | NHSO₂(2-napthyl) | |
| 351 | imidazolin-2-ylamino | 4 | 0 | H | NHSO₂NHCH₂Ph | |
| 352 | imidazolin-2-ylamino | 4 | 0 | H | NHSO₂NHPh | |
| 353 | imidazolin-2-ylamino | 4 | 0 | Ph | H | |
| 354 | imidazolin-2-ylamino | 4 | 0 | phenylsulfonylamino methyl | H | |
| 355 | imidazolin-2-ylamino | 4 | 0 | 3-azabicyclo[3.2.2]nonan-3-ylcarbonyl | H | |
| 356 | imidazolin-2-ylamino | 4 | 0 | adamantan-1-yl methylaminocarbonyl | H | |
| 357 | imidazolin-2-ylamino | 4 | 0 | adamantan-1-yl aminocarbonyl | H | |
| 358 | imidazolin-2-ylamino | 4 | 0 | adamantan-2-yl aminocarbonyl | H | |
| 359 | imidazolin-2-ylamino | 4 | 0 | tetrahydroisoquinolin-2-ylcarbonyl | H | |
| 360 | imidazolin-2-ylamino | 3 | 1 | H | NHSO₂(2,4,6-trimethylphenyl) | |
| 361 | imidazolin-2-ylamino | 3 | 1 | H | NHSO₂(2,4,6-trichlorophenyl) | |
| 362 | imidazolin-2-ylamino | 3 | 1 | H | NHSO₂(2,6-dichlorophenyl) | |
| 363 | imidazolin-2-ylamino | 3 | 1 | H | NHSO₂(2-chloro-6-methylphenyl) | |
| 364 | imidazolin-2-ylamino | 3 | 1 | H | NHSO₂C₆H₄(2-CH₃) | |
| 365 | imidazolin-2-ylamino | 3 | 1 | H | NHSO₂C₆H₄(2-Br) | |
| 366 | imidazolin-2-ylamino | 3 | 1 | H | NHSO2[4-(2,6-dimethylphenyl)phenyl | |
| 367 | imidazolin-2-ylamino | 3 | 1 | H | NHSO₂C₆H₄(4-Ph) | |
| 368 | imidazolin-2-ylamino | 3 | 1 | H | NHSO₂[4-(3,5-dimethyl)isoxazolyl] | |
| 369 | imidazolin-2-ylamino | 3 | 1 | H | NHSO₂(1-napthyl) | |
| 370 | imidazolin-2-ylamino | 3 | 1 | H | NHSO₂(2-napthyl) | |
| 371 | imidazolin-2-ylamino | 3 | 1 | H | NHSO₂NHCH₂Ph | |
| 372 | imidazolin-2-ylamino | 3 | 1 | H | NHSO₂NHPh | |
| 373 | imidazolin-2-ylamino | 3 | 1 | Ph | H | |
| 374 | imidazolin-2-ylamino | 3 | 1 | phenylsulfonylamino methyl | H | |
| 375 | imidazolin-2-ylamino | 3 | 1 | 3-azabicyclo[3.2.2]nonan-3-ylcarbonyl | H | |
| 376 | imidazolin-2-ylamino | 3 | 1 | adamantan-1-yl methylaminocarbonyl | H | |
| 377 | imidazolin-2-ylamino | 3 | 1 | adamantan-1-yl aminocarbonyl | H | |
| 378 | imidazolin-2-ylamino | 3 | 1 | adamantan-2-yl aminocarbonyl | H | |
| 379 | imidazolin-2-ylamino | 3 | 1 | tetrahydroisoquinolin-2-ylcarbonyl | H | |
| 380 | tetrahydropyrimidin-2-ylamino | 4 | 0 | H | NHSO₂(2,4,6-trimethylphenyl) | |
| 381 | tetrahydropyrimidin- | 4 | 0 | H | NHSO₂(2,4,6- | |

TABLE 1-continued $$R^1-U-(CH_2)_m-C(=N-O)-(CH_2)_n-C(=O)-NH-CR^8(R^9)-C(=O)OH$$ [structure shown with R⁹ and OH on α-carbon]

| Ex. No. | R¹-U | m | n | R⁸ | R⁹ | MS |
|---|---|---|---|---|---|---|
| | 2-ylamino | | | | trichlorophenyl) | |
| 382 | tetrahydropyrimidin-2-ylamino | 4 | 0 | H | NHSO₂(2,6-dichlorophenyl) | |
| 383 | tetrahydropyrimidin-2-ylamino | 4 | 0 | H | NHSO₂(2-chloro-6-methylphenyl) | |
| 384 | tetrahydropyrimidin-2-ylamino | 4 | 0 | H | NHSO₂C₆H₄(2-CH₃) | |
| 385 | tetrahydropyrimidin-2-ylamino | 4 | 0 | H | NHSO₂C₆H₄(2-Br) | |
| 386 | tetrahydropyrimidin-2-ylamino | 4 | 0 | H | NHSO2[4-(2,6-dimethylphenyl)phenyl | |
| 387 | tetrahydropyrimidin-2-ylamino | 4 | 0 | H | NHSO₂C₆H₄(4-Ph) | |
| 388 | tetrahydropyrimidin-2-ylamino | 4 | 0 | H | NHSO₂[4-(3,5-dimethyl)isoxazolyl] | |
| 389 | tetrahydropyrimidin-2-ylamino | 4 | 0 | H | NHSO₂(1-napthyl) | |
| 390 | tetrahydropyrimidin-2-ylamino | 4 | 0 | H | NHSO₂(2-napthyl) | |
| 391 | tetrahydropyrimidin-2-ylamino | 4 | 0 | H | NHSO₂NHCH₂Ph | |
| 392 | tetrahydropyrimidin-2-ylamino | 4 | 0 | H | NHSO₂NHPh | |
| 393 | tetrahydropyrimidin-2-ylamino | 4 | 0 | Ph | H | |
| 394 | tetrahydropyrimidin-2-ylamino | 4 | 0 | phenylsulfonylamino methyl | H | |
| 395 | tetrahydropyrimidin-2-ylamino | 4 | 0 | 3-azabicyclo[3.2.2]nonan-3-ylcarbonyl | H | |
| 396 | tetrahydropyrimidin-2-ylamino | 4 | 0 | adamantan-1-yl methylaminocarbonyl | H | |
| 397 | tetrahydropyrimidin-2-ylamino | 4 | 0 | adamantan-1-yl aminocarbonyl | H | |
| 398 | tetrahydropyrimidin-2-ylamino | 4 | 0 | adamantan-2-yl aminocarbonyl | H | |
| 399 | tetrahydropyrimidin-2-ylamino | 4 | 0 | tetrahydroisoquinolin-2-ylcarbonyl | H | |
| 400 | tetrahydropyrimidin-2-ylamino | 3 | 1 | H | NHSO₂(2,4,6-trimethylphenyl) | |
| 401 | tetrahydropyrimidin-2-ylamino | 3 | 1 | H | NHSO₂(2,4,6-trichlorophenyl) | |
| 402 | tetrahydropyrimidin-2-ylamino | 3 | 1 | H | NHSO₂(2,6-dichlorophenyl) | |
| 403 | tetrahydropyrimidin-2-ylamino | 3 | 1 | H | NHSO₂(2-chloro-6-methylphenyl) | |
| 404 | tetrahydropyrimidin-2-ylamino | 3 | 1 | H | NHSO₂C₆H₄(2-CH₃) | |
| 405 | tetrahydropyrimidin-2-ylamino | 3 | 1 | H | NHSO₂C₆H₄(2-Br) | |
| 406 | tetrahydropyrimidin-2-ylamino | 3 | 1 | H | NHSO2[4-(2,6-dimethylphenyl)phenyl | |
| 407 | tetrahydropyrimidin-2-ylamino | 3 | 1 | H | NHSO₂C₆H₄(4-Ph) | |
| 408 | tetrahydropyrimidin-2-ylamino | 3 | 1 | H | NHSO₂[4-(3,5-dimethyl)isoxazolyl] | |
| 409 | tetrahydropyrimidin-2-ylamino | 3 | 1 | H | NHSO₂(1-napthyl) | |
| 410 | tetrahydropyrimidin-2-ylamino | 3 | 1 | H | NHSO₂(2-napthyl) | |
| 411 | tetrahydropyrimidin-2-ylamino | 3 | 1 | H | NHSO₂NHCH₂Ph | |
| 412 | tetrahydropyrimidin-2-ylamino | 3 | 1 | H | NHSO₂NHPh | |
| 413 | tetrahydropyrimidin-2-ylamino | 3 | 1 | Ph | H | |
| 414 | tetrahydropyrimidin-2-ylamino | 3 | 1 | phenylsulfonylamino methyl | H | |
| 415 | tetrahydropyrimidin-2-ylamino | 3 | 1 | 3-azabicyclo[3.2.2]nonan-3-ylcarbonyl | H | |
| 416 | tetrahydropyrimidin- | 3 | 1 | adamantan-1-yl | H | |

TABLE 1-continued

Structure: R¹—U—(CH₂)ₘ—C(=N-O)—CH₂—(CH₂)ₙ—C(=O)—NH—CHR⁸—CHR⁹—C(=O)OH

| Ex. No. | R¹-U | m | n | R⁸ | R⁹ | MS |
|---|---|---|---|---|---|---|
| | 2-ylamino | | | methylaminocarbonyl | | |
| 417 | tetrahydropyrimidin-2-ylamino | 3 | 1 | adamantan-1-yl aminocarbonyl | H | |
| 418 | tetrahydropyrimidin-2-ylamino | 3 | 1 | adamantan-2-yl aminocarbonyl | H | |
| 419 | tetrahydropyrimidin-2-ylamino | 3 | 1 | tetrahydroisoquinolin-2-ylcarbonyl | H | |
| 420 | imidazol-2-ylamino | 4 | 0 | H | NHSO₂(2,4,6-trimethylphenyl) | |
| 421 | imidazol-2-ylamino | 4 | 0 | H | NHSO₂(2,4,6-trichlorophenyl) | |
| 422 | imidazol-2-ylamino | 4 | 0 | H | NHSO₂(2,6-dichlorophenyl) | |
| 423 | imidazol-2-ylamino | 4 | 0 | H | NHSO₂(2-chloro-6-methylphenyl) | |
| 424 | imidazol-2-ylamino | 4 | 0 | H | NHSO₂C₆H₄(2-CH₃) | |
| 425 | imidazol-2-ylamino | 4 | 0 | H | NHSO₂C₆H₄(2-Br) | |
| 426 | imidazol-2-ylamino | 4 | 0 | H | NHSO2[4-(2,6-dimethylphenyl)phenyl | |
| 427 | imidazol-2-ylamino | 4 | 0 | H | NHSO₂C₆H₄(4-Ph) | |
| 428 | imidazol-2-ylamino | 4 | 0 | H | NHSO₂[4-(3,5-dimethyl)isoxazolyl] | |
| 429 | imidazol-2-ylamino | 4 | 0 | H | NHSO₂(1-napthyl) | |
| 430 | imidazol-2-ylamino | 4 | 0 | H | NHSO₂(2-napthyl) | |
| 431 | imidazol-2-ylamino | 4 | 0 | H | NHSO₂NHCH₂Ph | |
| 432 | imidazol-2-ylamino | 4 | 0 | H | NHSO₂NHPh | |
| 433 | imidazol-2-ylamino | 4 | 0 | Ph | H | |
| 434 | imidazol-2-ylamino | 4 | 0 | phenylsulfonylamino methyl | H | |
| 435 | imidazol-2-ylamino | 4 | 0 | 3-azabicyclo[3.2.2] nonan-3-ylcarbonyl | H | |
| 436 | imidazol-2-ylamino | 4 | 0 | adamantan-1-yl methylaminocarbonyl | H | |
| 437 | imidazol-2-ylamino | 4 | 0 | adamantan-1-yl aminocarbonyl | H | |
| 438 | imidazol-2-ylamino | 4 | 0 | adamantan-2-yl aminocarbonyl | H | |
| 439 | imidazol-2-ylamino | 4 | 0 | tetrahydroisoquinolin-2-ylcarbonyl | H | |
| 440 | imidazol-2-ylamino | 3 | 1 | H | NHSO₂(2,4,6-trimethylphenyl) | |
| 441 | imidazol-2-ylamino | 3 | 1 | H | NHSO₂(2,4,6-trichlorophenyl) | |
| 442 | imidazol-2-ylamino | 3 | 1 | H | NHSO₂(2,6-dichlorophenyl) | |
| 443 | imidazol-2-ylamino | 3 | 1 | H | NHSO₂(2-chloro-6-methylphenyl) | |
| 444 | imidazol-2-ylamino | 3 | 1 | H | NHSO₂C₆H₄(2-CH₃) | |
| 445 | imidazol-2-ylamino | 3 | 1 | H | NHSO₂C₆H₄(2-Br) | |
| 446 | imidazol-2-ylamino | 3 | 1 | H | NHSO2[4-(2,6-dimethylphenyl)phenyl | |
| 447 | imidazol-2-ylamino | 3 | 1 | H | NHSO₂C₆H₄(4-Ph) | |
| 448 | imidazol-2-ylamino | 3 | 1 | H | NHSO₂[4-(3,5-dimethyl)isoxazolyl] | |
| 449 | imidazol-2-ylamino | 3 | 1 | H | NHSO₂(1-napthyl) | |
| 450 | imidazol-2-ylamino | 3 | 1 | H | NHSO₂(2-napthyl) | |
| 451 | imidazol-2-ylamino | 3 | 1 | H | NHSO₂NHCH₂Ph | |
| 452 | imidazol-2-ylamino | 3 | 1 | H | NHSO₂NHPh | |
| 453 | imidazol-2-ylamino | 3 | 1 | Ph | H | |
| 454 | imidazol-2-ylamino | 3 | 1 | phenylsulfonylamino methyl | H | |
| 455 | imidazol-2-ylamino | 3 | 1 | 3-azabicyclo[3.2.2] nonan-3-ylcarbonyl | H | |
| 456 | imidazol-2-ylamino | 3 | 1 | adamantan-1-yl methylaminocarbonyl | H | |
| 457 | imidazol-2-ylamino | 3 | 1 | adamantan-1-yl aminocarbonyl | H | |
| 458 | imidazol-2-ylamino | 3 | 1 | adamantan-2-yl aminocarbonyl | H | |
| 459 | imidazol-2-ylamino | 3 | 1 | tetrahydroisoquinolin- | H | |

TABLE 1-continued $$R^1-U-(CH_2)_m-\underset{N-O}{C}-(CH_2)_n-\underset{O}{\overset{H}{N}}-\underset{R^8}{\overset{R^9}{C}}-\underset{O}{\overset{OH}{C}}$$

| Ex. No. | R¹-U | m | n | R⁸ | R⁹ | MS |
|---|---|---|---|---|---|---|
| | | | | 2-ylcarbonyl | | |
| 460 | 2-aminoimidazol-4-yl | 3 | 0 | H | NHSO₂(2,4,6-trimethylphenyl) | |
| 461 | 2-aminoimidazol-4-yl | 3 | 0 | H | NHSO₂(2,4,6-trichlorophenyl) | |
| 462 | 2-aminoimidazol-4-yl | 3 | 0 | H | NHSO₂(2,6-dichlorophenyl) | |
| 463 | 2-aminoimidazol-4-yl | 3 | 0 | H | NHSO₂(2-chloro-6-methylphenyl) | |
| 464 | 2-aminoimidazol-4-yl | 3 | 0 | H | NHSO₂C₆H₄(2-CH₃) | |
| 465 | 2-aminoimidazol-4-yl | 3 | 0 | H | NHSO₂C₆H₄(2-Br) | |
| 466 | 2-aminoimidazol-4-yl | 3 | 0 | H | NHSO₂[4-(2,6-dimethylphenyl)phenyl | |
| 467 | 2-aminoimidazol-4-yl | 3 | 0 | H | NHSO₂C₆H₄(4-Ph) | |
| 468 | 2-aminoimidazol-4-yl | 3 | 0 | H | NHSO₂[4-(3,5-dimethyl)isoxazolyl] | |
| 469 | 2-aminoimidazol-4-yl | 3 | 0 | H | NHSO₂(1-napthyl) | |
| 470 | 2-aminoimidazol-4-yl | 3 | 0 | H | NHSO₂(2-napthyl) | |
| 471 | 2-aminoimidazol-4-yl | 3 | 0 | H | NHSO₂NHCH₂Ph | |
| 472 | 2-aminoimidazol-4-yl | 3 | 0 | H | NHSO₂NHPh | |
| 473 | 2-aminoimidazol-4-yl | 3 | 0 | Ph | H | |
| 474 | 2-aminoimidazol-4-yl | 3 | 0 | phenylsulfonylamino methyl | H | |
| 475 | 2-aminoimidazol-4-yl | 3 | 0 | 3-azabicyclo[3.2.2]nonan-3-ylcarbonyl | H | |
| 476 | 2-aminoimidazol-4-yl | 3 | 0 | adamantan-1-yl methylaminocarbonyl | H | |
| 477 | 2-aminoimidazol-4-yl | 3 | 0 | adamantan-1-yl aminocarbonyl | H | |
| 478 | 2-aminoimidazol-4-yl | 3 | 0 | adamantan-2-yl aminocarbonyl | H | |
| 479 | 2-aminoimidazol-4-yl | 3 | 0 | tetrahydroisoquinolin-2-ylcarbonyl | H | |
| 480 | 2-aminoimidazol-4-yl | 2 | 1 | H | NHSO₂(2,4,6-trimethylphenyl) | |
| 481 | 2-aminoimidazol-4-yl | 2 | 1 | H | NHSO₂(2,4,6-trichlorophenyl) | |
| 482 | 2-aminoimidazol-4-yl | 2 | 1 | H | NHSO₂(2,6-dichlorophenyl) | |
| 483 | 2-aminoimidazol-4-yl | 2 | 1 | H | NHSO₂(2-chloro-6-methylphenyl) | |
| 484 | 2-aminoimidazol-4-yl | 2 | 1 | H | NHSO₂C₆H₄(2-CH₃) | |
| 485 | 2-aminoimidazol-4-yl | 2 | 1 | H | NHSO₂C₆H₄(2-Br) | |
| 486 | 2-aminoimidazol-4-yl | 2 | 1 | H | NHSO2[4-(2,6-dimethylphenyl)phenyl | |
| 487 | 2-aminoimidazol-4-yl | 2 | 1 | H | NHSO₂C₆H₄(4-Ph) | |
| 488 | 2-aminoimidazol-4-yl | 2 | 1 | H | NHSO₂[4-(3,5-dimethyl)isoxazolyl] | |
| 489 | 2-aminoimidazol-4-yl | 2 | 1 | H | NHSO₂(1-napthyl) | |
| 490 | 2-aminoimidazol-4-yl | 2 | 1 | H | NHSO₂(2-napthyl) | |
| 491 | 2-aminoimidazol-4-yl | 2 | 1 | H | NHSO₂NHCH₂Ph | |
| 492 | 2-aminoimidazol-4-yl | 2 | 1 | H | NHSO₂NHPh | |
| 493 | 2-aminoimidazol-4-yl | 2 | 1 | Ph | H | |
| 494 | 2-aminoimidazol-4- | 2 | 1 | phenylsulfonylamino | H | |

TABLE 1-continued $$R^1-U-(CH_2)_m-\underset{N-O}{C}-CH_2-\underset{}{CH}-(CH_2)_n-\underset{O}{C}-\underset{H}{N}-\underset{R^8}{CH}-\underset{R^9}{CH}-\underset{O}{C}-OH$$

| Ex. No. | R¹-U | m | n | R⁸ | R⁹ | MS |
|---|---|---|---|---|---|---|
|  | yl |  |  | methyl |  |  |
| 495 | 2-aminoimidazol-4-yl | 2 | 1 | 3-azabicyclo[3.2.2]nonan-3-ylcarbonyl | H |  |
| 496 | 2-aminoimidazol-4-yl | 2 | 1 | adamantan-1-yl methylaminocarbonyl | H |  |
| 497 | 2-aminoimidazol-4-yl | 2 | 1 | adamantan-1-yl aminocarbonyl | H |  |
| 498 | 2-aminoimidazol-4-yl | 2 | 1 | adamantan-2-yl aminocarbonyl | H |  |
| 499a | 2-aminoimidazol-4-yl | 2 | 1 | tetrahydroisoquinolin-2-ylcarbonyl | H |  |
| 499b | benzimidazol-2-ylamino | 4 | 0 | H | NHSO$_2$(2,4,6-trimethylphenyl) |  |
| 499c | benzimidazol-2-ylamino | 4 | 0 | H | NHSO$_2$(2,4,6-trichlorophenyl) |  |
| 499d | benzimidazol-2-ylamino | 4 | 0 | H | NHSO$_2$(2,6-dichlorophenyl) |  |
| 499e | benzimidazol-2-ylamino | 4 | 0 | H | NHSO$_2$(2-chloro-6-methylphenyl) |  |
| 499f | benzimidazol-2-ylamino | 4 | 0 | H | NHSO$_2$C$_6$H$_4$(2-CH$_3$) |  |
| 499g | benzimidazol-2-ylamino | 4 | 0 | H | NHSO$_2$C$_6$H$_4$(2-Br) |  |
| 499h | benzimidazol-2-ylamino | 4 | 0 | H | NHSO2[4-(2,6-dimethylphenyl)phenyl |  |
| 499i | benzimidazol-2-ylamino | 4 | 0 | H | NHSO$_2$C$_6$H$_4$(4-Ph) |  |
| 499j | benzimidazol-2-ylamino | 4 | 0 | H | NHSO$_2$[4-(3,5-dimethyl)isoxazolyl] |  |
| 499k | benzimidazol-2-ylamino | 4 | 0 | H | NHSO$_2$(1-napthyl) |  |
| 499l | benzimidazol-2-ylamino | 4 | 0 | H | NHSO$_2$(2-napthyl) |  |
| 499m | benzimidazol-2-ylamino | 4 | 0 | H | NHSO$_2$NHCH$_2$Ph |  |
| 499 | benzimidazol-2-ylamino | 4 | 0 | H | NHSO$_2$NHPh |  |
| 499n | benzimidazol-2-ylamino | 4 | 0 | Ph | H |  |
| 499o | benzimidazol-2-ylamino | 4 | 0 | phenylsulfonylamino methyl | H |  |
| 499p | benzimidazol-2-ylamino | 4 | 0 | 3-azabicyclo[3.2.2]nonan-3-ylcarbonyl | H |  |
| 499q | benzimidazol-2-ylamino | 4 | 0 | adamantan-1-yl methylaminocarbonyl | H |  |
| 499r | benzimidazol-2-ylamino | 4 | 0 | adamantan-1-yl aminocarbonyl | H |  |
| 499s | benzimidazol-2-ylamino | 4 | 0 | adamantan-2-yl aminocarbonyl | H |  |
| 499t | benzimidazol-2-ylamino | 4 | 0 | tetrahydroisoquinolin-2-ylcarbonyl | H |  |
| 499u | benzimidazol-2-ylamino | 3 | 1 | H | NHSO$_2$(2,4,6-trimethylphenyl) |  |
| 499v | benzimidazol-2-ylamino | 3 | 1 | H | NHSO$_2$(2,4,6-trichlorophenyl) |  |
| 499w | benzimidazol-2-ylamino | 3 | 1 | H | NHSO$_2$(2,6-dichlorophenyl) |  |
| 499x | benzimidazol-2-ylamino | 3 | 1 | H | NHSO$_2$(2-chloro-6-methylphenyl) |  |
| 499y | benzimidazol-2-ylamino | 3 | 1 | H | NHSO$_2$C$_6$H$_4$(2-CH$_3$) |  |
| 499z | benzimidazol-2-ylamino | 3 | 1 | H | NHSO$_2$C$_6$H$_4$(2-Br) |  |
| 499aa | benzimidazol-2-ylamino | 3 | 1 | H | NHSO2[4-(2,6-dimethylphenyl)phenyl |  |
| 499ab | benzimidazol-2-ylamino | 3 | 1 | H | NHSO$_2$C$_6$H$_4$(4-Ph) |  |
| 499ac | benzimidazol-2-ylamino | 3 | 1 | H | NHSO$_2$[4-(3,5-dimethyl)isoxazolyl] |  |
| 499ad | benzimidazol-2- | 3 | 1 | H | NHSO$_2$(1-napthyl) |  |

TABLE 1-continued

R¹—U—(CH₂)ₘ—C(=N—O)—CH₂—(CH₂)ₙ—C(O)—N(H)—C(R⁸)—C(R⁹)(H)—C(O)OH

| Ex. No. | R¹-U | m | n | R⁸ | R⁹ | MS |
|---|---|---|---|---|---|---|
| | ylamino | | | | | |
| 499ae | benzimidazol-2-ylamino | 3 | 1 | H | NHSO₂(2-napthyl) | |
| 499af | benzimidazol-2-ylamino | 3 | 1 | H | NHSO₂NHCH₂Ph | |
| 499ag | benzimidazol-2-ylamino | 3 | 1 | H | NHSO₂NHPh | |
| 499ah | benzimidazol-2-ylamino | 3 | 1 | Ph | H | |
| 499ai | benzimidazol-2-ylamino | 3 | 1 | phenylsulfonylaminomethyl | H | |
| 499aj | benzimidazol-2-ylamino | 3 | 1 | 3-azabicyclo[3.2.2]nonan-3-ylcarbonyl | H | |
| 499ak | benzimidazol-2-ylamino | 3 | 1 | adamantan-1-yl methylaminocarbonyl | H | |
| 499al | benzimidazol-2-ylamino | 3 | 1 | adamantan-1-yl aminocarbonyl | H | |
| 499am | benzimidazol-2-ylamino | 3 | 1 | adamantan-2-yl aminocarbonyl | H | |
| 499an | benzimidazol-2-ylamino | 3 | 1 | tetrahydroisoquinolin-2-ylcarbonyl | H | |
| 499ao | 4-methylimidazol-2-ylamino | 4 | 0 | H | NHSO₂(2,4,6-trimethylphenyl) | |
| 499ap | 4-methylimidazol-2-ylamino | 4 | 0 | H | NHSO₂(2,4,6-trichlorophenyl) | |
| 499aq | 4-methylimidazol-2-ylamino | 4 | 0 | H | NHSO₂(2,6-dichlorophenyl) | |
| 499ar | 4-methylimidazol-2-ylamino | 4 | 0 | H | NHSO₂(2-chloro-6-methylphenyl) | |
| 499as | 4-methylimidazol-2-ylamino | 4 | 0 | H | NHSO₂C₆H₄(2-CH₃) | |
| 499at | 4-methylimidazol-2-ylamino | 4 | 0 | H | NHSO₂C₆H₄(2-Br) | |
| 499au | 4-methylimidazol-2-ylamino | 4 | 0 | H | NHSO2[4-(2,6-dimethylphenyl)phenyl | |
| 499av | 4-methylimidazol-2-ylamino | 4 | 0 | H | NHSO₂C₆H₄(4-Ph) | |
| 499aw | 4-methylimidazol-2-ylamino | 4 | 0 | H | NHSO₂[4-(3,5-dimethyl)isoxazolyl) | |
| 499ax | 4-methylimidazol-2-ylamino | 4 | 0 | H | NHSO₂(1-napthyl) | |
| 499ay | 4-methylimidazol-2-ylamino | 4 | 0 | H | NHSO₂(2-napthyl) | |
| 499az | 4-methylimidazol-2-ylamino | 4 | 0 | H | NHSO₂NHCH₂Ph | |
| 499ba | 4-methylimidazol-2-ylamino | 4 | 0 | H | NHSO₂NHPh | |
| 499bb | 4-methylimidazol-2-ylamino | 4 | 0 | Ph | H | |
| 499bc | 4-methylimidazol-2-ylamino | 4 | 0 | phenylsulfonylaminomethyl | H | |
| 499bd | 4-methylimidazol-2-ylamino | 4 | 0 | 3-azabicyclo[3.2.2]nonan-3-ylcarbonyl | H | |
| 499be | 4-methylimidazol-2-ylamino | 4 | 0 | adamantan-1-yl methylaminocarbonyl | H | |
| 499bf | 4-methylimidazol-2-ylamino | 4 | 0 | adamantan-1-yl aminocarbonyl | H | |
| 499bg | 4-methylimidazol-2 ylamino | 4 | 0 | adamantan-2-yl aminocarbonyl | H | |
| 499bh | 4-methylimidazol-2-ylamino | 4 | 0 | tetrahydroisoquinolin-2-ylcarbonyl | H | |
| 499bi | 4-methylimidazol-2-ylamino | 3 | 1 | H | NHSO₂(2,4,6-trimethylphenyl) | |
| 499bj | 4-methylimidazol-2-ylamino | 3 | 1 | H | NHSO₂(2,4,6-trichlorophenyl) | |
| 499bk | 4-methylimidazol-2-ylamino | 3 | 1 | H | NHSO₂(2,6-dichlorophenyl) | |
| 499bl | 4-methylimidazol-2-ylamino | 3 | 1 | H | NHSO₂(2-chloro-6-methylphenyl) | |
| 499bm | 4-methylimidazol-2- | 3 | 1 | H | NHSO₂C₆H₄(2-CH₃) | |

TABLE 1-continued $$R^1-U\diagup^{(CH_2)_m}\diagdown_{N-O}\diagup\diagdown_{(CH_2)_n}\diagup\overset{H}{\underset{O}{N}}\diagdown\underset{R^8}{\overset{R^9}{C}}\diagup^{OH}_{O}$$

| Ex. No. | R¹-U | m | n | R⁸ | R⁹ | MS |
|---|---|---|---|---|---|---|
| 499bn | 4-methylimidazol-2-ylamino | 3 | 1 | H | $NHSO_2C_6H_4$(2-Br) | |
| 499bo | 4-methylimidazol-2-ylamino | 3 | 1 | H | NHSO2[4-(2,6-dimethylphenyl)phenyl | |
| 499bp | 4-methylimidazol-2-ylamino | 3 | 1 | H | $NHSO_2C_6H_4$(4-Ph) | |
| 499bq | 4-methylimidazol-2-ylamino | 3 | 1 | H | $NHSO_2$[4-(3,5-dimethyl)isoxazolyl] | |
| 499br | 4-methylimidazol-2-ylamino | 3 | 1 | H | $NHSO_2$(1-napthyl) | |
| 499bs | 4-methylimidazol-2-ylamino | 3 | 1 | H | $NHSO_2$(2-napthyl) | |
| 499bt | 4-methylimidazol-2-ylamino | 3 | 1 | H | $NHSO_2NHCH_2Ph$ | |
| 499bu | 4-methylimidazol-2-ylamino | 3 | 1 | H | $NHSO_2NHPh$ | |
| 499bv | 4-methylimidazol-2-ylamino | 3 | 1 | Ph | H | |
| 499bw | 4-methylimidazol-2-ylamino | 3 | 1 | phenylsulfonylamino methyl | H | |
| 499bx | 4-methylimidazol-2-ylamino | 3 | 1 | 3-azabicyclo[3.2.2]nonan-3-ylcarbonyl | H | |
| 499by | 4-methylimidazol-2-ylamino | 3 | 1 | adamantan-1-yl methylaminocarbonyl | H | |
| 499bz | 4-methylimidazol-2-ylamino | 3 | 1 | adamantan-1-yl aminocarbonyl | H | |
| 499ca | 4-methylimidazol-2-ylamino | 3 | 1 | adamantan-2-yl aminocarbonyl | H | |
| 499cb | 4-methylimidazol-2-ylamino | 3 | 1 | tetrahydroisoquinolin-2-ylcarbonyl | H | |
| 499cc | 4,5-dimethylimidazol-2-ylamino | 4 | 0 | H | $NHSO_2$(2,4,6-trimethylphenyl) | |
| 499cd | 4,5-dimethylimidazol-2-ylamino | 4 | 0 | H | $NHSO_2$(2,4,6-trichlorophenyl) | |
| 499ce | 4,5-dimethylimidazol-2-ylamino | 4 | 0 | H | $NHSO_2$(2,6-dichlorophenyl) | |
| 499cf | 4,5-dimethylimidazol-2-ylamino | 4 | 0 | H | $NHSO_2$(2-chloro-6-methylphenyl) | |
| 499cg | 4,5-dimethylimidazol-2-ylamino | 4 | 0 | H | $NHSO_2C_6H_4$(2-$CH_3$) | |
| 499ch | 4,5-dimethylimidazol-2-ylamino | 4 | 0 | H | $NHSO_2C_6H_4$(2-Br) | |
| 499ci | 4,5-dimethylimidazol-2-ylamino | 4 | 0 | H | NHSO2[4-(2,6-dimethylphenyl)phenyl | |
| 499cj | 4,5-dimethylimidazol-2-ylamino | 4 | 0 | H | $NHSO_2C_6H_4$(4-Ph) | |
| 499ck | 4,5-dimethylimidazol-2-ylamino | 4 | 0 | H | $NHSO_2$[4-(3,5-dimethyl)isoxazolyl] | |
| 499cl | 4,5-dimethylimidazol-2-ylamino | 4 | 0 | H | $NHSO_2$(1-napthyl) | |
| 499cm | 4,5-dimethylimidazol-2-ylamino | 4 | 0 | H | $NHSO_2$(2-napthyl) | |
| 499cn | 4,5-dimethylimidazol-2-ylamino | 4 | 0 | H | $NHSO_2NHCH_2Ph$ | |
| 499co | 4,5-dimethylimidazol-2-ylamino | 4 | 0 | H | $NHSO_2NHPh$ | |

TABLE 1-continued $$R^1-U-(CH_2)_m-C(=N-O)-CH_2-(CH_2)_n-C(=O)-NH-CHR^8-CHR^9-C(=O)OH$$

| Ex. No. | R¹-U | m | n | R⁸ | R⁹ | MS |
|---|---|---|---|---|---|---|
| 499cp | 4,5-dimethylimidazol-2-ylamino | 4 | 0 | Ph | H | |
| 499cq | 4,5-dimethylimidazol-2-ylamino | 4 | 0 | phenylsulfonylaminomethyl | H | |
| 499cr | 4,5-dimethylimidazol-2-ylamino | 4 | 0 | 3-azabicyclo[3.2.2]nonan-3-ylcarbonyl | H | |
| 499cs | 4,5-dimethylimidazol-2-ylamino | 4 | 0 | adamantan-1-yl methylaminocarbonyl | H | |
| 499ct | 4,5-dimethylimidazol-2-ylamino | 4 | 0 | adamantan-1-yl aminocarbonyl | H | |
| 499cu | 4,5-dimethylimidazol-2-ylamino | 4 | 0 | adamantan-2-yl aminocarbonyl | H | |
| 499cv | 4,5-dimethylimidazol-2-ylamino | 4 | 0 | tetrahydroisoquinolin-2-ylcarbonyl | H | |
| 499cw | 4,5-dimethylimidazol-2-ylamino | 3 | 1 | H | $NHSO_2$(2,4,6-trimethylphenyl) | |
| 499cx | 4,5-dimethylimidazol-2-ylamino | 3 | 1 | H | $NHSO_2$(2,4,6-trichlorophenyl) | |
| 499cy | 4,5-dimethylimidazol-2-ylamino | 3 | 1 | H | $NHSO_2$(2,6-dichlorophenyl) | |
| 499cz | 4,5-dimethylimidazol-2-ylamino | 3 | 1 | H | $NHSO_2$(2-chloro-6-methylphenyl) | |
| 499da | 4,5-dimethylimidazol-2-ylamino | 3 | 1 | H | $NHSO_2C_6H_4$(2-$CH_3$) | |
| 499db | 4,5-dimethylimidazol-2-ylamino | 3 | 1 | H | $NHSO_2C_6H_4$(2-Br) | |
| 499dc | 4,5-dimethylimidazol-2-ylamino | 3 | 1 | H | $NHSO2$[4-(2,6-dimethylphenyl)phenyl | |
| 499de | 4,5-dimethylimidazol-2-ylamino | 3 | 1 | H | $NHSO_2C_6H_4$(4-Ph) | |
| 499df | 4,5-dimethylimidazol-2-ylamino | 3 | 1 | H | $NHSO_2$[4-(3,5-dimethyl)isoxazolyl] | |
| 499dg | 4,5-dimethylimidazol-2-ylamino | 3 | 1 | H | $NHSO_2$(1-napthyl) | |
| 499dh | 4,5-dimethylimidazol-2-ylamino | 3 | 1 | H | $NHSO_2$(2-napthyl) | |
| 499di | 4,5-dimethylimidazol-2-ylamino | 3 | 1 | H | $NHSO_2NHCH_2Ph$ | |
| 499dj | 4,5-dimethylimidazol-2-ylamino | 3 | 1 | H | $NHSO_2NHPh$ | |
| 499dk | 4,5-dimethylimidazol-2-ylamino | 3 | 1 | Ph | H | |
| 499dl | 4,5-dimethylimidazol-2-ylamino | 3 | 1 | phenylsulfonylaminomethyl | H | |
| 499dm | 4,5-dimethylimidazol-2-ylamino | 3 | 1 | 3-azabicyclo[3.2.2]nonan-3-ylcarbonyl | H | |
| 499dn | 4,5- | 3 | 1 | adamantan-1-yl | H | |

TABLE 1-continued $$R^1-U-(CH_2)_m-C(=N-O)-CH_2-(CH_2)_n-C(=O)-N(H)-C(R^8)-C(R^9)(H)-C(=O)-OH$$

| Ex. No. | R¹-U | m | n | R⁸ | R⁹ | MS |
|---|---|---|---|---|---|---|
| | dimethylimidazol-2-ylamino | | | methylaminocarbonyl | | |
| 499do | 4,5-dimethylimidazol-2-ylamino | 3 | 1 | adamantan-1-yl aminocarbonyl | H | |
| 499dp | 4,5-dimethylimidazol-2-ylamino | 3 | 1 | adamantan-2-yl aminocarbonyl | H | |
| 499dq | 4,5-dimethylimidazol-2-ylamino | 3 | 1 | tetrahydroisoquinolin-2-ylcarbonyl | H | |
| 499dr | 4,5,6,7-tetrahydrobenzimidazol-2-ylamino | 4 | 0 | H | $NHSO_2$(2,4,6-trimethylphenyl) | |
| 499ds | 4,5,6,7-tetrahydrobenzimidazol-2-ylamino | 4 | 0 | H | $NHSO_2$(2,4,6-trichlorophenyl) | |
| 499dt | 4,5,6,7-tetrahydrobenzimidazol-2-ylamino | 4 | 0 | H | $NHSO_2$(2,6-dichlorophenyl) | |
| 499du | 4,5,6,7-tetrahydrobenzimidazol-2-ylamino | 4 | 0 | H | $NHSO_2$(2-chloro-6-methylphenyl) | |
| 499dv | 4,5,6,7-tetrahydrobenzimidazol-2-ylamino | 4 | 0 | H | $NHSO_2C_6H_4$(2-$CH_3$) | |
| 499dw | 4,5,6,7-tetrahydrobenzimidazol-2-ylamino | 4 | 0 | H | $NHSO_2C_6H_4$(2-Br) | |
| 499dx | 4,5,6,7-tetrahydrobenzimidazol-2-ylamino | 4 | 0 | H | NHSO2[4-(2,6-dimethylphenyl)phenyl | |
| 499dy | 4,5,6,7-tetrahydrobenzimidazol-2-ylamino | 4 | 0 | H | $NHSO_2C_6H_4$(4-Ph) | |
| 499dz | 4,5,6,7-tetrahydrobenzimidazol-2-ylamino | 4 | 0 | H | $NHSO_2$[4-(3,5-dimethyl)isoxazolyl] | |
| 499ea | 4,5,6,7-tetrahydrobenzimidazol-2-ylamino | 4 | 0 | H | $NHSO_2$(1-napthyl) | |
| 499eb | 4,5,6,7-tetrahydrobenzimidazol-2-ylamino | 4 | 0 | H | $NHSO_2$(2-napthyl) | |
| 499ec | 4,5,6,7-tetrahydrobenzimidazol-2-ylamino | 4 | 0 | H | $NHSO_2NHCH_2Ph$ | |
| 499ed | 4,5,6,7-tetrahydrobenzimidazol-2-ylamino | 4 | 0 | H | $NHSO_2NHPh$ | |
| 499ee | 4,5,6,7-tetrahydrobenzimidazol-2-ylamino | 4 | 0 | Ph | H | |
| 499ef | 4,5,6,7-tetrahydrobenzimidazol-2-ylamino | 4 | 0 | phenylsulfonylamino methyl | H | |
| 499eg | 4,5,6,7-tetrahydrobenzimidazol-2-ylamino | 4 | 0 | 3-azabicyclo[3.2.2]nonan-3-ylcarbonyl | H | |
| 499eh | 4,5,6,7-tetrahydrobenzimidazol-2-ylamino | 4 | 0 | adamantan-1-yl methylaminocarbonyl | H | |
| 499ei | 4,5,6,7-tetrahydrobenzimidazol-2-ylamino | 4 | 0 | adamantan-1-yl aminocarbonyl | H | |
| 499ej | 4,5,6,7-tetrahydrobenzimidazol-2-ylamino | 4 | 0 | adamantan-2-yl aminocarbonyl | H | |
| 499ek | 4,5,6,7-tetrahydrobenzimidazol- | 4 | 0 | tetrahydroisoquinolin-2-ylcarbonyl | H | |

TABLE 1-continued $$R^1-U-(CH_2)_m-\underset{N-O}{C}-(CH_2)_n-\underset{O}{C}-\underset{R^8}{N}H-\underset{}{C}H-\underset{O}{C}R^9-OH$$

| Ex. No. | R¹-U | m | n | R⁸ | R⁹ | MS |
|---|---|---|---|---|---|---|
| 499el | 4,5,6,7-tetrahydrobenzimidazol-2-ylamino | 3 | 1 | H | NHSO₂(2,4,6-trimethylphenyl) | |
| 499em | 4,5,6,7-tetrahydrobenzimidazol-2-ylamino | 3 | 1 | H | NHSO₂(2,4,6-trichlorophenyl) | |
| 499en | 4,5,6,7-tetrahydrobenzimidazol-2-ylamino | 3 | 1 | H | NHSO₂(2,6-dichlorophenyl) | |
| 499eo | 4,5,6,7-tetrahydrobenzimidazol-2-ylamino | 3 | 1 | H | NHSO₂(2-chloro-6-methylphenyl) | |
| 499ep | 4,5,6,7-tetrahydrobenzimidazol-2-ylamino | 3 | 1 | H | NHSO₂C₆H₄(2-CH₃) | |
| 499eq | 4,5,6,7-tetrahydrobenzimidazol-2-ylamino | 3 | 1 | H | NHSO₂C₆H₄(2-Br) | |
| 499er | 4,5,6,7-tetrahydrobenzimidazol-2-ylamino | 3 | 1 | H | NHSO2[4-(2,6-dimethylphenyl)phenyl | |
| 499es | 4,5,6,7-tetrahydrobenzimidazol-2-ylamino | 3 | 1 | H | NHSO₂C₆H₄(4-Ph) | |
| 499et | 4,5,6,7-tetrahydrobenzimidazol-2-ylamino | 3 | 1 | H | NHSO₂[4-(3,5-dimethyl)isoxazolyl] | |
| 499eu | 4,5,6,7-tetrahydrobenzimidazol-2-ylamino | 3 | 1 | H | NHSO₂(1-napthyl) | |
| 499ev | 4,5,6,7-tetrahydrobenzimidazol-2-ylamino | 3 | 1 | H | NHSO₂(2-napthyl) | |
| 499ew | 4,5,6,7-tetrahydrobenzimidazol-2-ylamino | 3 | 1 | H | NHSO₂NHCH₂Ph | |
| 499ex | 4,5,6,7-tetrahydrobenzimidazol-2-ylamino | 3 | 1 | H | NHSO₂NHPh | |
| 499ey | 4,5,6,7-tetrahydrobenzimidazol-2-ylamino | 3 | 1 | Ph | H | |
| 499ez | 4,5,6,7-tetrahydrobenzimidazol-2-ylamino | 3 | 1 | phenylsulfonylaminomethyl | H | |
| 499fa | 4,5,6,7-tetrahydrobenzimidazol-2-ylamino | 3 | 1 | 3-azabicyclo[3.2.2]nonan-3-ylcarbonyl | H | |
| 499fb | 4,5,6,7-tetrahydrobenzimidazol-2-ylamino | 3 | 1 | adamantan-1-yl methylaminocarbonyl | H | |
| 499fc | 4,5,6,7-tetrahydrobenzimidazol-2-ylamino | 3 | 1 | adamantan-1-yl aminocarbonyl | H | |
| 499fd | 4,5,6,7-tetrahydrobenzimidazol-2-ylamino | 3 | 1 | adamantan-2-yl aminocarbonyl | H | |
| 499fe | 4,5,6,7-tetrahydrobenzimidazol-2-ylamino | 3 | 1 | tetrahydroisoquinolin-2-ylcarbonyl | H | |
| 499ff | pyridin-2-ylamino | 4 | 0 | H | NHSO₂(2,4,6-trimethylphenyl) | |
| 499fg | pyridin-2-ylamino | 4 | 0 | H | NHSO₂(2,4,6-trichlorophenyl) | |
| 499fh | pyridin-2-ylamino | 4 | 0 | H | NHSO₂(2,6-dichlorophenyl) | |
| 499fi | pyridin-2-ylamino | 4 | 0 | H | NHSO₂(2-chloro-6-methylphenyl) | |
| 499fj | pyridin-2-ylamino | 4 | 0 | H | NHSO₂C₆H₄(2-CH₃) | |

TABLE 1-continued $$R^1-U-(CH_2)_m-C(=N-O)-CH_2-(CH_2)_n-C(=O)-NH-CH(R^8)-CH(R^9)-C(=O)-OH$$

| Ex. No. | R¹-U | m | n | R⁸ | R⁹ | MS |
|---|---|---|---|---|---|---|
| 499fk | pyridin-2-ylamino | 4 | 0 | H | NHSO$_2$C$_6$H$_4$(2-Br) | |
| 499fl | pyridin-2-ylamino | 4 | 0 | H | NHSO2[4-(2,6-dimethylphenyl)phenyl | |
| 499fm | pyridin-2-ylamino | 4 | 0 | H | NHSO$_2$C$_6$H$_4$(4-Ph) | |
| 499fn | pyridin-2-ylamino | 4 | 0 | H | NHSO$_2$[4-(3,5-dimethyl)isoxazolyl] | |
| 499of | pyridin-2-ylamino | 4 | 0 | H | NHSO$_2$(1-napthyl) | |
| 499fp | pyridin-2-ylamino | 4 | 0 | H | NHSO$_2$(2-napthyl) | |
| 499fq | pyridin-2-ylamino | 4 | 0 | H | NHSO$_2$NHCH$_2$Ph | |
| 499fr | pyridin-2-ylamino | 4 | 0 | H | NHSO$_2$NHPh | |
| 499fs | pyridin-2-ylamino | 4 | 0 | Ph | H | |
| 499ft | pyridin-2-ylamino | 4 | 0 | phenylsulfonylamino methyl | H | |
| 499fu | pyridin-2-ylamino | 4 | 0 | 3-azabicyclo[3.2.2]nonan-3-ylcarbonyl | H | |
| 499fv | pyridin-2-ylamino | 4 | 0 | adamantan-1-yl methylaminocarbonyl | H | |
| 499fw | pyridin-2-ylamino | 4 | 0 | adamantan-1-yl aminocarbonyl | H | |
| 499fy | pyridin-2-ylamino | 4 | 0 | adamantan-2-yl aminocarbonyl | H | |
| 499fz | pyridin-2-ylamino | 4 | 0 | tetrahydroisoquinolin-2-ylcarbonyl | H | |
| 499ga | pyridin-2-ylamino | 3 | 1 | H | NHSO$_2$(2,4,6-trimethylphenyl) | |
| 499gb | pyridin-2-ylamino | 3 | 1 | H | NHSO$_2$(2,4,6-trichlorophenyl) | |
| 499gc | pyridin-2-ylamino | 3 | 1 | H | NHSO$_2$(2,6-dichlorophenyl) | |
| 499gd | pyridin-2-ylamino | 3 | 1 | H | NHSO$_2$(2-chloro-6-methylphenyl) | |
| 499ge | pyridin-2-ylamino | 3 | 1 | H | NHSO$_2$C$_6$H$_4$(2-CH$_3$) | |
| 499gf | pyridin-2-ylamino | 3 | 1 | H | NHSO$_2$C$_6$H$_4$(2-Br) | |
| 499gh | pyridin-2-ylamino | 3 | 1 | H | NHSO2[4-(2,6-dimethylphenyl)phenyl | |
| 499gi | pyridin-2-ylamino | 3 | 1 | H | NHSO$_2$C$_6$H$_4$(4-Ph) | |
| 499gk | pyridin-2-ylamino | 3 | 1 | H | NHSO$_2$[4-(3,5-dimethyl)isoxazolyl] | |
| 499gl | pyridin-2-ylamino | 3 | 1 | H | NHSO$_2$(1-napthyl) | |
| 499gm | pyridin-2-ylamino | 3 | 1 | H | NHSO$_2$(2-napthyl) | |
| 499gn | pyridin-2-ylamino | 3 | 1 | H | NHSO$_2$NHCH$_2$Ph | |
| 499go | pyridin-2-ylamino | 3 | 1 | H | NHSO$_2$NHPh | |
| 499gp | pyridin-2-ylamino | 3 | 1 | Ph | H | |
| 499gq | pyridin-2-ylamino | 3 | 1 | phenylsulfonylamino methyl | H | |
| 499gr | pyridin-2-ylamino | 3 | 1 | 3-azabicyclo[3.2.2]nonan-3-ylcarbonyl | H | |
| 499gs | pyridin-2-ylamino | 3 | 1 | adamantan-1-yl methylaminocarbonyl | H | |
| 499gt | pyridin-2-ylamino | 3 | 1 | adamantan-1-yl aminocarbonyl | H | |
| 499gu | pyridin-2-ylamino | 3 | 1 | adamantan-2-yl aminocarbonyl | H | |
| 499gv | pyridin-2-ylamino | 3 | 1 | tetrahydroisoquinolin-2-ylcarbonyl | H | |
| 499gw | benzimidazol-2-ylmethylaminocarbonyl | 0 | 0 | H | NHSO$_2$(2,4,6-trimethylphenyl) | |
| 499gx | benzimidazol-2-ylmethylaminocarbonyl | 0 | 0 | H | NHSO$_2$(2,4,6-trichlorophenyl) | |
| 499gy | benzimidazol-2-ylmethylaminocarbonyl | 0 | 0 | H | NHSO$_2$(2,6-dichlorophenyl) | |
| 499gz | benzimidazol-2-ylmethylaminocarbonyl | 0 | 0 | H | NHSO$_2$(2-chloro-6-methylphenyl) | |
| 499ha | benzimidazol-2-ylmethylaminocarbonyl | 0 | 0 | H | NHSO$_2$C$_6$H$_4$(2-CH$_3$) | |
| 499hb | benzimidazol-2-ylmethylaminocarbonyl | 0 | 0 | H | NHSO$_2$C$_6$H$_4$(2-Br) | |
| 499hc | benzimidazol-2-ylmethylaminocarbonyl | 0 | 0 | H | NHSO2[4-(2,6-dimethylphenyl)phenyl | |
| 499hd | benzimidazol-2- | 0 | 0 | H | NHSO$_2$C$_6$H$_4$(4-Ph) | |

TABLE 1-continued $$R^1-U-(CH_2)_m-\underset{N-O}{C}-(CH_2)_n-\underset{O}{\overset{H}{N}}-\underset{R^8}{\overset{R^9}{C}}-\underset{O}{C}-OH$$

| Ex. No. | R¹-U | m | n | R⁸ | R⁹ | MS |
|---|---|---|---|---|---|---|
| | ylmethylaminocarbonyl | | | | | |
| 499he | benzimidazol-2-ylmethylaminocarbonyl | 0 | 0 | H | NHSO₂[4-(3,5-dimethyl)isoxazolyl] | |
| 499hf | benzimidazol-2-ylmethylaminocarbonyl | 0 | 0 | H | NHSO₂(1-napthyl) | |
| 499hg | benzimidazol-2-ylmethylaminocarbonyl | 0 | 0 | H | NHSO₂(2-napthyl) | |
| 499hi | benzimidazol-2-ylmethylaminocarbonyl | 0 | 0 | H | NHSO₂NHCH₂Ph | |
| 499hj | benzimidazol-2-ylmethylaminocarbonyl | 0 | 0 | H | NHSO₂NHPh | |
| 499hk | benzimidazol-2-ylmethylaminocarbonyl | 0 | 0 | Ph | H | |
| 499hl | benzimidazol-2-ylmethylaminocarbonyl | 0 | 0 | phenylsulfonylaminomethyl | H | |
| 499hm | benzimidazol-2-ylmethylaminocarbonyl | 0 | 0 | 3-azabicyclo[3.2.2]nonan-3-ylcarbonyl | H | |
| 499hn | benzimidazol-2-ylmethylaminocarbonyl | 0 | 0 | adamantan-1-yl methylaminocarbonyl | H | |
| 499ho | benzimidazol-2-ylmethylaminocarbonyl | 0 | 0 | adamantan-1-yl aminocarbonyl | H | |
| 499hp | benzimidazol-2-ylmethylaminocarbonyl | 0 | 0 | adamantan-2-yl aminocarbonyl | H | |
| 499hq | benzimidazol-2-ylmethylaminocarbonyl | 0 | 0 | tetrahydroisoquinolin-2-ylcarbonyl | H | |
| 499hr | N-(benzimidazol-2-ylmethyl)-N-methyl-aminocarbonyl | 0 | 0 | H | NHSO₂(2,4,6-trimethylphenyl) | |
| 499hs | N-(benzimidazol-2-ylmethyl)-N-methyl-aminocarbonyl | 0 | 0 | H | NHSO₂(2,4,6-trichlorophenyl) | |
| 499ht | N-(benzimidazol-2-ylmethyl)-N-methyl-aminocarbonyl | 0 | 0 | H | NHSO₂(2,6-dichlorophenyl) | |
| 499hu | N-(benzimidazol-2-ylmethyl)-N-methyl-aminocarbonyl | 0 | 0 | H | NHSO₂(2-chloro-6-methylphenyl) | |
| 499hv | N-(benzimidazol-2-ylmethyl)-N-methyl-aminocarbonyl | 0 | 0 | H | NHSO₂C₆H₄(2-CH₃) | |
| 499hw | N-(benzimidazol-2-ylmethyl)-N-methyl-aminocarbonyl | 0 | 0 | H | NHSO₂C₆H₄(2-Br) | |
| 499hx | N-(benzimidazol-2-ylmethyl)-N-methyl-aminocarbonyl | 0 | 0 | H | NHSO2[4-(2,6-dimethylphenyl)phenyl | |
| 499hy | N-(benzimidazol-2-ylmethyl)-N-methyl-aminocarbonyl | 0 | 0 | H | NHSO₂C₆H₄(4-Ph) | |
| 499hz | N-(benzimidazol-2-ylmethyl)-N-methyl-aminocarbonyl | 0 | 0 | H | NHSO₂[4-(3,5-dimethyl)isoxazolyl] | |
| 499ia | N-(benzimidazol-2-ylmethyl)-N-methyl-aminocarbonyl | 0 | 0 | H | NHSO₂(1-napthyl) | |
| 499ib | N-(benzimidazol-2-ylmethyl)-N-methyl-aminocarbonyl | 0 | 0 | H | NHSO₂(2-napthyl) | |
| 499ic | N-(benzimidazol-2-ylmethyl)-N-methyl-aminocarbonyl | 0 | 0 | H | NHSO₂NHCH₂Ph | |
| 499id | N-(benzimidazol-2-ylmethyl)-N-methyl-aminocarbonyl | 0 | 0 | H | NHSO₂NHPh | |
| 499ie | N-(benzimidazol-2-ylmethyl)-N-methyl-aminocarbonyl | 0 | 0 | Ph | H | |
| 499if | N-(benzimidazol-2-ylmethyl)-N-methyl-aminocarbonyl | 0 | 0 | phenylsulfonylaminomethyl | H | |

TABLE 1-continued $R^1-U{-}(CH_2)_m{-}\text{[isoxazoline]}{-}(CH_2)_n{-}C(O){-}NH{-}CH(R^8){-}CH(R^9){-}COOH$ (N—O)

| Ex. No. | R¹-U | m | n | R⁸ | R⁹ | MS |
|---|---|---|---|---|---|---|
| 499ig | N-(benzimidazol-2-ylmethyl)-N-methyl-aminocarbonyl | 0 | 0 | 3-azabicyclo[3.2.2]nonan-3-ylcarbonyl | H | |
| 499ih | N-(benzimidazol-2-ylmethyl)-N-methyl-aminocarbonyl | 0 | 0 | adamantan-1-yl methylaminocarbonyl | H | |
| 499ii | N-(benzimidazol-2-ylmethyl)-N-methyl-aminocarbonyl | 0 | 0 | adamantan-1-yl aminocarbonyl | H | |
| 499ij | N-(benzimidazol-2-ylmethyl)-N-methyl-aminocarbonyl | 0 | 0 | adamantan-2-yl aminocarbonyl | H | |
| 499ik | N-benzimidazol-2-ylmethyl)-N-methyl-aminocarbonyl | 0 | 0 | tetrahydroisoquinolin-2-ylcarbonyl | H | |

TABLE 2

$R^1-U{-}(CH_2)_m{-}\text{[isoxazoline]}{-}(CH_2)_n{-}C(O){-}NH{-}CH(R^8){-}CH(R^9){-}COOH$ (O—N)

| Ex. No. | R¹—U | m | n | R⁸ | R⁹ | MS |
|---|---|---|---|---|---|---|
| 501 | tetrahydropyrimidin-2-ylamino | 3 | 1 | H | H | |
| 502 | tetrahydropyrimidin-2-ylamino | 3 | 1 | H | NHCbz | |
| 503 | tetrahydropyrimidin-2-ylamino | 3 | 1 | H | NHtBOC | |
| 504 | tetrahydropyrimidin-2-ylamino | 3 | 1 | H | NHCO₂-nBu | |
| 505 | tetrahydropyrimidin-2-ylamino | 3 | 1 | H | NHCO₂Et | |
| 506 | tetrahydropyrimidin-2-ylamino | 3 | 1 | H | NHCO₂Me | |
| 507 | tetrahydropyrimidin-2-ylamino | 3 | 1 | H | NHCO(CH₂)ₙPh | |
| 508 | tetrahydropyrimidin-2-ylamino | 3 | 1 | H | NHCOtBu | |
| 509 | tetrahydropyrimidin-2-ylamino | 3 | 1 | H | NHCO-n-C₅H₁₁ | |
| 510 | tetrahydropyrimidin-2-ylamino | 3 | 1 | H | NHCO-n-C₄H₉ | |
| 511 | tetrahydropyrimidin-2-ylamino | 3 | 1 | H | NHCOCH₂CH₃ | |
| 512 | tetrahydropyrimidin-2-ylamino | 3 | 1 | H | NHCOCH₃ | |
| 513 | tetrahydropyrimidin-2-ylamino | 3 | 1 | H | NHSO₂CH₃ | |
| 514 | tetrahydropyrimidin-2-ylamino | 3 | 1 | H | NHSO₂CH₂CH₃ | |
| 515 | tetrahydropyrimidin-2-ylamino | 3 | 1 | H | NHSO₂n-Bu | |
| 516 | tetrahydropyrimidin-2-ylamino | 3 | 1 | H | NHSO₂Ph | |
| 517 | tetrahydropyrimidin-2-ylamino | 3 | 1 | H | NHSO₂C₆H₄(4-CH₃) | |
| 518 | tetrahydropyrimidin-2-ylamino | 3 | 1 | H | NHSO₂Bn | |
| 519 | tetrahydropyrimidin-2-ylamino | 3 | 1 | H | NHCO(2-pyridyl) | |
| 520 | tetrahydropyrimidin-2-ylamino | 3 | 1 | H | NHCO(3-pyridyl) | |
| 521 | tetrahydropyrimidin- | 3 | 1 | H | NHCO(4-pyridyl) | |

TABLE 2-continued

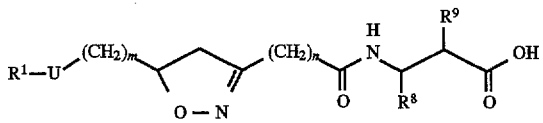

| Ex. No. | $R^1-U$ | m | n | $R^8$ | $R^9$ | MS |
|---|---|---|---|---|---|---|
| 522 | tetrahydropyrimidin-2-ylamino | 3 | 1 | H | NHCOCH$_2$(2-pyridyl) | |
| 523 | tetrahydropyrimidin-2-ylamino | 3 | 1 | H | NHCOCH$_2$(3-pyridyl) | |
| 524 | tetrahydropyrimidin-2-ylamino | 3 | 1 | H | NHCOCH$_2$(4-pyridyl) | |
| 525 | tetrahydropyrimidin-2-ylamino | 3 | 1 | H | NHCO$_2$CH$_2$(2-pyridyl) | |
| 526 | tetrahydropyrimidin-2-ylamino | 3 | 1 | H | NHCO$_2$CH$_2$(3-pyridyl) | |
| 527 | tetrahydropyrimidin-2-ylamino | 3 | 1 | H | NHCO$_2$CH$_2$(4-pyridyl) | |
| 528 | imidazolin-2-ylamino | 3 | 1 | H | H | |
| 529 | imidazolin-2-ylamino | 3 | 1 | H | NHCbz | |
| 530 | imidazolin-2-ylamino | 3 | 1 | H | NHtBOC | |
| 531 | imidazolin-2-ylamino | 3 | 1 | H | NHCO$_2$-nBu | |
| 532 | imidazolin-2-ylamino | 3 | 1 | H | NHCO$_2$Et | |
| 533 | imidazolin-2-ylamino | 3 | 1 | H | NHCO$_2$Me | |
| 534 | imidazolin-2-ylamino | 3 | 1 | H | NHCO(CH$_2$)$_n$Ph | |
| 535 | imidazolin-2-ylamino | 3 | 1 | H | NHCOtBu | |
| 536 | imidazolin-2-ylamino | 3 | 1 | H | NHCO-n-C$_5$H$_{11}$ | |
| 537 | imidazolin-2-ylamino | 3 | 1 | H | NHCO-n-C$_4$H$_9$ | |
| 538 | imidazolin-2-ylamino | 3 | 1 | H | NHCOCH$_2$CH$_3$ | |
| 539 | imidazolin-2-ylamino | 3 | 1 | H | NHCOCH$_3$ | |
| 540 | imidazolin-2-ylamino | 3 | 1 | H | NHSO$_2$CH$_3$ | |
| 541 | imidazolin-2-ylamino | 3 | 1 | H | NHSO$_2$CH$_2$CH$_3$ | |
| 542 | imidazolin-2-ylamino | 3 | 1 | H | NHSO$_2$n-Bu | |
| 543 | imidazolin-2-ylamino | 3 | 1 | H | NHSO$_2$Ph | |
| 544 | imidazolin-2-ylamino | 3 | 1 | H | NHSO$_2$C$_6$H$_4$(4-CH$_3$) | |
| 545 | imidazolin-2-ylamino | 3 | 1 | H | NHSO$_2$Bn | |
| 546 | imidazolin-2-ylamino | 3 | 1 | H | NHCO(2-pyridyl) | |
| 547 | imidazolin-2-ylamino | 3 | 1 | H | NHCO(3-pyridyl) | |
| 548 | imidazolin-2-ylamino | 3 | 1 | H | NHCO(4-pyridyl) | |
| 549 | imidazolin-2-ylamino | 3 | 1 | H | NHCOCH$_2$(2-pyridyl) | |
| 550 | imidazolin-2-ylamino | 3 | 1 | H | NHCOCH$_2$(3-pyridyl) | |
| 551 | imidazolin-2-ylamino | 3 | 1 | H | NHCOCH$_2$(4-pyridyl) | |
| 552 | imidazolin-2-ylamino | 3 | 1 | H | NHCO$_2$CH$_2$(2-pyridyl) | |
| 553 | imidazolin-2-ylamino | 3 | 1 | H | NHCO$_2$CH$_2$(3-pyridyl) | |
| 554 | imidazolin-2-ylamino | 3 | 1 | H | NHCO$_2$CH$_2$(4-pyridyl) | |
| 555 | tetrahydropyrimidin-2-ylamino | 4 | 0 | H | H | |

TABLE 2-continued

R¹—U—(CH₂)ₘ—[C(=N—O)]—(CH₂)ₙ—C(=O)—NH—CHR⁸—CH(R⁹)—COOH

| Ex. No. | R¹—U | m | n | R⁸ | R⁹ | MS |
|---|---|---|---|---|---|---|
| 556 | tetrahydropyrimidin-2-ylamino | 4 | 0 | H | NHCbz | |
| 557 | tetrahydropyrimidin-2-ylamino | 4 | 0 | H | NHtBOC | |
| 558 | tetrahydropyrimidin-2-ylamino | 4 | 0 | H | NHCO₂-nBu | |
| 559 | tetrahydropyrimidin-2-ylamino | 4 | 0 | H | NHCO₂Et | |
| 560 | tetrahydropyrimidin-2-ylamino | 4 | 0 | H | NHCO₂Me | |
| 561 | tetrahydropyrimidin-2-ylamino | 4 | 0 | H | NHCO(CH₂)ₙPh | |
| 562 | tetrahydropyrimidin-2-ylamino | 4 | 0 | H | NHCOtBu | |
| 563 | tetrahydropyrimidin-2-ylamino | 4 | 0 | H | NHCO-n-C₅H₁₁ | |
| 564 | tetrahydropyrimidin-2-ylamino | 4 | 0 | H | NHCO-n-C₄H₉ | |
| 565 | tetrahydropyrimidin-2-ylamino | 4 | 0 | H | NHCOCH₂CH₃ | |
| 566 | tetrahydropyrimidin-2-ylamino | 4 | 0 | H | NHCOCH₃ | |
| 567 | tetrahydropyrimidin-2-ylamino | 4 | 0 | H | NHSO₂CH₃ | |
| 568 | tetrahydropyrimidin-2-ylamino | 4 | 0 | H | NHSO₂CH₂CH₃ | |
| 569 | tetrahydropyrimidin-2-ylamino | 4 | 0 | H | NHSO₂n-Bu | |
| 570 | tetrahydropyrimidin-2-ylamino | 4 | 0 | H | NHSO₂Ph | |
| 571 | tetrahydropyrimidin 2-ylamino | 4 | 0 | H | NHSO₂C₆H₄(4-CH₃) | |
| 572 | tetrahydropyrimidin 2-ylamino | 4 | 0 | H | NHSO₂Bn | |
| 573 | tetrahydropyrimidin 2-ylamino | 4 | 0 | H | NHCO(2-pyridyl) | |
| 574 | tetrahydropyrimidin 2-ylamino | 4 | 0 | H | NHCO(3-pyridyl) | |
| 575 | tetrahydropyrimidin 2-ylamino | 4 | 0 | H | NHCO(4-pyridyl) | |
| 576 | tetrahydropyrimidin 2-ylamino | 4 | 0 | H | NHCOCH₂(2-pyridyl) | |
| 577 | tetrahydropyrimidin-2-ylamino | 4 | 0 | H | NHCOCH₂(3-pyridyl) | |
| 578 | tetrahydropyrimidin-2-ylamino | 4 | 0 | H | NHCOCH₂(4-pyridyl) | |
| 579 | tetrahydropyrimidin-2-ylamino | 4 | 0 | H | NHCO₂CH₂(2-pyridyl) | |
| 580 | tetrahydropyrimidin 2-ylamino | 4 | 0 | H | NHCO₂CH₂(3-pyridyl) | |
| 581 | tetrahydropyrimidin 2-ylamino | 4 | 0 | H | NHCO₂CH₂(4-pyridyl) | |
| 582 | imidazolin-2-ylamino | 4 | 0 | H | H | |
| 583 | imidazolin-2-ylamino | 4 | 0 | H | NHCbz | 475.4 |
| 584 | imidazolin-2-ylamino | 4 | 0 | H | NHtBOC | |
| 585 | imidazolin-2-ylamino | 4 | 0 | H | NHCO₂-nBu | |
| 586 | imidazolin-2-ylamino | 4 | 0 | H | NHCO₂Et | |
| 587 | imidazolin-2-ylamino | 4 | 0 | H | NHCO₂Me | |
| 588 | imidazolin-2-ylamino | 4 | 0 | H | NHCO(CH₂)ₙPh | |
| 589 | imidazolin-2-ylamino | 4 | 0 | H | NHCOtBu | |
| 590 | imidazolin-2- | 4 | 0 | H | NHCO-n-C₅H₁₁ | |

TABLE 2-continued

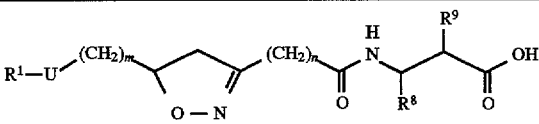

| Ex. No. | $R^1-U$ | m | n | $R^8$ | $R^9$ | MS |
|---|---|---|---|---|---|---|
| | ylamino | | | | | |
| 591 | imidazolin-2-ylamino | 4 | 0 | H | NHCO-n-$C_4H_9$ | |
| 592 | imidazolin-2-ylamino | 4 | 0 | H | NHCO$CH_2CH_3$ | |
| 593 | imidazolin-2-ylamino | 4 | 0 | H | NHCO$CH_3$ | |
| 594 | imidazolin-2-ylamino | 4 | 0 | H | NHSO$_2CH_3$ | |
| 595 | imidazolin-2-ylamino | 4 | 0 | H | NHSO$_2CH_2CH_3$ | |
| 596 | imidazolin-2-ylamino | 4 | 0 | H | NHSO$_2$n-Bu | |
| 597 | imidazolin-2-ylamino | 4 | 0 | H | NHSO$_2$Ph | 481.3 |
| 598 | imidazolin-2-ylamino | 4 | 0 | H | NHSO$_2C_6H_4$(4-$CH_3$) | |
| 599 | imidazolin-2-ylamino | 4 | 0 | H | NHSO$_2$Bn | |
| 600 | imidazolin-2-ylamino | 4 | 0 | H | NHCO(2-pyridyl) | |
| 601 | imidazolin-2-ylamino | 4 | 0 | H | NHCO(3-pyridyl) | |
| 602 | imidazolin-2-ylamino | 4 | 0 | H | NHCO(4-pyridyl) | |
| 603 | imidazolin-2-ylamino | 4 | 0 | H | NHCO$CH_2$(2-pyridyl) | |
| 604 | imidazolin-2-ylamino | 4 | 0 | H | NHCO$CH_2$(3-pyridyl) | |
| 605 | imidazolin-2-ylamino | 4 | 0 | H | NHCO$CH_2$(4-pyridyl) | |
| 606 | imidazolin-2-ylamino | 4 | 0 | H | NHCO$_2CH_2$(2-pyridyl) | |
| 607 | imidazolin-2-ylamino | 4 | 0 | H | NHCO$_2CH_2$(3-pyridyl) | |
| 608 | imidazolin-2-ylamino | 4 | 0 | H | NHCO$_2CH_2$(4-pyridyl) | |
| 609 | tetrahydropyrimidin-2-ylamino | 3 | 0 | H | H | |
| 610 | tetrahydropyrimidin-2-ylamino | 3 | 0 | H | NHCbz | |
| 611 | tetrahydropyrimidin-2-ylamino | 3 | 0 | H | NHtBOC | |
| 612 | tetrahydropyrimidin 2-ylamino | 3 | 0 | H | NHCO$_2$-nBu | |
| 613 | tetrahydropyrimidin-2-ylamino | 3 | 0 | H | NHCO$_2$Et | |
| 614 | tetrahydropyrimidin-2-ylamino | 3 | 0 | H | NHCO$_2$Me | |
| 615 | tetrahydropyrimidin-2-ylamino | 3 | 0 | H | NHCO$(CH_2)_n$Ph | |
| 616 | tetrahydropyrimidin-2-ylamino | 3 | 0 | H | NHCOtBu | |
| 617 | tetrahydropyrimidin-2-ylamino | 3 | 0 | H | NHCO-n-$C_5H_{11}$ | |
| 618 | tetrahydropyrimidin-2-ylamino | 3 | 0 | H | NHCO-n-$C_4H_9$ | |
| 619 | tetrahydropyrimidin-2-ylamino | 3 | 0 | H | NHCO$CH_2CH_3$ | |
| 620 | tetrahydropyrimidin-2-ylamino | 3 | 0 | H | NHCO$CH_3$ | |
| 621 | tetrahydropyrimidin-2-ylamino | 3 | 0 | H | NHSO$_2CH_3$ | |
| 622 | tetrahydropyrimidin-2-ylamino | 3 | 0 | H | NHSO$_2CH_2CH_3$ | |
| 623 | tetrahydropyrimidin-2-ylamino | 3 | 0 | H | NHSO$_2$n-Bu | |
| 624 | tetrahydropyrimidin-2-ylamino | 3 | 0 | H | NHSO$_2$Ph | |

TABLE 2-continued $$R^1-U-(CH_2)_m-\overset{}{\underset{O-N}{C}}-(CH_2)_n-\overset{O}{\underset{}{C}}-\overset{H}{\underset{R^8}{N}}-\overset{R^9}{\underset{}{C}H}-\overset{}{\underset{}{C}}-OH$$

| Ex. No. | R¹—U | m | n | R⁸ | R⁹ | MS |
|---|---|---|---|---|---|---|
| 625 | tetrahydropyrimidin-2-ylamino | 3 | 0 | H | NHSO$_2$C$_6$H$_4$(4-CH$_3$) | |
| 626 | tetrahydropyrimidin-2-ylamino | 3 | 0 | H | NHSO$_2$Bn | |
| 627 | tetrahydropyrimidin-2-ylamino | 3 | 0 | H | NHCO(2-pyridyl) | |
| 628 | tetrahydropyrimidin-2-ylamino | 3 | 0 | H | NHCO(3-pyridyl) | |
| 629 | tetrahydropyrimidin-2-ylamino | 3 | 0 | H | NHCO(4-pyridyl) | |
| 630 | tetrahydropyrimidin-2-ylamino | 3 | 0 | H | NHCOCH$_2$(2-pyridyl) | |
| 631 | tetrahydropyrimidin-2-ylamino | 3 | 0 | H | NHCOCH$_2$(3-pyridyl) | |
| 632 | tetrahydropyrimidin-2-ylamino | 3 | 0 | H | NHCOCH$_2$(4-pyridyl) | |
| 633 | tetrahydropyrimidin-2-ylamino | 3 | 0 | H | NHCO$_2$CH$_2$(2-pyridyl) | |
| 634 | tetrahydropyrimidin-2-ylamino | 3 | 0 | H | NHCO$_2$CH$_2$(3-pyridyl) | |
| 635 | tetrahydropyrimidin-2-ylamino | 3 | 0 | H | NHCO$_2$CH$_2$(4-pyridyl) | |
| 636 | imidazolin-2-ylamino | 3 | 0 | H | H | |
| 637 | imidazolin-2-ylamino | 3 | 0 | H | NHCbz | 461.3 |
| 638 | imidazolin-2-ylamino | 3 | 0 | H | NHtBOC | |
| 639 | imidazolin-2-ylamino | 3 | 0 | H | NHCO$_2$-nBu | |
| 640 | imidazolin-2-ylamino | 3 | 0 | H | NHCO$_2$Et | |
| 641 | imidazolin-2-ylamino | 3 | 0 | H | NHCO$_2$Me | |
| 642 | imidazolin-2-ylamino | 3 | 0 | H | NHCO(CH$_2$)$_n$Ph | |
| 643 | imidazolin-2-ylamino | 3 | 0 | H | NHCOtBu | |
| 644 | imidazolin-2-ylamino | 3 | 0 | H | NHCO-n-C$_5$H$_{11}$ | |
| 645 | imidazolin-2-ylamino | 3 | 0 | H | NHCO-n-C$_4$H$_9$ | |
| 646 | imidazolin-2-ylamino | 3 | 0 | H | NHCOCH$_2$CH$_3$ | |
| 647 | imidazolin-2-ylamino | 3 | 0 | H | NHCOCH$_3$ | |
| 648 | imidazolin-2-ylamino | 3 | 0 | H | NHSO$_2$CH$_3$ | |
| 649 | imidazolin-2-ylamino | 3 | 0 | H | NHSO$_2$CH$_2$CH$_3$ | |
| 650 | imidazolin-2-ylamino | 3 | 0 | H | NHSO$_2$n-Bu | |
| 651 | imidazolin-2-ylamino | 3 | 0 | H | NHSO$_2$Ph | |
| 652 | imidazolin-2-ylamino | 3 | 0 | H | NHSO$_2$C$_6$H$_4$(4-CH$_3$) | |
| 653 | imidazolin-2-ylamino | 3 | 0 | H | NHSO$_2$Bn | |
| 654 | imidazolin-2-ylamino | 3 | 0 | H | NHCO(2-pyridyl) | |
| 655 | imidazolin-2-ylamino | 3 | 0 | H | NHCO(3-pyridyl) | |
| 656 | imidazolin-2-ylamino | 3 | 0 | H | NHCO(4-pyridyl) | |
| 657 | imidazolin-2-ylamino | 3 | 0 | H | NHCOCH$_2$(2-pyridyl) | |
| 658 | imidazolin-2-ylamino | 3 | 0 | H | NHCOCH$_2$(3-pyridyl) | |
| 659 | imidazolin-2- | 3 | 0 | H | NHCOCH$_2$(4-pyridyl) | |

TABLE 2-continued $$R^1-U-(CH_2)_m-\underset{O-N}{C}=\underset{}{CH}-(CH_2)_n-\underset{O}{C}(=O)-\underset{R^8}{N}H-\underset{}{CH}(R^9)-C(=O)OH$$

| Ex. No. | R¹—U | m | n | R⁸ | R⁹ | MS |
|---|---|---|---|---|---|---|
| 660 | imidazolin-2-ylamino | 3 | 0 | H | NHCO$_2$CH$_2$(2-pyridyl) | |
| 661 | imidazolin-2-ylamino | 3 | 0 | H | NHCO$_2$CH$_2$(3-pyridyl) | |
| 662 | imidazolin-2-ylamino | 3 | 0 | H | NHCO$_2$CH$_2$(4-pyridyl) | |
| 663 | pyridin-2-ylamino | 3 | 1 | H | NHCbz | |
| 664 | pyridin-2-ylamino | 3 | 1 | H | NHCO$_2$-n-Bu | |
| 665 | pyridin-2-ylamino | 3 | 1 | H | NHSO$_2$Ph | |
| 666 | pyridin-2-ylamino | 3 | 1 | H | NHSO$_2$-nBu | |
| 667 | pyridin-2-ylamino | 4 | 0 | H | NHCbz | 484.3 |
| 668 | pyridin-2-ylamino | 4 | 0 | H | NHCO$_2$-n-Bu | |
| 669 | pyridin-2-ylamino | 4 | 0 | H | NHSO$_2$Ph | 490.2 |
| 670 | pyridin-2-ylamino | 4 | 0 | H | NHSO$_2$-nBu | |
| 671 | pyridin-2-ylamino | 3 | 0 | H | NHCbz | |
| 672 | pyridin-2-ylamino | 3 | 0 | H | NHCO$_2$-n-Bu | |
| 673 | pyridin-2-ylamino | 3 | 0 | H | NHSO$_2$Ph | |
| 674 | pyridin-2-ylamino | 3 | 0 | H | NHSO$_2$-nBu | |
| 675 | imidazol-2-ylamino | 3 | 1 | H | NHCbz | |
| 676 | imidazol-2-ylamino | 3 | 1 | H | NHCO$_2$-n-Bu | |
| 677 | imidazol-2-ylamino | 3 | 1 | H | NHSO$_2$Ph | |
| 678 | imidazol-2-ylamino | 3 | 1 | H | NHSO$_2$-nBu | |
| 679 | imidazol-2-ylamino | 4 | 0 | H | NHCbz | |
| 680 | imidazol-2-ylamino | 4 | 0 | H | NHCO$_2$-n-Bu | |
| 681 | imidazol-2-ylamino | 4 | 0 | H | NHSO$_2$Ph | |
| 682 | imidazol-2-ylamino | 4. | 0 | H | NHSO$_2$-nBu | |
| 683 | imidazol-2-ylamino | 3 | 0 | H | NHCbz | |
| 684 | imidazol-2-ylamino | 3 | 0 | H | NHCO$_2$-n-Bu | |
| 685 | imidazol-2-ylamino | 3 | 0 | H | NHSO$_2$Ph | |
| 686 | imidazol-2-ylamino | 3 | 0 | H | NHSO$_2$-nBu | |
| 687 | thiazol-2-ylamino | 3 | 1 | H | NHCbz | |
| 688 | 2-aminopyridin-6-yl | 3 | 1 | H | NHCO$_2$-n-Bu | |
| 689 | 2-aminopyridin-6-yl | 3 | 1 | H | NHSO$_2$Ph | |
| 690 | 2-aminopyridin-6-yl | 3 | 1 | H | NHSO$_2$-nBu | |
| 691 | 2-aminopyridin-6-yl | 4 | 0 | H | NHCbz | |
| 692 | 2-aminopyridin-6-yl | 4 | 0 | H | NHCO$_2$-n-Bu | |
| 693 | 2-aminopyridin-6-yl | 4 | 0 | H | NHSO$_2$Ph | |
| 694 | 2-aminopyridin-6-yl | 4 | 0 | H | NHSO$_2$-nBu | |
| 695 | 2-aminopyridin-6-yl | 3 | 0 | H | NHCbz | 470.5 |
| 696 | 2-aminopyridin-6-yl | 3 | 0 | H | NHCO$_2$-n-Bu | |
| 697 | 2-aminopyridin-6-yl | 3 | 0 | H | NHSO$_2$Ph | 476.4 |
| 698 | 2-aminopyridin-6-yl | 3 | 0 | H | NHSO$_2$-nBu | |
| 699 | 2-aminopyridin-3-yl | 2 | 0 | H | NHCbz | |
| 700 | 2-aminopyridin-3-yl | 2 | 0 | H | NHCO$_2$-n-Bu | |
| 701 | 2-aminopyridin-3-yl | 2 | 0 | H | NHSO$_2$Ph | |
| 702 | 2-aminopyridin-3-yl | 2 | 0 | H | NHSO$_2$-nBu | |
| 703 | 2-aminothiazol-4-yl | 3 | 1 | H | NHCbz | |
| 704 | 2-aminothiazol-4-yl | 3 | 1 | H | NHCO$_2$-n-Bu | |
| 705 | 2-aminothiazol-4-yl | 3 | 1 | H | NHSO$_2$Ph | |
| 706 | 2-aminothiazol-4-yl | 3 | 1 | H | NHSO$_2$-nBu | |
| 707 | 2-aminothiazol-4-yl | 4 | 0 | H | NHCbz | |
| 708 | 2-aminothiazol-4-yl | 4 | 0 | H | NHCO$_2$-n-Bu | |
| 709 | 2-aminothiazol-4-yl | 4 | 0 | H | NHSO$_2$Ph | |
| 710 | 2-aminopyridin-6-yl | 4 | 0 | H | NHSO$_2$-nBu | |
| 711 | 2-aminothiazol-4-yl | 3 | 0 | H | NHCbz | |
| 712 | 2-aminothiazol-4-yl | 3 | 0 | H | NHCO$_2$-n-Bu | |
| 713 | 2-aminothiazol-4-yl | 3 | 0 | H | NHSO$_2$Ph | |
| 714 | 2-aminothiazol-4-yl | 3 | 0 | H | NHSO$_2$-nBu | |
| 715 | 2-aminothiazol-4-yl | 3 | 1 | H | NHCbz | |
| 716 | 2-aminothiazol-4-yl | 3 | 1 | H | NHCO$_2$-n-Bu | |
| 775 | imidazolin-2-ylamino | 2 | 2 | H | NHCbz | |
| 776 | imidazolin-2-ylamino | 2 | 2 | H | NHCO$_2$-n-Bu | |
| 777 | imidazolin-2-ylamino | 2 | 2 | H | NHSO$_2$Ph | |
| 778 | imidazolin-2-ylamino | 2 | 2 | H | NHSO$_2$-nBu | |

TABLE 2-continued

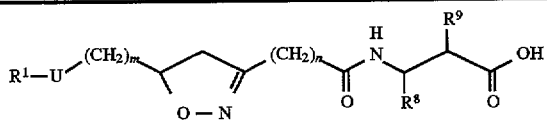

| Ex. No. | $R^1-U$ | m | n | $R^8$ | $R^9$ | MS |
|---|---|---|---|---|---|---|
| 779 | tetrahydropyrimidin-2-ylamino | 2 | 2 | H | NHCbz | |
| 780 | tetrahydropyrimidin-2-ylamino | 2 | 2 | H | $NHCO_2$-n-Bu | |
| 781 | tetrahydropyrimidin-2-ylamino | 2 | 2 | H | $NHSO_2Ph$ | |
| 782 | tetrahydropyrimidin-2-ylamino | 2 | 2 | H | $NHSO_2$-nBu | |
| 783 | benzimidazol-2-ylamino | 4 | 0 | H | NHCbz | |
| 784 | benzthiazol-2-ylamino | 4 | 0 | H | NHCbz | |
| 787 | imidazol-4-ylamino | 4 | 0 | H | NHCbz | |
| 794 | 2-iminopyrrolidin-5-yl | 3 | 1 | H | NHCbz | |
| 795 | 2-iminopyrrolidin-5-yl | 3 | 1 | H | $NHSO_2Ph$ | |
| 796 | 2-iminopyrrolidin-5-yl | 3 | 0 | H | NHCbz | |
| 797 | 2-iminopyrrolidin-5-yl | 3 | 0 | H | $NHSO_2Ph$ | |
| 798 | 2-iminopyrrolidin-5-yl | 2 | 1 | H | NHCbz | |
| 799 | 2-iminopyrrolidin-5-yl | 2 | 1 | H | $NHSO_2Ph$ | |
| 800 | 2-iminopiperidin-6-yl | 3 | 1 | H | NHCbz | |
| 801 | 2-iminopiperidin-6-yl | 3 | 1 | H | $NHSO_2Ph$ | |
| 802 | 2-iminopiperidin-6-yl | 3 | 0 | H | NHCbz | |
| 803 | 2-iminopiperidin-6-yl | 3 | 0 | H | $NHSO_2Ph$ | |
| 804 | 2-iminopiperidin-6-yl | 2 | 1 | H | NHCbz | |
| 805 | 2-iminopiperidin-6-yl | 2 | 1 | H | $NHSO_2Ph$ | |
| 806 | 2-iminoazepin-7-yl | 3 | 1 | H | NHCbz | |
| 807 | 2-iminoazepin-7-yl | 3 | 1 | H | $NHSO_2Ph$ | |
| 808 | 2-iminoazepin-7-yl | 3 | 0 | H | NHCbz | |
| 809 | 2-iminoazepin-7-yl | 3 | 0 | H | $NHSO_2Ph$ | |
| 810 | 2-iminoazepin-7-yl | 2 | 1 | H | NHCbz | |
| 811 | 2-iminoazepin-7-yl | 2 | 1 | H | $NHSO_2Ph$ | |
| 812 | benzimidazol-2-ylamino | 4 | 0 | n-Bu | H | |
| 813 | benzthiazol-2-ylamino | 4 | 0 | n-Bu | H | |
| 816 | imidazol-4-ylamino | 4 | 0 | n-Bu | H | |
| 823 | imidazolin-2-ylamino | 2 | 0 | H | NHCbz | 447.4 |
| 824 | imidazolin-2-ylamino | 2 | 0 | H | NHSO2Ph | |
| 830 | pyridin-2-ylamino | 4 | 0 | H | $N(Me)SO_2C_6H_4$-(3-Me) | 518.2 |
| 831 | pyridin-2-ylamino | 4 | 0 | H | $NHSO_2C_6H_4$-(2-Me) | 504.3 |
| 832 | pyridin-2-ylamino | 4 | 0 | H | $NHSO_2C_6H_4$-(3-Me) | 504.2 |
| 833 | pyridin-2-ylamino | 4 | 0 | H | $NHSO_2C_6H_4$-(4-Me) | 504.2 |
| 834 | pyridin-2-ylamino | 4 | 0 | H | $NHSO_2C_6H_4$-(2-Br) | 568.1 |
| 835 | pyridin-2-ylamino | 4 | 0 | H | $NHSO_2C_6H_4$-(3-Br) | 570.0 |
| 836 | pyridin-2-ylamino | 4 | 0 | H | $NHSO_2C_6H_4$-(4-Br) | 570.0 |
| 837 | pyridin-2-ylamino | 4 | 0 | H | $NHSO_2C_6H_4$-(2-F) | 508.2 |
| 838 | pyridin-2-ylamino | 4 | 0 | H | $NHSO_2C_6H_4$-(4-F) | 508.2 |
| 839 | pyridin-2-ylamino | 4 | 0 | H | $NHSO_2C_6H_4$-(2-$CF_3$) | 558.3 |
| 840 | pyridin-2-ylamino | 4 | 0 | H | $NHSO_2C_6H_4$-(3-$CF_3$) | 558.1 |
| 841 | pyridin-2-ylamino | 4 | 0 | H | $NHSO_2C_6H_4$-(4-$CF_3$) | |
| 842 | pyridin-2-ylamino | 4 | 0 | H | $NHSO_2C_6H_4$-(4-$OCH_3$) | 520.1 |
| 843 | pyridin-2-ylamino | 4 | 0 | H | $NHSO_2C_6H_4$-(4-CN) | 515.2 |
| 844 | pyridin-2-ylamino | 4 | 0 | H | $NHSO_2$[4-(acetylamino)phenyl] | 547.3 |
| 845 | pyridin-2-ylamino | 4 | 0 | H | $NHSO_2C_6H_4$-(4-$OCF_3$) | 574.3 |

TABLE 2-continued

Structure: $R^1-U-(CH_2)_m-$ [isoxazoline with O-N] $-(CH_2)_n-C(O)-N(H)-CH(R^8)-CH(R^9)-C(O)-OH$

| Ex. No. | $R^1-U$ | m | n | $R^8$ | $R^9$ | MS |
|---|---|---|---|---|---|---|
| 846 | pyridin-2-ylamino | 4 | 0 | H | $NHSO_2C_6H_4$-(4-isopropyl) | 532.4 |
| 847 | pyridin-2-ylamino | 4 | 0 | H | NHSO2(2,6-dichlorophenyl) | 558.3 |
| 848 | pyridin-2-ylamino | 4 | 0 | H | NHSO2(2-chloro-6-methylphenyl) | 538.3 |
| 849 | pyridin-2-ylamino | 4 | 0 | H | NHSO2(2,4,6-trimethylphenyl) | 532.2 |
| 850 | pyridin-2-ylamino | 4 | 0 | H | NHSO2(2,4,6-triisopropylphenyl) | 616.4 |
| 851 | pyridin-2-ylamino | 4 | 0 | H | $NHSO_2C_6H_4$-(4-Ph) | 566.1 |
| 852 | pyridin-2-ylamino | 4 | 0 | H | $NHSO_2$[4-(2,6-dimethylphenyl)phenyl | |
| 853 | pyridin-2-ylamino | 4 | 0 | H | $NHSO_2$(1-napthyl) | 540.1 |
| 854 | pyridin-2-ylamino | 4 | 0 | H | $NHSO_2$(2-napthyl) | 540.3 |
| 855 | pyridin-2-ylamino | 4 | 0 | H | $NHSO_2$(8-quinolinyl) | 541.1 |
| 856 | pyridin-2-ylamino | 4 | 0 | H | $NHSO_{2(CH}=CH)C_6H_5$ | 516.1 |
| 857 | pyridin-2-ylamino | 4 | 0 | H | $NHSO_2CH_2Ph$ | 504.3 |
| 858 | pyridin-2-ylamino | 4 | 0 | H | $NHSO_2$(2-thienyl) | 496.1 |
| 859 | pyridin-2-ylamino | 4 | 0 | H | $NHSO_2$[2-(5-chloro)thienyl] | 530.2 |
| 860 | pyridin-2-ylamino | 4 | 0 | H | $NHSO_2$[2-(5-pyridin-2-yl)thienyl] | 573.0 |
| 861 | pyridin-2-ylamino | 4 | 0 | H | $NHSO_2$[3-(2-(methoxycarbonyl)thienyl] | 554.1 |
| 862 | pyridin-2-ylamino | 4 | 0 | H | $NHSO_2$[2-(5-isoxazol-3-yl)thienyl] | 563.3 |
| 863 | pyridin-2-ylamino | 4 | 0 | H | $NHSO_2$[2-(4-phenylsulfonyl)thienyl] | 636.1 |
| 864 | pyridin-2-ylamino | 4 | 0 | H | $NHSO_2$[3-(2-(1-$CH_3$-5-$CF_3$-pyrazol-3-yl))thienyl] | 644.0 |
| 865 | pyridin-2-ylamino | 4 | 0 | H | $NHSO_2$[2-(5-(5-$CF_3$-pyridine-2-yl)sulfonyl)thienyl] | 705.2 |
| 866 | pyridin-2-ylamino | 4 | 0 | H | NHSO2[2-(5-(5-CF3-3-chloropyridine-2-yl)sulfonyl)thienyl] | 739.2 |
| 867 | pyridin-2-ylamino | 4 | 0 | H | $NHSO_2$[2-(4,5-dichloro)thienyl] | 564.2 |
| 868 | pyridin-2-ylamino | 4 | 0 | H | $NHSO_2$[2-(3-bromo-5-chloro)thienyl] | 610.0 |
| 869 | pyridin-2-ylamino | 4 | 0 | H | $NHSO_2$[3-(2,5-dichloro)thienyl] | 564.0 |
| 870 | pyridin-2-ylamino | 4 | 0 | H | $NHSO_2$[4-(1-methyl)imidazolyl] | 494.1 |
| 871 | pyridin-2-ylamino | 4 | 0 | H | $NHSO_2$[4-(1,3-dimethyl-5-chloropyrazolyl] | 542.1 |
| 872 | pyridin-2-ylamino | 4 | 0 | H | $NHSO_2$[4-(3,5-dimethyl)isoxazolyl] | 509.2 |
| 873 | pyridin-2-ylamino | 4 | 0 | H | $NHSO_2$NH(cyclohexyl) | |
| 874 | pyridin-2-ylamino | 4 | 0 | H | $NHSO_2$NHCH2Ph | |
| 875 | pyridin-2-ylamino | 4 | 0 | H | $NHSO_2$NHPh | |
| 876 | pyridin-2-ylamino | 4 | 0 | H | $NHSO_2$NH(2,6-dichloro)Ph | |
| 877 | pyridin-2-ylamino | 4 | 0 | H | $NHSO_2$NH(2,6-dimethoxy)Ph | |
| 878 | pyridin-2-ylamino | 4 | 0 | H | $NHSO_2$NH(2,4,6-trimethyl)Ph | |
| 879 | pyridin-2-ylamino | 4 | 0 | H | $NHSO_2$NH(4-Ph)Ph | |
| 880 | pyridin-2-ylamino | 4 | 0 | H | $NHSO_2$NH(1-napthyl) | |
| 881 | pyridin-2-ylamino | 4 | 0 | H | $NHSO_2$NH(2-napthyl) | |
| 882 | pyridin-2-ylamino | 4 | 0 | Et | H | |
| 883 | pyridin-2-ylamino | 4 | 0 | Ph | H | |
| 884 | pyridin-2-ylamino | 4 | 0 | 3-pyridyl | H | 412.2 |
| 885 | pyridin-2-ylamino | 4 | 0 | $CH_2Ph$ | H | |
| 886 | pyridin-2-ylamino | 4 | 0 | phenylsulfonylamino | H | |

TABLE 2-continued

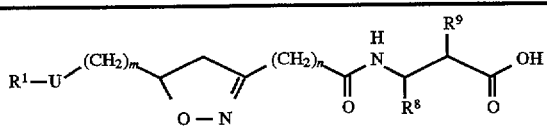

| Ex. No. | R¹—U | m | n | R⁸ | R⁹ | MS |
|---|---|---|---|---|---|---|
| 887 | pyridin-2-ylamino | 4 | 0 | methyl 3-azabicyclo[3.2.2] nonan-3-ylcarbonyl | H | |
| 888 | pyridin-2-ylamino | 4 | 0 | adamantan-1-yl methylaminocarbonyl | H | |
| 889 | pyridin-2-ylamino | 4 | 0 | adamantan-2-yl aminocarbonyl | H | |
| 890 | pyridin-2-ylamino | 4 | 0 | tetrahydroisoquinolin-2-ylcarbonyl | H | |
| 891 | pyridin-2-ylamino | 4 | 0 | phenylethylaminocarbonyl | H | |
| 892 | pyridin-2-ylamino | 4 | 0 | [N-(phenylethyl)N-(methyl)amino]carbonyl | H | |
| 893 | imidazolin-2-ylamino | 4 | 0 | H | $NHSO_2(2,4,6$-trimethylphenyl) | |
| 894 | imidazolin-2-ylamino | 4 | 0 | H | $NHSO_2(2,4,6$-trichlorophenyl) | |
| 895 | imidazolin-2-ylamino | 4 | 0 | H | $NHSO_2(2,6$-dichlorophenyl) | |
| 896 | imidazolin-2-ylamino | 4 | 0 | H | $NHSO_2(2$-chloro-6-methylphenyl) | |
| 897 | imidazolin-2-ylamino | 4 | 0 | H | $NHSO_2C_6H_4(2$-$CH_3)$ | |
| 898 | imidazolin-2-ylamino | 4 | 0 | H | $NHSO_2C_6H_4(2$-Br$)$ | |
| 899 | imidazolin-2-ylamino | 4 | 0 | H | $NHSO2[4$-$(2,6$-dimethylphenyl)phenyl | |
| 900 | imidazolin-2-ylamino | 4 | 0 | H | $NHSO_2C_6H_4(4$-Ph$)$ | |
| 901 | imidazolin-2-ylamino | 4 | 0 | H | $NHSO_2[4$-$(3,5$-dimethyl)isoxazolyl] | |
| 902 | imidazolin-2-ylamino | 4 | 0 | H | $NHSO_2(1$-napthyl$)$ | |
| 903 | imidazolin-2-ylamino | 4 | 0 | H | $NHSO_2(2$-napthyl$)$ | |
| 904 | imidazolin-2-ylamino | 4 | 0 | H | $NHSO_2NHCH_2Ph$ | |
| 905 | imidazolin-2-ylamino | 4 | 0 | H | $NHSO_2NHPh$ | |
| 906 | imidazolin-2-ylamino | 4 | 0 | Ph | H | |
| 907 | Imidazolin-2-ylamino | 4 | 0 | phenylsulfonylamino methyl | H | |
| 908 | imidazolin-2-ylamino | 4 | 0 | 3-azabicyclo[3.2.2] nonan-3-ylcarbonyl | H | |
| 909 | imidazolin-2-ylamino | 4 | 0 | adamantan-1-yl methylaminocarbonyl | H | |
| 910 | imidazolin-2-ylamino | 4 | 0 | adamantan-1-yl aminocarbonyl | H | |
| 911 | imidazolin-2-ylamino | 4 | 0 | adamantan-2-yl aminocarbonyl | H | |
| 912 | imidazolin-2-ylamino | 4 | 0 | tetrahydroisoquinolin-2-ylcarbonyl | H | |
| 913 | tetrahydropyrimidin-2-ylamino | 4 | 0 | H | $NHSO_2(2,4,6$-trimethylphenyl) | |
| 914 | tetrahydropyrimidin-2-ylamino | 4 | 0 | H | $NHSO_2(2,4,6$-trichlorophenyl) | |
| 915 | tetrahydropyrimidin-2-ylamino | 4 | 0 | H | $NHSO_2(2,6$-dichlorophenyl) | |
| 916 | tetrahydropyrimidin-2-ylamino | 4 | 0 | H | $NHSO_2(2$-chloro-6-methylphenyl) | |
| 917 | tetrahydropyrimidin-2-ylamino | 4 | 0 | H | $NHSO_2C_6H_4(2$-$CH_3)$ | |
| 918 | tetrahydropyrimidin-2-ylamino | 4 | 0 | H | $NHSO_2C_6H_4(2$-Br$)$ | |
| 919 | tetrahydropyrimidin-2-ylamino | 4 | 0 | H | $NHSO2[4$-$(2,6$-dimethylphenyl)phenyl | |
| 920 | tetrahydropyrimidin-2-ylamino | 4 | 0 | H | $NHSO_2C_6H_4(4$-Ph$)$ | |

TABLE 2-continued structure with R¹—U—(CH₂)ₘ—[ring with O—N]—(CH₂)ₙ—C(O)—NH—CHR⁸—CHR⁹—C(O)OH

| Ex. No. | R¹—U | m | n | R⁸ | R⁹ | MS |
|---|---|---|---|---|---|---|
| 921 | tetrahydropyrimidin-2-ylamino | 4 | 0 | H | NHSO₂[4-(3,5-dimethyl)isoxazolyl] | |
| 922 | tetrahydropyrimidin-2-ylamino | 4 | 0 | H | NHSO₂(1-napthyl) | |
| 923 | tetrahydropyrimidin-2-ylamino | 4 | 0 | H | NHSO₂(2-napthyl) | |
| 924 | tetrahydropyrimidin-2-ylamino | 4 | 0 | H | NHSO₂NHCH₂Ph | |
| 925 | tetrahydropyrimidin-2-ylamino | 4 | 0 | H | NHSO₂NHPh | |
| 926 | tetrahydropyrimidin-2-ylamino | 4 | 0 | Ph | H | |
| 927 | tetrahydropyrimidin-2-ylamino | 4 | 0 | phenylsulfonylamino methyl | H | |
| 928 | tetrahydropyrimidin-2-ylamino | 4 | 0 | 3-azabicyclo[3.2.2]nonan-3-ylcarbonyl | H | |
| 929 | tetrahydropyrimidin-2-ylamino | 4 | 0 | adamantan-1-yl methylaminocarbonyl | H | |
| 930 | tetrahydropyrimidin-2-ylamino | 4 | 0 | adamantan-1-yl aminocarbonyl | H | |
| 931 | tetrahydropyrimidin-2-ylamino | 4 | 0 | adamantan-2-yl aminocarbonyl | H | |
| 932 | tetrahydropyrimidin-2-ylamino | 4 | 0 | tetrahydroisoquinolin-2-ylcarbonyl | H | |
| 933 | imidazol-2-ylamino | 4 | 0 | H | NHSO₂C₆H₄-(2-Me) | |
| 934 | imidazol-2-ylamino | 4 | 0 | H | NHSO₂C₆H₄-(3-Me) | |
| 935 | imidazol-2-ylamino | 4 | 0 | H | NHSO₂C₆H₄-(4-Me) | |
| 936 | imidazol-2-ylamino | 4 | 0 | H | NHSO₂C₆H₄-(2-Br) | |
| 937 | imidazol-2-ylamino | 4 | 0 | H | NHSO₂C₆H₄-(3-Br) | |
| 938 | imidazol-2-ylamino | 4 | 0 | H | NHSO₂C₆H₄-(4-Br) | |
| 939 | imidazol-2-ylamino | 4 | 0 | H | NHSO₂C₆H₄-(2-F) | |
| 940 | imidazol-2-ylamino | 4 | 0 | H | NHSO₂C₆H₄-(4-F) | |
| 941 | imidazol-2-ylamino | 4 | 0 | H | NHSO₂C₆H₄-(2-CF₃) | |
| 942 | imidazol-2-ylamino | 4 | 0 | H | NHSO₂C₆H₄-(3-CF₃) | |
| 943 | imidazol-2-ylamino | 4 | 0 | H | NHSO₂C₆H₄-(4-CF₃) | |
| 944 | imidazol-2-ylamino | 4 | 0 | H | NHSO₂C₆H₄-(4-OCH₃) | |
| 945 | imidazol-2-ylamino | 4 | 0 | H | NHSO₂C₆H₄-(4-CN) | |
| 946 | imidazol-2-ylamino | 4 | 0 | H | NHSO₂[4-(acetylamino)phenyl] | |
| 947 | imidazol-2-ylamino | 4 | 0 | H | NHSO₂C₆H₄-(4-OCF₃) | |
| 948 | imidazol-2-ylamino | 4 | 0 | H | NHSO₂C₆H₄-(4-isopropyl) | |
| 949 | imidazol-2-ylamino | 4 | 0 | H | NHSO2(2,6-dichlorophenyl) | 547.2 |
| 950 | imidazol-2-ylamino | 4 | 0 | H | NHSO2(2-chloro-6-methylphenyl) | 527.3 |
| 951 | imidazol-2-ylamino | 4 | 0 | H | NHSO2(2,4,6-trimethylphenyl) | 521.4 |
| 952 | imidazol-2-ylamino | 4 | 0 | H | NHSO2(2,4,6-triisopropylphenyl) | |
| 953 | imidazol-2-ylamino | 4 | 0 | H | NHSO₂C₆H₄-(4-Ph) | |
| 954 | imidazol-2-ylamino | 4 | 0 | H | NHSO₂C₆H₄-(3-Ph) | |
| 955 | imidazol-2-ylamino | 4 | 0 | H | NHSO₂C₆H₄-(2-Ph) | |
| 956 | imidazol-2-ylamino | 4 | 0 | H | NHSO₂[4-(2,6-dimethylphenyl)phenyl | |
| 957 | imidazol-2-ylamino | 4 | 0 | H | NHSO₂(1-napthyl) | 529.3 |
| 958 | imidazol-2-ylamino | 4 | 0 | H | NHSO₂(2-napthyl) | |
| 959 | imidazol-2-ylamino | 4 | 0 | H | NHSO₂(8-quinolinyl) | |
| 960 | imidazol-2-ylamino | 4 | 0 | H | NHSO₂(CH=CH)C₆H₅ | |
| 961 | imidazol-2-ylamino | 4 | 0 | H | NHSO₂CH₂Ph | |
| 962 | imidazol-2-ylamino | 4 | 0 | H | NHSO₂(2-thienyl) | |
| 963 | imidazol-2-ylamino | 4 | 0 | H | NHSO₂[2-(5-chloro)thienyl] | |
| 964 | imidazol-2-ylamino | 4 | 0 | H | NHSO₂[2-(5-pyridin-2-yl)thienyl] | |
| 965 | imidazol-2-ylamino | 4 | 0 | H | NHSO₂[3-(2-(methoxycarbonyl)thienyl] | |
| 966 | imidazol-2-ylamino | 4 | 0 | H | NHSO₂[2-(5-isoxazol-3- | |

TABLE 2-continued $$R^1-U\underset{(CH_2)_m}{\diagup}\underset{O-N}{\diagdown}\underset{}{\diagup}(CH_2)_n\underset{O}{\diagdown}\underset{}{\overset{H}{N}}\underset{R^8}{\diagdown}\underset{O}{\overset{R^9}{\diagdown}}OH$$

| Ex. No. | $R^1-U$ | m | n | $R^8$ | $R^9$ | MS |
|---|---|---|---|---|---|---|
| 967 | imidazol-2-ylamino | 4 | 0 | H | NHSO$_2$[2-(4-phenylsulfonyl) thienyl] | |
| 968 | imidazol-2-ylamino | 4 | 0 | H | NHSO$_2$[3-(2-(1-CH$_3$-5-CF$_3$-pyrazol-3-yl)) thienyl] | |
| 969 | imidazol-2-ylamino | 4 | 0 | H | NHSO$_2$[2-(5-(5-CF$_3$-pyridine-2-yl)sulfonyl)thienyl] | |
| 970 | imidazol-2-ylamino | 4 | 0 | H | NHSO2[2-(5-(5-CF3-3-chloropyridine-2-yl)sulfonyl)thienyl] | |
| 971 | imidazol-2-ylamino | 4 | 0 | H | NHSO$_2$[2-(4,5-dichloro) thienyl] | |
| 972 | imidazol-2-ylamino | 4 | 0 | H | NHSO$_2$[2-(3-bromo-5-chloro)thienyl] | |
| 973 | imidazol-2-ylamino | 4 | 0 | H | NHSO$_2$[3-(2,5-dichloro)thienyl] | |
| 974 | imidazol-2-ylamino | 4 | 0 | H | NHSO$_2$[4-(1-methyl)imidazolyl] | |
| 975 | imidazol-2-ylamino | 4 | 0 | H | NHSO$_2$[4-(1,3-dimethyl-5-chloro)pyrazolyl] | |
| 975 | imidazol-2-ylamino | 4 | 0 | H | NHSO$_2$[4-(3,5-dimethyl)isoxazolyl] | 498.3 |
| 976 | imidazol-2-ylamino | 4 | 0 | H | NHSO$_2$NH(cyclohexyl) | |
| 977 | imidazol-2-ylamino | 4 | 0 | H | NHSO$_2$NHCH2Ph | |
| 978 | imidazol-2-ylamino | 4 | 0 | H | NHSO$_2$NHPh | |
| 979 | imidazol-2-ylamino | 4 | 0 | H | NHSO$_2$NH(2,6-dichloro) Ph | |
| 980 | imidazol-2-ylamino | 4 | 0 | H | NHSO$_2$NH(2,6-dimethoxy) Ph | |
| 981 | imidazol-2-ylamino | 4 | 0 | H | NHSO$_2$NH(2,4,6-trimethyl)Ph | |
| 982 | imidazol-2-ylamino | 4 | 0 | H | NHSO$_2$NH(4-Ph)Ph | |
| 983 | imidazol-2-ylamino | 4 | 0 | H | NHSO$_2$NH(1-napthyl) | |
| 984 | imidazol-2-ylamino | 4 | 0 | H | NHSO$_2$H(2-napthyl) | |
| 985 | imidazol-2-ylamino | 4 | 0 | Et | H | |
| 986 | imidazol-2-ylamino | 4 | 0 | Ph | H | |
| 987 | imidazol-2-ylamino | 4 | 0 | 3-pyridyl | H | |
| 988 | imidazol-2-ylamino | 4 | 0 | CH$_2$Ph | H | |
| 989 | imidazol-2-ylamino | 4 | 0 | phenylsulfonylamino methyl | H | |
| 990 | imidazol-2-ylamino | 4 | 0 | 3-azabicyclo[3.2.2] nonan-3-ylcarbonyl | H | |
| 991 | imidazol-2-ylamino | 4 | 0 | adamantan-1-yl methylaminocarbonyl | H | |
| 992 | imidazol-2-ylamino | 4 | 0 | adamantan-2-yl aminocarbonyl | H | |
| 993 | imidazol-2-ylamino | 4 | 0 | tetrahydroisoquinol in-2-ylcarbonyl | H | |
| 994 | imidazol-2-ylamino | 4 | 0 | phenylethylaminocar bonyl | H | |
| 995 | imidazol-2-ylamino | 4 | 0 | [N-(phenylethyl)N-(methyl)amino]carbo nyl | H | |
| 996 | 2-aminoimidazol-4-yl | 3 | 0 | H | NHSO$_2$Ph | |
| 997 | 2-aminoimidazol-4-yl | 3 | 0 | H | NHSO$_2$(2,4,6-trimethylphenyl) | |
| 998 | 2-aminoimidazol-4-yl | 3 | 0 | H | NHSO$_2$(2,4,6-trichlorophenyl) | |
| 999 | 2-aminoimidazol-4-yl | 3 | 0 | H | NHSO$_2$(2,6-dichlorophenyl) | |
| 999a | 2-aminoimidazol-4-yl | 3 | 0 | H | NHSO$_2$(2-chloro-6-methylphenyl) | |
| 999b | 2-aminoimidazol-4-yl | 3 | 0 | H | NHSO$_2$C$_6$H$_4$(2-CH$_3$) | |
| 999c | 2-aminoimidazol-4- | 3 | 0 | H | NHSO$_2$C$_6$H$_4$(2-Br) | |

TABLE 2-continued $$R^1-U-(CH_2)_m-\underset{O-N}{\overset{|}{C}}-(CH_2)_n-\underset{O}{\overset{H}{N}}-\underset{R^8}{\overset{R^9}{C}}-\underset{O}{\overset{}{C}}-OH$$

| Ex. No. | R¹—U | m | n | R⁸ | R⁹ | MS |
|---|---|---|---|---|---|---|
| | yl | | | | | |
| 999d | 2-aminoimidazol-4-yl | 3 | 0 | H | NHSO2[4-(2,6-dimethylphenyl]phenyl | |
| 999e | 2-aminoimidazol-4-yl | 3 | 0 | H | NHSO₂C₆H₄(4-Ph) | |
| 999f | 2-aminoimidazol-4-yl | 3 | 0 | H | NHSO₂[4-(3,5-dimethyl)isoxazolyl] | |
| 999g | 2-aminoimidazol-4-yl | 3 | 0 | H | NHSO₂(1-napthyl) | |
| 999h | 2-aminoimidazol-4-yl | 3 | 0 | H | NHSO₂(2-napthyl) | |
| 999i | 2-aminoimidazol-4-yl | 3 | 0 | H | NHSO₂NHCH₂Ph | |
| 999j | 2-aminoimidazol-4-yl | 3 | 0 | H | NHSO₂NHPh | |
| 999k | 2-aminoimidazol-4-yl | 3 | 0 | Ph | H | |
| 999l | 2-aminoimidazol-4-yl | 3 | 0 | phenylsulfonylamino methyl | H | |
| 999m | 2-aminoimidazol-4-yl | 3 | 0 | 3-azabicyclo[3.2.2]nonan-3-ylcarbonyl | H | |
| 999n | 2-aminoimidazol-4-yl | 3 | 0 | adamantan-1-yl methylaminocarbonyl | H | |
| 999o | 2-aminoimidazol-4-yl | 3 | 0 | adamantan-1-yl aminocarbonyl | H | |
| 999p | 2-aminoimidazol-4-yl | 3 | 0 | adamantan-2-yl aminocarbonyl | H | |
| 999a | 2-aminoimidazol-4-yl | 3 | 0 | tetrahydroisoquinolin-2-ylcarbonyl | H | |
| 999r | benzylimidazol-2-yl | 4 | 0 | H | NHSO₂Ph | |
| 999s | benzylimidazol-2-yl | 4 | 0 | H | NHSO₂(2,4,6-trimethylphenyl) | |
| 999t | benzylimidazol-2-yl | 4 | 0 | H | NHSO₂(2,4,6-trichlorophenyl) | |
| 999u | benzylimidazol-2-yl | 4 | 0 | H | NHSO₂(2,6-dichlorophenyl) | |
| 999v | benzylimidazol-2-yl | 4 | 0 | H | NHSO₂(2-chloro-6-methylphenyl) | |
| 999w | benzylimidazol-2-yl | 4 | 0 | H | NHSO₂C₆H₄(2-CH₃) | |
| 999x | benzylimidazol-2-yl | 4 | 0 | H | NHSO₂C₆H₄(2-Br) | |
| 999y | benzylimidazol-2-yl | 4 | 0 | H | NHSO2[4-(2,6-dimethylphenyl)phenyl | |
| 999z | benzylimidazol-2-yl | 4 | 0 | H | NHSO₂C₆H₄(4-Ph) | |
| 999aa | benzylimidazol-2-yl | 4 | 0 | H | NHSO2[4-(3,5-dimethyl)isoxazolyl] | |
| 999ab | benzylimidazol-2-yl | 4 | 0 | H | NHSO₂(1-napthyl) | |
| 999ac | benzylimidazol-2-yl | 4 | 0 | H | NHSO₂(2-napthyl) | |
| 999ad | benzylimidazol-2-yl | 4 | 0 | H | NHSO₂NHCH₂Ph | |
| 999ae | benzylimidazol-2-yl | 4 | 0 | H | NHSO₂NHPh | |
| 999af | benzylimidazol-2-yl | 4 | 0 | Ph | H | |
| 999ag | benzylimidazol-2-yl | 4 | 0 | phenylsulfonylamino methyl | H | |
| 999ah | benzylimidazol-2-yl | 4 | 0 | 3-azabicyclo[3.2.2]nonan-3-ylcarbonyl | H | |
| 999ai | benzylimidazol-2-yl | 4 | 0 | adamantan-1-yl methylaminocarbonyl | H | |
| 999aj | benzylimidazol-2-yl | 4 | 0 | adamantan-1-yl aminocarbonyl | H | |
| 999ak | benzylimidazol-2-yl | 4 | 0 | adamantan-2-yl aminocarbonyl | H | |
| 999al | benzylimidazol-2-yl | 4 | 0 | tetrahydroisoquinolin-2-ylcarbonyl | H | |
| 999am | 4-methylimidazol-2-ylamino | 4 | 0 | H | NHSO₂Ph | |
| 999an | 4-methylimidazol-2-ylamino | 4 | 0 | H | NHSO₂(2,4,6-trimethylphenyl) | |
| 999ao | 4-methylimidazol-2-ylamino | 4 | 0 | H | NHSO₂(2,4,6-trichlorophenyl) | |
| 999ap | 4-methylimidazol-2- | 4 | 0 | H | NHSO₂(2,6- | |

TABLE 2-continued $$R^1-U-(CH_2)_m-\overset{\underset{O-N}{\|}}{C}-(CH_2)_n-\overset{O}{\underset{\|}{C}}-\overset{H}{\underset{R^8}{N}}-\overset{R^9}{\underset{}{C}}H-\overset{O}{\underset{\|}{C}}-OH$$

| Ex. No. | R¹—U | m | n | R⁸ | R⁹ | MS |
|---|---|---|---|---|---|---|
| 999aq | 4-methylimidazol-2-ylamino | 4 | 0 | H | NHSO₂(2-chloro-6-methylphenyl) dichlorophenyl) | |
| 999ar | 4-methylimidazol-2-ylamino | 4 | 0 | H | NHSO₂C₆H₄(2-CH₃) | |
| 999as | 4-methylimidazol-2-ylamino | 4 | 0 | H | NHSO₂C₆H₄(2-Br) | |
| 999at | 4-methylimidazol-2-ylamino | 4 | 0 | H | NHSO2[4-(2,6-dimethylphenyl)phenyl | |
| 999au | 4-methylimidazol-2-ylamino | 4 | 0 | H | NHSO₂C₆H₄(4-Ph) | |
| 999av | 4-methylimidazol-2-ylamino | 4 | 0 | H | NHSO₂4-(3,5-dimethyl)isoxazolyl] | |
| 999aw | 4-methylimidazol-2-ylamino | 4 | 0 | H | NHSO₂(1-napthyl) | |
| 999ax | 4-methylimidazol-2-ylamino | 4 | 0 | H | NHSO₂(2-napthyl) | |
| 999az | 4-methylimidazol-2-ylamino | 4 | 0 | H | NHSO₂NHCH₂Ph | |
| 999ba | 4-methylimidazol-2-ylamino | 4 | 0 | H | NHSO₂NHPh | |
| 999bb | 4-methylimidazol-2-ylamino | 4 | 0 | Ph | H | |
| 999bc | 4-methylimidazol-2-ylamino | 4 | 0 | phenylsulfonylamino methyl | H | |
| 999bd | 4-methylimidazol-2-ylamino | 4 | 0 | 3-azabicyclo[3.2.2]nonan-3-ylcarbonyl | H | |
| 999be | 4-methylimidazol-2-ylamino | 4 | 0 | adamantan-1-yl methylaminocarbonyl | H | |
| 999bf | 4-methylimidazol-2-ylamino | 4 | 0 | adamantan-1-yl aminocarbonyl | H | |
| 999bg | 4-methylimidazol-2-ylamino | 4 | 0 | adamantan-2-yl aminocarbonyl | H | |
| 999bh | 4-methylimidazol-2-ylamino | 4 | 0 | tetrahydroisoquinolin-2-ylcarbonyl | H | |
| 999bi | 4,5-dimethylimidazol-2-ylamino | 4 | 0 | H | NHSO₂Ph | |
| 999bj | 4,5-dimethylimidazol-2-ylamino | 4 | 0 | H | NHSO₂(2,4,6-trimethylphenyl) | |
| 999bk | 4,5-dimethylimidazol-2-ylamino | 4 | 0 | H | NHSO₂(2,4,6-trichlorophenyl) | |
| 999bl | 4,5-dimethylimidazol-2-ylamino | 4 | 0 | H | NHSO₂(2,6-dichlorophenyl) | |
| 999bm | 4,5-dimethylimidazol-2-ylamino | 4 | 0 | H | NHSO₂(2-chloro-6-methylphenyl) | |
| 999bn | 4,5-dimethylimidazol-2-ylamino | 4 | 0 | H | NHSO₂C₆H₄(2-CH₃) | |
| 999bo | 4,5-dimethylimidazol-2-ylamino | 4 | 0 | H | NHSO₂C₆H₄(2-Br) | |
| 999bp | 4,5-dimethylimidazol-2-ylamino | 4 | 0 | H | NHSO₂[4-(2,6-dimethylphenyl)phenyl | |
| 999bq | 4,5-dimethylimidazol-2-ylamino | 4 | 0 | H | NHSO₂C₆H₄(4-Ph) | |
| 999br | 4,5-dimethylimidazol-2-ylamino | 4 | 0 | H | NHSO₂4-(3,-5-dimethyl)isoxazolyl] | |
| 999bs | 4,5-dimethylimidazol-2-ylamino | 4 | 0 | H | NHSO₂(1-napthyl) | |
| 999bt | 4,5- | 4 | 0 | H | NHSO₂(2-napthyl) | |

TABLE 2-continued $$R^1-U-(CH_2)_m-\underset{O-N}{C}-(CH_2)_n-\underset{O}{C}-\underset{R^8}{\overset{H}{N}}-\underset{}{\overset{R^9}{C}H}-OH$$

| Ex. No. | R¹—U | m | n | R⁸ | R⁹ | MS |
|---|---|---|---|---|---|---|
| 999bu | 4,5-dimethylimidazol-2-ylamino | 4 | 0 | H | NHSO₂NHCH₂Ph | |
| 999bv | 4,5-dimethylimidazol-2-ylamino | 4 | 0 | H | NHSO₂NHPh | |
| 999bw | 4,5-dimethylimidazol-2-ylamino | 4 | 0 | Ph | H | |
| 999bx | 4,5-dimethylimidazol-2-ylamino | 4 | 0 | phenylsulfonylamino methyl | H | |
| 999by | 4,5-dimethylimidazol-2-ylamino | 4 | 0 | 3-azabicyclo[3.2.2]nonan-3-ylcarbonyl | H | |
| 999bz | 4,5-dimethylimidazol-2-ylamino | 4 | 0 | adamantan-1-yl methylaminocarbonyl | H | |
| 999ca | 4,5-dimethylimidazol-2-ylamino | 4 | 0 | adamantan-1-yl aminocarbonyl | H | |
| 999cb | 4,5-dimethylimidazol-2-ylamino | 4 | 0 | adamantan-2-yl aminocarbonyl | H | |
| 999cc | 4,5-dimethylimidazol-2-ylamino | 4 | 0 | tetrahydroisoquinolin-2-ylcarbonyl | H | |
| 999cd | 4,5,6,7-tetrahydrobenzimidazol-2-ylamino | 4 | 0 | H | NHSO₂Ph | |
| 999ce | 4,5,6,7-tetrahydrobenzimidazol-2-ylamino | 4 | 0 | H | NHSO₂(2,4,6-trimethylphenyl) | |
| 999cf | 4,5,6,7-tetrahydrobenzimidazol-2-ylamino | 4 | 0 | H | NHSO₂(2,4,6-trichlorophenyl) | |
| 999cg | 4,5,6,7-tetrahydrobenzimidazol-2-ylamino | 4 | 0 | H | NHSO₂(2,6-dichlorophenyl) | |
| 999ch | 4,5,6,7-tetrahydrobenzimidazol-2-ylamino | 4 | 0 | H | NHSO₂(2-chloro-6-methylphenyl) | |
| 999ci | 4,5,6,7-tetrahydrobenzimidazol-2-ylamino | 4 | 0 | H | NHSO₂C₆H₄(2-CH₃) | |
| 999cj | 4,5,6,7-tetrahydrobenzimidazol-2-ylamino | 4 | 0 | H | NHSO₂C₆H₄(2-Br) | |
| 999ck | 4,5,6,7-tetrahydrobenzimidazol-2-ylamino | 4 | 0 | H | NHSO₂[4-(2,6-dimethylphenyl)phenyl] | |
| 999cl | 4,5,6,7-tetrahydrobenzimidazol-2-ylamino | 4 | 0 | H | NHSO₂C₆H₄(4-Ph) | |
| 999cm | 4,5,6,7-tetrahydrobenzimidazol-2-ylamino | 4 | 0 | H | NHSO₂[4-(3,5-dimethyl)isoxazolyl] | |
| 999cn | 4,5,6,7-tetrahydrobenzimidazol-2-ylamino | 4 | 0 | H | NHSO₂(1-napthyl) | |
| 999co | 4,5,6,7-tetrahydrobenzimidazol-2-ylamino | 4 | 0 | H | NHSO₂(2-napthyl) | |
| 999cp | 4,5,6,7-tetrahydrobenzimidazol-2-ylamino | 4 | 0 | H | NHSO₂NHCH₂Ph | |
| 999cq | 4,5,6,7- | 4 | 0 | H | NHSO₂NHPh | |

TABLE 2-continued

Structure:
R¹—U—(CH₂)ₘ—CH(O—N=)—CH₂—(CH₂)ₙ—C(O)—NH—CH(R⁸)—CH(R⁹)—C(O)—OH

| Ex. No. | R¹—U | m | n | R⁸ | R⁹ | MS |
|---|---|---|---|---|---|---|
| | tetrahydrobenzimidazol-2-ylamino | | | | | |
| 999cr | 4,5,6,7-tetrahydrobenzimidazol-2-ylamino | 4 | 0 | Ph | H | |
| 999cs | 4,5,6,7-tetrahydrobenzimidazol-2-ylamino | 4 | 0 | phenylsulfonylaminomethyl | H | |
| 999ct | 4,5,6,7-tetrahydrobenzimidazol-2-ylamino | 4 | 0 | 3-azabicyclo[3.2.2]nonan-3-ylcarbonyl | H | |
| 999cu | 4,5,6,7-tetrahydrobenzimidazol-2-ylamino | 4 | 0 | adamantan-1-yl methylaminocarbonyl | H | |
| 999cv | 4,5,6,7-tetrahydrobenzimidazol-2-ylamino | 4 | 0 | adamantan-1-yl aminocarbonyl | H | |
| 999cw | 4,5,6,7-tetrahydrobenzimidazol-2-ylamino | 4 | 0 | adamantan-2-yl aminocarbonyl | H | |
| 999cx | 4,5,6,7-tetrahydrobenzimidazol-2-ylamino | 4 | 0 | tetrahydroisoquinolin-2-ylcarbonyl | H | |
| 999cy | 2-aminopyridin-6-yl | 3 | 0 | H | $NHSO_2(2,4,6$-trimethylphenyl) | |
| 999cz | 2-aminopyridin-6-yl | 3 | 0 | H | $NHSO_2(2,4,6$-trichlorophenyl) | |
| 999da | 2-aminopyridin-6-yl | 3 | 0 | H | $NHSO_2(2,6$-dichlorophenyl) | |
| 999db | 2-aminopyridin-6-yl | 3 | 0 | H | $NHSO_2(2$-chloro-6-methylphenyl) | |
| 999dc | 2-aminopyridin-6-yl | 3 | 0 | H | $NHSO_2C_6H_4(2\text{-}CH_3)$ | |
| 999de | 2-aminopyridin-6-yl | 3 | 0 | H | $NHSO_2C_6H_4(2\text{-Br})$ | |
| 999df | 2-aminopyridin-6-yl | 3 | 0 | H | $NHSO_2[4\text{-}(2,6$-dimethylphenyl)phenyl | |
| 999dg | 2-aminopyridin-6-yl | 3 | 0 | H | $NHSO_2C_6H_4(4\text{-Ph})$ | |
| 999dh | 2-aminopyridin-6-yl | 3 | 0 | H | $NHSO2[4\text{-}(3,5$-dimethyl)isoxazolyl) | |
| 999di | 2-aminopyridin-6-yl | 3 | 0 | H | $NHSO_2(1$-napthyl) | |
| 999dj | 2-aminopyridin-6-yl | 3 | 0 | H | $NHSO_2(2$-napthyl) | |
| 999dk | 2-aminopyridin-6-yl | 3 | 0 | H | $NHSO_2NHCH_2Ph$ | |
| 999dl | 2-aminopyridin-6-yl | 3 | 0 | H | $NHSO_2NHPh$ | |
| 999dm | 2-aminopyridin-6-yl | 3 | 0 | Ph | H | |
| 999dn | 2-aminopyridin-6-yl | 3 | 0 | phenylsulfonylaminomethyl | H | |
| 999do | 2-aminopyridin-6-yl | 3 | 0 | 3-azabicyclo[3.2.2]nonan-3-ylcarbonyl | H | |
| 999dp | 2-aminopyridin-6-yl | 3 | 0 | adamantan-1-yl methylaminocarbonyl | H | |
| 999dq | 2-aminopyridin-6-yl | 3 | 0 | adamantan-1-yl aminocarbonyl | H | |
| 999dr | 2-aminopyridin-6-yl | 3 | 0 | adamantan-2-yl aminocarbonyl | H | |
| 999ds | 2-aminopyridin-6-yl | 3 | 0 | tetrahydroisoquinolin-2-ylcarbonyl | H | |
| 999dt | imidazol-2-ylamino | 3 | 0 | H | $NHSO_2(2,4,6$-trimethylphenyl) | |
| 999du | imidazol-2-ylamino | 3 | 0 | H | $NHSO_2(2,4,6$-trichlorophenyl) | |
| 999dv | imidazol-2-ylamino | 3 | 0 | H | $NHSO_2(2,6$-dichlorophenyl) | |
| 999dw | imidazol-2-ylamino | 3 | 0 | H | $NHSO_2(2$-chloro-6-methylphenyl) | |
| 999dx | imidazol-2-ylamino | 3 | 0 | H | $NHSO_2C_6H_4(2\text{-}CH_3)$ | |
| 999dy | imidazol-2-ylamino | 3 | 0 | H | $NHSO_2C_6H_4(2\text{-Br})$ | |
| 999dz | imidazol-2-ylamino | 3 | 0 | H | $NHSO2[4\text{-}(2,6$-dimethylphenyl)phenyl | |
| 999ea | imidazol-2-ylamino | 3 | 0 | H | $NHSO_2C_6H_4(4\text{-Ph})$ | |
| 999eb | imidazol-2-ylamino | 3 | 0 | H | $NHSO_2[4\text{-}(3,5$- | |

TABLE 2-continued

Structure: $R^1-U-(CH_2)_m$ — [isoxazoline ring with O—N] — $(CH_2)_n$—C(O)—N(H)—CH($R^8$)—CH($R^9$)—C(O)—OH

| Ex. No. | R¹—U | m | n | R⁸ | R⁹ | MS |
|---|---|---|---|---|---|---|
| 999ef | imidazol-2-ylamino | 3 | 0 | H | NHSO₂(1-napthyl) | |
| 999eg | imidazol-2-ylamino | 3 | 0 | H | NHSO₂(2-napthyl) | |
| 999eh | imidazol-2-ylamino | 3 | 0 | H | NHSO₂NHCH₂Ph | |
| 999ei | imidazol-2-ylamino | 3 | 0 | H | NHSO₂NHPh | |
| 999ej | imidazol-2-ylamino | 3 | 0 | Ph | H | |
| 999ek | imidazol-2-ylamino | 3 | 0 | phenylsulfonylamino methyl | H | |
| 999el | imidazol-2-ylamino | 3 | 0 | 3-azabicyclo[3.2.2]nonan-3-ylcarbonyl | H | |
| 999em | imidazol-2-ylamino | 3 | 0 | adamantan-1-yl methylaminocarbonyl | H | |
| 999en | imidazol-2-ylamino | 3 | 0 | adamantan-1-yl aminocarbonyl | H | |
| 999eo | imidazol-2-ylamino | 3 | 0 | adamantan-2-yl aminocarbonyl | H | |
| 999ep | imidazol-2-ylamino | 3 | 0 | tetrahydroisoquinolin-2-ylcarbonyl | H | |
| 999eq | imidazol-2-ylamino | 2 | 0 | H | NHSO₂(2,4,6-trimethylphenyl) | |
| 999er | imidazol-2-ylamino | 2 | 0 | H | NHSO₂(2,4,6-trichlorophenyl) | |
| 999es | imidazol-2-ylamino | 2 | 0 | H | NHSO₂(2,6-dichlorophenyl) | |
| 999et | imidazol-2-ylamino | 2 | 0 | H | NHSO₂(2-chloro-6-methylphenyl) | |
| 999eu | imidazol-2-ylamino | 2 | 0 | H | NHSO₂C₆H₄(2-CH₃) | |
| 999ev | imidazol-2-ylamino | 2 | 0 | H | NHSO₂C₆H₄(2-Br) | |
| 999ew | imidazol-2-ylamino | 2 | 0 | H | NHSO2[4-(2,6-dimethylphenyl)phenyl | |
| 999ex | imidazol-2-ylamino | 2 | 0 | H | NHSO₂C₆H₄(4-Ph) | |
| 999ey | imidazol-2-ylamino | 2 | 0 | H | NHSO2[4-(3,5-dimethyl)isoxazolyl] | |
| 999ez | imidazol-2-ylamino | 2 | 0 | H | NHSO₂(1-napthyl) | |
| 999fa | imidazol-2-ylamino | 2 | 0 | H | NHSO₂(2-napthyl) | |
| 999fb | imidazol-2-ylamino | 2 | 0 | H | NHSO₂NHCH₂Ph | |
| 999fc | imidazol-2-ylamino | 2 | 0 | H | NHSO₂NHPh | |
| 999fd | imidazol-2-ylamino | 2 | 0 | Ph | H | |
| 999fe | imidazol-2-ylamino | 2 | 0 | phenylsulfonylamino methyl | H | |
| 999ff | imidazol-2-ylamino | 2 | 0 | 3-azabicyclo[3.2.2]nonan-3-ylcarbonyl | H | |
| 999fg | imidazol-2-ylamino | 2 | 0 | adamantan-1-yl methylaminocarbonyl | H | |
| 999fh | imidazol-2-ylamino | 2 | 0 | adamantan-1-yl aminocarbonyl | H | |
| 999fi | imidazol-2-ylamino | 2 | 0 | adamantan-2-yl aminocarbonyl | H | |
| 999fj | imidazol-2-ylamino | 2 | 0 | tetrahydroisoquinolin-2-ylcarbonyl | H | |
| 999fk | 2-aminoimidazol-4-yl | 2 | 0 | H | NHSO₂Ph | |
| 999fl | 2-aminoimidazol-4-yl | 2 | 0 | H | NHSO₂(2,4,6-trimethylphenyl) | |
| 999fm | 2-aminoimidazol-4-yl | 2 | 0 | H | NHSO₂(2,4,6-trichlorophenyl) | |
| 999fn | 2-aminoimidazol-4-yl | 2 | 0 | H | NHSO₂(2,6-dichlorophenyl) | |
| 999fo | 2-aminoimidazol-4-yl | 2 | 0 | H | NHSO₂(2-chloro-6-methylphenyl) | |
| 999fq | 2-aminoimidazol-4-yl | 2 | 0 | H | NHSO₂C₆H₅(2-Br) | |
| 999fr | 2-aminoimidazol-4-yl | 2 | 0 | H | NHSO2[4-(2,6-dimethylphenyl)phenyl | |
| 999fs | 2-aminoimidazol-4-yl | 2 | 0 | H | NHSO₂C₆H₄(4-Ph) | |
| 999ft | 2-aminoimidazol-4-yl | 2 | 0 | H | NHSO2[4-(3,5-dimethyl)isoxazolyl] | |
| 999fu | 2-aminoimidazol-4-yl | 2 | 0 | H | NHSO₂(1-napthyl) | |
| 999fv | 2-aminoimidazol-4-yl | 2 | 0 | H | NHSO₂(2-napthyl) | |
| 999fw | 2-aminoimidazol-4-yl | 2 | 0 | H | NHSO₂NHCH₂Ph | |
| 999fx | 2-aminoimidazol-4-yl | 2 | 0 | H | NHSO₂NHPh | |

TABLE 2-continued $$R^1-U\diagdown^{(CH_2)_m}\diagdown\diagdown^{(CH_2)_n}\diagdown\underset{O}{\overset{H}{N}}\diagdown\underset{R^8}{\overset{R^9}{\diagdown}}\diagdown OH$$
$$O-N$$

| Ex. No. | R¹—U | m | n | R⁸ | R⁹ | MS |
|---|---|---|---|---|---|---|
| 999fy | 2-aminoimidazol-4-yl | 2 | 0 | Ph | H | |
| 999fz | 2-aminoimidazol-4-yl | 2 | 0 | phenylsulfonylamino methyl | H | |
| 999ga | 2-aminoimidazol-4-yl | 2 | 0 | 3-azabicyclo[3.2.2] nonan-3-ylcarbonyl | H | |
| 999gb | 2-aminoimidazol-4-yl | 2 | 0 | adamantan-1-yl methylaminocarbonyl | H | |
| 999gc | 2-aminoimidazol-4-yl | 2 | 0 | adamantan-1-yl aminocarbonyl | H | |
| 999gd | 2-aminoimidazol-4-yl | 2 | 0 | adamantan-2-yl aminocarbonyl | H | |
| 999ge | 2-aminoimidazol-4-yl | 2 | 0 | tetrahydroisoquinolin-2-ylcarbonyl | H | |
| 999gf | 2-aminoimidazol-4-yl | 1 | 0 | H | NHSO$_2$Ph | |
| 999gg | 2-aminoimidazol-4-yl | 1 | 0 | H | NHSO$_2$(2,4,6-trimethylphenyl) | |
| 999gh | 2-aminoimidazol-4-yl | 1 | 0 | H | NHSO$_2$(2,4,6-trichlorophenyl) | |
| 999gi | 2-aminoimidazol-4-yl | 1 | 0 | H | NHSO$_2$(2,6-dichlorophenyl) | |
| 999gj | 2-aminoimidazol-4-yl | 1 | 0 | H | NHSO$_2$(2-chloro-6-methylphenyl) | |
| 999gk | 2-aminoimidazol-4-yl | 1 | 0 | H | NHSO$_2$C$_6$H$_4$(2-CH$_3$) | |
| 999gl | 2-aminoimidazol-4-yl | 1 | 0 | H | NHSO$_2$C$_6$H$_4$(2-Br) | |
| 999gm | 2-aminoimidazol-4-yl | 1 | 0 | H | NHSO2[4-(2,6-dimethylphenyl)phenyl | |
| 999gn | 2-aminoimidazol-4-yl | 1 | 0 | H | NHSO$_2$C$_6$H$_4$(4-Ph) | |
| 999go | 2-aminoimidazol-4-yl | 1 | 0 | H | NHSO2[4-(3,5-dimethyl)isoxazolyl] | |
| 999gp | 2-aminoimidazol-4-yl | 1 | 0 | H | NHSO$_2$(1-napthyl) | |
| 999gq | 2-aminoimidazol-4-yl | 1 | 0 | H | NHSO$_2$(2-napthyl) | |
| 999gr | 2-aminoimidazol-4-yl | 1 | 0 | H | NHSO$_2$NHCH$_2$Ph | |
| 999gs | 2-aminoimidazol-4-yl | 1 | 0 | H | NHSO$_2$NHPh | |
| 999gt | 2-aminoimidazol-4-yl | 1 | 0 | Ph | H | |
| 999gu | 2-aminoimidazol-4-yl | | 0 | H | phenylsulfonylamino methyl | H |
| 999gv | 2-aminoimidazol-4-yl | | 0 | H | 3-azabicyclo[3.2.2] nonan-3-ylcarbonyl | H |
| 999gw | 2-aminoimidazol-4-yl | | 0 | H | adamantan-1-yl methylaminocarbonyl | H |
| 999gx | 2-aminoimidazol-4-yl | | 0 | H | adamantan-1-yl aminocarbonyl | H |
| 999gy | 2-aminoimidazol-4-yl | | 0 | H | adamantan-2-yl aminocarbonyl | H |
| 999gz | 2-aminoimidazol-4-yl | | 0 | H | tetrahydroisoquinolin-2-ylcarbonyl | H |
| 999ha | imidazol-2-ylaminocarbonyl | 3 | 0 | H | NHSO$_2$(2,4,6-trimethylphenyl) | |
| 999hb | imidazol-2-ylaminocarbonyl | 3 | 0 | H | NHSO$_2$(2,4,6-trichlorophenyl) | |
| 999hc | imidazol-2-ylaminocarbonyl | 3 | 0 | H | NHSO$_2$(2,6-dichlorophenyl) | |
| 999hd | imidazol-2-ylaminocarbonyl | 3 | 0 | H | NHSO$_2$(2-chloro-6-methylphenyl) | |
| 999he | imidazol-2-ylaminocarbonyl | 3 | 0 | H | NHSO$_2$C$_6$H$_4$(2-CH$_3$) | |
| 999hf | imidazol-2-ylaminocarbonyl | 3 | 0 | H | NHSO$_2$C$_6$H$_4$(2-Br) | |
| 999hf | imidazol-2-ylaminocarbonyl | 3 | 0 | H | NHSO2[4-(2,6-dimethylphenyl)phenyl | |
| 999hh | imidazol-2-ylaminocarbonyl | 3 | 0 | H | NHSO$_2$C$_6$H$_4$(4-Ph) | |
| 999hi | imidazol-2-ylaminocarbonyl | 3 | 0 | H | NHSO2[4-(3,5-dimethyl)isoxazolyl] | |
| 999hj | imidazol-2-ylaminocarbonyl | 3 | 0 | H | NHSO$_2$(1-napthyl) | |
| 999hk | imidazol-2-ylaminocarbonyl | 3 | 0 | H | NHSO$_2$(2-napthyl) | |
| 999hl | imidazol-2-ylamino- | 3 | 0 | H | NHSO$_2$NHCH$_2$Ph | |

TABLE 2-continued

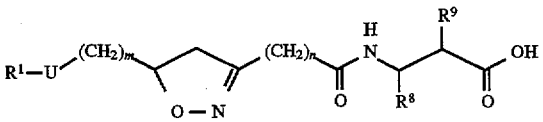

| Ex. No. | $R^1$—U | m | n | $R^8$ | $R^9$ | MS |
|---|---|---|---|---|---|---|
| 999hm | imidazol-2-ylaminocarbonyl | 3 | 0 | H | $NHSO_2NHPh$ | |
| 999hn | imidazol-2-ylaminocarbonyl | 3 | 0 | Ph | H | |
| 999ho | imidazol-2-ylaminocarbonyl | 3 | 0 | phenylsulfonylaminomethyl | H | |
| 999hp | imidazol-2-ylaminocarbonyl | 3 | 0 | 3-azabicyclo[3.2.2]nonan-3-ylcarbonyl | H | |
| 999hq | imidazol-2-ylaminocarbonyl | 3 | 0 | adamantan-1-yl methylaminocarbonyl | H | |
| 999hr | imidazol-2-ylaminocarbonyl | 3 | 0 | adamantan-1-yl aminocarbonyl | H | |
| 999hs | imidazol-2-ylaminocarbonyl | 3 | 0 | adamantan-2-yl aminocarbonyl | H | |
| 999ht | imidazol-2-ylaminocarbonyl | 3 | 0 | tetrahydroisoquinolin-2-ylcarbonyl | H | |
| 99hu | benzimidazol-2-ylmethylaminocarbonyl | 0 | 0 | H | $NHSO_2Ph$ | |
| 999hv | benzimidazol-2-ylmethylaminocarbonyl | 0 | 0 | H | $NHSO_2$(2,4,6-trimethylphenyl) | |
| 999hw | benzimidazol-2-ylmethylaminocarbonyl | 0 | 0 | H | $NHSO_2$(2,4,6-trichlorophenyl) | |
| 999hx | benzimidazol-2-ylmethylaminocarbonyl | 0 | 0 | H | $NHSO_2$(2,6-dichlorophenyl) | |
| 999hy | benzimidazol-2-ylmethylaminocarbonyl | 0 | 0 | H | $NHSO_2$(2-chloro-6-methylphenyl) | |
| 999hz | benzimidazol-2-ylmethylaminocarbonyl | 0 | 0 | H | $NHSO_2C_6H_4$(2-$CH_3$) | |
| 999ia | benzimidazol-2-ylmethylaminocarbonyl | 0 | 0 | H | $NHSO_2C_6H_4$(2-Br) | |
| 999ib | benzimidazol-2-ylmethylaminocarbonyl | 0 | 0 | H | NHSO2[4-(2,6-dimethylphenyl)phenyl] | |
| 999ic | benzimidazol-2-ylmethylaminocarbonyl | 0 | 0 | H | $NHSO_2C_6H_4$(4-Ph) | |
| 999id | benzimidazol-2-ylmethylaminocarbonyl | 0 | 0 | H | $NHSO_2$[4-(3,5-dimethyl)isoxazoyl] | |
| 999ie | benzimidazol-2-ylmethylaminocarbonyl | 0 | 0 | H | $NHSO_2$(1-napthyl) | |
| 999if | benzimidazol-2-ylmethylaminocarbonyl | 0 | 0 | H | $NHSO_2$(2-napthyl) | |
| 999ig | benzimidazol-2-ylmethylaminocarbonyl | 0 | 0 | H | $NHSO_2NHCH_2Ph$ | |
| 999ih | benzimidazol-2-ylmethylaminocarbonyl | 0 | 0 | H | $NHSO_2NHPh$ | |
| 999ii | benzimidazol-2-ylmethylaminocarbonyl | 0 | 0 | Ph | H | |
| 999ij | benzimidazol-2-ylmethylaminocarbonyl | 0 | 0 | phenylsulfonylaminomethyl | H | |
| 999ik | benzimidazol-2-methylaminocarbonyl | 0 | 0 | 3-azabicyclo[3.2.2]nonan-3-ylcarbonyl | H | |
| 999il | benzimidazol-2-ylmethylaminocarbonyl | 0 | 0 | adamantan-1-yl methylaminocarbonyl | H | |
| 999im | benzimidazol-2-ylmethylaminocarbonyl | 0 | 0 | adamantan-1-yl aminocarbonyl | H | |
| 999in | benzimidazol-2-ylmethylaminocarbonyl | 0 | 0 | adamantan-2-yl aminocarbonyl | H | |
| 999io | benzimidazol-2-ylmethylaminocarbonyl | 0 | 0 | tetrahydroisoquinolin-2-ylcarbonyl | H | |
| 999ip | N-(benzimidazol-2-ylmethyl)-N-methyl-aminocarbonyl | 0 | 0 | H | $NHSO_2Ph$ | |
| 999iq | N-benzimidazol-2-ymethyl-N-methyl-aminocarbonyl | 0 | 0 | H | $NHSO_2$(2,4,6-trimethylphenyl) | |
| 999ir | N-benzimidazol-2-ymethyl-N-methyl-aminocarbonyl | 0 | 0 | H | $NHSO_2$(2,4,6-trichlorophenyl) | |
| 999is | N-benzimidazol-2- | 0 | 0 | H | $NHSO_2$(2,6- | |

TABLE 2-continued

Structure:
R¹—U—(CH₂)ₘ—[C with O—N]—(CH₂)ₙ—C(O)—NH—CHR⁸—CHR⁹—C(O)OH

| Ex. No. | R¹—U | m | n | R⁸ | R⁹ | MS |
|---|---|---|---|---|---|---|
| | ylmethyl-N-methyl-aminocarbonyl | | | | dichlorophenyl) | |
| 999it | N-benzimidazol-2-ylmethyl-N-methyl-aminocarbonyl | 0 | 0 | H | NHSO₂(2-chloro-6-methylphenyl) | |
| 999iu | N-benzimidazol-2-ylmethyl-N-methyl-aminocarbonyl | 0 | 0 | H | NHSO₂C₆H₄(2-CH₃) | |
| 999iv | N-benzimidazol-2-ylmethyl)-N-methyl-aminocarbonyl | 0 | 0 | H | NHSO₂C₆H₄(2-Br) | |
| 999iw | N-benzimidazol-2-ylmethyl)-N-methyl-aminocarbonyl | 0 | 0 | H | NHSO2[4-(2,6-dimethylphenyl)phenyl | |
| 999ix | N-benzimidazol-2-ylmethyl)-N-methyl-aminocarbonyl | 0 | 0 | H | NHSO₂C₆H₄(4-Ph) | |
| 999iy | N-benzimidazol-2-ylmethyl-N-methyl-aminocarbonyl | 0 | 0 | H | NHSO₂[4-(3,5-dimethyl)isoxazolyl] | |
| 999iz | N-benzimidazol-2-ylmethyl)-N-methyl-aminocarbonyl | 0 | 0 | H | NHSO₂(1-napthyl) | |
| 999ja | N-benzimidazol-2-ylmethyl)-N-methyl-aminocarbonyl | 0 | 0 | H | NHSO₂(2-napthyl) | |
| 999jb | N-benzimidazol-2-ylmethyl)-N-methyl-aminocarbonyl | 0 | 0 | H | NHSO₂NHCH₂Ph | |
| 999jc | N-benzimidazol-2-ylmethyl)-N-methyl-aminocarbonyl | 0 | 0 | H | NHSO₂NHPh | |
| 999jd | N-benzimidazol-2-ylmethyl)-N-methyl-aminocarbonyl | 0 | 0 | Ph | H | |
| 999je | N-benzimidazol-2-ylmethyl)-N-methyl-aminocarbonyl | 0 | 0 | phenylsulfonylamino methyl | H | |
| 999jf | N-benzimidazol-2-ylmethyl)-N-methyl-aminocarbonyl | 0 | 0 | 3-azabicyclo[3.2.2]nonan-3-ylcarbonyl | H | |
| 999jg | N-benzimidazol-2-ylmethyl)-N-methyl-aminocarbonyl | 0 | 0 | adamantan-1-yl methylaminocarbonyl | H | |
| 999jh | N-benzimidazol-2-ylmethyl)-N-methyl-aminocarbonyl | 0 | 0 | adamantan-1-yl aminocarbonyl | H | |
| 999ji | N-benzimidazol-2-ylmethyl)-N-methyl-aminocarbonyl | 0 | 0 | adamantan-2-yl aminocarbonyl | H | |
| 999jj | N-benzimidazol-2-ylmethyl)-N-methyl-aminocarbonyl | 0 | 0 | tetrahydroisoquinolin-2-ylcarbonyl | H | |
| 999jk | 3,4,5,6,-tetrahydro-pyridin-2-ylamino | 4 | 0 | H | NHSO₂Ph | 494.3 |
| 999jl | 3,4,5,6,-tetrahydro-pyridin-2-ylamino | 4 | 0 | H | NHSO₂(2,4,6-trimethylphenyl) | 536.5 |
| 999jm | 3,4,5,6,-tetrahydro-pyridin-2-ylamino | 4 | 0 | H | NHSO₂(2,4,6-trichlorophenyl) | |
| 999jn | 3,4,5,6,-tetrahydro-pyridin-2-ylamino | 4 | 0 | H | NHSO₂(2,6-dichlorophenyl) | |
| 999jo | 3,4,5,6,-tetrahydro-pyridin-2-ylamino | 4 | 0 | H | NHSO₂(2-chloro-6-methylphenyl) | |
| 999jp | 3,4,5,6,-tetrahydro-pyridin-2-ylamino | 4 | 0 | H | NHSO₂C₆H₄(2-CH₃) | |
| 999jq | 3,4,5,6,-tetrahydro-pyridin-2-ylamino | 4 | 0 | H | NHSO₂C₆H₄(2-Br) | |
| 999jr | 3,4,5,6,-tetrahydro-pyridin-2-ylamino | 4 | 0 | H | NHSO2[4-(2,6-dimethylphenyl)phenyl | |

TABLE 2-continued $$R^1-U-(CH_2)_m \overset{}{\underset{O-N}{\diagdown}} (CH_2)_n-\overset{O}{\underset{}{C}}-\overset{H}{\underset{R^8}{N}}-\overset{R^9}{\underset{}{C}}-COOH$$

| Ex. No. | R¹—U | m | n | R⁸ | R⁹ | MS |
|---|---|---|---|---|---|---|
| 999js | 3,4,5,6,-tetrahydro-pyridin-2-ylamino | 4 | 0 | H | NHSO₂C₆H₄(4-Ph) | |
| 999jt | 3,4,5,6,-tetrahydro-pyridin-2-ylamino | 4 | 0 | H | NHSO₂[4-(3,5-dimethyl)isoxazolyl] | |
| 999ju | 3,4,5,6,-tetrahydro-pyridin-2-ylamino | 4 | 0 | H | NHSO₂(1-napthyl) | |
| 999jv | 3,4,5,6,-tetrahydro-pyridin-2-ylamino | 4 | 0 | H | NHSO₂(2-napthyl) | |
| 999jw | 3,4,5,6,-tetrahydro-pyridin-2-ylamino | 4 | 0 | H | NHSO₂NHCH₂Ph | |
| 999jx | 3,4,5,6,-tetrahydro-pyridin-2-ylamino | 4 | 0 | H | NHSO₂NHPh | |
| 999jy | 3,4,5,6,-tetrahydro-pyridin-2-ylamino | 4 | 0 | Ph | N | |
| 999jz | 3,4,5,6,-tetrahydro-pyridin-2-ylamino | 4 | 0 | phenylsulfonylamino methyl | H | |
| 999ka | 3,4,5,6,-tetrahydro-pyridin-2-ylamino | 4 | 0 | 3-azabicyclo[3.2.2] nonan-3-ylcarbonyl | H | |
| 999kb | 3,4,5,6,-tetrahydro-pyridin-2-ylamino | 4 | 0 | adamantan-1-yl methylaminocarbonyl | H | |
| 999kc | 3,4,5,6,-tetrahydro-pyridin-2-ylamino | 4 | 0 | adamantan-1-yl aminocarbonyl | H | |
| 999kd | 3,4,5,6,-tetrahydro-pyridin-2-ylamino | 4 | 0 | adamantan-2-yl aminocarbonyl | H | |
| 999ke | 3,4,5,6,-tetrahydro-pyridin-2-ylamino | 4 | 0 | tetrahydroisoquinolin-2-ylcarbonyl | H | |

TABLE 3

$$R^1-U-(CH_2)_m-Q\underset{N-O}{\overset{R^{14}}{\diagdown}}(CH_2)_n-\overset{O}{\underset{}{C}}-\overset{H}{\underset{R^8}{N}}-\overset{R^9}{\underset{}{C}}-COOH$$

| Ex. No. | R¹-U | m | n | Q | R⁸ | R⁹ | R¹⁴ | MS |
|---|---|---|---|---|---|---|---|---|
| 1001 | imidazolin-2-ylamino | 3 | 0 | O | H | H | H | 326.2 |
| 1002 | imidazolin-2-ylamino | 2 | 0 | O | H | H | H | |
| 1003 | imidazolin-2-ylamino | 2 | 0 | O | H | NHCbz | H | |
| 1004 | imidazolin-2-ylamino | 3 | 0 | O | H | NHCbz | H | 475.2 |
| 1005 | imidazolin-2-ylamino | 2 | 0 | S | H | NHCbz | H | |
| 1006 | imidazolin-2-ylamino | 3 | 0 | S | H | NHCbz | H | |
| 1007 | imidazolin-2-ylamino | 2 | 0 | NH | H | NHCbz | H | |
| 1008 | imidazolin-2-ylamino | 3 | 0 | NH | H | NHCbz | H | |
| 1009 | tetrahydropyrimidin-2-ylamino | 2 | 0 | O | H | H | H | |
| 1010 | tetrahydropyrimidin-2-ylamino | 2 | 0 | O | H | NHCbz | H | |
| 1011 | tetrahydropyrimidin-2-ylamino | 3 | 0 | O | H | H | H | |
| 1012 | tetrahydropyrimidin-2-ylamino | 3 | 0 | O | H | NHCbz | H | |
| 1013 | tetrahydropyrimidin-2-ylamino | 2 | 0 | S | H | NHCbz | H | |
| 1014 | tetrahydropyrimidin-2-ylamino | 3 | 0 | S | H | NHCbz | H | |
| 1015 | tetrahydropyrimidin-2-ylamino | 2 | 0 | NH | H | NHCbz | H | |
| 1016 | tetrahydropyrimidin-2-ylamino | 3 | 0 | NH | H | NHCbz | H | |
| 1017 | imidazolin-2-ylamino | 2 | 0 | O | H | NHCO2-n-Bu | H | |
| 1018 | imidazolin-2-ylamino | 3 | 0 | O | H | NHCO2-n-Bu | H | |
| 1019 | imidazolin-2-ylamino | 2 | 0 | S | H | NHCO2-n-Bu | H | |
| 1020 | imidazolin-2-ylamino | 3 | 0 | S | H | NHCO2-n-Bu | H | |
| 1021 | imidazolin-2-ylamino | 2 | 0 | NH | H | NHCO2-n-Bu | H | |
| 1022 | imidazolin-2-ylamino | 3 | 0 | NH | H | NHCO2-n-Bu | H | |

TABLE 3-continued $$R^1-U-(CH_2)_m-Q\underset{N-O}{\overset{R^{14}}{\diagdown}}(\phantom{x})_n\overset{H}{\underset{O}{N}}\underset{R^8}{\overset{R^9}{\diagdown}}\overset{OH}{\underset{O}{\diagdown}}$$

| Ex. No. | R¹-U | m | n | Q | R⁸ | R⁹ | R¹⁴ | MS |
|---|---|---|---|---|---|---|---|---|
| 1023 | tetrahydropyrimidin-2-ylamino | 2 | 0 | O | H | NHCO2-n-Bu | H | |
| 1024 | tetrahydropyrimidin-2-ylamino | 3 | 0 | O | H | NHCO2-n-Bu | H | |
| 1025 | tetrahydropyrimidin-2-ylamino | 2 | 0 | S | H | NHCO2-n-Bu | H | |
| 1026 | tetrahydropyrimidin-2-ylamino | 3 | 0 | S | H | NHCO2-n-Bu | H | |
| 1027 | tetrahydropyrimidin-2-ylamino | 2 | 0 | NH | H | NHCO2-n-Bu | H | |
| 1028 | tetrahydropyrimidin-2-ylamino | 3 | 0 | NH | H | NHCO2-n-Bu | H | |
| 1029 | imidazolin-2-ylamino | 2 | 0 | O | H | NHSO$_2$Ph(o-CH$_3$) | H | |
| 1030 | imidazolin-2-ylamino | 3 | 0 | O | H | NHSO$_2$Ph(o-CH$_3$) | H | |
| 1031 | imidazolin-2-ylamino | 2 | 0 | S | H | NHSO$_2$Ph(o-CH$_3$) | H | |
| 1032 | imidazolin-2-ylamino | 3 | 0 | S | H | NHSO$_2$Ph(o-CH$_3$) | H | |
| 1033 | imidazolin-2-ylamino | 2 | 0 | O | H | NHSO$_2$Ph(m-CH$_3$) | H | |
| 1034 | imidazolin-2-ylamino | 3 | 0 | O | H | NHSO$_2$Ph(m-CH$_3$) | H | 495.3 |
| 1035 | imidazolin-2-ylamino | 2 | 0 | S | H | NHSO$_2$Ph(m-CH$_3$) | H | |
| 1036 | imidazolin-2-ylamino | 3 | 0 | S | H | NHSO$_2$Ph(m-CH$_3$) | H | |
| 1037 | imidazolin-2-ylamino | 2 | 0 | O | H | NHSO$_2$Ph(p-CH$_3$) | H | |
| 1038 | imidazolin-2-ylamino | 3 | 0 | O | H | NHSO$_2$Ph(p-CH$_3$) | H | |
| 1039 | imidazolin-2-ylamino | 2 | 0 | S | H | NHSO$_2$Ph(p-CH$_3$) | H | |
| 1040 | imidazolin-2-ylamino | 3 | 0 | S | H | NHSO$_2$Ph(p-CH$_3$) | H | |
| 1041 | imidazolin-2-ylamino | 2 | 0 | O | H | NHSO$_2$Ph(o-Cl) | H | |
| 1042 | imidazolin-2-ylamino | 3 | 0 | O | H | NHSO$_2$Ph(o-Cl) | H | |
| 1043 | imidazolin-2-ylamino | 2 | 0 | O | H | NHSO$_2$Ph(m-Cl) | H | |
| 1044 | imidazolin-2-ylamino | 3 | 0 | O | H | NHSO$_2$Ph(m-Cl) | H | |
| 1045 | imidazolin-2-ylamino | 2 | 0 | O | H | NHSO$_2$Ph(p-Cl) | H | |
| 1046 | imidazolin-2-ylamino | 3 | 0 | O | H | NHSO$_2$Ph(p-Cl) | H | |
| 1047 | tetrahydropyrimidin-2-ylamino | 2 | 0 | O | H | NHSO$_2$Ph(p-Cl) | H | |
| 1048 | tetrahydropyrimidin-2-ylamino | 3 | 0 | O | H | NHSO$_2$Ph(p-Cl) | H | |
| 1049 | tetrahydropyrimidin-2-ylamino | 2 | 0 | O | H | NHSO$_2$Ph(m-Cl) | H | |
| 1050 | tetrahydropyrimidin-2-ylamino | 3 | 0 | O | H | NHSO$_2$Ph(m-Cl) | H | |
| 1051 | tetrahydropyrimidin-2-ylamino | 2 | 0 | O | H | NHSO$_2$Ph(p-Cl) | | |
| 1052 | tetrahydropyrimidin-2-ylamino | 3 | 0 | O | H | NHSO$_2$Ph(p-Cl) | H | |
| 1053 | imidazolin-2-ylamino | 2 | 0 | O | H | NHSO$_2$Ph(m-F) | H | |
| 1054 | imidazolin-2-ylamino | 3 | 0 | O | H | NHSO$_2$Ph(m-F) | H | |
| 1055 | tetrahydropyrimidin-2-ylamino | 2 | 0 | O | H | NHSO$_2$Ph(m-F) | H | |
| 1056 | tetrahydropyrimidin-2-ylamino | 3 | 0 | O | H | NHSO$_2$Ph(m-F) | H | |
| 1057 | imidazolin-2-ylamino | 2 | 0 | O | H | NHSO$_2$Ph(p-F) | H | |
| 1058 | imidazolin-2-ylamino | 3 | 0 | O | H | NHSO$_2$Ph(p-F) | H | |
| 1059 | tetrahydropyrimidin-2-ylamino | 2 | 0 | O | H | NHSO$_2$Ph(p-F) | H | |
| 1060 | tetrahydropyrimidin-2-ylamino | 3 | 0 | O | H | NHSO$_2$Ph(p-F) | H | |
| 1061 | imidazolin-2-ylamino | 2 | 0 | O | H | NHSO$_2$Ph(m-Br) | H | |
| 1062 | imidazolin-2-ylamino | 3 | 0 | O | H | NHSO$_2$Ph(m-Br) | H | |
| 1063 | tetrahydropyrimidin-2-ylamino | 2 | 0 | O | H | NHSO$_2$Ph(m-Br) | H | |
| 1064 | tetrahydropyrimidin-2-ylamino | 3 | 0 | O | H | NHSO$_2$Ph(m-Br) | H | |
| 1065 | imidazolin-2-ylamino | 2 | 0 | O | H | NHSO$_2$Ph(p-Br) | H | |
| 1066 | imidazolin-2-ylamino | 3 | 0 | O | H | NHSO$_2$Ph(p-Br) | H | |
| 1067 | tetrahydropyrimidin-2-ylamino | 2 | 0 | O | H | NHSO$_2$Ph(p-Br) | H | |
| 1068 | tetrahydropyrimidin-2-ylamino | 3 | 0 | O | H | NHSO$_2$Ph(p-Br) | H | |
| 1069 | imidazolin-2-ylamino | 2 | 0 | O | H | NHSO$_2$Ph(m-OCH$_3$) | H | |
| 1070 | imidazolin-2-ylamino | 3 | 0 | O | H | NHSO$_2$Ph(m-OCH$_3$) | H | |
| 1071 | tetrahydropyrimidin-2-ylamino | 2 | 0 | O | H | NHSO$_2$Ph(m-OCH$_3$) | H | |

TABLE 3-continued $$R^1-U-(CH_2)_m-Q-\underset{N-O}{\overset{R^{14}}{\diagdown}}(\phantom{)})_n\underset{O}{\overset{H}{-C-N}}\underset{R^8}{\overset{R^9}{-C-C}}OH$$

| Ex. No. | R¹-U | m | n | Q | R⁸ | R⁹ | R¹⁴ | MS |
|---|---|---|---|---|---|---|---|---|
| 1072 | tetrahydropyrimidin-2-ylamino | 3 | 0 | O | H | NHSO₂Ph(m-OCH₃) | H | |
| 1073 | imidazolin-2-ylamino | 2 | 0 | O | H | NHSO₂Ph(p-OCH₃) | H | |
| 1074 | imidazolin-2-ylamino | 3 | 0 | O | H | NHSO₂Ph(p-OCH₃) | H | |
| 1075 | tetrahydropyrimidin-2-ylamino | 2 | 0 | O | H | NHSO₂Ph(p-OCH₃) | H | |
| 1076 | tetrahydropyrimidin-2-ylamino | 3 | 0 | O | H | NHSO₂Ph(p-OCH₃) | H | |
| 1077 | imidazolin-2-ylamino | 2 | 0 | O | H | NHSO₂Bn | H | |
| 1078 | imidazolin-2-ylamino | 3 | 0 | O | H | NHSO₂Bn | H | |
| 1079 | tetrahydropyrimidin-2-ylamino | 2 | 0 | O | H | NHSO₂Bn | H | |
| 1080 | tetrahydropyrimidin-2-ylamino | 3 | 0 | O | H | NHSO₂Bn | H | |
| 1081 | imidazolin-2-ylamino | 2 | 0 | O | H | NHSO₂Et | H | |
| 1082 | imidazolin-2-ylamino | 3 | 0 | O | H | NHSO₂Et | H | |
| 1083 | tetrahydropyrimidin-2-ylamino | 2 | 0 | O | H | NHSO₂Et | H | |
| 1084 | tetrahydropyrimidin-2-ylamino | 3 | 0 | O | H | NHSO₂Et | H | |
| 1085 | imidazolin-2-ylamino | 2 | 0 | O | H | NHSO₂-n-Pr | H | |
| 1086 | imidazolin-2-ylamino | 3 | 0 | O | H | NHSO₂-n-Pr | H | |
| 1087 | tetrahydropyrimidin-2-ylamino | 2 | 0 | O | H | NHSO₂-n-Pr | H | |
| 1088 | tetrahydropyrimidin-2-ylamino | 3 | 0 | O | H | NHSO₂-n-Pr | H | |
| 1089 | imidazolin-2-ylamino | 2 | 0 | O | H | NHSO₂-n-(C₅H₁₁) | H | |
| 1090 | imidazolin-2-ylamino | 3 | 0 | O | H | NHSO₂-n-(C₅H₁₁) | H | |
| 1091 | tetrahydropyrimidin-2-ylamino | 2 | 0 | O | H | NHSO₂-n-(C₅H₁₁) | H | |
| 1092 | tetrahydropyrimidin-2-ylamino | 3 | 0 | O | H | NHSO₂-n-(C₅H₁₁) | H | |
| 1093 | imidazolin-2-ylamino | 2 | 0 | O | H | NHCO₂Et | H | |
| 1094 | imidazolin-2-ylamino | 3 | 0 | O | H | NHCO₂Et | H | |
| 1095 | tetrahydropyrimidin-2-ylamino | 2 | 0 | O | H | NHCO₂Et | H | |
| 1096 | tetrahydropyrimidin-2-ylamino | 3 | 0 | O | H | NHCO₂Et | H | |
| 1097 | imidazolin-2-ylamino | 2 | 0 | O | H | NHCO₂-n-C₅H₁₁ | H | |
| 1098 | imidazolin-2-ylamino | 3 | 0 | O | H | NHCO₂-n-C₅H₁₁ | H | |
| 1099 | tetrahydropyrimidin-2-ylamino | 2 | 0 | O | H | NHCO₂-n-C₅H₁₁ | H | |
| 1100 | tetrahydropyrimidin-2-ylamino | 3 | 0 | O | H | NHCO₂-n-C₅H₁₁ | H | |
| 1101 | imidazolin-2-ylamino | 4 | 0 | O | H | NHCbz | H | |
| 1102 | tetrahydropyrimidin-2-ylamino | 4 | 0 | O | H | NHCbz | H | |
| 1103 | imidazolin-2-ylamino | 4 | 0 | O | H | NHCO₂-n-Bu | H | |
| 1104 | tetrahydropyrimidin-2-ylamino | 4 | 0 | O | H | NHCO₂-n-Bu | H | |
| 1105 | imidazolin-2-ylamino | 4 | 0 | O | H | NHSO₂Ph | H | |
| 1106 | tetrahydropyrimidin-2-ylamino | 4 | 0 | O | H | NHSO₂Ph | H | |
| 1107 | imidazolin-2-ylamino | 4 | 0 | O | H | NHSO₂-n-Bu | H | |
| 1108 | tetrahydropyrimidin-2-ylamino | 4 | 0 | O | H | NHSO₂-n-Bu | H | |
| 1109 | imidazolin-2-ylamino | 4 | 0 | S | H | NHCbz | H | |
| 1110 | tetrahydropyrimidin-2-ylamino | 4 | 0 | S | H | NHCbz | H | |
| 1111 | imidazolin-2-ylamino | 4 | 0 | S | H | NHSO₂Bu | H | |
| 1112 | tetrahydropyrimidin-2-ylamino | 4 | 0 | S | H | NHSO₂Bu | H | |
| 1113 | imidazolin-2-ylamino | 2 | 0 | O | Me | H | H | |
| 1114 | imidazolin-2-ylamino | 3 | 0 | O | Me | H | H | |
| 1115 | tetrahydropyrimidin-2-ylamino | 2 | 0 | O | Me | H | H | |
| 1116 | tetrahydropyrimidin-2-ylamino | 3 | 0 | O | Me | H | H | |
| 1117 | imidazolin-2-ylamino | 3 | 0 | S | Me | H | | |
| 1118 | tetrahydropyrimidin- | 3 | 0 | S | Me | H | H | |

TABLE 3-continued

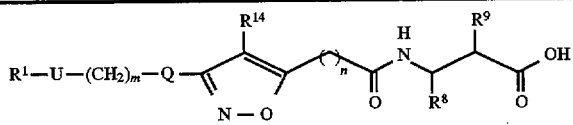

| Ex. No. | R¹-U | m | n | Q | R⁸ | R⁹ | R¹⁴ | MS |
|---|---|---|---|---|---|---|---|---|
| | 2-ylamino | | | | | | | |
| 1119 | imidazolin-2-ylamino | 2 | 0 | O | Me | NHCbz | H | |
| 1120 | imidazolin-2-ylamino | 3 | 0 | O | Me | NHCbz | H | |
| 1121 | tetrahydropyrimidin-2-ylamino | 2 | 0 | O | Me | NHSO$_2$-n-Bu | H | |
| 1122 | tetrahydropyrimidin-2-ylamino | 3 | 0 | O | Me | NHSO$_2$-n-Bu | H | |
| 1123 | imidazolin-2-ylamino | 2 | 0 | O | Et | H | H | |
| 1124 | imidazolin-2-ylamino | 3 | 0 | O | Et | H | H | |
| 1125 | tetrahydropyrimidin-2-ylamino | 2 | 0 | O | Et | H | H | |
| 1126 | tetrahydropyrimidin-2-ylamino | 3 | 0 | O | Et | H | H | |
| 1127 | imidazolin-2-ylamino | 3 | 0 | S | Et | H | H | |
| 1128 | tetrahydropyrimidin-2-ylamino | 3 | 0 | S | Et | H | H | |
| 1129 | imidazolin-2-ylamino | 2 | 0 | O | Ph | H | H | |
| 1130 | imidazolin-2-ylamino | 3 | 0 | O | Ph | H | H | |
| 1131 | tetrahydropyrimidin-2-ylamino | 2 | 0 | O | Ph | H | H | |
| 1132 | tetrahydropyrimidin-2-ylamino | 3 | 0 | O | Ph | H | H | |
| 1133 | imidazolin-2-ylamino | 3 | 0 | S | Ph | H | H | |
| 1134 | tetrahydropyrimidin-2-ylamino | 3 | 0 | S | Ph | H | H | |
| 1135 | imidazolin-2-ylamino | 2 | 0 | O | Bn | H | H | |
| 1136 | imidazolin-2-ylamino | 3 | 0 | O | Bn | H | H | |
| 1137 | tetrahydropyrimidin-2-ylamino | 2 | 0 | O | Bn | H | H | |
| 1138 | tetrahydropyrimidin-2-ylamino | 3 | 0 | O | Bn | H | H | |
| 1139 | imidazolin-2-ylamino | 3 | 0 | S | Bn | H | H | |
| 1140 | tetrahydropyrimidin-2-ylamino | 3 | 0 | S | Bn | H | H | |
| 1141 | imidazolin-2-ylamino | 2 | 0 | O | H | NHCbz | Me | |
| 1142 | imidazolin-2-ylamino | 3 | 0 | O | H | NHCbz | Me | |
| 1143 | tetrahydropyrimidin-2-ylamino | 2 | 0 | O | H | NHCbz | Me | |
| 1144 | tetrahydropyrimidin-2-ylamino | 3 | 0 | O | H | NHCbz | Me | |
| 1145 | imidazolin-2-ylamino | 2 | 0 | O | H | NHSO$_2$-n-Bu | Me | |
| 1146 | imidazolin-2-ylamino | 3 | 0 | O | H | NHSO$_2$-n-Bu | Me | |
| 1147 | tetrahydropyrimidin-2-ylamino | 2 | 0 | O | H | NHSO$_2$-n-Bu | Me | |
| 1148 | tetrahydropyrimidin-2-ylamino | 3 | 0 | O | H | NHSO$_2$-n-Bu | Me | |
| 1149 | imidazolin-2-ylamino | 3 | 0 | S | H | NHCbz | Me | |
| 1150 | tetrahydropyrimidin-2-ylamino | 3 | 0 | S | H | NHCbz | Me | |
| 1151 | imidazolin-2-ylamino | 3 | 0 | S | H | NHSO$_2$-n-Bu | Me | |
| 1152 | tetrahydropyrimidin-2-ylamino | 3 | 0 | S | H | NHSO$_2$-n-Bu | Me | |
| 1153 | imidazolin-2-ylamino | 2 | 0 | O | H | NHCbz. | Bn | |
| 1154 | imidazolin-2-ylamino | 3 | 0 | O | H | NHCbz | Bn | |
| 1155 | tetrahydropyrimidin-2-ylamino | 2 | 0 | O | H | NHCbz | Bn | |
| 1156 | tetrahydropyrimidin-2-ylamino | 3 | 0 | O | H | NHCbz | Bn | |
| 1157 | imidazolin-2-ylamino | 2 | 0 | O | H | NHSO$_2$-n-Bu | Bn | |
| 1158 | imidazolin-2-ylamino | 3 | 0 | O | H | NHSO$_2$-n-Bu | Bn | |
| 1159 | tetrahydropyrimidin-2-ylamino | 2 | 0 | O | H | NHSO$_2$-n-Bu | Bn | |
| 1160 | tetrahydropyrimidin-2-ylamino | 3 | 0 | O | H | NHSO$_2$-n-Bu | Bn | |
| 1161 | imidazolin-2-ylamino | 3 | 0 | S | H | NHCbz | Bn | |
| 1162 | tetrahydropyrimidin-2-ylamino | 3 | 0 | S | H | NHCbz | Bn | |
| 1163 | imidazolin-2-ylamino | 3 | 0 | S | H | NHSO$_2$-n-Bu | Bn | |
| 1164 | tetrahydropyrimidin-2-ylamino | 3 | 0 | S | H | NHSO$_2$-n-Bu | Bn | |

TABLE 3-continued $$R^1-U-(CH_2)_m-Q-\underset{N-O}{\overset{R^{14}}{\diagup}}(\phantom{X})_n-\underset{O}{\overset{H}{N}}-\underset{R^8}{\overset{R^9}{C}}-\underset{O}{\overset{OH}{C}}$$

| Ex. No. | R¹-U | m | n | Q | R⁸ | R⁹ | R¹⁴ | MS |
|---|---|---|---|---|---|---|---|---|
| 1165 | imidazolin-2-ylamino | 3 | 0 | O | Me | NHCbz | Me | |
| 1166 | tetrahydropyrimidin-2-ylamino | 3 | 0 | O | Me | NHSO$_2$Bu | Me | |
| 1167 | imidazolin-2-ylamino | 3 | 0 | O | Bn | NHCbz | Me | |
| 1168 | tetrahydropyrimidin-2-ylamino | 3 | 0 | O | Bn | NHCbz | Me | |
| 1169 | imidazolin-2-ylamino | 3 | 0 | O | Me | NHSO$_2$-n-Bu | Me | |
| 1170 | tetrahydropyrimidin-2-ylamino | 3 | 0 | O | Me | NHCbz | Me | |
| 1171 | imidazolin-2-ylamino | 3 | 0 | O | Bn | NHSO$_2$-n-Bu | Me | |
| 1172 | tetrahydropyrimidin-2-ylamino | 3 | 0 | O | Bn | NHCbz | Me | |
| 1173 | (4-oxoimidazolin-2-yl)amino | 2 | 0 | O | H | NHCBz | H | |
| 1174 | (4-oxoimidazolin-2-yl)amino | 3 | 0 | O | H | NHCBz | H | |
| 1175 | (4-oxoimidazolin-2-yl)amino | 2 | 0 | O | H | NHCO$_2$-n-Bu | H | |
| 1176 | (4-oxoimidazolin-2-yl)amino | 3 | 0 | O | H | NHCO$_2$-n-Bu | H | |
| 1177 | (4-oxoimidazolin-2-yl)amino | 2 | 0 | O | H | NHSO$_2$Ph | H | |
| 1178 | (4-oxoimidazolin-2-yl)amino | 3 | 0 | O | H | NHSO$_2$Ph | H | |
| 1179 | (4-oxoimidazolin-2-yl)amino | 2 | 0 | O | H | NHSO$_2$-n-Bu | H | |
| 1180 | (4-oxoimidazolin-2-yl)amino | 3 | 0 | O | H | NHSO$_2$-n-Bu | H | |
| 1181 | (4-oxotetrahydropyrimidin-2-yl)amino | 3 | 0 | O | H | NHCbz | H | |
| 1182 | (4-oxotetrahydropyrimidin-2-yl)amino | 3 | 0 | O | H | NHCO$_2$-n-Bu | H | |
| 1183 | (4-oxotetrahydropyrimidin-2-yl)amino | 3 | 0 | O | H | NHSO$_2$Ph | H | |
| 1184 | (4-oxotetrahydropyrimidin-2-yl)amino | 3 | 0 | O | H | NHSO$_2$-n-Bu | H | |
| 1185 | (4-oxoimidazolin-2-yl)amino | 3 | 0 | S | H | NHCbz | H | |
| 1186 | (4-oxoimidazolin-2-yl)amino | 3 | 0 | S | H | NHSO$_2$-n-Bu | H | |
| 1187 | (4-oxotetrahydropyrimidin-2-yl)amino | 3 | 0 | S | H | NHCbz | H | |
| 1188 | (4-oxotetrahydropyrimidin-2-yl)amino | 3 | 0 | S | H | NHSO$_2$-n-Bu | H | |
| 1189 | (4-oxoimidazolin-2-yl)amino | 3 | 0 | O | Me | H | H | |
| 1190 | (4-oxotetrahydropyrimidin-2-yl)amino | 3 | 0 | O | Me | H | H | |
| 1191 | (4-oxoimidazolin-2-yl)amino | 3 | 0 | O | Bn | H | H | |
| 1192 | (4-oxotetrahydropyrimidin-2-yl)amino | 3 | 0 | O | Bn | H | | |
| 1193 | (4-oxomidazolin-2-yl)amino | 3 | 0 | O | Me | NHCbz | H | |
| 1194 | (4-oxotetrahydropyrimidin-2-yl)amino | 3 | 0 | O | Me | NHSO$_2$-n-Bu | H | |
| 1195 | (4-oxoimidazolin-2-yl)amino | 3 | 0 | O | H | NHCbz | Me | |
| 1196 | (4-oxotetrahydropyrimidin-2-yl)amino | 3 | 0 | O | H | NHCbz | Bn | |

TABLE 3-continued $$R^1-U-(CH_2)_m-Q-\underset{N-O}{\overset{R^{14}}{C}}=CH-(CH_2)_n-\underset{O}{\overset{H}{C}}-N-\underset{R^8}{\overset{R^9}{C}H}-\underset{O}{\overset{}{C}}-OH$$

| Ex. No. | R¹-U | m | n | Q | R⁸ | R⁹ | R¹⁴ | MS |
|---|---|---|---|---|---|---|---|---|
| 1197 | imidazolin-2-ylaminocarbonyl | 1 | 0 | O | H | NHCbz | H | |
| 1198 | imidazolin-2-ylaminocarbonyl | 2 | 0 | O | H | NHCbz | H | |
| 1199 | tetrahydropyrimidin-2-ylaminocarbonyl | 1 | 0 | O | H | NHSO₂-n-Bu | H | |
| 1200 | tetrahydropyrimidin-2-ylaminocarbonyl | 2 | 0 | O | H | NHSO₂-n-Bu | H | |
| 1201 | imidazolin-2-ylaminocarbonyl | 2 | 0 | O | H | NHCbz | H | |
| 1202 | tetrahydropyrimidin-2-ylaminocarbonyl | 2 | 0 | O | H | NHSO₂-n-Bu | H | |
| 1203 | imidazolin-2-ylaminocarbonyl | 1 | 0 | O | H | NHCO₂-n-Bu | H | |
| 1204 | imidazolin-2-ylaminocarbonyl | 2 | 0 | O | H | NHCO₂-n-Bu | H | |
| 1205 | tetrahydropyrimidin-2-ylaminocarbonyl | 1 | 0 | O | H | NHSO₂Ph | H | |
| 1206 | tetrahydropyrimidin-2-ylaminocarbonyl | 2 | 0 | O | H | NHSO₂Ph | H | |
| 1207 | imidazolin-2-ylaminocarbonyl | 2 | 0 | O | Me | NHCbz | H | |
| 1208 | tetrahydropyrimidin-2-ylaminocarbonyl | 2 | 0 | O | Me | NHSO₂-n-Bu | H | |
| 1209 | imidazolin-2-ylaminocarbonyl | 2 | 0 | O | Bn | H | H | |
| 1210 | tetrahydropyrimidin-2-ylaminocarbonyl | 2 | 0 | O | Bn | H | H | |
| 1211 | imidazolin-2-ylaminocarbonyl | 2 | 0 | O | Me | H | H | |
| 1212 | tetrahydropyrimidin-2-ylaminocarbonyl | 2 | 0 | O | Me | H | H | |
| 1213 | imidazolin-2-ylaminocarbonyl | 2 | 0 | O | H | NHCbz | Me | |
| 1214 | tetrahydropyrimidin-2-ylaminocarbonyl | 2 | 0 | O | H | NHCbz | Me | |
| 1215 | imidazolin-2-ylaminocarbonyl | 2 | 0 | O | H | NHSO₂-n-Bu | Me | |
| 1216 | tetrahydropyrimidin-2-ylaminocarbonyl | 2 | 0 | O | H | NHSO₂-n-Bu | Me | |
| 1217 | imidazolin-2-ylaminocarbonyl | 2 | 0 | S | Me | H | H | |
| 1218 | tetrahydropyrimidin-2-ylaminocarbonyl | 2 | 0 | S | Bn | H | H | |
| 1219 | imidazolin-2-ylaminocarbonyl | 2 | 0 | S | H | NHCbz | Me | |
| 1220 | tetrahydropyrimidin-2-ylaminocarbonyl | 2 | 0 | S | H | NHSO₂-n-Bu | Me | |
| 1221 | imidazolin-2-ylamino | 2 | 1 | O | H | NHCbz | H | |
| 1222 | imidazolin-2-ylamino | 3 | 1 | O | H | NHCbz | H | |
| 1223 | tetrahydropyrimidin-2-ylamino | 2 | 1 | O | H | NHCbz | H | |
| 1224 | tetrahydropyrimidin-2-ylamino | 3 | 1 | O | H | NHCbz | H | |
| 1225 | imidazolin-2-ylamino | 2 | 1 | O | H | NHSO₂-n-Bu | H | |
| 1226 | imidazolin-2-ylamino | 3 | 1 | O | H | NHSO₂-n-Bu | H | |
| 1227 | tetrahydropyrimidin-2-ylamino | 2 | 1 | O | H | NHSO₂-n-Bu | H | |
| 1228 | tetrahydropyrimidin-2-ylamino | 3 | 1 | O | H | NHSO₂-n-Bu | H | |
| 1229 | imidazolin-2-ylamino | 2 | 1 | S | H | NHCbz | H | |
| 1230 | imidazolin-2-ylamino | 3 | 1 | S | H | NHCbz | H | |
| 1231 | tetrahydropyrimidin-2-ylamino | 2 | 1 | S | H | NHCbz | H | |
| 1232 | tetranydropyrimidin-2-ylamino | 3 | 1 | S | H | NHCbz | H | |
| 1233 | imidazolin-2-ylamino | 2 | 1 | O | Me | H | H | |
| 1234 | imidazolin-2-ylamino | 3 | 1 | O | Me | H | H | |
| 1235 | tetrahydropyrimidin-2-ylamino | 2 | 1 | O | Bn | H | H | |

TABLE 3-continued $$R^1-U-(CH_2)_m-Q-\underset{N-O}{\overset{R^{14}}{\diagdown}}(\phantom{)}_n\overset{O}{\underset{}{\parallel}}-N\overset{H}{\underset{R^8}{\diagdown}}\overset{R^9}{\underset{}{\diagup}}COOH$$

| Ex. No. | R¹-U | m | n | Q | R⁸ | R⁹ | R¹⁴ | MS |
|---|---|---|---|---|---|---|---|---|
| 1236 | tetrahydropyrimidin-2-ylamino | 3 | 1 | O | Bn | H | H | |
| 1237 | imidazolin-2-ylamino | 2 | 1 | S | Me | H | H | |
| 1238 | tetrahydropyrimidin-2-ylamino | 2 | 1 | S | Bn | H | H | |
| 1239 | imidazolin-2-ylamino | 2 | 1 | O | Me | NHCbz | H | |
| 1240 | tetrahydropyrimidin-2-ylamino | 2 | 1 | O | Me | NHCbz | H | |
| 1241 | imidazolin-2-ylamino | 2 | 1 | O | H | NHCbz | H | |
| 1242 | tetrahydropyrimidin-2-ylamino | 2 | 1 | O | H | NHCbz | H | |
| 1243 | imidazolin-2-ylamino | 3 | 1 | O | H | NHCbz | H | |
| 1244 | tetrahydropyrimidin-2-ylamino | 3 | 1 | O | H | NHCbz | H | |
| 1245 | pyridin-2-ylamino | 2 | 1 | O | H | NHCbz | H | |
| 1246 | imidazol-2-ylamino | 2 | 1 | O | H | NHCbz | H | |
| 1251 | benzimidazol-2-ylamino | 2 | 1 | O | H | NHCbz | H | |
| 1252 | benzthiazol-2-ylamino | 2 | 1 | O | H | NHCbz | H | |
| 1255 | imidazol-4-ylamino | 2 | 1 | O | H | NHCbz | H | |
| 1262 | pyridin-2-ylamino | 3 | 0 | O | H | NHCbz | H | |
| 1263 | imidazol-2-ylamino | 3 | 0 | O | H | NHCbz | H | |
| 1268 | benzimidazol-2-ylamino | 3 | 0 | O | H | NHCbz | H | |
| 1269 | benzthiazol-2-ylamino | 3 | 0 | O | H | NHCbz | H | |
| 1272 | imidazol-4-ylamino | 3 | 0 | O | H | NHCbz | H | |
| 1279 | pyridin-2-ylamino | 2 | 0 | O | H | NHCbz | H | |
| 1280 | imidazol-2-ylamino | 2 | 0 | O | H | NHCbz | H | |
| 1285 | benzimidazol-2-ylamino | 2 | 0 | O | H | NHCbz | H | |
| 1286 | benzthiazol-2-ylamino | 2 | 0 | O | H | NHCbz | H | |
| 1289 | imidazol-4-ylamino | 2 | 0 | O | H | NHCbz | H | |
| 1297 | imidazolin-2-ylamino | 2 | 0 | O | H | NHSO₂-n-Bu | H | 447.5 |
| 1298 | imidazolin-2-ylamino | 3 | 0 | O | H | NHSO₂Ph | H | 481.4 |
| 1299 | imidazolin-2-ylamino | 2 | 0 | O | H | NHSO₂Ph | H | 467.3 |
| 1300 | imidazolin-2-ylamino | 3 | 0 | O | H | NHSO₂[4-(3,5-dimethyl)isoxazolyl] | H | 500.3 |
| 1301 | 5-nitropyridin-2-ylamino | 3 | 0 | O | H | NHCbz | H | 498.2 |
| 1302 | imidazol-2-ylamino | 3 | 0 | O | H | NHSO₂(2,4,6-trimethylphenyl) | H | |
| 1303 | imidazol-2-ylamino | 3 | 0 | O | H | NHSO₂(2,4,6-trichlorophenyl) | H | |
| 1304 | imidazol-2-ylamino | 3 | 0 | 0 | H | NHSO₂(2,6-dichlorophenyl) | H | |
| 1305 | imidazol-2-ylamino | 3 | 0 | O | H | NHSO₂(2-chloro-6-methylphenyl) | H | |
| 1306 | imidazol-2-ylamino | 3 | 0 | O | H | NHSO₂C₆H₄(2-CH₃) | H | |
| 1307 | imidazol-2-ylamino | 3 | 0 | O | H | NHSO₂C₆H₄(2-Br) | H | |
| 1308 | imidazol-2-ylamino | 3 | 0 | O | H | NHSO2[4-(2,6-dimethylphenyl)phenyl | H | |
| 1309 | imidazol-2-ylamino | 3 | 0 | O | H | NHSO₂C₆H₄(4-Ph) | H | |
| 1310 | imidazol-2-ylamino | 3 | 0 | O | H | NHSO₂[4-(3,5-dimethyl)isoxazolyl] | H | |
| 1311 | imidazol-2-ylamino | 3 | 0 | O | H | NHSO₂(1-napthyl) | H | |
| 1312 | imidazol-2-ylamino | 3 | 0 | O | H | NHSO₂(2-napthyl) | H | |
| 1313 | imidazol-2-ylamino | 3 | 0 | O | H | NHSO₂NHCH₂Ph | H | |
| 1314 | imidazol-2-ylamino | 3 | 0 | O | H | NHSO₂NHPh | H | |
| 1315 | imidazol-2-ylamino | 3 | 0 | O | Ph | H | H | |
| 1316 | imidazol-2-ylamino | 3 | 0 | O | phenylsulfonyl-aminomethyl | H | H | |
| 1317 | imidazol-2-ylamino | 3 | 0 | 0 | 3-azabicyclo[3.2.2]nonan-3-ylcarbonyl | H | H | |
| 1318 | imidazol-2-ylamino | 3 | 0 | O | adamantan-1- | H | H | |

TABLE 3-continued $$R^1-U-(CH_2)_m-Q\diagdown\overset{R^{14}}{\underset{N-O}{\diagup}}\diagdown(\ )_n\overset{O}{\underset{}{C}}-\overset{H}{\underset{R^8}{N}}\diagdown\overset{R^9}{\underset{}{C}}-COOH$$

| Ex. No. | R¹-U | m | n | Q | R⁸ | R⁹ | R¹⁴ | MS |
|---|---|---|---|---|---|---|---|---|
| 1319 | imidazol-2-ylamino | 3 | 0 | O | yl methylaminocarbonyl adamantan-1-yl aminocarbonyl | H | H | |
| 1320 | imidazol-2-ylamino | 3 | 0 | O | adamantan-2-yl aminocarbonyl | H | H | |
| 1321 | imidazol-2-ylamino | 3 | 0 | O | tetrahydroisoquinolin-2-ylcarbonyl | H | H | |
| 1322 | imidazol-2-ylaminocarbonyl | 2 | 0 | O | H | NHSO₂(2,4,6-trimethylphenyl) | H | |
| 1323 | imidazol-2-ylaminocarbonyl | 2 | 0 | O | H | NHSO₂(2,4,6-trichlorophenyl) | H | |
| 1324 | imidazol-2-ylaminocarbonyl | 2 | 0 | O | H | NHSO₂(2,6-dichlorophenyl) | H | |
| 1325 | imidazol-2-ylaminocarbonyl | 2 | 0 | O | H | NHSO₂(2-chloro-6-methylphenyl) | H | |
| 1326 | imidazol-2-ylaminocarbonyl | 2 | 0 | O | H | NHSO₂C₆H₄(2-CH₃) | H | |
| 1327 | imidazol-2-ylaminocarbonyl | 2 | 0 | O | H | NHSO₂C₆H₄(2-Br) | H | |
| 1328 | imidazol-2-ylaminocarbonyl | 2 | 0 | O | H | NHSO₂[4-(2,6-dimethylphenyl)phenyl] | H | |
| 1329 | imidazol-2-ylaminocarbonyl | 2 | 0 | O | H | NHSO₂C₆H₄(4-Ph) | H | |
| 1330 | imidazol-2-ylaminocarbonyl | 2 | 0 | O | H | NHSO₂[4-(3,5-dimethyl)isoxazolyl] | H | |
| 1331 | imidazol-2-ylaminocarbonyl | 2 | 0 | O | H | NHSO₂(1-napthyl) | H | |
| 1332 | imidazol-2-ylaminocarbonyl | 2 | 0 | O | H | NHSO₂(2-napthyl) | H | |
| 1333 | imidazol-2-ylaminocarbonyl | 2 | 0 | O | H | NHSO₂NHCH₂Ph | H | |
| 1334 | imidazol-2-ylaminocarbonyl | 2 | 0 | O | H | NHSO₂NHPh | H | |

TABLE 4

$$R^1-U-V-Q\diagdown\diagup\diagdown\overset{O}{\underset{}{C}}-\overset{H}{\underset{R^8}{N}}\diagdown\overset{R^9}{\underset{}{C}}-COOH$$

| NO. | R¹-U | V | Q | R⁸ | R⁹ | MS |
|---|---|---|---|---|---|---|
| 1501 | imidazolin-2-ylamino | 1,4-phenylene | O | H | NHCBz | |
| 1502 | tetrahydropyrimidin-2-ylamino | 1,4-phenylene | O | H | NHCBz | |
| 1503 | imidazolin-2-ylamino | 1,4-phenylene | O | H | NHSO₂-n-Bu | |
| 1504 | tetrahydropyrimidin-2-ylamino | 1,4-phenylene | O | H | NHSO₂-n-Bu | |
| 1505 | imidazolin-2-ylamino | 1,4-phenylene | S | H | NHCbz | |
| 1506 | tetrahydropyrimidin-2-ylamino | 1,4-phenylene | S | H | NHCbz | |
| 1507 | imidazolin-2-ylamino | 1,4-phenylene | S | H | NHSO₂-n-Bu | |
| 1508 | tetrahydropyrimidin-2-ylamino | 1,4-phenylene | S | H | NHSO₂-n-Bu | |
| 1509 | imidazolin-2-ylamino | 1,4-phenylene | NH | H | NHCbz | |
| 1510 | tetrahydropyrimidin-2-ylamino | 1,4-phenylene | NH | H | NHCbz | |
| 1511 | imidazolin-2-ylamino | 1,4-phenylene | NH | H | NHSO₂-n-Bu | |
| 1512 | tetrahydropyrimidin-2-ylamino | 1,4-phenylene | NH | H | NHSO₂-n-Bu | |
| 1513 | imidazolin-2-ylamino | 1,4-phenylene | O | Me | H | |
| 1514 | tetrahydropyrimidin-2-ylamino | 1,4-phenylene | O | Me | H | |
| 1515 | imidazolin-2-ylamino | 1,4-phenylene | O | Bn | H | |
| 1516 | tetrahydropyrimidin-2-ylamino | 1,4-phenylene | O | Bn | H | |

TABLE 4-continued $$R^1-U-V-Q-\underset{N-O}{\overset{}{\diagdown}}\diagup\diagdown C(O)-NH-CH(R^8)-CH(R^9)-C(O)OH$$

| NO. | R¹—U | V | Q | R⁸ | R⁹ | MS |
|---|---|---|---|---|---|---|
| 1517 | imidazolin-2-ylamino | 1,4-phenylene | S | Me | H | |
| 1518 | tetrahydropyrimidin-2-ylamino | 1,4-phenylene | S | Me | H | |
| 1519 | imidazolin-2-ylamino | 1,4-phenylene | S | Bn | H | |
| 1520 | tetrahydropyrimidin-2-ylamino | 1,4-phenylene | S | Bn | H | |
| 1521 | imidazolin-2-ylamino | 1,4-phenylene | O | Me | NHCbz | |
| 1522 | tetrahydropyrimidin-2-ylamino | 1,4-phenylene | O | Me | NHCbz | |
| 1523 | imidazolin-2-ylamino | 1,4-phenylene | O | H | NHCbz | |
| 1524 | tetrahydropyrimidin-2-ylamino | 1,4-phenylene | O | H | NHCbz | |
| 1525 | imidazolin-2-ylamino | 1,3-phenylene | O | H | NHCbz | |
| 1526 | tetrahydropyrimidin-2-ylamino | 1,3-phenylene | O | H | NHCbz | |
| 1527 | imidazolin-2-ylamino | 1,3-phenylene | O | H | NHSO₂-n-Bu | |
| 1528 | tetrahydropyrimidin-2-ylamino | 1,3-phenylene | O | H | NHSO₂-n-Bu | |
| 1529 | imidazolin-2-ylamino | 1,3-phenylene | S | H | NHCbz | |
| 1530 | tetrahydropyrimidin-2-ylamino | 1,3-phenylene | S | H | NHCbz | |
| 1531 | imidazolin-2-ylamino | 1,3-phenylene | S | H | NHSO₂-n-Bu | |
| 1532 | tetrahydropyrimidin-2-ylamino | 1,3-phenylene | S | H | NHSO₂-n-Bu | |
| 1533 | imidazolin-2-ylamino | 1,3-phenylene | NH | H | NHCbz | |
| 1534 | tetrahydropyrimidin-2-ylamino | 1,3-phenylene | NH | H | NHCbz | |
| 1535 | imidazolin-2-ylamino | 1,3-phenylene | NH | H | NHCbz | |
| 1536 | tetrahydropyrimidin-2-ylamino | 1,3-phenylene | NH | H | NHCbz | |
| 1537 | imidazolin-2-ylamino | 1,3-phenylene | O | Me | H | |
| 1538 | tetrahydropyrimidin-2-ylamino | 1,3-phenylene | O | Me | H | |
| 1539 | imidazolin-2-ylamino | 1,3-phenylene | O | Bn | H | |
| 1540 | tetrahydropyrimidin-2-ylamino | 1,3-phenylene | O | Bn | H | |
| 1541 | imidazolin-2-ylamino | 1,3-phenylene | O | Me | NHCbz | |
| 1542 | tetrahydropyrimidin-2-ylamino | 1,3-phenylene | O | Me | NHCbz | |
| 1543 | imidazolin-2-ylamino | 1,3-phenylene | S | Me | H | |
| 1544 | tetrahydropyrimidin-2-ylamino | 1,3-phenylene | S | Me | H | |
| 1545 | imidazolin-2-ylamino | 1,3-phenylene | S | Bn | H | |
| 1546 | tetrahydropyrimidin-2-ylamino | 1,3-phenylene | S | Bn | H | |
| 1547 | imidazolin-2-ylamino | 1,3-phenylene | O | H | NHCbz | |
| 1548 | tetrahydropyrimidin-2-ylamino | 1,3-phenylene | O | H | NHCbz | |

TABLE 5

$$R^1-U-(CH_2)_m-Q-\underset{N-O}{\overset{}{\diagdown}}\diagup\diagdown(R^{14})-CH_2-C(O)-NH-CH(R^8)-C(O)OH$$

| NO. | R¹—U | m | Q | R⁸ | R¹⁴ | MS |
|---|---|---|---|---|---|---|
| 1601 | imidazolin-2-ylamino | 2 | O | Bn | H | |
| 1602 | imidazolin-2-ylamino | 3 | O | Bn | H | |
| 1603 | tetrahydropyrimidin-2-ylamino | 2 | O | Bn | H | |
| 1604 | tetrahydropyrimidin-2-ylamino | 3 | O | Bn | H | |
| 1605 | imidazolin-2-ylamino | 2 | O | Bn(p-OCH₃) | H | |
| 1606 | tetrahydropyrimidin-2-ylamino | 2 | O | Bn(p-OCH₃) | H | |
| 1607 | imidazolin-2-ylamino | 3 | O | Bn(p-OCH₃) | H | |
| 1608 | tetrahydropyrimidin-2-ylamino | 3 | O | Bn(p-OCH₃) | H | |
| 1609 | imidazolin-2-ylamino | 2 | O | Bn(p-F) | H | |
| 1610 | imidazolin-2-ylamino | 3 | O | Bn(p-F) | | |
| 1611 | tetrahydropyrimidin-2-ylamino | 2 | O | Bn(p-F) | H | |
| 1612 | tetrahydropyrimidin-2-ylamino | 3 | O | Bn(p-F) | H | |
| 1613 | imidazolin-2-ylamino | 2 | S | Bn | H | |
| 1614 | imidazolin-2-ylamino | 3 | S | Bn | H | |
| 1615 | tetrahydropyrimidin-2-ylamino | 2 | S | Bn | H | |
| 1616 | tetrahydropyrimidin-2-ylamino | 3 | S | Bn | H | |
| 1617 | imidazolin-2-ylamino | 2 | O | Bn | Me | |
| 1618 | imidazolin-2-ylamino | 3 | O | Bn | Me | |
| 1619 | tetrahydropyrimidin-2-ylamino | 2 | O | Bn | Me | |
| 1620 | tetrahydropyrimidin-2-ylamino | 3 | O | Bn | Me | |
| 1621 | imidazolin-2-ylamino | 2 | NH | Bn | H | |
| 1622 | imidazolin-2-ylamino | 3 | NH | Bn | H | |
| 1623 | tetrahydropyrimidin-2-ylamino | 2 | NH | Bn | H | |
| 1624 | tetrahydropyrimidin-2-ylamino | 3 | NH | Bn | H | |

Utility

The compounds of Formula I of the present invention possess activity as antagonists of integrins such as, for example, the $\alpha_v\beta_3$ or vitronectin receptor, $\alpha_v\beta_5$ or $\alpha_5\beta_1$, and as such have utility in the treatment and diagnosis of cell adhesion, angiogenic disorders, inflammation, bone degradation, cancer metastases, diabetic retinopathy, thrombosis, restenosis, macular degeneration, and other conditions mediated by cell adhesion and/or cell migration and/or angiogenesis. The integrin antagonist activity of the compounds of the present invention is demonstrated using assays which measure the binding of a specific integrin to a native ligand, for example, using the ELISA assay described below for the binding of vitronectin to the $\alpha_v\beta_3$ receptor.

The compounds of the present invention possess selectivity for the $\alpha_v\beta_3$ receptor relative to the GPIIb/IIIa receptor as demonstrated by their lack of activity in standard assays of platelet aggregation, such as the platelet aggregation assay described below.

One of the major roles of integrins in vivo is to mediate cellular interactions with adjacent cells. Cell based adhesion assays can be used to mimic these interactions in vitro. A cell based assay is more representative of the in vivo situation than an ELISA since the receptor is maintained in membranes in the native state. The compounds of the present invention have activity in cell-based assays of adhesion, for example as demonstrated in using the cell adhesion assays described below.

The compounds of Formula I of the present invention may be useful for the treatment or prevention of other diseases which involve cell adhesion processes, including, but not limited to, osteoporosis, rheumatoid arthritis, autoimmune disorders, bone degradation, rheumatoid arthritis, asthma, allergies, adult respiratory distress syndrome, graft versus host disease, organ transplantation, septic shock, psoriasis, eczema, contact dermatitis, osteoarthritis, atherosclerosis, metastasis, wound healing, inflammatory bowel disease and other angiogenic disorders.

The compounds of Formula I have the ability to suppress/inhibit angiogenesis in vivo, for example, as demonstrated using animal models of ocular neovascularization.

The compounds provided by this invention are also useful as standards and reagents in determining the ability of a potential pharmaceutical to inhibit integrin-ligand binding. These may be provided in a commercial kit comprising a compound of this invention.

As used herein "µg" denotes microgram, "mg" denotes milligram, "g" denotes gram, "µL" denotes microliter, "mL" denotes milliliter, "L" denotes liter, "nM" denotes nanomolar, "µM" denotes micromolar, "mM" denotes millimolar, "M" denotes molar and "nm" denotes nanometer. "Sigma" stands for the Sigma-Aldrich Corp. of St. Louis, Mo.

The utility of the compounds of the present invention may be assessed by testing in one or more of the following assays as described in detail below: Purified $\alpha_v\beta_3$ (human placenta) —Vitronectin ELISA, $\alpha_v\beta_3$-Vitronectin Binding Assay, Human Aortic Smooth Muscle Cell Migration Assay, In Vivo Angiogenesis Model, Pig Restenosis Model, Mouse Retinopathy Model. A compound of the present invention is considered to be active if it has an $IC_{50}$ or $K_i$ value of less than about 10 µM for the inhibition of $\alpha_v\beta_3$-Vitronectin Binding Assay, with compounds preferably having $K_i$ values of less than about 0.1 µM. Tested compounds of the present invention are active in the $\alpha_v\beta_3$-Vitronectin Binding Assay.

Purified $\alpha_v\beta_3$ (human placenta)—Vitronectin ELISA

The $\alpha_v\beta_3$ receptor was isolated from human placental extracts prepared using octylglucoside. The extracts were passed over an affinity column composed of anti-$\alpha_v\beta_3$ monoclonal antibody (LM609) to Affigel. The column was subsequently washed extensively at pH 7 and pH 4.5 followed by elution at pH 3. The resulting sample was concentrated by wheat germ agglutinin chromatography to provide gave two bands on SDS gel which were confirmed as $\alpha_v\beta_3$ by western blotting.

Affinity purified protein was diluted at different levels and plated to 96 well plates. ELISA was performed using fixed concentration of biotinylated vitronectin (approximately 80 nM/well). This receptor preparation contains the $\alpha_v\beta_3$ with no detectable levels of $\alpha_v\beta_5$ according to the gel ($\alpha_v\beta_3$) and according to effects of blocking antibodies for the $\alpha_v\beta_3$ or $\alpha_v\beta_5$ in the ELISA.

A submaximal concentration of biotinylated vitronectin was selected based on conc. response curve with fixed receptor conc. and variable concentrations of biotinylated vitronectin.

$\alpha_v\beta_3$-Vitronectin Binding Assay

The purified receptor is diluted with coating buffer (20 mM Tris HCl, 150 mM NaCl, 2.0 mM $CaCl_2$, 1.0 mM $MgCl_2 \cdot 6H_2O$, 1.0 mM $MnCl_2 \cdot 4H_2O$) and coated (100 µL/well) on Costar (3590) high capacity binding plates overnight at 4° C. The coating solution is discarded and the plates washed once with blocking/binding buffer (B/B buffer, 50 mM Tris HCl, 100 mM NaCl, 2.0 mM $CaCl_2$, 1.0 mM $MgCl_2 \cdot 6H_2O$, 1.0 mM $MnCl_2 \cdot 4H_2O$). Receptor is then blocked (200 µL/well) with 3.5% BSA in B/B buffer for 2 hours at room temperature. After washing once with 1.0% BSA in B/B buffer, biotinylated vitronectin (100 µL) and either inhibitor (11 µL) or B/B buffer w/1.0% BSA (11 µL) is added to each well. The plates are incubated 2 hours at room temperature. The plates are washed twice with B/B buffer and incubated 1 hour at room temperature with anti-biotin alkaline phosphatase (100 µL/well) in B/B buffer containing 1.0% BSA. The plates are washed twice with B/B buffer and alkaline phosphatase substrate (100 µL) is added. Color is developed at room temperature. Color development is stopped by addition of 2N NaOH (25 µL/well) and absorbance is read at 405 nm. The $IC_{50}$ is the concentration of test substance needed to block 50% of the vitronectin binding to the receptor.

Integrin Cell-Based Adhesion Assays

In the adhesion assays, a 96 well plate was coated with the ligand (i.e., fibrinogen) and incubated overnight at 4° C. The following day, the cells were harvested, washed and loaded with a fluorescent dye. Compounds and cells were added together and then were immediately added to the coated plate. After incubation, loose cells are removed from the plate, and the plate (with adherent cells) is counted on a fluorometer. The ability of test compounds to inhibit cell adhesion by 50% is given by the $IC_{50}$ value and represents a measure of potency of inhibition of integrin mediated binding. Compounds were tested for their ability to block cell adhesion using assays specific for $\alpha_v\beta_3$, $\alpha_v\beta_5$ and $\alpha_5\beta_1$ integrin interactions.

Platelet Aggregation Assay

Venous blood was obtained from anesthetized mongrel dogs or from healthy human donors who were drug- and aspirin-free for at least two weeks prior to blood collection. Blood was collected into citrated Vacutainer tubes. The blood was centrifuged for 15 minutes at 150×g (850 RPM in a Sorvall RT6000 Tabletop Centrifuge with H-1000 B rotor) at room temperature, and platelet-rich plasma (PRP) was removed. The remaining blood was centrifuged for 15 minutes at 1500×g (26,780 RPM) at room temperature, and platelet-poor plasma (PPP) was removed. Samples were assayed on a PAP-4 Platelet Aggregation Profiler, using PPP as the blank (100% transmittance). 200 µL of PRP ($5 \times 10^8$ platelets/mL) were added to each micro test tube, and transmittance was set to 0%. 20 µL of ADP (10 µM) was added to each tube, and the aggregation profiles were plotted (% transmittance versus time). Test agent (20 μL) was added at different concentrations prior to the addition of the platelet agonist. Results are expressed as % inhibition of agonist-induced platelet aggregation.

Human Aortic Smooth Muscle Cell Migration Assay

A method for assessing $\alpha_v\beta_3$-mediated smooth muscle cell migration and agents which inhibit $\alpha_v\beta_3$-mediated smooth muscle cell migration is described in Liaw et al., *J. Clin. Invest.* (1995) 95: 713–724).

In Vivo Angiogenesis Model

A quantitative method for assessing angiogenesis and antiangiogenic agents is described in Passaniti et al., *Laboratory Investigation* (1992) 67:519–528

Pig Restenosis Model

A method for assessing restenosis and agents which inhibit restenosis is described in Schwartz et al., *J. Am. College of Cardiology* (1992) 19: 267–274.

Mouse Retinopathy Model

A method for assessing retinopathy and agents which inhibit retinopathy is described in Smith et al., *Invest. Ophthal. & Visual Science* (1994) 35: 101–111.

Dosage and Formulation

The compounds of this invention can be administered by any means that produces contact of the active agent with the agent's site of action, the $\alpha_v\beta_3$ integrin, in the body of a mammal. They can be administered by any conventional means available for use in conjunction with pharmaceuticals, either as individual therapeutic agents or in a combination of therapeutic agents, such as a antiplatelet agent such as aspirin, piroxicam, or ticlopidine which are agonist-specific, or an anti-coagulant such as warfarin or heparin, or a thrombin inhibitor such as a boropeptide, hirudin or argatroban, or a thrombolytic agent such as tissue plasminogen activator, anistreplase, urokinase or streptokinase, or combinations thereof. The compounds of the invention, or compounds of the invention in combination with other therapeutic agents, can be administered alone, but generally administered with a pharmaceutical carrier selected on the basis of the chosen route of administration and standard pharmaceutical practice.

The dosage of the novel cyclic compounds of this invention administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 10 milligrams per kilogram of body weight.

Dosage forms (compositions suitable for administration) contain from about 0.1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 10 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 10 milligrams of the active ingredient. The capsules are washed and dried.

Tablets

A large number of tablets are prepared by conventional procedures so that the dosage unit was 10 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

The active ingredient can be administered intranasally to a mammal at a dosage range of about 0.01 to 0.5 mg/kg while the preferred dosage range is about 0.01–0.1 mg/kg.

Compositions of the active ingredients can be administered intranasally by preparing a suitable formulation of the active ingredient by procedures well known to those skilled in the art. Preferably the formulations are prepared with suitable nontoxic pharmaceutically acceptable ingredients. These ingredients are known to those skilled in the preparation of nasal dosage forms and some of these can be found in *REMINGTON'S PHARMACEUTICAL SCIENCES*. 17th edition, 1985 a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, jelling agents, or buffering and other stabilizing and solubilizing agents may also be present. Preferably, the nasal dosage form should be isotonic with nasal secretions.

An example of a nasal solution composition of this invention includes:

| Active Drug | 0.2–2 g |
|---|---|
| Sorbitol | 0.6 g |
| Benzalkonium chloride | 0.002 g |
| Hydrochloric acid | to adjust pH |
| Sodium hydroxide | to adjust pH |
| Purified water | to 10 mL |

In this example the active drug can be in one vial and the rest of the formulation can be in another vial. The drug can be reconstituted when needed.

The formulation of this invention may be varied to include: (1) other acids and bases to adjust the pH; (2) other tonicity imparting agents such as glycerin and dextrose; (3) other antimicrobial preservatives such as other parahydroxy benzoic acid esters, sorbate, benzoate, propionate, chlorbutanol, phenylethyl alcohol, and mercurials; (4) other viscosity imparting agents such as sodium carboxymethylcellulose microcrystalline cellulose, polyvinylpyrrolidone, polyvinyl alcohol and other gums; (5) suitable absorption enhancers; (6) stabilizing agents such as antioxidants, like bisulfite and ascorbate, metal chelating agents such as sodium edetate and drug solubility enhancers such as polyethylene glycols.

The above formulation can be administered as drops, sprays, aerosols or by any other intranasal dosage form. Optionally, the delivery system can be a unit dose delivery system. The volume of solution or suspension delivered per dose can be anywhere from 5 to 400 µL, and preferably between 50 and 150 µL. Delivery systems for these various dosage forms can be dropper bottles, plastic squeeze units, atomizers, nebulizers or pharmaceutical aerosols in either unit dose or multiple dose packages.

The combination products of this invention, such as the novel $\alpha_v\beta_3$ antagonist compounds of this invention in combination with an anti-coagulant agent such as warfarin or heparin, or an anti-platelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, can be in any dosage form, such as those described above, and can also be administered in various ways, as described above.

In a preferred embodiment, the combination products of the invention are formulated together, in a single dosage form (that is, combined together in one capsule, tablet, powder, or liquid, etc.). When the combination products are not formulated together in a single dosage form, the $\alpha_v\beta_3$ antagonist compounds of this invention and the anti-coagulant agent, anti-platelet agent, thrombin inhibitor, and/or thrombolytic agent may be administered at the same time (that is, together), or in any order, for example the compounds of this invention are administered first, followed by administration of the anti-coagulant agent, anti-platelet agent, thrombin inhibitor, and/or thrombolytic agent. When not administered at the same time, preferably the administration of the compound of this invention and any anti-coagulant agent, anti-platelet agent, thrombin inhibitor, and/or thrombolytic agent occurs less than about one hour apart, more preferably less than about 30 minutes apart, even more preferably less than about 15 minutes apart, and most preferably less than about 5 minutes apart. Preferably, administration of the combination products of the invention is oral. The terms oral agent, oral inhibitor, oral compound, or the like, as used herein, denote compounds which may be orally administered. Although it is preferable that the $\alpha_v\beta_3$ antagonist compounds of this invention and the anti-coagulant agent, anti-platelet agent, thrombin inhibitor, and/or thrombolytic agent are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

As discussed above, where two or more of the foregoing therapeutic agents are combined or co-administered with the compounds of this invention, generally the amount of each component in a typical daily dosage and typical dosage form may be reduced relative to the usual dosage of the agent when administered alone, in view of the additive or synergistic effect which would be obtained as a result of addition of further agents in accordance with the present invention.

Particularly when provided as a single dosage form, the potential exists for a chemical interaction between the combined active ingredients (for example, a novel compound of this invention and an anti-coagulant such as warfarin or heparin, or a novel compound of this invention and an anti-platelet agent such as aspirin, piroxicam or ticlopidine, or a novel compound of this invention and a thrombin inhibitor such as a boropeptide, hirudin or argatroban, or a novel compound of this invention and a thrombolytic agent such as tissue plasminogen activator, anistreplase, urokinase or streptokinase, or combinations thereof). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

Pharmaceutical kits useful in, for example, the inhibition of thrombus formation, the prevention of blood clots, and/or the treatment of thromboembolic disorders, which comprise a therapeutically effective amount of a compound according to the method of the present invention along with a therapeutically effective amount of an anti-coagulant agent such as warfarin or heparin, or an anti-platelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The compounds according to the method of the invention and the anti-coagulant agent, anti-platelet agent, thrombin inhibitor, thrombolytic agent, and/or combinations thereof, may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

What is claimed is:
1. A compound of Formula I:

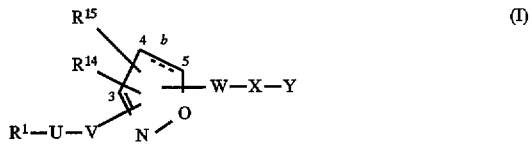

including stereoisomeric forms thereof, or mixtures of stereoisomeric forms thereof, or a pharmaceutically acceptable salt thereof wherein:

b, the bond between carbon atoms numbered 4 and 5, is a carbon-carbon single or double bond;

$R^1$ is selected from:

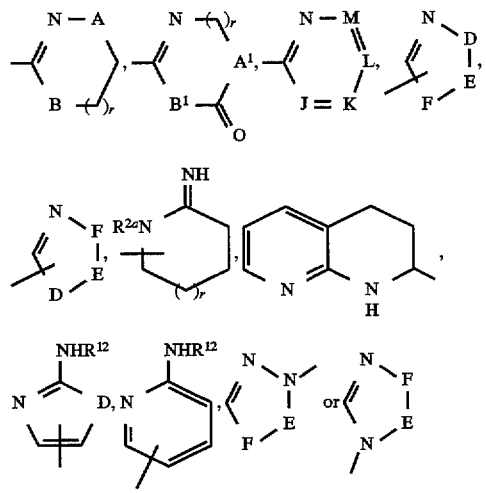

A and B are independently —$CH_2$—, —O—, —$N(R^{12})$—, or —$C(=O)$—;

$A^1$ and $B^1$ are independently —$CH_2$— or —$N(R^{10})$—;

D is —$N(R^{2a})$—, —O—, —S—, —$C(=O)$— or —$SO_2$—;

E—F is —$C(R^2)=C(R^3)$—, —$N=C(R^2)$—, —$C(R^2)=N$—, —$N=N$—, or —$C(R^2)_2C(R^3)_2$—;

J, K, L and M are independently selected from —$C(R^2)$— or —N—, provided that at least one of J, K, L and M is —$C(R^2)$—;

$R^2$ and $R^3$ are independently selected from: H, $C_1$–$C_4$ alkoxy, $NR^{11}R^{12}$, =$NR^{12}$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, $C_6$–$C_{10}$ aryl, $C_7$–$C_{11}$ arylalkyl, $C_2$–$C_7$ alkylcarbonyl, $C_6$–$C_{10}$ carbonyl or $C_7$–$C_{11}$ arylcarbonyl;

alternatively, $R^2$ and $R^3$, when substituents on adjacent atoms, are taken together with the carbon atoms to which they are attached to form a 5–7 membered carbocyclic or 5–7 membered heterocyclic aromatic or nonaromatic ring system, said carbocyclic or heterocyclic ring being optionally substituted with 0–2 $R^7$;

$R^{2a}$ is absent or $R^{12}$;

U is selected from:
—$(CH_2)_n$—,
—$(CH_2)_nO(CH_2)_m$—,
—$(CH_2)_nN(R^{12})(CH_2)_m$—,
—$(CH_2)_nC(=O)(CH_2)_m$—,
—$(CH_2)_nS(O)_p(CH_2)_m$—, —(CH$_2$)$_n$NHNH(CH$_2$)$_m$—,
—N(R$^{10}$)C(=O)—, or
—C(=O)N(R$^{10}$)—;
—N(R$^{10}$)S(O)$_p$—, or V is selected from:
—(CH$_2$)$_n$—,
—(C$_1$–C$_6$ alkylene)-Q—, substituted with 0–3 groups independently selected from R$^{13}$,
—(C$_2$–C$_7$ alkenylene)-Q—, substituted with 0–3 groups independently selected from R$^{13}$,
—(C$_2$–C$_7$ alkynylene)-Q—, substituted with 0–3 groups independently selected from R$^{13}$,
-(phenyl)-Q—, said phenyl substituted with 0–2 groups independently selected from R$^{13}$,
-(pyridyl)-Q—, said pyridyl substituted with 0–2 groups independently selected from R$^{13}$, or
-(pyridazinyl)-Q—, said pyridazinyl substituted with 0–2 groups independently selected from R$^{13}$;

Q is selected from:
—(CH$_2$)$_n$—,
—(CH$_2$)$_n$O(CH$_2$)$_m$—,
—(CH$_2$)$_n$N(R$^{12}$)(CH$_2$)$_m$—,
—(CH$_2$)$_n$C(=O)(CH$_2$)$_m$—,
—(CH$_2$)$_n$S(O)$_p$(CH$_2$)$_m$—,
—(CH$_2$)$_n$NHNH(CH$_2$)$_m$—,
—N(R$^{10}$)C(=O)—, or
—C(=O)N(R$^{10}$)—;

W is selected from:
—(C(R$^4$)$_2$)$_q$C(=O)N(R$^{10}$)—,
—C(=O)—N(R$^{10}$)—(C(R$^4$)$_2$)$_q$—;

X is selected from:
a single bond,
—(C(R$^4$)$_2$)$_q$—[C(R$^4$)(R$^8$)]$_s$—C(R$^4$)(R$^9$)—;
alternatively, W is

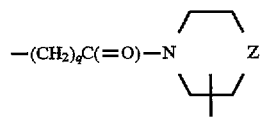

and X is absent or —CH$_2$—

Y is selected from:
—COR$^{20}$—, —SO$_3$H, —PO$_3$H, —CONHNHSO$_2$CF$_3$,
—CONHSO$_2$R$^{18a}$, —CONHSO$_2$NHR$^{18b}$,
—NHCOCF$_3$, —NHCONHSO$_2$R$^{18a}$,
—NHSO$_2$R$^{18a}$, —OPO$_3$H$_2$, —OSO$_3$H, —PO$_3$H$_2$,
—SO$_3$H, —SO$_2$NHCOR$^{18a}$, —SO$_2$NHCO$_2$R$^{18a}$, or

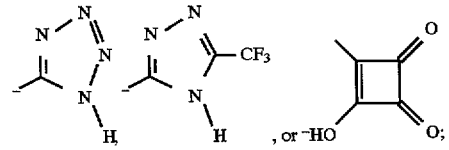

Z is selected from —CH(R$^9$)—, or —N(R$^{16}$)—;
R$^4$ is selected from H, C$_1$–C$_{10}$ alkyl, C$_1$–C$_{10}$ alkylcarbonyl, aryl, arylalkyl, cycloalkyl, or cycloalkylalkyl;
alternatively, two R$^4$ groups on adjacent carbon atoms join to form a bond, thereby forming a carbon-carbon double or triple bond between the adjacent carbon atoms;

R$^5$ is selected from H, C$_1$–C$_6$ alkyl, C$_2$–C$_6$ alkenyl, C$_2$–C$_6$ alkynyl, C$_3$–C$_7$ cycloalkyl, C$_7$–C$_{14}$ bicycloalkyl, hydroxy, C$_1$–C$_6$ alkoxy, C$_1$–C$_6$ alkylthio, C$_1$–C$_6$ alkylsulfinyl, C$_1$–C$_6$ alkylsulfonyl, nitro, C$_1$–C$_6$ alkylcarbonyl, C$_6$–C$_{10}$ aryl, —N(R$^{11}$)R$^{12}$, halo, CF$_3$, CN, C$_1$–C$_6$ alkoxycarbonyl, carboxy, piperidinyl, morpholinyl or pyridinyl;

R$^6$ is selected from:
H, C$_1$–C$_{10}$ alkyl, hydroxy, C$_1$–C$_{10}$ alkoxy, nitro, C$_1$–C$_{10}$ alkylcarbonyl, —N(R$^{11}$)R$^{12}$, cyano, halo, CF$_3$, CHO, CO$_2$R$^{18b}$, C(=O)R$^{18b}$, CONR$^{17}$R$^{18b}$, OC(=O)R$^{10}$, OC(=O)OR$^{21}$, OR$^{10}$, OC(=O)NR$^{10}$R$^{11}$, OCH$_2$CO$_2$R$^{10}$, CO$_2$CH$_2$CO$_2$R$^{10}$, NO$_2$, NR$^{10}$C(=O)R$^{10}$, NR$^{10}$C(=O)OR$^{21}$, NR$^{10}$C(=O) NR$^{10}$R$^{11}$, NR$^{10}$SO$_2$NR$^{10}$R$^{11}$, NR$^{10}$SO$_2$R$^{21}$, S(O)$_p$ R$^{11}$, SO$_2$NR$^{10}$R$^{11}$, SiMe$_3$, C$_2$ to C$_6$ alkenyl, C$_3$ to C$_{11}$ cycloalkyl, C$_4$ to C$_{11}$ cycloalkylmethyl,
C$_6$ to C$_{10}$ aryl optionally substituted with 1–3 groups selected from halogen, C$_1$–C$_6$ alkoxy, C$_1$–C$_6$ alkyl, CF$_3$, S(O)$_m$Me, or —NMe$_2$;
C$_7$ to C$_{11}$ arylalkyl, said aryl being optionally substituted with 1–3 groups selected from halogen, C$_1$–C$_6$ alkoxy, C$_1$–C$_6$ alkyl, CF$_3$, S(O)$_p$Me, or —NMe$_2$,
methylenedioxy when R$^6$ is a substituent on aryl, or
a 5–10 membered heterocyclic ring containing 1–3 N, O, or S heteroatoms, wherein said heterocyclic ring is saturated, partially saturated, or fully unsaturated, said heterocyclic ring being substituted with 0–2 R$^7$;

R$^7$ is selected from:
H, C$_1$–C$_{10}$ alkyl, hydroxy, C$_1$–C$_{10}$ alkoxy, nitro, C$_1$–C$_{10}$ alkylcarbonyl, —N(R$^{11}$) R$^{12}$, cyano, halo, CF$_3$, CHO, CO$_2$R$^{10}$, C(=O)R$^{10}$, CONR$^{10}$R$^{11}$, OC(=O)R$^{10}$, OC(=O)OR$^{21}$, OR$^{10}$, OC(=O) NR$^{10}$R$^{11}$, OCH$_2$CO$_2$R$^{10}$, CO$_2$CH$_2$CO$_2$R$^{10}$, NO$_2$, NR$^{10}$C(=O)R$^{10}$, NR$^{10}$C(=O)OR$^{21}$, NR$^{10}$C(=O) NR$^{10}$R$^{11}$, NR$^{10}$SO$_2$NR$^{10}$R$^{11}$, NR$^{10}$SO$_2$R$^{21}$, S(O)$_p$ R$^{11}$, SO$_2$NR$^{10}$R$^{11}$, SiMe$_3$, C$_2$ to C$_6$ alkenyl, C$_3$ to C$_{11}$ cycloalkyl, C$_4$ to C$_{11}$ cycloalkylmethyl, C$_6$ to C$_{10}$ aryl, or C$_7$ to C$_{11}$ arylalkyl;

R$^8$ is selected from:
H, R$^6$,
C$_1$–C$_{10}$ alkyl, substituted with 0–3 R$^6$,
C$_2$–C$_{10}$ alkenyl, substituted with 0–3 R$^6$,
C$_2$–C$_{10}$ alkynyl, substituted with 0–3 R$^6$,
C$_3$–C$_8$ cycloalkyl, substituted with 0–3 R$^6$,
C$_5$–C$_6$ cycloalkenyl, substituted with 0–3 R$^6$,
aryl, substituted with 0–3 R$^6$, or
5–10 membered heterocyclic ring containing 1–3 N, O, or S heteroatoms, wherein said heterocyclic ring is saturated, partially saturated, or fully unsaturated, said heterocyclic ring being substituted with 0–2 R$^7$;

R$^9$ is selected from H, hydroxy, C$_1$–C$_{10}$ alkoxy, nitro, N(R$^{10}$)R$^{11}$, —N(R$^{16}$)R$^{17}$, OR$^{22}$, C$_1$–C$_{10}$ alkyl substituted with 0–3 R$^7$, aryl substituted with 0–3 R$^7$, heteroaryl substituted with 0–3 R$^7$, C$_1$–C$_{10}$ alkylcarbonyl; aryl(C$_0$–C$_6$ alkyl)carbonyl, C$_1$–C$_{10}$ alkenyl, C$_1$–C$_{10}$ alkynyl, C$_3$–C$_{10}$ cycloalkyl, C$_3$–C$_{10}$ cycloalkylalkyl, aryl(C$_1$–C$_6$ alkyl)-, heteroaryl(C$_1$–C$_6$ alkyl)-, CO$_2$R$^{18a}$, C(=O)R$^{18a}$, CONR$^{18a}$R$^{20}$, SO$_2$R$^{18a}$, or SO$_2$NR$^{18a}$R$^{20}$, provided that any of the above alkyl, cycloalkyl, aryl or heteroaryl groups are unsubstituted or substituted independently with 0–2 R$^7$;

R$^{10}$ is selected from H, C$_1$–C$_8$ alkyl, C$_3$–C$_6$ alkenyl, C$_3$–C$_{11}$ cycloalkyl, C$_4$–C$_{11}$ cycloalkylmethyl, C$_6$–C$_{10}$ aryl, C$_7$–C$_{11}$ arylalkyl, or C$_1$–C$_{10}$ alkyl substituted with 0–2 R$^4$;

R$^{11}$ is selected from hydrogen, hydroxy, C$_1$ to C$_8$ alkyl, C$_3$–C$_6$ alkenyl, C$_3$ to C$_{11}$ cycloalkyl, C$_4$ to C$_{11}$ cycloalkylmethyl, $C_1$–$C_6$ alkoxy, benzyloxy, $C_6$ to $C_{10}$ aryl, heteroaryl, heteroarylalkyl, $C_7$ to $C_{11}$ arylalkyl, adamantylmethyl, or $C_1$–$C_{10}$ alkyl substituted with 0–2 $R^4$;

alternatively, $R^{10}$ and $R^{11}$ when both are substituents on the same nitrogen atom are taken together with the nitrogen atom to which they are attached to form a heterocycle selected from: 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl; said heterocycle being optionally substituted with 0–3 groups selected from: $C_1$–$C_6$ alkyl, $C_6$–$C_{10}$ aryl, heteroaryl, $C_7$–$C_{11}$ arylalkyl, $C_1$–$C_6$ alkylcarbonyl, $C_3$–$C_7$ cycloalkylcarbonyl, $C_1$–$C_6$ alkoxycarbonyl, $C_7$–$C_{11}$ arylalkoxycarbonyl, $C_1$–$C_6$ alkylsulfonyl or $C_6$–$C_{10}$ arylsulfonyl;

$R^{12}$ is selected from:
H, $C_1$–$C_{10}$ alkyl, triphenylmethyl, methoxyphenyldiphenylmethyl, trimethylsilylethoxymethyoxy, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl($C_2$–$C_{10}$ alkenyl)sulfonyl, heteroarylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_7$–$C_{11}$ arylcarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylcarbonyl, heteroarylalkylcarbonyl, or aryl ($C_1$–$C_{10}$ alkoxy)carbonyl; wherein said aryl groups are optionally substituted with 0–3 substituents selected from the group consisting of: $C_1$–$C_4$ alkyl, $C_1$–$C_4$ alkoxy, halo, $CF_3$, and $NO_2$;

$R^{13}$ is selected from: H, hydroxy, $C_1$–$C_{10}$ alkoxy, nitro, $N(R^{10})R^{11}$, —$N(R^{16})R^{17}$, $C_1$–$C_{10}$ alkyl substituted with 0–3 $R^7$, aryl substituted with 0–3 $R^7$, heteroaryl substituted with 0–3 $R^7$, or $C_1$–$C_{10}$ alkylcarbonyl;

$R^{14}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^{10}$ or —$C(=O)N(R^{10})R^{11}$;

$R^{15}$ is selected from:
H, $R^6$, —$CO_2R^{10}$, —$C(=O)N(R^{10})R^{11}$;
$C_1$–$C_{10}$ alkoxycarbonyl substituted with 0–2 $R^6$;
$C_1$–$C_{10}$ alkyl, substituted with 0–3 $R^6$;
$C_2$–$C_{10}$ alkenyl, substituted with 0–3 $R^6$;
$C_1$–$C_{10}$ alkoxy, substituted with 0–3 $R^6$;
aryl, substituted with 0–3 $R^6$; or
5–10 membered heterocyclic ring containing 1–3 N, O, or S heteroatoms, wherein said heterocyclic ring is saturated, partially saturated, or fully unsaturated, said heterocyclic ring being substituted with 0–2 $R^7$;

$R^{16}$ is selected from:
—C(=O)—O—$R^{18a}$,
—C(=O)—$R^{18b}$,
—C(=O)N($R^{18b}$)$_2$,
—C(=O)NHSO$_2R^{18a}$,
—C(=O)NHC(=O)$R^{18b}$,
—C(=O)NHC(=O)O$R^{18a}$,
—C(=O)NHSO$_2$NH$R^{18b}$,
—C(=S)—NH—$R^{18b}$,
—NH—C(=O)—O—$R^{18a}$,
—NH—C(=O)—$R^{18b}$,
—NH—C(=O)—NH—$R^{18b}$,
—SO$_2$—O—$R^{18a}$,
—SO$_2$—$R^{18a}$,
—SO$_2$—N($R^{18b}$)$_2$,
—SO$_2$—NHC(=O)O$R^{18b}$;

$R^{17}$ is selected from: H, $C_1$–$C_{10}$ alkyl, $C_2$–$C_6$ alkenyl, $C_3$–$C_{11}$ cycloalkyl, $C_4$–$C_{15}$ cycloalkylalkyl, aryl, aryl ($C_1$–$C_{10}$ alkyl)-;

$R^{18a}$ is selected from:
$C_1$–$C_8$ alkyl substituted with 0–2 $R^{19}$,
$C_2$–$C_8$ alkenyl substituted with 0–2 $R^{19}$,
$C_2$–$C_8$ alkynyl substituted with 0–2 $R^{19}$,
$C_3$–$C_8$ cycloalkyl substituted with 0–2 $R^{19}$,
aryl substituted with 0–4 $R^{19}$,
aryl($C_1$–$C_6$ alkyl)- substituted with 0–4 $R^{19}$,
a 5–10 membered heterocyclic ring system having 1–3 heteroatoms selected independently from O, S, and N, said heterocyclic ring being substituted with 0–4 $R^{19}$,
$C_1$–$C_6$ alkyl substituted with a 5–10 membered heterocyclic ring system having 1–3 heteroatoms selected independently from O, S, and N, said heterocyclic ring being substituted with 0–4 $R^{19}$;

$R^{18b}$ is selected from $R^{18a}$ or H;

$R^{19}$ is selected from H, halogen, $CF_3$, $CO_2H$, CN, $NO_2$, $NR^{11}R^{12}$, $C_1$–$C_8$ alkyl, $C_2$–$C_6$ alkenyl, $C_2$–$C_6$ alkynyl, $C_3$–$C_{11}$ cycloalkyl, $C_4$–$C_{11}$ cycloalkylalkyl, aryl ($C_1$–$C_6$ alkyl)-, $C_1$–$C_6$ alkoxy, $OCF_3$, or $C_1$–$C_4$ alkoxycarbonyl, aryl, —O-aryl, —$SO_2$-aryl, heteroaryl, or —$SO_2$-heteroaryl, wherein said aryl and heteroaryl groups are substituted with 0–4 groups selected from hydrogen, halogen, $CF_3$, $C_1$–$C_3$ alkyl, or $C_1$–$C_3$ alkoxy;

$R^{20}$ is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ arylalkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonylomyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, $C_{10}$ to $C_{14}$ (5-aryl-1,3-dioxa-cyclopenten-2-one-yl)methyloxy, ($R^{11}$)($R^{12}$)N—($C_1$–$C_{10}$ alkoxy)-;

$R^{21}$ is selected from: $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^5$;

$R^{22}$ is selected from:
—C(=O)—$R^{18b}$,
—C(=O)N($R^{18b}$)$_2$,
—C(=O)NHSO$_2R^{18a}$,
—C(=O)NHC(=O)$R^{18b}$,
—C(=O)NHC(=O)O$R^{18a}$,
—C(=O)NHSO$_2$NH$R^{18b}$,
—C(=S)—NH—$R^{18b}$,
—SO$_2$—$R^{18a}$,
—SO$_2$—N($R^{18b}$)$_2$,
—SO$_2$—NHC(=O)O$R^{18b}$;

m is 0–2;
n is 0–4;
p is 0–2;
q is 0–4;

r is 0–2;
s is 0–1;
with the following provisos:
(1) when b is a double bond, only one of $R^{14}$ or $R^{15}$ is present and Q and U are not —(CH$_2$)—; and
(2) n, m and q are chosen such that the number of atoms connecting $R^1$ and Y is in the range of 8–14; and
(3) when V is -(phenyl)-Q—, then either: U is not a direct bond or Q is not a direct bond.

2. A compound of claim 1 of Formula I:

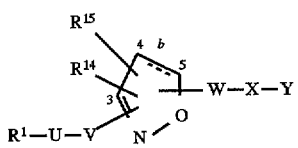

including stereoisomeric forms thereof, or mixtures of stereoisomeric forms thereof, or a pharmaceutically acceptable salt thereof wherein:

b, the bond between carbon atoms numbered 4 and 5, is a carbon-carbon single or double bond;

$R^1$ is selected from:

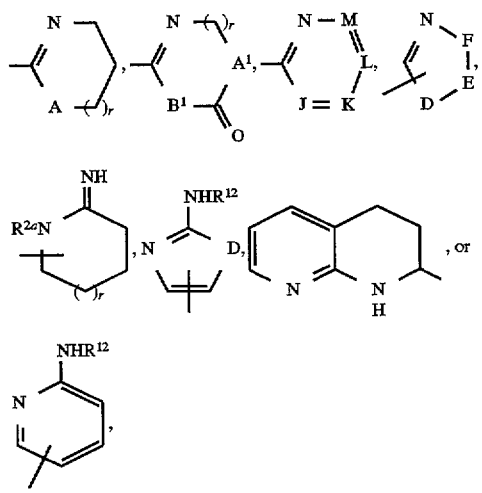

A is selected from —CH$_2$—, or —N(R$^{12}$)—;
$A^1$ and B are independently —CH$_2$— or —N(R$^{10}$)—;
D is —N(R$^{12}$)—, or —S—;
E—F is —C(R$^2$)=C(R$^3$)—, or —C(R$^2$)$_2$C(R$^3$)$_2$—;
J is either —C(R$^2$)— or —N—, and K, L and M are independently selected from —C(R$^2$)— or —C(R$^3$)—;
$R^2$ and $R^3$ are independently selected from: H, $C_1$–$C_4$ alkoxy, NR$^{11}$R$^{12}$, =NR$^{12}$, halogen, NO$_2$, CN, CF$_3$, $C_1$–$C_6$ alkyl, $C_3$–$C_6$ alkenyl, $C_3$–$C_7$ cycloalkyl, $C_4$–$C_{11}$ cycloalkylalkyl, $C_6$–$C_{10}$ aryl substituted with 0–4 R$^7$, $C_7$–$C_{11}$ arylalkyl, $C_2$–$C_7$ alkylcarbonyl, $C_1$–$C_4$ alkoxycarbonyl, or $C_7$–$C_{11}$ arylcarbonyl; alternatively, $R^2$ and $R^3$ when substituents on adjacent atoms, are taken together when substituents on adjacent atoms, with the carbon atoms to which they are attached, to form a 5–7 membered carbocyclic or 5–7 membered heterocyclic with the carbon atoms to which they are attached, aromatic or nonaromatic ring system, said carbocyclic or heterocyclic ring being optionally substituted with 0–2 groups selected from $C_1$–$C_4$ alkyl, $C_1$–$C_4$ alkoxy, halo, cyano, amino, CF$_3$ or NO$_2$;
$R^{2a}$ is absent or $R^{12}$;

U is selected from:
—(CH$_2$)$_n$—,
—(CH$_2$)$_n$O(CH$_2$)$_m$—,
—(CH$_2$)$_n$N(R$^{12}$)(CH$_2$)$_m$—,
—(CH$_2$)$_n$C(=O)(CH$_2$)$_m$—,
—(CH$_2$)$_n$S(O)$_p$(CH$_2$)$_m$—,
—(CH$_2$)$_n$NHNH(CH$_2$)$_m$—,
—N(R$^{10}$)C(=O)—, or
—C(=O)N(R$^{10}$)—;
—N(R$^{10}$)S(O)$_p$—, or V is selected from:
—(CH$_2$)$_n$—,
—($C_1$–$C_6$ alkylene)-Q—, substituted with 0–3 groups independently selected from R$^{13}$,
—($C_2$–$C_7$ alkenylene)-Q—, substituted with 0–3 groups independently selected from R$^{13}$,
—($C_2$–$C_7$ alkynylene)-Q—, substituted with 0–3 groups independently selected from R$^{13}$,
-(phenyl)-Q—, said phenyl substituted with 0–2 groups independently selected from R$^{13}$,
-(pyridyl)-Q—, said pyridyl substituted with 0–2 groups independently selected from R$^{13}$, or
-(pyridazinyl)-Q—, said pyridazinyl substituted with 0–2 groups independently selected from R$^{13}$;

Q is selected from:
—(CH$_2$)$_n$—,
—(CH$_2$)$_n$O(CH$_2$)$_m$—,
—(CH$_2$)$_n$N(R$^{12}$)(CH$_2$)$_m$—,
—(CH$_2$)$_n$C(=O)(CH$_2$)$_m$—,
—(CH$_2$)$_n$S(O)$_p$(CH$_2$)$_m$—,
—(CH$_2$)$_n$NHNH(CH$_2$)$_m$—,
—N(R$^{10}$)C(=O)—, or
—C(=O)N(R$^{10}$)—;

W is selected from:
—(C(R$^4$)$_2$)$_q$C(=O)N(R$^{10}$)— or,
—C(=O)—N(R$^{10}$)—(C(R$^4$)$_2$)$_q$—;

X is selected from:
a single bond or,
—(C(R$^4$)$_2$)$_q$—[C(R$^4$)(R$^8$)]$_s$—C(R$^4$)(R$^9$)—;
alternatively, W is

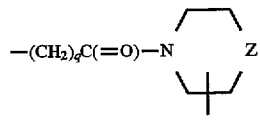

and X is either absent or —CH$_2$—

Y is selected from:
—COR$^{20}$, —SO$_3$H, —PO$_3$H, —CONHNHSO$_2$CF$_3$,
—CONHSO$_2$R$^{18a}$, —CONHSO$_2$NHR$^{18b}$,
—NHCOCF$_3$,
—NHCONHSO$_2$R$^{18a}$, —NHSO$_2$R$^{18a}$, —OPO$_3$H$_2$,
—OSO$_3$H,
—PO$_3$H$_2$, —SO$_3$H, —SO$_2$NHCOR$^{18a}$,
—SO$_2$NHCO$_2$R$^{18a}$, or

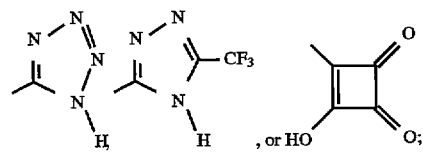

Z is selected from —CH(R$^9$)—, or —N(R$^{16}$)—;
$R^4$ is selected from H, $C_1$–$C_{10}$ alkyl, $C_1$–$C_{10}$ alkylcarbonyl, aryl, arylalkyl, cycloalkyl, or cycloalkylalkyl;

alternatively, two $R^4$ groups on adjacent carbon atoms join to form a bond, thereby forming a carbon-carbon double or triple bond between the adjacent carbon atoms;

$R^6$ is selected from:
H, $C_1-C_{10}$ alkyl, hydroxy, $C_1-C_{10}$ alkoxy, nitro, $C_1-C_{10}$ alkylcarbonyl, —N($R^{11}$)$R^{12}$, cyano, halo, $CF_3$, CHO, $CO_2R^{18b}$, C(=O)$R^{18b}$, CONR$^{17}$R$^{18b}$, OC(=O)$R^{10}$, O$R^{10}$, OC(=O)NR$^{10}$R$^{11}$, NR$^{10}$C(=O)$R^{10}$, NR$^{10}$C(=O)O$R^{21}$, NR$^{10}$C(=O)NR$^{10}$R$^{11}$, NR$^{10}$SO$_2$NR$^{10}$R$^{11}$, NR$^{10}$SO$_2$R$^{21}$, S(O)$_p$R$^{11}$, SO$_2$NR$^{10}$R$^{11}$, $C_6$ to $C_{10}$ aryl optionally substituted with 0-3 groups selected from halogen, $C_1-C_6$ alkoxy, $C_1-C_6$ alkyl, $CF_3$, S(O)$_m$Me, or —NMe$_2$;

$C_7$ to $C_{11}$ arylalkyl, said aryl being optionally substituted with 1-3 groups selected from halogen, $C_1-C_6$ alkoxy, $C_1-C_6$ alkyl, $CF_3$, S(O)$_p$Me, or —NMe$_2$, a 5-10 membered heterocyclic ring containing 1-3 N, O, or S heteroatoms, wherein said heterocyclic ring is saturated, partially saturated, or fully unsaturated, said heterocyclic ring being substituted with 0-2 $R^7$;

$R^7$ is selected from selected from H, $C_1-C_4$ alkyl, hydroxy, $C_1-C_4$ alkoxy, $C_6-C_{10}$ aryl, $C_7-C_{11}$ arylalkyl, ($C_1-C_4$ alkyl)carbonyl, $CO_2R^{18a}$, $SO_2R^{11}$, $SO_2NR^{10}R^{11}$, $OR^{10}$, or $N(R^{11})R^{12}$;

$R^8$ is selected from:
H, $CO_2R^{18a}$, C(=O)$R^{18a}$, or CONR$^{17}$R$^{18a}$
$C_1-C_{10}$ alkyl, substituted with 0-1 $R^6$,
$C_2-C_{10}$ alkenyl, substituted with 0-1 $R^6$,
$C_2-C_{10}$ alkynyl, substituted with 0-1 $R^6$,
$C_3-C_8$ cycloalkyl, substituted with 0-1 $R^6$,
$C_5-C_6$ cycloalkenyl, substituted with 0-1 $R^6$,
aryl, substituted with 0-3 $R^6$, or
5-10 membered heterocyclic ring containing 1-3 N, O, or S heteroatoms, wherein said heterocyclic ring is saturated, partially saturated, or fully unsaturated, said heterocyclic ring being substituted with 0-2 $R^7$;

$R^9$ is selected from H, hydroxy, $C_1-C_{10}$ alkoxy, nitro, N($R^{10}$)$R^{11}$, —N($R^{16}$)$R^{17}$, O$R^{22}$, $C_1-C_{10}$ alkyl substituted with 0-3 $R^7$, aryl substituted with 0-3 $R^7$, heteroaryl substituted with 0-3 $R^7$, $C_1-C_{10}$ alkylcarbonyl; aryl($C_0-C_6$ alkyl)carbonyl, $C_1-C_{10}$ alkenyl, $C_1-C_{10}$ alkynyl, $C_3-C_{10}$ cycloalkyl, $C_3-C_{10}$ cycloalkylalkyl, aryl($C_1-C_6$ alkyl)-, heteroaryl($C_1-C_6$ alkyl)-, $CO_2R^{18a}$, C(=O)$R^{18a}$, CONR$^{18a}$R$^{20}$, SO$_2$R$^{18a}$, or SO$_2$NR$^{18a}$R$^{20}$, provided that any of the above alkyl, cycloalkyl, aryl or heteroaryl groups are unsubstituted or substituted independently with 0-2 $R^7$;

$R^{10}$ is selected from H, $C_1-C_8$ alkyl, $C_3-C_6$ alkenyl, $C_3-C_{11}$ cycloalkyl, $C_4-C_{11}$ cycloalkylmethyl, $C_6-C_{10}$ aryl, $C_7-C_{11}$ arylalkyl, or $C_1-C_{10}$ alkyl substituted with 0-2 $R^4$;

$R^{11}$ is selected from hydrogen, hydroxy, $C_1$ to $C_8$ alkyl, $C_3-C_6$ alkenyl, $C_3$ to $C_{11}$ cycloalkyl, $C_4$ to $C_{11}$ cycloalkylmethyl, $C_1-C_6$ alkoxy, benzyloxy, $C_6$ to $C_{10}$ aryl, heteroaryl, heteroarylalkyl, $C_7$ to $C_{11}$ arylalkyl, adamantylmethyl, or $C_1-C_{10}$ alkyl substituted with 0-2 $R^4$;

alternatively, $R^{10}$ and $R^{11}$ when both are substituents on the same nitrogen atom are taken together with the nitrogen atom to which they are attached to form a heterocycle selected from: 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl; said heterocycle being optionally substituted with 0-3 groups selected from: $C_1-C_6$ alkyl, $C_6-C_{10}$ aryl, heteroaryl, $C_7-C_{11}$ arylalkyl, $C_1-C_6$ alkylcarbonyl, $C_3-C_7$ cycloalkylcarbonyl, $C_1-C_6$ alkoxycarbonyl, $C_7-C_{11}$ arylalkoxycarbonyl, $C_1-C_6$ alkylsulfonyl or $C_6-C_{10}$ arylsulfonyl;

$R^{12}$ is selected from:
H, $C_1-C_6$ alkyl, triphenylmethyl, methoxyphenyldiphenylmethyl, trimethylsilylethoxymethyoxy, ($C_1-C_6$ alkyl)carbonyl, ($C_1-C_6$ alkoxy)carbonyl; ($C_1-C_6$ alkyl)aminocarbonyl, $C_3-C_6$ alkenyl, $C_3-C_7$ cycloalkyl, $C_4-C_{11}$ cycloalkylalkyl, aryl, heteroaryl($C_1-C_6$ alkyl)carbonyl, heteroarylcarbonyl, aryl $C_1-C_6$ alkyl, ($C_1-C_6$ alkyl)carbonyl, or arylcarbonyl, $C_1-C_6$ alkylsulfonyl, arylsulfonyl, aryl($C_1-C_6$ alkyl)sulfonyl, heteroarylsulfonyl, heteroaryl($C_1-C_6$ alkyl)sulfonyl, aryloxycarbonyl, or aryl($C_1-C_6$ alkoxy)carbonyl, wherein said aryl groups are substituted with 0-2 substituents selected from the group consisting of $C_1-C_4$ alkyl, $C_1-C_4$ alkoxy, halo, $CF_3$, and nitro;

$R^{13}$ is selected from: H, hydroxy, $C_1-C_{10}$ alkoxy, nitro, N($R^{10}$)$R^{11}$, —N($R^{16}$)$R^{17}$, $C_1-C_{10}$ alkyl substituted with 0-3 $R^7$, aryl substituted with 0-3 $R^7$, heteroaryl substituted with 0-3 $R^7$, or $C_1-C_{10}$ alkylcarbonyl;

$R^{14}$ is selected from H, $C_1-C_{10}$ alkyl, $C_2-C_{10}$ alkenyl, $C_2-C_{10}$ alkynyl, $C_1-C_{10}$ alkoxy, aryl, heteroaryl or $C_1-C_{10}$ alkoxycarbonyl, $CO_2R^{10}$ or —C(=O)N($R^{10}$)$R^{11}$;

$R^{15}$ is selected from: H, $CO_2R^{18a}$, C(=O)$R^{18a}$, CONR$^{18a}$R$^{17}$, —SO$_2$R$^{18a}$, —SO$_2$NR$^{18a}$R$^{17}$, $C_1-C_6$ alkyl substituted with 0-1 $R^9$, $C_3-C_6$ alkenyl substituted with 0-1 $R^9$, $C_3-C_7$ cycloalkyl substituted with 0-1 $R^9$, $C_4-C_{11}$ cycloalkylalkyl substituted with 0-1 $R^9$, aryl substituted with 0-1 $R^9$ or 0-2 $R^7$, or aryl ($C_1-C_6$ alkyl)- substituted with 0-1 $R^9$ or 0-2 $R^7$;

$R^{16}$ is selected from:
—C(=O)—O—$R^{18a}$,
—C(=O)—$R^{18b}$,
—C(=O)N($R^{18b}$)$_2$,
—C(=O)NHSO$_2$R$^{18a}$,
—C(=O)NHC(=O)$R^{18b}$,
—C(=O)NHC(=O)O$R^{18a}$,
—C(=O)NHSO$_2$NHR$^{18b}$,
—SO$_2$—$R^{18a}$,
—SO$_2$—N($R^{18b}$)$_2$ or,
—SO$_2$—NHC(=O)O$R^{18b}$;

$R^{17}$ is selected from: H, $C_1-C_6$ alkyl, $C_3-C_7$ cycloalkyl, $C_4-C_{11}$ cycloalkylalkyl, aryl, aryl($C_1-C_6$ alkyl)-, or heteroaryl ($C_1-C_6$ alkyl);

$R^{18a}$ is selected from: $C_1-C_8$ alkyl, $C_3-C_{11}$ cycloalkyl, aryl($C_1-C_6$ alkyl)-, ($C_1-C_6$ alkyl)aryl, heteroaryl ($C_1-C_6$ alkyl)-, ($C_1-C_6$ alkyl)heteroaryl, biaryl($C_1-C_6$ alkyl), heteroaryl, or aryl, wherein said aryl or heteroaryl groups are optionally substituted with 0-4 $R^{19}$;

$R^{18b}$ is selected from $R^{18a}$ or H;

$R^{19}$ is selected from H, halogen, $CF_3$, $CO_2H$, CN, $NO_2$, N$R^{11}$R$^{12}$, $C_1-C_8$ alkyl, $C_2-C_6$ alkenyl, $C_2-C_6$ alkynyl, $C_3-C_{11}$ cycloalkyl, $C_4-C_{11}$ cycloalkylalkyl, aryl ($C_1-C_6$ alkyl)-, $C_1-C_6$ alkoxy, $OCF_3$, or $C_1-C_4$ alkoxycarbonyl, aryl, —O-aryl, —SO$_2$-aryl, heteroaryl, or —SO$_2$-heteroaryl, wherein said aryl and heteroaryl groups are substituted with 0-4 groups selected from hydrogen, halogen, $CF_3$, $C_1-C_3$ alkyl, or $C_1-C_3$ alkoxy;

$R^{20}$ is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, $C_{10}$ to $C_{14}$ (5-aryl-1,3-dioxa-cyclopenten-2-one-yl)methyloxy, or $(R^{11})(R^{12})N$—$(C_1$-$C_{10}$ alkoxy)-;

$R^{21}$ is selected from: $C_1$-$C_8$ alkyl, $C_2$-$C_6$ alkenyl, $C_3$-$C_{11}$ cycloalkyl, $C_4$-$C_{11}$ cycloalkylmethyl, $C_6$-$C_{10}$ aryl, $C_7$-$C_{11}$ arylalkyl, or $C_1$-$C_{10}$ alkyl substituted with 0–2 $R^7$;

$R^{22}$ is selected from:
—C(=O)—$R^{18b}$,
—C(=O)N($R^{18b}$)$_2$,
—C(=O)NHSO$_2$$R^{18a}$,
—C(=O)NHC(=O)$R^{18b}$,
—C(=O)NHC(=O)O$R^{18a}$ or,
—C(=O)NHSO$_2$NH$R^{18b}$, m is 0–2;

n is 0–4;

p is 0–2;

q is 0–4;

r is 0–2;

s is 0–1;

with the following provisos:
(1) when b is a double bond, only one of $R^{14}$ or $R^{15}$ is present and Q and U are not —(CH$_2$)—; and
(2) n, m and q are chosen such that the number of atoms connecting $R^1$ and Y is in the range of 8—14; and
(3) when V is -(phenyl)-Q—, then either: U is not a direct bond (i.e., U is not —(CH$_2$)$_n$— where n=0) or Q is not a direct bond (i.e., Q is not —(CH$_2$)$_n$— where n=0).

3. A compound of claim 2 of Formula II:

(II)

including enantiomeric or diastereomeric forms thereof, or mixtures of enantiomeric or diastereomeric forms thereof, or a pharmaceutically acceptable salt thereof wherein:

b, the bond between carbon atoms numbered 4 and 5, is a carbon-carbon single or double bond;

$R^1$ is selected from:

$R^2$ and $R^3$ are independently selected from: H, $C_1$-$C_4$ alkoxy, NR$^{11}$R$^{12}$, halogen, NO$_2$, CN, CF$_3$, $C_1$-$C_6$ alkyl, $C_3$-$C_6$ alkenyl, $C_3$-$C_7$ cycloalkyl, $C_4$-$C_{11}$ cycloalkylalkyl, $C_6$-$C_{10}$ aryl substituted with 0–2 $R^7$, $C_7$-$C_{11}$ arylalkyl, $C_2$-$C_7$ alkylcarbonyl, or $C_7$-$C_{11}$ arylcarbonyl;

alternatively, $R^2$ and $R^3$ are taken together with the carbon atoms to which they are attached to form a 5–7 membered carbocyclic or 5–7 membered heterocyclic aromatic or nonaromatic ring system, said carbocyclic or heterocyclic ring being optionally substituted with 0–2 $R^7$;

U is selected from:
—(CH$_2$)$_r$—,
—N($R^{12}$)(CH$_2$)$_m$—,
—N($R^{10}$)C(=O)—, or
—C(=O)N($R^{10}$)—;
—N($R^{10}$)S(O)$_p$—, or V is selected from:
—(CH$_2$)$_n$—,
—($C_1$-$C_6$ alkylene)-Q—, substituted with 0–3 groups independently selected from $R^{13}$,
—($C_2$-$C_7$ alkenylene)-Q—, substituted with 0–3 groups independently selected from $R^{13}$,
—($C_2$-$C_7$ alkynylene)-Q—, substituted with 0–3 groups independently selected from $R^{13}$,
-(phenyl)-Q—, said phenyl substituted with 0–2 groups independently selected from $R^{13}$,
-(pyridyl)-Q—, said pyridyl substituted with 0–2 groups independently selected from $R^{13}$, or
-(pyridazinyl)-Q—, said pyridazinyl substituted with 0–2 groups independently selected from $R^{13}$;

Q is selected from:
—(CH$_2$)$_n$—,
—(CH$_2$)$_n$O(CH$_2$)$_m$—,
—(CH$_2$)$_n$N($R^{12}$)(CH$_2$)$_m$—,
—N($R^{10}$)C(=O)—, or
—C(=O)N($R^{10}$)—;

W is selected from:
—(CH$_2$)$_q$C(=O)N(R$^{10}$)—, or
—C(=O)—N(R$^{10}$)—(CH$_2$)$_q$—;
X is —(CH$_2$)$_q$—CH(R$^8$)—CH(R$^9$)—;
Y is —COR$^{20}$;
R$^6$ is selected from:
  H, C$_1$–C$_4$ alkyl, hydroxy, C$_1$–C$_4$ alkoxy, nitro, C$_1$–C$_6$ alkylcarbonyl, —N(R$^{11}$)R$^{12}$, cyano, halo, CF$_3$, —S(O)$_p$R$^{10}$, CO$_2$R$^{18a}$, CONR$^{17}$R$^{18a}$, —COR$^{18a}$, OR$^{10}$,
  C$_6$ to C$_{10}$ aryl optionally substituted with 0–3 groups selected from halogen, C$_1$–C$_6$ alkoxy, C$_1$–C$_6$ alkyl, CF$_3$, S(O)$_m$Me, or —NMe$_2$;
  a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, benzimidazolyl, piperidinyl, tetrahydrofuranyl, pyranyl, 3H-indolyl, carbazolyl, pyrrolidinyl, piperidinyl, isoxazolinyl, isoxazolyl, or morpholinyl;

R$^7$ is selected from:
  H, C$_1$–C$_4$ alkyl, hydroxy, C$_1$–C$_4$ alkoxy, nitro, C$_1$–C$_4$ alkylcarbonyl, —N(R$^{11}$)R$^{12}$, CO$_2$R$^{18a}$, SO$_2$R$^{11}$, SO$_2$NR$^{10}$R$^{11}$ or OR$^{10}$;

R$^8$ is selected from:
  H, CONR$^{17}$R$^{18a}$, —CO$_2$R$^{18a}$, —COR$^{18a}$
  C$_1$–C$_{10}$ alkyl, substituted with 0–1 R$^6$,
  C$_2$–C$_{10}$ alkenyl, substituted with 0–1 R$^6$,
  C$_2$–C$_{10}$ alkynyl, substituted with 0–1 R$^6$,
  C$_3$–C$_8$ cycloalkyl, substituted with 0–1 R$^6$,
  aryl, substituted with 0–1 R$^6$ or,
  a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, benzimidazolyl, piperidinyl, tetrahydrofuranyl, pyranyl, 3H-indolyl, carbazolyl, pyrrolidinyl, piperidinyl, isoxazolinyl, isoxazolyl or morpholinyl, said heterocycle optionally substituted with 0–2 R$^7$;

R$^9$ is selected from: H or —N(R$^{16}$)R$^{17}$;

R$^{10}$ is selected from H or C$_1$–C$_{10}$ alkyl, or C$_7$–C$_{10}$ arylalkyl;

R$^{11}$ is selected from hydrogen, hydroxy, C$_1$ to C$_8$ alkyl, C$_3$–C$_6$ alkenyl, C$_3$ to C$_{11}$ cycloalkyl, C$_4$ to C$_{11}$ cycloalkylmethyl, C$_1$–C$_6$ alkoxy, benzyloxy, C$_6$ to C$_{10}$ aryl, heteroaryl, heteroarylalkyl, C$_7$ to C$_{11}$ arylalkyl, adamantylmethyl, or C$_1$–C$_{10}$ alkyl substituted with 0–2 R$^4$;

alternatively, R$^{10}$ and R$^{11}$ when both are substituents on the same nitrogen atom are taken together with the nitrogen atom to which they are attached to form a heterocycle selected from: 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl; said heterocycle being optionally substituted with 1–3 groups selected from: C$_1$–C$_6$ alkyl, C$_6$–C$_{10}$ aryl, heteroaryl, C$_7$–C$_{11}$ arylalkyl, C$_1$–C$_6$ alkylcarbonyl, C$_3$–C$_7$ cycloalkylcarbonyl, C$_1$–C$_6$ alkoxycarbonyl, C$_7$–C$_{11}$ arylalkoxycarbonyl, C$_1$–C$_6$ alkylsulfonyl or C$_6$–C$_{10}$ arylsulfonyl;

R$^{12}$ is selected from:
  H, C$_1$–C$_6$ alkyl, triphenylmethyl, methoxyphenyldiphenylmethyl, trimethylsilylethoxymethyoxy, C$_1$–C$_4$ alkoxycarbonyl, C$_1$–C$_6$ alkylcarbonyl, C$_1$–C$_6$ alkylsulfonyl, aryl(C$_1$–C$_4$ alkyl)sulfonyl, arylsulfonyl, aryl, heteroarylcarbonyl, or heteroarylalkylcarbonyl, wherein said aryl groups are substituted with 0–3 substituents selected from the group consisting of: C$_1$–C$_4$ alkyl, C$_1$–C$_4$ alkoxy, halo, CF$_3$, and NO$_2$;

R$^{13}$ is selected from: H, hydroxy, C$_1$–C$_{10}$ alkoxy, N(R$^{10}$) R$^{11}$, —N(R$^{16}$)R$^{17}$, C$_1$–C$_{10}$ alkyl substituted with 0–3 R$^7$, aryl substituted with 0–3 R$^7$, heteroaryl substituted with 0–3 R$^7$, or C$_1$–C$_{10}$ alkylcarbonyl;

R$^{14}$ is selected from H, C$_1$–C$_{10}$ alkyl, C$_2$–C$_{10}$ alkenyl, C$_2$–C$_{10}$ alkynyl, C$_1$–C$_{10}$ alkoxy, aryl, heteroaryl or C$_1$–C$_{10}$ alkoxycarbonyl, CO$_2$R$^{10}$ or —C(=O)N(R$^{10}$) R$^{11}$;

R$^{16}$ is selected from:
  —C(=O)—O—R$^{18a}$,
  —C(=O)—R$^{18b}$,
  —SO$_2$—R$^{18a}$ or,
  —SO$_2$—N(18$^b$)$_2$;

R$^{17}$ is selected from H or C$_1$–C$_4$ alkyl;

R$^{18a}$ is selected from: C$_1$–C$_8$ alkyl, C$_3$–C$_{11}$ cycloalkyl, aryl(C$_1$–C$_6$ alkyl)-, (C$_1$–C$_6$ alkyl)aryl, heteroaryl (C$_1$–C$_6$ alkyl)-, (C$_1$–C$_6$ alkyl)heteroaryl, biaryl(C$_1$–C$_6$ alkyl), heteroaryl, or aryl, wherein said aryl or heteroaryl groups are optionally substituted with 0–2 R$^{19}$;

R$^{18b}$ is selected from R$^{18a}$ or H;

R$^{19}$ is selected from H, halogen, CF$_3$, CO$_2$H, CN, NO$_2$, NR$^{11}$R$^{12}$, C$_1$–C$_8$ alkyl, C$_2$–C$_6$ alkenyl, C$_2$–C$_6$ alkynyl, C$_3$–C$_{11}$ cycloalkyl, C$_4$–C$_{11}$ cycloalkylalkyl, aryl (C$_1$–C$_6$ alkyl)-, C$_1$–C$_6$ alkoxy, OCF$_3$, or C$_1$–C$_4$ alkoxycarbonyl, aryl, —O-aryl, —SO$_2$-aryl, heteroaryl, or —SO$_2$-heteroaryl, wherein said aryl and heteroaryl groups are substituted with 0–4 groups selected from hydrogen, halogen, CF$_3$, C$_1$–C$_3$ alkyl, or C$_1$–C$_3$ alkoxy;

R$^{20}$ is selected from:
  hydroxy;
  C$_1$ to C$_{10}$ alkoxy;
  methylcarbonyloxymethoxy-;
  ethylcarbonyloxymethoxy-;
  t-butyl carbonyloxymethoxy-;
  cyclohexylcarbonyloxymethoxy-;
  1-(methylcarbonyloxy)ethoxy-;
  1-(ethylcarbonyloxy)ethoxy-;
  1-(t-butylcarbonyloxy)ethoxy-;
  1-(cyclohexylcarbonyloxy)ethoxy-;
  i-propyloxycarbonyloxymethoxy-;
  t-butyloxycarbonyloxymethoxy-;
  1-(i-propyloxycarbonyloxy)ethoxy-;
  1-(cyclohexyloxycarbonyloxy)ethoxy-;
  1-(t-butyloxycarbonyloxy)ethoxy-;
  dimethylaminoethoxy-;
  diethylaminoethoxy-;
  (5-methyl-1,3-dioxacyclopenten-2-on-4-yl)methoxy-;
  (5-(t-butyl)-1,3-dioxacyclopenten-2-on-4-yl) methoxy-;
  (1,3-dioxa-5-phenyl-cyclopenten-2-on-4-yl)methoxy-or;
  1-(2-(2-methoxypropyl)carbonyloxy)ethoxy-;

R$^{21}$ is selected from C$_1$–C$_8$ alkyl, C$_2$–C$_6$ alkenyl, C$_3$–C$_{11}$ cycloalkyl, C$_4$–C$_{11}$ cycloalkylmethyl, C$_6$–C$_{10}$ aryl, C$_7$–C$_{11}$ arylalkyl, or C$_1$–C$_{10}$ alkyl substituted with 0–2 R$^4$;

m is 0–2;

n is 0–4;

p is 0–2;

q is 0–1; and r is 0–2;

with the following provisos:
(1) when b is a double bond, Q and U are not —(CH$_2$)—; and
(2) n, m and q are chosen such that the number of atoms connecting R$^1$ and Y is in the range of 8–14; and
(3) when V is -(phenyl)-Q—, then either: U is not a direct bond (i.e., U is not —(CH$_2$)$_n$— where n=0) or Q is not a direct bond (i.e., Q is not —(CH$_2$)$_n$— where n=0).

4. A compound of claim 2 of Formula IIIa, IIIb or IIIc:

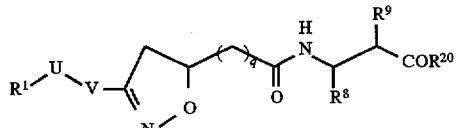
IIIa

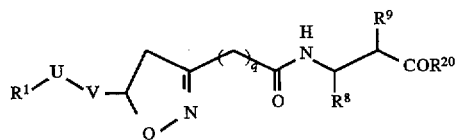
IIIb

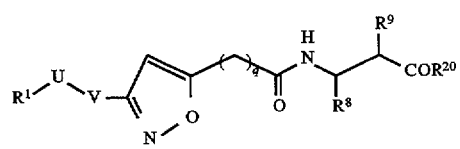
IIIc including enantiomeric or diasteriomeric forms thereof, or mixtures of enantiomeric or diasteriomeric forms thereof, or pharmaceutically acceptable salt thereof wherein:

R$^1$—U taken together are selected from:

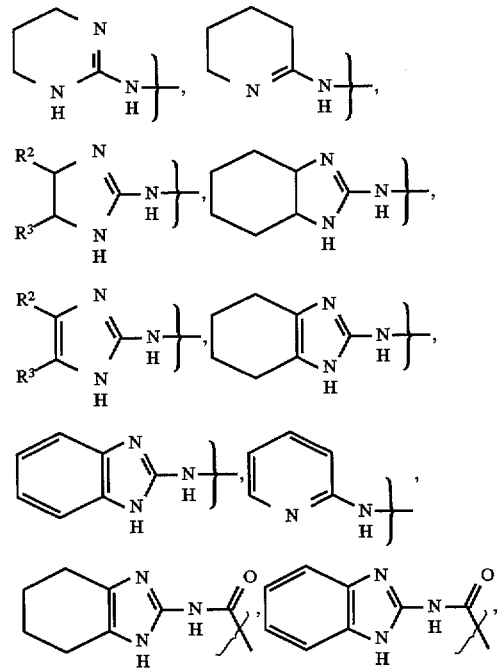

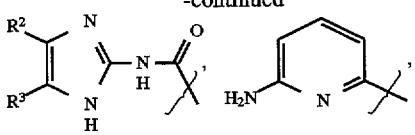

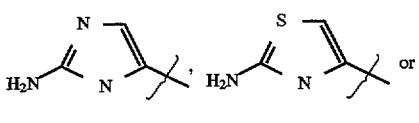

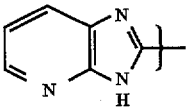

R$^2$ and R$^3$ are independently selected from: H, C$_1$–C$_4$ alkoxy, halogen, C$_1$–C$_6$ alkyl, or C$_3$–C$_6$ alkenyl;

V is selected from:
—(CH$_2$)$_n$—,
—(C$_1$–C$_6$ alkylene)-Q—, substituted with 0–1 groups independently selected from R$^{13}$ or,
—(C$_2$–C$_7$ alkenylene)-Q—, substituted with 0–1 groups independently selected from R$^{13}$, or
-(phenyl)-Q—, said phenyl substituted with 0–1 groups independently selected from R$^{13}$, Q is selected from:
—(CH$_2$)$_n$—,
—O—,
—N(R$^{12}$)—,
—N(R$^{10}$)C(=O)—, or
—C(=O)N(R$^{10}$)—;

R$^7$ is selected from:
H, hydroxy, C$_1$–C$_4$ alkoxy, C$_1$–C$_4$ alkylcarbonyl, —N(R$^{10}$)(R$^{11}$), CO$_2$R$^{18a}$, SO$_2$N(R$^{10}$)R$^{11}$, or OR$^{10}$;

R$^8$ is selected from:
H, CONR$^{17}$R$^{18a}$, C$_1$–C$_{10}$ alkyl, C$_2$–C$_{10}$ alkenyl, C$_2$–C$_{10}$ alkynyl, C$_3$–C$_8$ cycloalkyl, pyridinyl, or aryl, wherein said aryl or pyridinyl groups are optionally substituted with 0–3 substituents selected from the group consisting of: C$_1$–C$_4$ alkyl, C$_1$–C$_4$ alkoxy, aryl, halo, cyano, CF$_3$, and NO$_2$ R$^9$ is selected from: H or —NHR$^{16}$;

R$^{10}$ is selected from H or C$_1$–C$_{10}$ alkyl;

R$^{11}$ is selected from hydrogen, hydroxy, C$_1$ to C$_8$ alkyl, C$_3$–C$_6$ alkenyl, C$_3$ to C$_{11}$ cycloalkyl, C$_4$ to C$_{11}$ cycloalkylmethyl, C$_1$–C$_6$ alkoxy, benzyloxy, C$_6$ to C$_{10}$ aryl, heteroaryl, heteroarylalkyl, C$_7$ to C$_{11}$ arylalkyl, or adamantylmethyl;

R$^{13}$ is selected from: H, hydroxy, C$_1$–C$_{10}$ alkoxy, N(R$^{10}$)R$^{11}$, —N(R$^{16}$)R$^{17}$, C$_1$–C$_{10}$ alkyl substituted with 0–2 R$^7$, aryl substituted with 0–3 R$^7$, heteroaryl substituted with 0–2 R$^7$, or C$_1$–C$_6$ alkylcarbonyl;

R$^{16}$ is selected from:
—C(=O)—O—R$^{18a}$,
—SO$_2$—R$^{18a}$ or,
—SO$_2$—NHR$^{18a}$;

R$^{18a}$ is selected from: C$_1$–C$_8$ alkyl, C$_3$–C$_{11}$ cycloalkyl, aryl(C$_1$–C$_6$ alkyl)-, (C$_1$–C$_6$ alkyl)aryl, heteroaryl (C$_1$–C$_6$ alkyl)-, (C$_1$–C$_6$ alkyl)heteroaryl, biaryl(C$_1$–C$_6$ alkyl), heteroaryl, or aryl, wherein said aryl or heteroaryl groups are optionally substituted with 0–2 R$^{19}$;

R$^{19}$ is selected from: H, Br, F, Cl, CF$_3$, CN, NO$_2$, NHR$^{11}$, C$_1$–C$_4$ alkyl, aryl, aryl(C$_1$–C$_4$ alkyl)-, C$_1$–C$_4$ alkoxy, $C_1$–$C_4$ alkoxycarbonyl, or —O-aryl, wherein said aryl groups are optionally substituted with 0–3 substituents selected from a group consisting of halogen, $CF_3$, $C_1$–$C_3$ alkyl, or $C_1$–$C_3$ alkoxy;

$R^{20}$ is selected from:
  hydroxy;
  $C_1$ to $C_{10}$ alkoxy;
  methylcarbonyloxymethoxy-;
  ethylcarbonyloxymethoxy-;
  t-butylcarbonyloxymethoxy-;
  cyclohexylcarbonyloxymethoxy-;
  1-(methylcarbonyloxy)ethoxy-;
  1-(ethylcarbonyloxy)ethoxy-;
  1-(t-butylcarbonyloxy)ethoxy-;
  1-(cyclohexylcarbonyloxy)ethoxy-;
  i-propyloxycarbonyloxymethoxy-;
  t-butyloxycarbonyloxymethoxy-;
  1-(i-propyloxycarbonyloxy)ethoxy-;
  1-(cyclohexyloxycarbonyloxy)ethoxy-;
  1-(t-butyloxycarbonyloxy)ethoxy-;
  dimethylaminoethoxy-;
  diethylaminoethoxy-;
  (5-methyl-1,3-dioxacyclopenten-2-on-4-yl)methoxy-;
  (5-(t-butyl)-1,3-dioxacyclopenten-2-on-4-yl)methoxy-;
  (1,3-dioxa-5-phenyl-cyclopenten-2-on-4-yl)methoxy- or;
  1-(2-(2-methoxypropyl)carbonyloxy)ethoxy-;

n is 0–4;
q is 0–1;
with the proviso that n, and q are chosen such that the number of atoms connecting $R^1$ and $COR^{20}$ is in the range of 8–14.

5. A compound of claim 1, and enantiomeric or diasteriomeric forms thereof, or mixtures of enantiomeric or diastereomeric forms thereof, or pharmaceutically acceptable salt forms thereof selected from the group consisting of:

3-[3-[3-(imidazolin-2-ylamino)propyl]isoxazolin-5-ylmethylcarbonylamino]-2-(benzyloxycarbonylamino)-propionic acid, 3-[3-[3-(imidazolin-2-ylamino)propyl]isoxazolin-5-ylmethylcarbonylamino]-2-(n-butyloxycarbonylamino)propionic acid, 3-[3-[3-(imidazolin-2-ylamino)propyl]isoxazolin-5-ylmethylcarbonylamino]-2-(phenylsulfonylamino)propionic acid, 3-[3-[3-(imidazolin-2-ylamino)propyl]isoxazolin-5-ylmethylcarbonylamino]-2-(n-butylsulfonylamino)-propionic acid, 3-[3-[3-(tetrahydropyrimid-2-ylamino)propyl]isoxazolin-5-ylmethylcarbonylamino]-2-(benzyloxycarbonylamino)propionic acid, 3-[3-[3-(tetrahydropyrimid-2-ylamino)propyl]isoxazolin-5-ylmethylcarbonyl amino]-2-(n-butyloxycarbonylamino)propionic acid, 3-[3-[3-(tetrahydropyrimid-2-ylamino)propyl]isoxazolin-5-ylmethylcarbonylamino]-2-(phenylsulfonylamino)propionic acid, 3-[3-[3-(tetrahydropyrimid-2-ylamino)propyl]isoxazolin-5-ylmethylcarbonylamino]-2-(n-butylsulfonyl)aminopropionic acid, 3-[3-[4-(imidazolin-2-ylamino)butyl]isoxazolin-5-ylcarbonylamino]-2-(benzyloxycarbonylamino)-propionic acid, 3-[3-[4-(imidazolin-2-ylamino)butyl]isoxazolin-5-ylcarbonylamino]-2-(n-butyloxycarbonyl-amino)propionic acid, 3-[3-[4-(imidazolin-2-ylamino)butyl]isoxazolin-5-ylcarbonylamino]-2-(phenylsulfonylamino)propionic acid, 3-[3-[4-(imidazolin-2-ylamino)butyl]isoxazolin-5-ylcarbonylamino]-2-(n-butylsulfonylamino)propionic acid, 3-[3-[4-(tetrahydropyrimid-2-ylamino)butyl]isoxazolin-5-ylcarbonylamino]-2-(benzyloxycarbonylamino) propionic acid, 3-[3-[4-(tetrahydropyrimid-2-ylamino)butyl]isoxazolin-5-ylcarbonyl amino]-2-(n-butyloxycarbonylamino) propionic acid, 3-[3-[4-(tetrahydropyrimid-2-ylamino)butyl]isoxazolin-5-ylcarbonylamino]-2-(phenylsulfonylamino) propionic acid, 3-[3-[4-(tetrahydropyrimid-2-ylamino)butyl]isoxazolin-5-ylcarbonylamino]-2-(n-butylsulfonyl) aminopropionic acid, 3-[3-[3-(imidazolin-2-ylamino)propyl]isoxazolin-5-ylcarbonylamino]-2-(benzyloxycarbonylamino)-propionic acid, 3-[3-[3-(imidazolin-2-ylamino)propyl]isoxazolin-5-ylcarbonylamino]-2-(phenylsulfonylamino)propionic acid, 3-[3-[3-(tetrahydropyrimid-2-ylamino)propyl]isoxazolin-5-ylcarbonylamino]-2-(benzyloxycarbonylamino) propionic acid, 3-[3-[3-(tetrahydropyrimid-2-ylamino)propyl]isoxazolin-5-ylcarbonylamino]-2-(phenylsulfonylamino) propionic acid, 3-[3-[3-(2-aminothiazol-4-yl)propyl]isoxazolin-5-ylcarbonylamino]-2-(phenylsulfonylamino)propionic acid, 3-[3-[3-(2-aminothiazol-4-yl)propyl]isoxazolin-5-ylcarbonylamino]-2-(benzyloxycarbonylamino) propionic acid, 3-[3-[4-(imidazolin-2-ylamino)butyl]isoxazolin-5-ylcarbonylamino]-2-((2,4,6-trimethylphenyl)sulfonylamino)propionic acid, 3-[3-[4-(tetrahydropyrimid-2-ylamino)butyl]isoxazolin-5-ylcarbonylamino]-2-((2,4,6-trimethylphenyl)sulfonylamino)propionic acid, 3-[3-[4-(imidazol-2-ylamino)butyl]isoxazolin-5-ylcarbonylamino]-2-(benzyloxycarbonylamino)-propionic acid, 3-[3-[4-(imidazol-2-ylamino)butyl]isoxazolin-5-ylcarbonylamino]-2-(phenylsulfonylamino)-propionic acid, 3-[3-[4-(imidazol-2-ylamino)butyl]isoxazolin-5-ylcarbonylamino]-2-((2,6,dichlorophenyl)sulfonylamino)propionic acid, 3-[3-[4-(imidazol-2-ylamino)butyl]isoxazolin-5-ylcarbonylamino]-2-((2,4,6,trimethylphenyl)sulfonylamino)propionic acid, 3-[3-[4-(imidazol-2-ylamino)butyl]isoxazolin-5-ylcarbonylamino]-2-((4-biphenyl)sulfonyl-amino) propionic acid, 3-[3-[4-(imidazol-2-ylamino)butyl]isoxazolin-5-ylcarbonylamino]-2-(1-naphthylsulfonylamino) propionic acid, 3-[3-[3-(imidazol-2-ylamino)propyl]isoxazolin-5-ylmethylcarbonylamino]-2-benzyloxycarbonylamino) propionic acid, 3-[3-[3-(imidazol-2-ylamino)propyl]isoxazolin-5-ylmethylcarbonylamino]-2-(phenylsulfonylamino)propionic acid, 3-[3-[3-(imidazol-2-ylamino)propyl]isoxazolin-5-ylmethylcarbonylamino]-2-((2,6,dichlorophenyl)sulfonylamino)propionic acid, 3-[3-[3-(imidazol-2-ylamino)propyl]isoxazolin-5-ylmethylcarbonylamino]-2-((2,4,6,trimethylphenyl)sulfonylamino)propionic acid, 3-[3-[3-(imidazol-2-ylamino)propyl]isoxazolin-5-ylmethylcarbonylamino]-2-((4-biphenyl)sulfonylamino)propionic acid, 3-[3-[3-(imidazol-2-ylamino)propyl]isoxazolin-5-ylmethylcarbonylamino]-2-(1-naphthylsulfonylamino)propionic acid, 3-[3-[2-(imidazol-2-ylamino)ethyl]isoxazolin-5-ylcarbonylamino]-2-(benzyloxycarbonylamino)-propionic acid, 3-[3-[2-(imidazol-2-ylamino)ethyl]isoxazolin-5-ylcarbonylamino]-2-(phenylsulfonylamino)-propionic acid, 3-[3-[2-(imidazol-2-ylamino)ethyl]isoxazolin-5-ylcarbonylamino]-2-((2,6,dichlorophenyl)sulfonylamino)propionic acid, 3-[3-[2-(imidazol-2-ylamino)ethyl]isoxazolin-5-ylcarbonylamino]-2-((2,4,6,trimethylphenyl)sulfonylamino)propionic acid, 3-[3-[2-(imidazol-2-ylamino)ethyl]isoxazolin-5-ylcarbonylamino]-2-((4-biphenyl)sulfonyl-amino)propionic acid, 3-[3-[2-(imidazol-2-ylamino)ethyl]isoxazolin-5-ylcarbonylamino]-2-(1-naphthylsulfonylamino)propionic acid, 3-[3-[3-(imidazol-2-ylaminocarbonyl)propyl]isoxazolin-5-ylcarbonylamino]-2-((2,4,6,trimethylphenyl)sulfonylamino)propionic acid, 3-[3-[3-(2-aminoimidazol-4-yl)propyl]isoxazolin-5-ylcarbonylamino]-2-((2,4,6,trimethylphenyl)sulfonylamino)propionic acid, 3-[3-[2-(2-aminoimidazol-4-yl)ethyl]isoxazolin-5-ylmethylcarbonylamino]-2-((2,4,6,trimethylphenyl)sulfonylamino)propionic acid, 3-[3-[4-(benzimidazol-2-ylamino)butyl]isoxazolin-5-ylcarbonylamino]-2-((2,4,6,trimethylphenyl)sulfonylamino)propionic acid, 3-[3-[3-(benzimidazol-2-ylamino)propyl]isoxazolin-5-ylmethylcarbonylamino]-2-((2,4,6,trimethylphenyl)sulfonylamino)propionic acid, 3-[3-[3-(benzimidazol-2-ylaminocarbonyl)propyl]isoxazolin-5-ylcarbonylamino]-2-((2,4,6,trimethylphenyl)sulfonylamino)propionic acid, 3-[3-[4-(4-methylimidazol-2-ylamino)butyl]isoxazolin-5-ylcarbonylamino]-2-((2,4,6,trimethylphenyl)sulfonylamino)propionic acid, 3-[3-[3-(4-methylimidazol-2-ylamino)propyl]isoxazolin-5-ylmethylcarbonylamino]-2-((2,4,6,trimethylphenyl)sulfonylamino)propionic acid, 3-[3-[4-(4,5-dimethylimidazol-2-ylamino)butyl]-isoxazolin-5-ylcarbonylamino]-2-((2,4,6,trimethylphenyl)sulfonylamino)propionic acid, 3-[3-[3-(4,5-dimethylimidazol-2-ylamino)propyl]-isoxazolin-5-ylmethylcarbonylamino]-2-((2,4,6,trimethylphenyl)sulfonylamino)propionic acid, 3-[3-[3-(4,5-dimethylimidazol-2-ylaminocarbonyl)propyl]isoxazolin-5-ylcarbonylamino]-2-((2,4,6,trimethylphenyl)sulfonylamino)propionic acid, 3-[3-[4-(4,5,6,7-tetrahydrobenzimidazol-2-ylamino)butyl]isoxazolin-5-ylcarbonylamino]-2-((2,4,6,trimethylphenyl)sulfonylamino)propionic acid, 3-[3-[3-(4,5,6,7-tetrahydrobenzimidazol-2-ylamino)propyl]isoxazolin-5-ylmethylcarbonylamino]-2-((2,4,6,trimethylphenyl)sulfonylamino)propionic acid, 3-[3-[4-(pyridin-2-ylamino)butyl]isoxazolin-5-ylcarbonylamino]-2-((2,4,6,trimethylphenyl)sulfonylamino)propionic acid, 3-[3-[3-(pyridin-2-ylamino)propyl]isoxazolin-5-ylmethylcarbonylamino]-2-((2,4,6,trimethylphenyl)sulfonylamino)propionic acid, 3-[3-[3-(2-pyridin-6-yl)propyl]isoxazolin-5-ylcarbonylamino]-2-((2,4,6,trimethylphenyl)sulfonylamino)propionic acid, 3-[3-[2-(2-aminopyridin-6-yl)ethyl]isoxazolin-5-ylmethylcarbonylamino]-2-((2,4,6,trimethylphenyl)sulfonylamino)propionic acid, 3-[3-[3-(7-azabenzimidazol-2-yl)propyl]isoxazolin-5-ylcarbonylamino]-2-((2,4,6,trimethylphenyl)sulfonylamino)propionic acid, 3-[5-[3-(imidazolin-2-ylamino)propyl]isoxazolin-3-ylmethylcarbonylamino]-2-(benzyloxycarbonylamino)-propionic acid, 3-[5-[3-(imidazolin-2-ylamino)propyl]isoxazolin-3-ylmethylcarbonylamino]-2-(n-butyloxycarbonylamino)propionic acid, 3-[5-[3-(imidazolin-2-ylamino)propyl]isoxazolin-3-ylmethylcarbonylamino]-2-(phenylsulfonylamino)propionic acid, 3-[5-[3-(imidazolin-2-ylamino)propyl]isoxazolin-3-ylmethylcarbonylamino]-2-(2,4,6-trimethylphenylsulfonylamino)propionic acid, 3-[5-[3-(imidazolin-2-ylamino)propyl]isoxazolin-3-ylmethylcarbonylamino]-2-(n-butylsulfonylamino)-propionic acid, 3-[5-[3-(tetrahydropyrimid-2-ylamino)propyl]isoxazolin-3-ylmethylcarbonylamino]-2-(benzyloxycarbonylamino)propionic acid, 3-[5-[3-(tetrahydropyrimid-2-ylamino)propyl]isoxazolin-3-ylmethylcarbonyl amino]-2-(n-butyloxycarbonylamino)propionic acid, 3-[5-[3-(tetrahydropyrimid-2-ylamino)propyl]isoxazolin-3-ylmethylcarbonylamino]-2-(phenylsulfonylamino)propionic acid, 3-[5-[3-(tetrahydropyrimid-2-ylamino)propyl]isoxazolin-3-ylmethylcarbonylamino]-2-(2,4,6-trimethylphenylsulfonylamino)propionic acid, 3-[5-[3-(tetrahydropyrimid-2-ylamino)propyl]isoxazolin-3-ylmethylcarbonylamino]-2-(n-butylsulfonyl)aminopropionic acid, 3-[5-[4-(imidazolin-2-yl amino)butyl]isoxazolin-3-ylcarbonylamino]-2-(benzyloxycarbonylamino)-propionic acid, 3-[5-[4-(imidazolin-2-ylamino)butyl]isoxazolin-3-ylcarbonylamino]-2-(n-butyloxycarbonylamino)propionic acid, 3-[5-[4-(imidazolin-2-ylamino)butyl]isoxazolin-3-ylcarbonylamino]-2-(phenylsulfonylamino)propionic acid, 3-[5-[4-(imidazolin-2-ylamino)butyl]isoxazolin-3-ylcarbonylamino]-2-(n-butylsulfonylamino)propionic acid, 3-[5-[4-(tetrahydropyrimid-2-ylamino)butyl]isoxazolin-3-ylcarbonylamino]-2-(benzyloxycarbonylamino)propionic acid, 3-[5-[4-(tetrahydropyrimid-2-ylamino)butyl]isoxazolin-3-ylcarbonyl amino]-2-(n-butyloxycarbonylamino)propionic acid, 3-[5-[4-(tetrahydropyrimid-2-ylamino)butyl]isoxazolin-3-ylcarbonylamino]-2-(phenylsulfonylamino)propionic acid, 3-[5-[4-(tetrahydropyrimid-2-ylamino)butyl]isoxazolin-3-ylcarbonylamino]-2-(n-butylsulfonyl)aminopropionic acid, 3-[5-[3-(imidazol-2-yl amino)propyl]isoxazolin-3-ylcarbonylamino]-2-(benzyloxycarbonylamino)-propionic acid, 3-[5-[3-(imidazolin-2-ylamino)propyl]isoxazolin-3-ylcarbonylamino]-2-(n-propyloxycarbonylamino)propionic acid, 3-[5-[3-(imidazolin-2-ylamino)propyl]isoxazolin-3-ylcarbonylamino]-2-(phenylsulfonylamino)propionic acid, 3-[5-[3-(imidazolin-2-ylamino)propyl]isoxazolin-3-ylcarbonylamino]-2-(n-propylsulfonylamino)propionic acid, 3-[5-[3-(tetrahydropyrimid-2-ylamino)propyl]isoxazolin-3-ylcarbonylamino]-2-(benzyloxycarbonylamino)propionic acid, 3-[5-[3-(tetrahydropyrimid-2-ylamino)propyl]isoxazolin-3-ylmethylcarbonylamino]-2-(n-propyloxycarbonylamino)propionic acid, 3-[5-[3-(tetrahydropyrimid-2-ylamino)propyl]isoxazolin-3-ylcarbonylamino]-2-(phenylsulfonylamino)propionic acid, 3-[5-[3-(tetrahydropyrimid-2-ylamino)propyl]isoxazolin-3-ylcarbonylamino]-2-(n-propylsulfonyl)aminopropionic acid, 3-[5-[2-(imidazolin-2-ylamino)ethyl]isoxazolin-3-ylcarbonylamino]-2-(phenylsulfonylamino)propionic acid, 3-[5-[4-(pyridin-2-ylamino)butyl]isoxazolin-3-ylcarbonylamino]-2-(phenylsulfonylamino)propionic acid, 3-[5-[4-(pyridin-2-ylamino)butyl]isoxazolin-3-ylcarbonylamino]-2-(2,6-dichlorophenylsulfonylamino)propionic acid, 3-[5-[4-(pyridin-2-ylamino)butyl]isoxazolin-3-ylcarbonylamino]-2-(2,4,6-trimethylphenylsulfonylamino)propionic acid, 3-[5-[4-(pyridin-2-ylamino)butyl]isoxazolin-3-ylcarbonylamino]-2-(4-biphenylsulfonylamino)propionic acid, 3-[5-[4-(pyridin-2-ylamino)butyl]isoxazolin-3-ylcarbonylamino]-2-(1-naphthylsulfonylamino)propionic acid, 3-[5-[3-(2-aminopyridin-6-yl)propyl]isoxazolin-3-ylcarbonylamino]-2-(2,4,6-trimethylphenyl sulfonylamino)propionic acid, 3-[5-[4-(imidazol-2-ylamino)butyl]isoxazolin-3-ylcarbonylamino]-2-(phenylsulfonylamino)-propionic acid, 3-[5-[4-(imidazol-2-ylamino)butyl]isoxazolin-3-ylcarbonylamino]-2-(2,6-dichlorophenylsulfonylamino)propionic acid, 3-[5-[4-(imidazol-2-ylamino)butyl]isoxazolin-3-ylcarbonylamino]-2-(2,4,6-trimethylphenylsulfonylamino)propionic acid, 3-[5-[4-(imidazol-2-ylamino)butyl]isoxazolin-3-ylcarbonylamino]-2-(4-biphenylsulfonylamino)propionic acid, 3-[5-[4-(imidazol-2-ylamino)butyl]isoxazolin-3-ylcarbonylamino]-2-(1-naphthylsulfonylamino)propionic acid, 3-[5-[3-(2-aminoimidazol-4-yl)propyl]isoxazolin-3-ylcarbonylamino]-2-(phenylsulfonylamino)-propionic acid, 3-[5-[3-(2-aminoimidazol-4-yl)propyl]isoxazolin-3-ylcarbonylamino]-2-(2,6-dichlorophenylsulfonylamino)propionic acid, 3-[5-[3-(2-aminoimidazol-4-yl)propyl]isoxazolin-3-ylcarbonylamino]-2-(2,4,6-trimethylphenyl sulfonylamino)propionic acid, 3-[5-[3-(2-aminoimidazol-4-yl)propyl]isoxazolin-3-ylcarbonylamino]-2-(4-biphenylsulfonylamino)propionic acid, 3-[5-[3-(2-aminoimidazol-4-yl)propyl]isoxazolin-3-ylcarbonylamino]-2-(1-naphthylsulfonylamino)propionic acid, 3-[5-[2-(imidazol-2-ylamino)ethyl]isoxazolin-3-ylcarbonylamino]-2-(phenylsulfonylamino)-propionic acid, 3-[5-[2-(imidazol-2-ylamino)ethyl]isoxazolin-3-ylcarbonylamino]-2-(2,6-dichlorophenylsulfonylamino)propionic acid, 3-[5-[2-(imidazol-2-ylamino)ethyl]isoxazolin-3-ylcarbonylamino]-2-(2,4,6-trimethylphenylsulfonylamino)propionic acid, 3-[5-[2-(imidazol-2-ylamino)ethyl]isoxazolin-3-ylcarbonylamino]-2-(4-biphenylsulfonylamino)propionic acid, 3-[5-[2-(imidazol-2-ylamino)ethyl]isoxazolin-3-ylcarbonylamino]-2-(1-naphthylsulfonylamino)propionic acid, 3-[5-[3-(imidazol-2-ylaminocarbonyl)propyl]isoxazolin-3-ylcarbonylamino]-2-(2,4,6-trimethylphenylsulfonylamino)propionic acid, 3-[5-[3-(benzimidazol-2-ylaminocarbonyl)propyl]isoxazolin-3-ylcarbonylamino]-2-(2,4,6-trimethylphenylsulfonylamino)propionic acid, 3-[5-[4-(benzimidazol-2-ylamino)butyl]isoxazolin-3-ylcarbonylamino]-2-(phenylsulfonylamino)propionic acid, 3-[5-[4-(benzimidazol-2-ylamino)butyl]isoxazolin-3-ylcarbonylamino]-2-(2,6-dichlorophenylsulfonylamino)propionic acid, 3-[5-[4-(benzimidazol-2-ylamino)butyl]isoxazolin-3-ylcarbonylamino]-2-(2,4,6-trimethylphenylsulfonylamino)propionic acid, 3-[5-[4-(benzimidazol-2-ylamino)butyl]isoxazolin-3-ylcarbonylamino]-2-(4-biphenylsulfonylamino)propionic acid, 3-[5-[4-(benzimidazol-2-ylamino)butyl]isoxazolin-3-ylcarbonylamino]-2-(1-naphthylsulfonylamino)propionic acid, 3-[5-[4-(4-methylimidazol-2-ylamino)butyl]isoxazolin-3-ylcarbonylamino]-2-(phenylsulfonylamino) propionic acid, 3-[5-[4-(4-methylimidazol-2-ylamino)butyl]isoxazolin-3-ylcarbonylamino]-2-(2,6-dichlorophenylsulfonylamino)propionic acid, 3-[5-[4-(4-methylimidazol-2-ylamino)butyl]isoxazolin-3-ylcarbonylamino]-2-(2,4,6-trimethylphenylsulfonylamino)propionic acid, 3-[5-[4-(4-methylimidazol-2-ylamino)butyl]isoxazolin-3-ylcarbonylamino]-2-(4-biphenylsulfonylamino) propionic acid, 3-[5-[4-(4-methylimidazol-2-ylamino)butyl]isoxazolin-3-ylcarbonylamino]-2-(1-naphthylsulfonylamino) propionic acid, 3-[5-[4-(4,5-dimethylimidazol-2-ylamino)butyl]-isoxazolin-3-ylcarbonylamino]-2-(phenylsulfonylamino)propionic acid, 3-[5-[4-(4,5-dimethylimidazol-2-ylamino)butyl]-isoxazolin-3-ylcarbonylamino]-2-(2,6-dichlorophenylsulfonylamino)propionic acid, 3-[5-[4-(4,5-dimethylimidazol-2-ylamino)butyl]-isoxazolin-3-ylcarbonylamino]-2-(2,4,6-trimethylphenylsulfonylamino)propionic acid, 3-[5-[4-(4,5-dimethylimidazol-2-ylamino)butyl]-isoxazolin-3-ylcarbonylamino]-2-(4-biphenylsulfonylamino)propionic acid, 3-[5-[4-(4,5-dimethylimidazol-2-ylamino)butyl]-isoxazolin-3-ylcarbonylamino]-2-(1-naphthylsulfonylamino)propionic acid, 3-[5-[4-(4,5,6,7-tetrahydrobenzimidazol-2-ylamino) butyl]-isoxazolin-3-ylcarbonylamino]-2-(phenylsulfonylamino)propionic acid, 3-[5-[4-(4,5,6,7-tetrahydrobenzimidazol-2-ylamino) butyl]-isoxazolin-3-ylcarbonylamino]-2-(2,6-dichlorophenylsulfonylamino)propionic acid, 3-[5-[4-(4,5,6,7-tetrahydrobenzimidazol-2-ylamino) butyl]-isoxazolin-3-ylcarbonylamino]-2-(2,4,6-trimethylphenylsulfonylamino)propionic acid, 3-[5-[4-(4,5,6,7-tetrahydrobenzimidazol-2-ylamino) butyl]isoxazolin-3-ylcarbonylamino]-2-(4-biphenylsulfonylamino)propionic acid, 3-[5-[4-(4-,5,6,7-tetrahydrobenzimidazol-2-ylamino) butyl]-isoxazolin-3-ylcarbonylamino]-2-(1-naphthylsulfonylamino)propionic acid, 3-[5-[3-(7-azabenzimidazol-2-yl)propyl]isoxazolin-3-ylcarbonylamino]-2-(2,4,6-trimethylphenylsulfonylamino)propionic acid, 3-[5-[4-(imidazol-2-ylamino)butyl]isoxazolin-3-ylcarbonylamino]-2-[(2,6-dimethyl-4-phenyl) phenylsulfonylamino]propionic acid, 3-[5-[4-(4-methylimidazol-2-ylamino)butyl]isoxazolin-3-ylcarbonylamino]-2-[(2,6-dimethyl-4-phenyl) phenylsulfonylamino]propionic acid, 3-[5-[4-(4,5-dimethylimidazol-2-ylamino)butyl] isoxazolin-3-ylcarbonylamino]-2-[(2,6-dimethyl-4-phenyl)phenylsulfonylamino]propionic acid, 3-[5-[4-(4,5,6,7-tetrahydrobenzimidazol-2-ylamino) butyl]isoxazolin-3-ylcarbonylamino]-2-[(2,6-dimethyl-4-phenyl)phenylsulfonylamino]propionic acid, 3-[5-[4-(imidazol-2-ylamino)butyl]isoxazolin-3-ylcarbonylamino]-2-[(2,6-dichloro-4-phenyl) phenylsulfonylamino]propionic acid, 3-[5-[4-(4-methylimidazol-2-ylamino)butyl]isoxazolin-3-ylcarbonylamino]-2-[(2,6-dichloro-4-phenyl) phenylsulfonylamino]propionic acid, 3-[5-[4-(4,5-dimethylimidazol-2-ylamino)butyl] isoxazolin-3-ylcarbonylamino]-2-[(2,6-dichloro-4-phenyl)phenylsulfonylamino]propionic acid, 3-[5-[4-(4,5,6,7-tetrahydrobenzimidazol-2-ylamino) butyl]isoxazolin-3-ylcarbonylamino]-2-[(2,6-dichloro-4-phenyl)phenylsulfonylamino]propionic acid, 3-[5-[4-(imidazol-2-ylamino)butyl]isoxazolin-3-ylcarbonylamino]-3-(phenylsulfonylmethyl)propionic acid, 3-[5-[4-(imidazol-2-ylamino)butyl]isoxazolin-3-ylcarbonylamino]-3-(1-adamantylmethylaminocarbonyl)propionic acid, 3-[5-[4-(imidazol-2-ylamino)butyl]isoxazolin-3-ylcarbonylamino]-3-(3-pyridinyl)propionic acid, 3-[3-[3-(imidazolin-2-ylamino)propyloxy]isoxazol-5-ylcarbonylamino]-2-(benzyloxycarbonylamino)-propionic acid, 3-[3-[3-(imidazolin-2-ylamino)propyloxy]isoxazol-5-yl carbonyl amino]-2-(n-butyloxycarbonyl-amino) propionic acid, 3-[3-[3-(imidazolin-2-ylamino)propyloxy]isoxazol-5-yl carbonylamino]-2-(phenylsulfonylamino)propionic acid, 3-[3-[3-(imidazolin-2-ylamino)propyloxy]isoxazol-5-yl carbonyl amino]-2-(n-butylsulfonylamino)-propionic acid, 3-[3-[3-(tetrahydropyrimid-2-ylamino)propyloxy]-isoxazol-5-ylcarbonylamino]-2-(benzyloxycarbonylamino)propionic acid, 3-[3-[3-(tetrahydropyrimid-2-ylamino)propyloxy]-isoxazol-5-ylcarbonyl amino]-2-(n-butyloxycarbonylamino)propionic acid, 3-[3-[3-(tetrahydropyrimid-2-ylamino)propyloxy]-isoxazol-5-ylcarbonylamino]-2-(phenylsulfonylamino) propionic acid, 3-[3-[3-(tetrahydropyrimid-2-ylamino)propyloxy]-isoxazol-5-yl carbonylamino]-2-(n-butylsulfonyl) aminopropionic acid, 3-[3-[2-(imidazolin-2-yl amino)ethyloxy]isoxazol-5-yl carbonylamino]-2-(benzyloxycarbonylamino)-propionic acid, 3-[3-[3-(imidazolin-2-ylamino)ethyloxy]isoxazol-5-yl carbonylamino]-2-(n-butyloxycarbonylamino) propionic acid, 3-[3-[3-(imidazolin-2-ylamino)ethyloxy]isoxazol-5-yl carbonylamino]-2-(phenylsulfonylamino)propionic acid, 3-[3-[3-(imidazolin-2-ylamino)ethyloxy]isoxazol-5-ylcarbonylamino]-2-(n-butylsulfonylamino)propionic acid, 3-[3-[3-(tetrahydropyrimid-2-yl amino)ethyloxy]-isoxazol-5-ylcarbonylamino]-2-(benzyloxycarbonylamino)propionic acid, 3-[3-[3-(tetrahydropyrimid-2-ylamino)ethyloxy]-isoxazol-5-ylcarbonylamino]-2-(n-butyloxycarbonylamino)propionic acid, 3-[3-[3-(tetrahydropyrimid-2-ylamino)ethyloxy]-isoxazol-5-ylcarbonylamino]-2-(phenylsulfonylamino) propionic acid, 3-[3-[3-(tetrahydropyrimid-2-ylamino)ethyloxy]-isoxazol-5-ylcarbonylamino]-2-(n-butylsulfonylamino)propionic acid, 3-[3-[3-(imidazol-2-ylamino)propyloxy]isoxazol-5-ylcarbonylamino]-2-(phenylsulfonylamino)propionic acid, 3-[3-[3-(benzimidazol-2-ylamino)propyloxy]isoxazol-5-ylcarbonylamino]-2-(phenylsulfonylamino)propionic acid, 3-[3-[3-(4-methylimidazol-2-ylamino)propyloxy]-isoxazol-5-ylcarbonylamino]-2-(phenylsulfonylamino)propionic acid, 3-[3-[3-(4,5-dimethylimidazol-2-ylamino)propyloxy]-isoxazol-5-ylcarbonylamino]-2-(phenylsulfonylamino)propionic acid, 3-[3-[3-(4,5,6,7-tetrahydrobenzimidazol-2-ylamino)propyloxy]-isoxazol-5-ylcarbonylamino]-2-(phenylsulfonylamino)propionic acid, 3-[3-[3-(pyridin-2-ylamino)propyloxy]isoxazol-5-ylcarbonylamino]-2-(phenylsulfonylamino)propionic acid, 3-[3-[3-(imidazol-2-ylaminocarbonyl)ethoxy]isoxazol-5-ylcarbonylamino]-2-(phenylsulfonylamino)propionic acid, and prodrug ester forms thereof, wherein the hydrogen of the hydroxy group of the propionic acid moiety is substituted with a group selected from:

$C_1$–$C_{10}$ alkyl;
methylcarbonyloxymethyl-;
ethylcarbonyloxymethyl-;
t-butylcarbonyloxymethyl-;
cyclohexylcarbonyloxymethyl-;
1-(methylcarbonyloxy)ethyl-;
1-(ethylcarbonyloxy)ethyl-;
1(t-butylcarbonyloxy)ethyl-;
1-(cyclohexylcarbonyloxy)ethyl-;
i-propyloxycarbonyloxymethyl-;
t-butyloxycarbonyloxymethyl-;
1-(i-propyloxycarbonyloxy)ethyl-;
1-(cyclohexyloxycarbonyloxy)ethyl-;
1-(t-butyloxycarbonyloxy)ethyl-;
dimethylaminoethyl-;
diethylaminoethyl-:
(5-methyl-1,3-dioxacyclopenten-2-on-4-yl)methyl-;
(5-(t-butyl)-1,3-dioxacyclopenten-2-on-4-yl)methyl-;
(1,3-dioxa-5-phenyl-cyclopenten-2-on-4-yl)methyl-; or
1-(2-(2-methoxypropyl)carbonyloxy)ethyl-.

6. A method of treating angiogenic disorders, inflammation, bone degradation, or thrombosis, comprising administering to a host in need of such treatment a therapeutically effective amount of a compound of claim 1.

7. A method of treating angiogenic disorders, inflammation, bone degradation, or thrombosis, comprising administering to a host in need of such treatment a therapeutically effective amount of a compound of claim 2.

8. A method of treating angiogenic disorders, inflammation, bone degradation, or thrombosis, comprising administering to a host in need of such treatment a therapeutically effective amount of a compound of claim 3.

9. A method of treating angiogenic disorders, inflammation, bone degradation, or thrombosis, comprising administering to a host in need of such treatment a therapeutically effective amount of a compound of claim 4.

10. A method of treating angiogenic disorders, inflammation, bone degradation, or thrombosis, comprising administering to a host in need of such treatment a therapeutically effective amount of a compound of claim 5.

11. A pharmaceutical composition comprising a therapeutically effective amount of a compound of claim 1 and a pharmaceutically acceptable carrier.

12. A pharmaceutical composition comprising a therapeutically effective amount of a compound of claim 2 and a pharmaceutically acceptable carrier.

13. A pharmaceutical composition comprising a therapeutically effective amount of a compound of claim 3 and a pharmaceutically acceptable carrier.

14. A pharmaceutical composition comprising a therapeutically effective amount of a compound of claim 4 and a pharmaceutically acceptable carrier.

15. A pharmaceutical composition comprising a therapeutically effective amount of a compound of claim 5 and a pharmaceutically acceptable carrier.

16. A method for the treatment of thrombosis which comprises administering to a host in need of such treatment a therapeutically effective amount of a compound of claim 1 in combination with one or more additional therapeutic agents selected from: a thrombolytic agent, an anti-coagulant agent, or an anti-platelet agent.

17. A method of inhibiting angiogenesis, comprising administering to a host in need of such inhibition a therapeutically effective amount of a compound of claim 1.

18. A method of inhibiting angiogenesis, comprising administering to a host in need of such inhibition a therapeutically effective amount of a compound of claim 2.

19. A method of inhibiting angiogenesis, comprising administering to a host in need of such inhibition a therapeutically effective amount of a compound of claim 3.

20. A method of inhibiting angiogenesis, comprising administering to a host in need of such inhibition a therapeutically effective amount of a compound of claim 4.

21. A method of inhibiting angiogenesis, comprising administering to a host in need of such inhibition a therapeutically effective amount of a compound of claim 5.

* * * * *